US009284562B2

(12) United States Patent
Collins et al.

(10) Patent No.: US 9,284,562 B2
(45) Date of Patent: Mar. 15, 2016

(54) BIOLOGICAL CIRCUIT CHEMOTACTIC CONVERTERS

(75) Inventors: James J. Collins, Newton, MA (US); Timothy Kuan-Ta Lu, Charlestown, MA (US)

(73) Assignees: Trustees of Boston University, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/512,453

(22) PCT Filed: Nov. 30, 2010

(86) PCT No.: PCT/US2010/058341
§ 371 (c)(1),
(2), (4) Date: Oct. 2, 2012

(87) PCT Pub. No.: WO2011/066541
PCT Pub. Date: Jun. 3, 2011

(65) Prior Publication Data
US 2013/0034907 A1    Feb. 7, 2013

Related U.S. Application Data

(60) Provisional application No. 61/265,219, filed on Nov. 30, 2009.

(51) Int. Cl.
*C12N 15/00* (2006.01)
*C12N 15/09* (2006.01)
(Continued)

(52) U.S. Cl.
CPC .............. *C12N 15/63* (2013.01); *C12N 15/635* (2013.01)

(58) Field of Classification Search
CPC ............. C12N 15/635; C12N 2320/50; C12N 2830/05; C12Q 1/6897
See application file for complete search history.

(56) References Cited

U.S. PATENT DOCUMENTS 6,737,269 B2 * 5/2004 Gardner et al. ............... 435/325
6,828,140 B2 * 12/2004 Gardner et al. ............ 435/252.3
(Continued)

FOREIGN PATENT DOCUMENTS

WO    2008051854    5/2008
WO    2011/066539    6/2011

OTHER PUBLICATIONS

Hideki Kobayashi, et al., Programmable cells: Interfacing natural and engineered gene networks. 2004, PNAS, 101:8414-8419.*
(Continued)

*Primary Examiner* — Kevin Hill
*Assistant Examiner* — Arthur S Leonard
(74) *Attorney, Agent, or Firm* — Nixon Peabody LLP; Ronald I. Eisenstein; Leena H. Karttunen Contarino

(57) ABSTRACT

Described herein are novel biological circuit chemotactic converter that utilize modular components, such as genetic toggle switches and single invertase memory modules (SIMMs), for detecting and converting external inputs, such as chemoattractants, into outputs that allow for autonomous chemotaxis in cellular systems. Flexibility in these biological circuit chemotactic converter is provided by combining individual modular components, i.e., SIMMs and genetic toggle switches, together. These biological converter switches can be combined in a variety of network topologies to create network systems that regulate chemotactic responses based on the combination and nature of input signals received.

20 Claims, 15 Drawing Sheets

(51) Int. Cl.
*C07H 21/04* (2006.01)
*C12Q 1/68* (2006.01)
*H03M 1/66* (2006.01)
*H03M 1/12* (2006.01)
*C12N 15/63* (2006.01)

(56) References Cited

U.S. PATENT DOCUMENTS 6,841,376 B2 * 1/2005 Gardner et al. ............ 435/252.3
2003/0166191 A1 9/2003 Gardner et al.

OTHER PUBLICATIONS

Voigt et al, Genetic parts to program bacteria. Current Opinion in Biotechnology 2006, 17:548-557.*
Weiss et al., Genetic circuit building blocks for cellular computation, communications, and signal processing. Natural Computing 2: 47-84. 2003.*
Fritz et al., Designing sequential transcription logic: a simple genetic circuit for conditional memory. Syst Synth Biol (2007) 1:89-98.*
Gardner et al, "Constrcution of a genetic toggle switch in *Ecscherichia coli*", Nature, vol. 403, No. 6767, pp. 339-342, 2000.
Friedland et al, "Synthetic gene networks that count", Science, vol. 324, No. 5931, pp. 1199-1302, 2009.
Lu et al, "Next Generation Synthetic Gene Networks", Nat. Biotechnol., vol. 27, pp. 1139-1150, 2009.
Ajo-Franklin et al. Rational design of memory in eukaryotic cells. Genes Dev 21, 2271-2276 (2007).
An and Chin, Synthesis of orthogonal transcription-translation networks. Proc Natl Acad Sci U S A 106, 8477-8482 (2009).
Anderson et al., Environmentally controlled invasion of cancer cells by engineered bacteria. J Mol Biol 355, 619-627 (2006).
Bae et al, Nature Biotechnology 2003: 21, p. 275-280. "Human zinc fingers as building blocks in the construction of artificial transcription factors."
Basu et al., A synthetic multicellular system for programmed pattern formation. Nature 434, 1130-1134 (2005).
Bayer et al., Programmable ligand-controlled riboregulators of eukaryotic gene expression. Nat Biotechnol 23, 337-343 (2005).
Beerli et al., 3rd Positive and negative regulation of endogenous genes by designed transcription factors. Proc Natl Acad Sci U S A 97, 1495-1500 (2000).
Blancafort et al., Nature Biotechnology 2003: 21, p. 269-274. "Scanning the human genome with combinatorial transcription factor libraries."
Blancafort et al., PNAS, 2005, 102: 33, p. 11716-11721. "Genetic reprogramming of tumor cells by zinc finger transcription factors."
Booth et al., Mechanosensitive channels in bacteria: signs of closure? Nat Rev Microbiol 5, 431-440 (2007).
Canton et al., Refinement and standardization of synthetic biological parts and devices. Nat Biotechnol 26, 787-793 (2008).
Czar et al., Writing DNA with GenoCAD. Nucleic Acids Res 37, W40-47 (2009).
Datsenko et al., Proc Natl Acad Sci U S A 97, 6640 (2000). "One-step inactivation of chromosomal genes in *Escherichia coli* K-12 using PCR products."
Deans et al., A tunable genetic switch based on RNAi and repressor proteins for regulating gene expression in mammalian cells. Cell 130, 363-372 (2007).
Ellis et al., Diversity-based, model-guided construction of synthetic gene networks with predicted functions. Nat Biotechnol 27, 465-471 (2009).
Elowitz and Leibler, A synthetic oscillatory network of transcriptional regulators. Nature 403, 335-338 (2000).
Falke et al., The two-component signaling pathway of bacterial chemotaxis: a molecular view of signal transduction by receptors, kinases, and adaptation enzymes. Annu Rev Cell Dev Biol 13, 457-512 (1997).

Fung et al, A synthetic gene-metabolic oscillator. Nature 435, 118-122 (2005).
Guido et al., A bottom-up approach to gene regulation. Nature 439, 856-860 (2006).
Ham et al., A tightly regulated inducible expression system utilizing the fim inversion recombination switch. Biotechnol Bioeng 94, 1-4 (2006).
Ham et al., Design and construction of a double inversion recombination switch for heritable sequential genetic memory. PLoS ONE 3, e2815 (2008).
Hooshangi et al., Ultrasensitivity and noise propagation in a synthetic transcriptional cascade. Proc Natl Acad Sci U S A 102, 3581-3586 (2005).
Isaacs et al., Engineered riboregulators enable post-transcriptional control of gene expression. Nat Biotechnol 22, 841-847 (2004).
Isaacs et al., Prediction and measurement of an autoregulatory genetic module. Proc Natl Acad Sci U S A 100, 7714-7719 (2003).
Lee et al., Nucleic Acids Research,36:16 (2008). "Phenotypic engineering by reprogramming gene transcription using novel artificial transcription factors in *Escherichia coli*."
Lee et al., Genome Res., 2003, 13: 2708-2716. "Toward a functional annotation of the human genome using artificial transcription factors."
Jogler et al., Genomics, genetics, and cell biology of magnetosome formation. Annu Rev Microbiol 63, 501-521 (2009).
Haynes et al., J Biol Eng 2, 8 (2008). "Engineering bacteria to solve the Burnt Pancake problem."
Kitano et al., Nat Rev Genet 5, 826-837 (2004). "Biological robustness."
Kobayashi et al., Programmable cells: interfacing natural and engineered gene networks. Proc Natl Acad Sci U S A 101, 8414-8419 (2004).
Kramer et al., An engineered epigenetic transgene switch in mammalian cells. Nat Biotechnol 22, 867-870 (2004).
Kwon et al., Biotechnology Letters (2006) 28: 9-15. "Artificial transcription factors increase production of recombinant antibodies in Chinese hamster ovary cells."
Levskaya et al., Synthetic biology: engineering *Escherichia coli* to see light. Nature 438, 441-442 (2005).
Levskaya et al., Spatiotemporal control of cell signalling using a light-switchable protein interaction. Nature (2009).
Looger et al., Computational design of receptor and sensor proteins with novel functions. Nature 423, 185-190 (2003).
Lu et al., Dispersing biofilms with engineered enzymatic bacteriophage. Proc Natl Acad Sci USA 104, 11197-11202 (2007).
Lu and Collins, Engineered bacteriophage targeting gene networks as adjuvants for antibiotic therapy. Proc Natl Acad Sci U S A 106, 4629-4634 (2009).
Maeder et al. Rapid "open-source" engineering of customized zinc-finger nucleases for highly efficient gene modification. Mol Cell 31, 294-301 (2008).
Park et al. Phenotypic alteration of eukaryotic cells using randomized libraries of artificial transcription factors. Nat Biotechnol 21, 1208-1214 (2003).
Purnick and Weiss, The second wave of synthetic biology: from modules to systems. Nat Rev Mol Cell Biol 10, 410-422 (2009).
Rackham and Chin, A network of orthogonal ribosome x mRNA pairs. Nat Chem Biol 1, 159-166 (2005).
Rinaudo et al., A universal RNAi-based logic evaluator that operates in mammalian cells. Nat Biotechnol 25, 795-801 (2007).
Ro et al., Production of the antimalarial drug precursor artemisinic acid in engineered yeast. Nature 440, 940-943 (2006).
Shetty et al., Engineering BioBrick vectors from BioBrick parts. J Biol Eng 2, 5 (2008).
Skerker et al., Rewiring the specificity of two-component signal transduction systems. Cell 133, 1043-1054 (2008).
Sohka et al., An externally tunable bacterial band-pass filter. Proc Nati Acad Sci U S A 106, 10135-10140 (2009).
Stege et al., The Plant Journal (2002) 32, 1077-1086. "Controlling gene expression in plants using synthetic zinc finger transcription factors."
Stricker et al., A fast, robust and tunable synthetic gene oscillator. Nature 456, 516-519 (2008).

(56) References Cited

OTHER PUBLICATIONS

Tigges et al., A tunable synthetic mammalian oscillator. Nature 457, 309-312 (2009).
Wang et al., Programming cells by multiplex genome engineering and accelerated evolution. Nature 460, 894-898 (2009).
Wang et al., Evolved orthogonal ribosomes enhance the efficiency of synthetic genetic code expansion. Nat Biotechnol 25, 770-777 (2007).
Wang et al., Expanding the genetic code for biological studies. Chem Biol 16, 323-336 (2009).
Win and Smolke, A modular and extensible RNA-based gene-regulatory platform for engineering cellular function. Proc Natl Acad Sci U S A 104, 14283-14288 (2007).
Win and Smolke, Higher-order cellular information processing with synthetic RNA devices. Science 322, 456-460 (2008).
Win et al., Codeine-binding RNA aptamers and rapid determination of their binding constants using a direct coupling surface plasmon resonance assay. Nucleic Acids Res 34, 5670-5682 (2006).
Win et al., Frameworks for programming biological function through RNA parts and devices. Chem Biol 16, 298-310 (2009).
Xu and Lavan, Designing artificial cells to harness the biological ion concentration gradient. Nat Nanotechnol 3, 666-670 (2008).
Friedland et al., Science, 324:1199-1202 (2009). "Synthetic gene networks that count."
Kilby, Trends Genet, 9(12):413-421 (1993). "Site-specific recombinases: tools for genome engineering."

* cited by examiner

BIOLOGICAL CIRCUIT CHEMOTACTIC CONVERTERS

CROSS REFERENCE TO RELATED APPLICATIONS

This application is a 35 U.S.C. §371 National Phase Entry Application of International Application No. PCT/US2010/058341, filed Nov. 30, 2010, which designates the United States, and which claims the benefit under 35 U.S.C. §119(e) of U.S. Provisional Application No. 61/265,219, filed on Nov. 30, 2009 the contents of which are incorporated herein in their entireties by reference.

SEQUENCE LISTING

The instant application contains a Sequence Listing which has been submitted in ASCII format via EFS-Web and is hereby incorporated by reference in its entirety. Said ASCII copy, created on Nov. 23, 2010, is named 70158651.txt and is 259,985 bytes in size.

FIELD OF THE INVENTION

The present invention relates to biological chemotactic converters and methods of use thereof.

BACKGROUND OF THE INVENTION

Circuits and circuit designs are typically based on electrical and electronic components and properties and are useful for a variety of functions. An electrical circuit is an interconnection of electrical elements, such as resistors, inductors, capacitors, transmission lines, voltage sources, current sources, and switches, and when it also contains active electronic components is known as an electronic circuit. Electronic circuits can usually be categorized as analog, digital or mixed-signal (a combination of analog and digital) electronic circuits. The basic units of analog circuits are passive (resistors, capacitors, inductors, and memristors) and active (independent power sources and dependent power sources). Components such as transistors may be represented by a model containing passive components and dependent sources. In digital electronic circuits, electric signals take on discrete values, which are not dependent upon time, to represent logical and numeric values. These values represent the information that is being processed. The transistor is one of the primary components used in discrete circuits, and combinations of these can be used to create logic gates. These logic gates can then be used in combination to create a desired output from an input.

In contrast, while some biological circuits have been developed, the utility of these circuits has been minimal, and it has been difficult to replicate the versatility and flexibility of standard electronic circuits. Many challenges remain in advancing synthetic biology from low-level gene circuitry to higher-order networks. Controlling the state of cells is a difficult but important task in biotechnology. For example, controlling transcriptional activity in cells currently relies on either constitutive promoters which are hardwired to have distinct activities or by using transcriptional activators or repressors which can be tuned by the application of inducer molecules. However, inducer molecules are expensive, can be difficult to control in complex environments used in biotechnology, and can be toxic. Constitutive promoters cannot be easily shut off and therefore can be difficult to use when there are toxic products that are being expressed. Furthermore, constitutive promoters severely limit the flexibility of biological systems to adapt to different conditions.

SUMMARY OF THE INVENTION

We have created and describe herein novel biological chemotactic converters that provide modular systems for converting external inputs, such as chemoattractants, into outputs that allow for autonomous chemotaxis of biological systems, such as cells. To provide such functionalities, the biological circuit chemotactic converters of the invention comprise modular components that facilitate feedback loops and are capable of responding to external inputs by expressing sensors or receptors useful for detecting and responding to external signals, such as chemoattractants. For example, a biological circuit chemotactic converter can be used to convert an input chemoattractant signal into upregulation of a specific sensor receptor that permits a chemotactic response to the chemoattractant.

Provided herein are biological chemotactic converters for use in biological systems, and systems and methods for responding to specific chemotactic inputs. These biological chemotactic converters are extensible, highly modular and can function with a variety of combinations of various component parts, such as toggle switches and recombinases. Depending on the combinations of modules and component parts used in the biological chemotactic converters described herein, a chemotactic converter can respond to one or to multiple inputs.

Thus, described herein, in some aspects, are biological circuit chemotactic converters comprising at least one input module $(IM)_n$, at least one genetic toggle switch $(TS)_n$, at least one logic module $(LM)_n$, and at least two sensor modules $(SM_A$ and $SM_B)_{n+1}$, where $n \geq 1$.

In some aspects, the input module comprises an inducible promoter sequence $(iP_A)$ operably linked to a repressor sequence encoding a repressor protein $(R_A)$. In some embodiments of these aspects, the input module further comprises at least one ribosome binding sequence. In some embodiments of these aspects, the input module further comprises at least one terminator sequence. In some embodiments of these aspects, the input module further comprises at least one degradation tag sequence. In some embodiments of these aspects, the input module further comprises at least one sequence encoding an iRNA molecule specific for a protein encoded by another module. In some embodiments of these aspects, the repressor sequence encodes for an engineered zinc-finger protein.

In other embodiments of these aspects, the input module consists essentially of an inducible promoter sequence $(iP_A)$ operably linked to a repressor sequence $(R_A)$. In some embodiments of these aspects, the input module consists of an inducible promoter sequence $(iP_A)$ operably linked to a repressor sequence $(R_A)$.

In some aspects, the genetic toggle switch comprises a first repressible promoter sequence $(rP_1)$ that drives expression of a second repressor sequence $(R_2)$, and a second repressible promoter sequence $(rP_2)$ that drives expression of a first repressor sequence $(R_1)$, i.e., $(rP_1-R_2$ and $rP_2-R_1)$. In other embodiments of these aspect, the genetic toggle switch consists essentially of a first repressible promoter sequence $(rP_1)$ that drives expression of a second repressor sequence $(R_2)$, and a second repressible promoter sequence $(rP_2)$ that drives expression of a first repressor sequence $(R_1)$, i.e., $(rP_1-R_2$ and $rP_2-R_1)$. In some embodiments of the aspect, the genetic toggle switch consists of a first repressible promoter sequence $(rP_1)$ that drives expression of a second repressor sequence ($R_2$), and a second repressible promoter sequence ($rP_2$) that drives expression of a first repressor sequence ($R_1$), i.e., ($rP_1$-$R_2$ and $rP_2$-$R_1$).

In some such embodiments, the first and second repressor sequences encode first and second repressor molecules, such that the first repressible promoter sequence is inhibited by the first repressor molecule and the second repressible promoter sequence is inhibited by the second repressor molecule. In some embodiments of these aspects, at least one repressor molecule is a protein. In some embodiments of these aspects, at least one repressor molecule is an RNA molecule.

In other such embodiments, the first and second repressor sequences encode first and second repressor proteins, such that the first repressible promoter sequence is inhibited by the first repressor protein and the second repressible promoter sequence is inhibited by the second repressor protein. In other embodiments, the first and second repressor sequences encode first and second repressor molecules, such that the first repressible promoter sequence is inhibited by the first repressor molecule and the second repressible promoter sequence is inhibited by the second repressor molecule.

In some embodiments of these aspects, the genetic toggle switch further comprises at least one ribosome binding sequence. In some embodiments of these aspects, the genetic toggle switch further comprises at least one terminator sequence. In some embodiments of these aspects, the genetic toggle switch further comprises at least one degradation tag sequence. In some embodiments of these aspects, the genetic toggle switch further comprises at least one sequence encoding an iRNA molecule specific for a protein encoded by another module. In some embodiments of these aspects, at least one repressor sequence, $R_1$, $R_2$, or both, encodes for an engineered zinc-finger protein.

In some aspects, the logic module comprises a repressible promoter sequence ($rP_B$) operably linked to a repressor sequence encoding a repressor protein ($R_B$). In some embodiments of these aspects, the logic module further comprises at least one ribosome binding sequence. In some embodiments of these aspects, the logic module further comprises at least one terminator sequence. In some embodiments of these aspects, the logic module further comprises at least one degradation tag sequence. In some embodiments of these aspects, the logic module further comprises at least one sequence encoding an iRNA molecule specific for a protein encoded by another module. In some embodiments of these aspects, the repressor sequence of the logic module encodes for a protein or an RNA molecule. In some embodiments, the protein is an engineered zinc-finger protein. In other embodiments, the logic module consists essentially of a repressible promoter sequence ($rP_B$) operably linked to a repressor sequence encoding a repressor protein ($R_B$). In other embodiments, the logic module consists of a repressible promoter sequence ($rP_B$) operably linked to a repressor sequence encoding a repressor protein ($R_B$).

In some aspects, each sensor module comprises a repressible promoter sequence ($rP_C$ and $rP_D$) operably linked to a nucleic acid sequence encoding a sensor molecule (i.e., sensor A and sensor B), i.e., $rP_C$-sensor A, and $rP_D$-sensor B. In some embodiments of these aspects, at least one sensor module further comprises at least one ribosome binding sequence. In some embodiments of these aspects, at least one sensor module further comprises at least one terminator sequence. In some embodiments of these aspects, at least one sensor module further comprises at least one degradation tag sequence. In some embodiments of these aspects, at least one sensor module further comprises at least one sequence encoding an iRNA molecule specific for a protein encoded by another module. In other embodiments, each sensor module consists essentially of a repressible promoter sequence ($rP_C$ and $rP_D$) operably linked to a nucleic acid sequence encoding a sensor (sensor A and sensor B), i.e., $rP_C$-sensor A and $rP_D$-sensor B. In other embodiments, each sensor module consists of a repressible promoter sequence ($rP_C$ and $rP_D$) operably linked to a nucleic acid sequence encoding a sensor (sensor A and sensor B), i.e., $rP_C$-sensor A and $rP_D$-sensor B. In some embodiments of these aspects and all such aspects described herein, the at least two sensor modules encode for different sensor molecules.

In some embodiments of these aspects and all such aspects described herein, the inducible promoter sequence of the input module is induced by a biological agent, a chemical agent, a metal ion, a toxin, or a pollutant.

In some embodiments of these aspects and all such aspects described herein, the repressor encoded by the first repressor sequence of the toggle switch ($R_1$) and the repressor encoded by the input module ($R_A$) are the same repressor.

In some embodiments of these aspects and all such aspects described herein, the repressors encoded by the logic module and the input module are different repressors.

In some embodiments of these aspects and all such aspects described herein, the repressors encoded by the logic module and the genetic toggle switch are different repressors.

In some embodiments of these aspects and all such aspects described herein, the second repressible promoter sequence of the genetic toggle switch ($rP_2$), the repressible promoter sequence of the logic module ($rP_B$), and the repressible promoter sequence of one sensor module ($rP_D$) are repressed by the same repressor.

In some embodiments of these aspects and all such aspects described herein, the second repressible promoter sequence encoded by the genetic toggle switch ($rP_2$), the repressible promoter sequence encoded by the logic module ($rP_B$), and the repressible promoter sequence encoded by one sensor module ($rP_D$) comprise the same repressible promoter sequence.

In some embodiments of these aspects and all such aspects described herein, the repressible promoter sequence of one sensor module ($rP_C$) is repressed by the repressor encoded by the logic module ($R_B$).

In some embodiments of these aspects and all such aspects described herein, n is an integer value between and including 1 and 100. In some embodiments of these aspects and all such aspects described herein, n is an integer value between and including 1 and 50. In some embodiments of these aspects and all such aspects described herein, n is an integer value between and including 1 and 20. In some embodiments of these aspects and all such aspects described herein, n is an integer value between and including 1 and 15. In some embodiments of these aspects and all such aspects described herein, n is an integer value selected from the group consisting of 1, 2, 3, 4, 5, 6, 7, 8, 9, and 10.

In other aspects, described herein are methods of modulating chemotaxis in a biological system using a biological circuit chemotactic converter comprising at least one input module $(IM)_n$, at least one genetic toggle switch $(TS)_n$, at least one logic module $(LM)_n$, and at least two sensor modules $(SMA$ and $SMB)_{n+1}$, where $n \geq 1$.

In some embodiments of these aspects, the biological system is a cell. In some embodiments of these aspects, the cell is a eukaryotic cell, a prokaryotic cell, or a synthetic cell. In other embodiments, the cell is a bacterial cell.

In other aspects, the invention provides a system that comprises one or more biological circuit chemotactic converters for converting a chemoattractant signal into a chemotactic response. In some embodiments of these aspects and all such aspects described herein, the system further comprises a cell, such as a eukaryotic cell, a prokaryotic cell, or a synthetic cell.

BRIEF DESCRIPTION OF THE DRAWINGS

FIG. 1A shows a chemotactic environment made up of three chemoattractant gradients (A, B, C). FIG. 1B depicts an exemplary biological circuit chemotactic converter, whereby toggle switches control the sequential expression of three chemotaxis sensor receptors, for autonomously navigating bacteria down three chemoattractant gradients. Inputs into promoters and logic operations are shown explicitly except when the promoter name is italicized, which represents an inducible promoter. FIG. 1C depicts the Boolean on/off values for the network genes that illustrate the sequential order of operations in the exemplary biological circuit chemotactic converter.

FIG. 2A depicts an exemplary SIMM comprising a first inducible promoter sequence (P inducible,1) linked to a forward recombinase recognition site (R1RS), an inverted sequence of a second inducible promoter (P inducible,2), a recombinase sequence (Recombinase 1), and a reverse recombinase recognition site (R1RS). Further upstream of the first inducible promoter sequence of the SIMM is an inverted sequence of a constitutively active inducer agent that is specific for the second inducible promoter. Downstream of the reverse recombinase recognition site of the SIMM is an inverted sequence of a third inducible promoter (P inducible,3) and a sequence encoding a dominant negative version of the inducer agent specific for the second inducible promoter. A further component of the exemplary circuit is a sequence of the second inducible promoter operably linked to an output product. In the absence of any inducing agent, constitutive expression of the inducer agent that is specific for the second inducible promoter drives expression from the inducible promoter operably linked to an output product. Addition of the inducing agent specific for the first inducible promoter sequence (P inducible,1) of the SIMM causes expression of the recombinase sequence and subsequent inversion of the recombinase sequence and the inverted sequence of the second inducible promoter (P inducible,2) of the SIMM, such that the second inducible promoter can now drive expression of the dominant negative inducer agent that is specific for the second inducible promoter sequence. Expression of the dominant negative inducer agent inhibits transcription of the output product. Addition of the inducing agent specific for the third inducible promoter (P inducible,3) causes reexpression of the inverted recombinase sequence and subsequent restoration to the initial state, and consequent expression of the output product. FIG. 2B depicts an exemplary SIMM, as shown in FIG. 2A, where the first inducible promoter sequence (P inducible,1) is $P_{LtetO}$, the forward recombinase recognition site (R1RS) is loxP, the second inducible promoter (P inducible, 2) is $P_{BAD}$, the recombinase sequence encodes Cre recombinase, the reverse recombinase recognition site (R1RS) is LoxP, the constitutively active inducer agent is arabinose C, the third inducible promoter (P inducible, 3) is $P_{LlacO}$, the dominant negative version of the inducer agent is a dominant negative arabinose C, and the output product is GFP. FIG. 2C shows data obtained from the exemplary circuit of FIG. 2B, where in the initial state, in the absence of any inducing agent, GFP is expressed. Addition of anhydrous tetracycline to the circuit inhibits GFP expression by permitting expression of the dominant negative arabinose C via Cre recombinase activity. Addition of IPTG then restores the circuit to its initial state whereby GFP is expressed.

FIG. 3A shows an exemplary analog-to-digital biological converter switch that enables the discretization of analog inputs. The analog-to-digital biological converter switch is composed of a bank of modules, i.e., genetic toggle switches that have increasing response thresholds so that sequential toggling is achieved as input levels increase. The design shown enables different natural or synthetic pathways to be activated depending on distinct input ranges, which is useful in cell-based biosensing applications. Inputs into promoters and logic operations are shown explicitly except when the promoter name is italicized, which represents an inducible promoter. FIG. 3B depicts an exemplary digital-to-analog biological converter switch that enables the programming of defined promoter activity based on combinatorial inputs. The digital-to-analog biological converter switch comprises a bank of recombinase-based switches, known as single-invertase memory modules (SIMMs) (A. E. Friedland et al., Science (2009) 324:1199-1202). Each SIMM comprises an inverted promoter and a recombinase gene located between its cognate recognition site, as indicated by the arrows. Upon the combinatorial addition of inducers that activate specific P promoters, different SIMMs are flipped, enabling promoters of varying strength to drive GFP expression. This allows combinatorial programming of different levels of promoter activity.

FIG. 5A depicts an associative memory circuit that enables association between two simultaneous inputs (Activator A and Activator B), so that the subsequent presence of only a single input can drive its own pathway and the pathway of the other input. Associations between inputs are recorded by a promoter $P_{AND}$ that is activated in the presence of Activator A and Activator B to toggle the memory switch. Inputs into promoters and logic operations are shown explicitly except when the promoter name is italicized, which represents an inducible promoter. FIG. 5B depicts a winner-take-all circuit, which allows only one input out of many inputs to be recorded. This effect is achieved by a global repressor protein that gates all inputs and prevents them from being recorded if there has already been an input recorded in memory.

FIG. 6A demonstrates that amyloid-based memory can be implemented by fusing a prion-determining region (PD) to an effector gene, such as a transcriptional activator. FIG. 6B shows that overexpressing the prion-determining region via promoter $P_{OFF}$ causes aggregation of the fusion protein, rendering the effector inactive. FIG. 6C shows that subsequent overexpression of chaperone proteins (HSP104), which act to disaggregate amyloids, via promoter $P_{ON}$ releases the effector from the amyloid state and enables it to fulfill its function. Inputs into promoters and logic operations are shown explicitly except when the promoter name is italicized, which represents an inducible promoter.

DETAILED DESCRIPTION

Figure 1A:
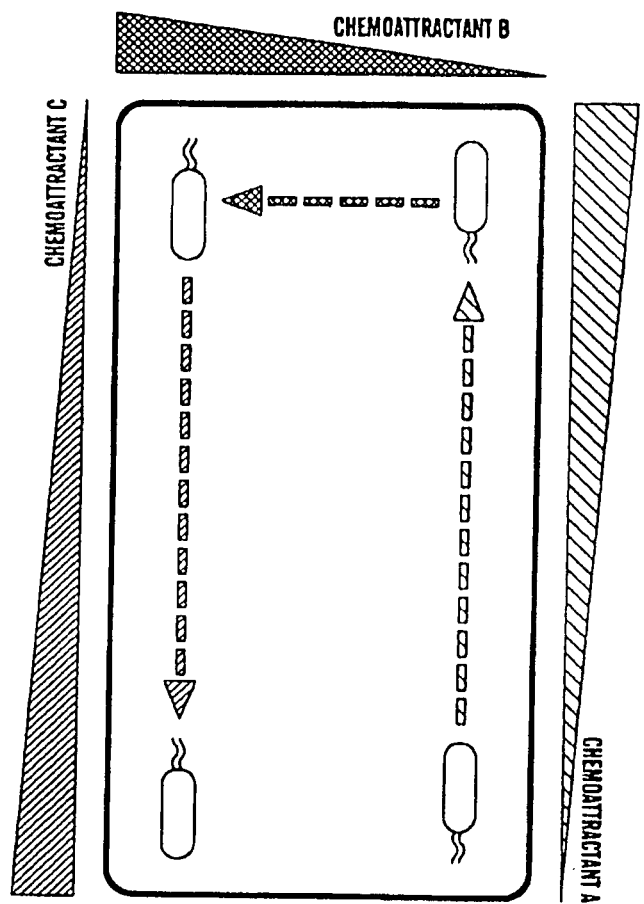
FIGS. 1A-1C depicts exemplary modules for autonomous chemotactic converters.

Described herein are novel biological circuit chemotactic converters that provide modular designs for the conversion of changes in external signals, such as concentrations of chemoattractants, to biological responses, such as expression of sensors necessary for chemotactic responses in biological systems, such as cells. Flexibility in the biological circuit chemotactic converters described herein is provided by incorporating and utilizing various combinations of individual modular components. The biological circuit chemotactic converters are easily extendable to detect large ranges and diversity of input signals, as well as to express a variety of sensors that can translate the input signals into coordinated movements in response to chemoattractants. In other embodiments, the biological circuit chemotactic converters can be used in quorum sensing.

"Chemotaxis" refers to a biological phenomenon in which bodily cells, bacteria, and other single-cell or multicellular organisms direct their movements according to certain chemicals, termed herein as "chemoattractants" in their environment. For bacteria, such chemotactic responses are important for finding food, for example, glucose, such that the bacteria swim towards the highest concentration of food molecules. Bacteria also use such chemotactic responses to flee from poisons, such as phenol. In multicellular organisms, chemotaxis is critical to both early and subsequent phases of development, for example, movement of sperm towards the egg during fertilization; and migration of neurons or lymphocytes, respectively, as well as in normal function. In addition, it has been recognized that mechanisms that allow chemotaxis in animals can be subverted during cancer metastasis. Chemotaxis or a chemotactic response is called positive if the movement is in the direction of a higher concentration of the chemical in question, and negative if the direction is opposite. Accordingly, in some embodiments of the aspects described herein, biological circuit chemotactic converters can be designed to undergo positive chemotaxis, and in other embodiments, biological circuit chemotactic converters can be designed to undergo negative chemotaxis.

The ability of some cells to move or migrate in response chemoattractants is a useful functionality to incorporate into biological systems, such as cells, in order to provide directed and specific movements. Accordingly, provided herein are novel "biological circuit chemotactic converters," which are engineered biological circuits comprised of modular components, that comprise an input module that can detect chemoattractants as inputs, and convert these input information into the upregulation of appropriate sensor molecules, via a series of engineered modular components, including genetic toggle switches, logic modules, and sensor modules. The upregulation of an appropriate sensor allows the biological circuit chemotactic converters to direct the chemotactic movement of a biological system, such as a cell.

In some embodiments of the aspects described herein, the biological circuit chemotactic converters can be designed to incorporate quorum sensing responses. As defined herein, "quorum sensing" refers to a type of decision-making process used by decentralized groups to coordinate behavior. Many species of bacteria use quorum sensing to coordinate their gene expression according to the local density of their population. Similarly, some social insects use quorum sensing to make collective decisions about where to nest.

Some of the best-known examples of quorum sensing come from studies of bacteria. Bacteria use quorum sensing to coordinate certain behaviors based on the local density of the bacterial population. Quorum sensing can occur within a single bacterial species as well as between diverse species, and can regulate a host of different processes, essentially serving as a simple communication network. A variety of different molecules can be used as signals, defined herein as "quorum sensing signals." Common classes of signaling molecules are oligopeptides in Gram-positive bacteria, N-Acyl Homoserine Lactones (AHL) in Gram-negative bacteria and a family of autoinducers known as AI-2 in both Gram-negative and Gram-positive bacteria. In some embodiments of the aspects described herein, the biological circuit chemotactic converters use quorum sensing signals as input signals.

Bacteria that use quorum sensing constantly produce and secrete certain signaling molecules (called autoinducers or pheromones). These bacteria also have a receptor that can specifically detect the signaling molecule (inducer). When the inducer binds the receptor, it activates transcription of certain genes, including those for inducer synthesis. As in natural systems, there is a low likelihood of a bacterium detecting its own secreted inducer, in order for gene transcription to be activated, the cell must encounter signaling molecules secreted by other cells in its environment. When only a few other bacteria of the same kind are in the vicinity, diffusion reduces the concentration of the inducer in the surrounding medium to almost zero, so the bacteria produce little inducer. However, as the population grows the concentration of the inducer passes a threshold, causing more inducer to be synthesized. This forms a positive feedback loop, and the receptor becomes fully activated. Activation of the receptor induces the up regulation of other specific genes, causing all of the cells to begin transcription at approximately the same time. This coordinated behavior of bacterial cells can be useful in a variety of situations. Quorum sensing was first observed in *Vibrio fischeri*, a bioluminiscent bacterium that lives as a mutualistic symbiont in the photophore (or light-producing organ) of the Hawaiian bobtail squid. When *V. fischeri* cells are free-living (or planktonic), the autoinducer is at low concentration and thus cells do not luminesce. However, when they are highly concentrated in the photophore (about $10^{11}$ cells/ml) transcription of luciferase is induced, leading to bioluminescence. The bioluminescent luciferase produced by *V. fischeri* would not be visible if it was produced by a single cell. By using quorum sensing to limit the production of luciferase to situations when cell populations are large, *V. fischeri* cells are able to avoid wasting energy on the production of useless product. Accordingly, in some embodiments of the aspects described herein, one or more of the sensor genes of a biological circuit chemotactic converter encodes for a receptor that can detect an autoinducer.

In the Gram-negative bacteria *Escherichia coli*, cell division may be partially regulated by AI-2-mediated quorum sensing. This species uses AI-2, which is produced and processed by the lsr operon. Part of it encodes an ABC transporter which imports AI-2 into the cells during the early stationary (latent) phase of growth. AI-2 is then phosphorylated by the LsrK kinase, and the newly produced phospho-AI-2 can either be internalized or used to suppress LsrR, a repressor of the lsr operon (thereby activating the operon). Transcription of the lsr operon is also thought to be inhibited by dihydroxyacetone phosphate (DHAP) through its competitive binding to LsrR. Glyceraldehyde 3-phosphate has also been shown to inhibit the lsr operon through cAMP-CAPK-mediated inhibition. When grown normally, AI-2 presence is transient.

E. coli and Salmonella enterica do not produce AHL signals commonly found in other gram negative bacteria. However, they have a receptor that detects AHLs from other bacteria and change their gene expression in accordance with the presence of other 'quorate' populations of gram-negative bacteria.

The opportunistic bacteria Pseudomonas aeruginosa use quorum sensing to coordinate the formation of biofilms, swarming motility, exopolysaccharide production, and cell aggregation. These bacteria can grow within a host without harming it, until they reach a certain concentration. Then they become aggressive, their numbers sufficient to overcome the host's immune system and form a biofilm, leading to disease. In this species, AI-2 was found to increase expression of sdiA, a transcriptional regulator of promoters which promote ftsQ, part of the ftsQAZ operon essential for cell division. Another form of gene regulation which allows the bacteria to rapidly adapt to surrounding changes is through environmental signaling. Recent studies have discovered that anaerobiosis can significantly impact the major regulatory circuit of quorum sensing. This important link between quorum sensing and anaerobiosis has a significant impact on production of virulence factors of this organism. Garlic reportedly blocks quorum sensing in Pseudomonas aeruginosa. As defined herein, disrupting the quorum sensing signalling process in this way is called "quorum quenching."

Genetic Toggle Switches

Provided herein are biological modules, such as genetic toggle switches, comprising different nucleic acid and protein components, such as promoters, transcriptional activators, transcriptional repressors, recombinases, and output products, to be used in the biological circuit chemotactic converters described herein. The ability to manipulate and combine different components and modules provides flexibility in input and output responses of the biological circuit chemotactic converters described herein.

In some aspects, genetic toggle switches are provided for use as a biological module in the biological circuit chemotactic converters described herein. A "genetic toggle switch," as defined herein, refers to a synthetic, addressable cellular memory unit or module that can be constructed from any two repressible promoters arranged in a mutually inhibitory network. A genetic toggle switch exhibits robust bistable behaviour. By "robust bistable behaviour" is meant that the toggle switch exhibits bistability over a wide range of parameter values and that the two states are tolerant of fluctuations inherent in gene expression, i.e., a genetic toggle switch does not flip randomly between states. Bistability of a genetic toggle switch is possible with any set of promoters and repressors as long as a minimum set of conditions are fulfilled, as described, for example, in T. S. Gardner et al., Nature (2000) 403: 339-342.

Bistability of a genetic toggle switch, as described herein, arises from a mutually inhibitory arrangement of at least two repressor sequences. The product of each repressor sequence, i.e., the repressor, can inhibit, at a transcriptional level, a translational level, or a combination thereof, the expression of a product encoded by the other repressor sequence. Thus, in the absence of an appropriate input or inducing agent, such as a transcriptional activating agent, two stable states are possible: a first state in which a first repressor is expressed and inhibits expression of a second repressor sequence, and a second state in which the second repressor is expressed and inhibits expression of the first repressor sequence. For example, in some aspects, repressors act at the transcriptional level, whereby a first promoter sequence drives expression of a first repressor sequence that encodes for a repressor specific for a second promoter sequence. The second promoter sequence, in turn, drives expression of a second repressor sequence that encodes for a repressor specific for a second promoter sequence. In such an aspect, switching between the two states (i.e., expression of the first or second repressor) is mediated by the presence of an exogenous or endogenous input agent, such as an agent that prevents repressor binding to the currently inactive promoter. In such an embodiment, the agent permits the opposing repressor to be maximally transcribed until it stably represses the originally active promoter. In other embodiments of the aspects described herein, repressors in a genetic toggle switch can act at the translational level, whereby a first repressor encodes a product, such as an inhibitory RNA molecule, that inhibits or prevents translation of the second repressor, or causes degaration of the second repressor mRNA. In other embodiments of the aspects described herein, different repressors in a genetic toggle switch can use different mechanisms of repression, i.e., transcriptional, translational, or combinations thereof.

In one embodiment of this aspect and all such aspects described herein, a genetic toggle switch comprises two different repressible promoter sequences driving expression of two sequences encoding different repressors, such that each promoter can be inhibited by the repressor transcribed by the other promoter. In such an embodiment, the genetic toggle switch comprises a first repressible promoter sequence ($rP_1$) that drives the transcription of a second repressor sequence ($R_2$), which encodes a repressor specific for the second repressible promoter sequence, and a second repressible promoter sequence ($rP_2$) that drives the transcription of a first repressor sequence ($R_1$), which encodes a repressor specific for the first repressible promoter sequence.

In some embodiments, the genetic toggle switches are implemented on plasmids, such as plasmids derived from E. coli. In some embodiments, the nucleic acid sequences of the promoters and repressors of the genetic toggle switch are contained or present on a single plasmid. In other embodiments, the nucleic acid sequences of the promoters and repressors of the genetic toggle switch are contained or present on multiple plasmids.

In one embodiment of this aspect and all such aspects described herein, the genetic toggle switch comprises a Ptrc-2 promoter that drives the expression of a temperature-sensitive λ repressor (cIts), and a $P_L$s1con promoter that drives the expression of a Lac repressor. In such an embodiment, the genetic toggle is switched between states by pulses of isopropyl-b-D-thiogalactopyranoside (IPTG) and thermal pulses. For example, a pulse of IPTG permits expression of cIts driven by the Ptrc-2 promoter, as the IPTG prevents the Lac repressor from binding to the Ptrc-2 promoter. Expression of cIts maintains the state of transcription from the Ptrc-2 promoter by binding and repressing the $P_L$s1con promoter, thus preventing Lac repressor expression and inhibition of the Ptrc-2 promoter. In contrast, a thermal pulse inhibits the cIts repressor, thus preventing cIts binding to the $P_L$s1con promoter, and permitting expression of the Lac repressor.

Expression of the Lac repressor further maintains the state of transcription from the $P_Ls1con$ promoter by binding to and repressing the Ptrc-2 promoter, thus preventing cIts repressor expression and inhibition of the $P_Ls1con$ promoter.

In another embodiment of this aspect and all such aspects described herein, the genetic toggle switch comprises a Ptrc-2 promoter that drives the expression of a Tet repressor (Tet), and a $P_L$tetO-1 promoter that drives the expression of a Lac repressor. In such an embodiment, the genetic toggle switch is switched between states by a pulse of IPTG or a pulse of anhydrotetracycline (aTc). For example, a pulse of IPTG permits expression of Tet driven by the Ptrc-2 promoter, as the IPTG will prevent the Lac repressor from binding to the Ptrc-2 promoter. Expression of Tet maintains the state of transcription from the Ptrc-2 promoter by binding and repressing the $P_L$tetO-1 promoter, thus preventing Lac repressor expression and inhibition of the Ptrc-2 promoter. In contrast, a pulse of anhydrotetracycline inhibits the Tet repressor, thus preventing Tet binding to the $P_L$tetO-1 promoter, and permitting expression of the Lac repressor. Expression of the Lac repressor further maintains the state of transcription from the $P_L$tetO-1 promoter by binding to and repressing the Ptrc-2 promoter, thus preventing Tet repressor expression and inhibition of the $P_L$tetO-1 promoter.

Libraries of Toggle Switches

For use in the genetic toggle switches described herein, it is possible to use any set of promoters and repressors as long as they fulfill a minimum set of conditions, as described, for example, in T. S. Gardner et al., Nature (2000) 403: 339-342. In some embodiments of the invention, the promoters useful in the genetic toggle switches are presented under the section entitled Promoters and provided in SEQ ID NOs: 1-7, SEQ ID NOs: 41-843, and SEQ ID NOs: 1005-1010.

In order to further enhance and expand the range and sensitivity of genetic toggle switches for use in the biological circuit chemotactic converters described herein, it is useful to create libraries of genetic toggle switches with multiple interoperable repressors, such as transcriptional repressors. Thus, in some embodiments of the aspects described herein, a library of transcriptional repressors and activators can be targeted towards unique promoters with minimum crossover, using engineered zinc-finger proteins fused to transcriptional activation and repression domains.

To create such libraries, unique promoters containing sequence sites known to bind to engineered zinc-finger proteins can be synthesized. These sites are made up of three sequences, each of which is at least 3 DNA base pairs long. Each 3 base pair sequence binds to a single zinc-finger domain. Thus, in some embodiments, each complete engineered zinc-finger transcription factor contains three zinc-finger domains to target a total 9 base pair region of DNA. In some embodiments, the number of zinc-finger domains used in a complete engineered zinc-finger transcription factor is 1. In some embodiments, the number of zinc-finger domains used in a complete engineered zinc-finger transcription factor is 2. In some embodiments, the number of zinc-finger domains used in a complete engineered zinc-finger transcription factor is 3. In some embodiments, the number of zinc-finger domains used in a complete engineered zinc-finger transcription factor is 4. In some embodiments, the number of zinc-finger domains used in a complete engineered zinc-finger transcription factor is 5. In some embodiments, the number of zinc-finger domains used in a complete engineered zinc-finger transcription factor is 6. In some embodiments, the number of zinc-finger domains used in a complete engineered zinc-finger transcription factor is 7. In some embodiments, the number of zinc-finger domains used in a complete engineered zinc-finger transcription factor is 8. In some embodiments, the number of zinc-finger domains used in a complete engineered zinc-finger transcription factor is 9. In some embodiments, the number of zinc-finger domains used in a complete engineered zinc-finger transcription factor is 10. In some embodiments, the number of zinc-finger domains used in a complete engineered zinc-finger transcription factor is 11. In some embodiments, the number of zinc-finger domains used in a complete engineered zinc-finger transcription factor is 12. In some embodiments, the number of zinc-finger domains used in a complete engineered zinc-finger transcription factor is 13. In some embodiments, the number of zinc-finger domains used in a complete engineered zinc-finger transcription factor is 14. In some embodiments, the number of zinc-finger domains used in a complete engineered zinc-finger transcription factor is 15. In some embodiments, the number of zinc-finger domains used in a complete engineered zinc-finger transcription factor is 15. In some embodiments, the number of zinc-finger domains used in a complete engineered zinc-finger transcription factor is 17. In some embodiments, the number of zinc-finger domains used in a complete engineered zinc-finger transcription factor is 18. In some embodiments, the number of zinc-finger domains used in a complete engineered zinc-finger transcription factor is 19. In some embodiments, the number of zinc-finger domains used in a complete engineered zinc-finger transcription factor is 20. In some embodiments, the number of zinc-finger domains used in a complete engineered zinc-finger transcription factor is at least 25, at least 50, at least 100, or more.

Representative examples of zinc-finger pools created for the shaded 3 base pair sequences are shown below (M L Maeder et al., *Molecular Cell* 2008: 31, 294-301):

F1

| GAA | GCA | GGA | GTA |
|-----|-----|-----|-----|
| GAC | GCC | CGC | GTC |
| GAG | GCG | CGG | GTG |
| GAT | GCT | GGT | GTT |

| TAA | TCA | TGA | TTA |
|-----|-----|-----|-----|
| TAC | TCC | TGC | TTC |
| TAG | TCG | TGG | TTG |
| TAT | TCT | TGT | TTT |

F2

| GAA | GCA | GGA | GTA |
|-----|-----|-----|-----|
| GAC | GCC | CGC | GTC |
| GAG | GCG | CGG | GTG |
| GAT | GCT | GGT | GTT |

| TAA | TCA | TGA | TTA |
|-----|-----|-----|-----|
| TAC | TCC | TGC | TTC |
| TAG | TCG | TGG | TTG |
| TAT | TCT | TGT | TTT |

F3

| GAA | GCA | GGA | GTA |
|-----|-----|-----|-----|
| GAC | GCC | CGC | GTC |
| GAG | GCG | CGG | GTG |
| GAT | GCT | GGT | GTT |

| TAA | TCA | TGA | TTA |
|-----|-----|-----|-----|
| TAC | TCC | TGC | TTC |
| TAG | TCG | TGG | TTG |
| TAT | TCT | TGT | TTT |

Using such pools, complete engineered zinc-finger proteins containing at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more zinc-fingers that can target synthetic promoters can be selected.

In some embodiments, the engineered zinc-finger proteins are fused to transcriptional activation domains, for e.g., VP16, VP64, p65, Gal4, α-subunit of RNA polymerase, Wild-type CRP (amino acid residues 1-209), CRP D1 (residues 1-180), CRP D2 (residues 137-190), CRP D3 (residues 137-180) and CRP D4 (residues 151-168). In other embodiments, the engineered zinc-finger proteins are fused to transcriptional repressor domains e.g., SKD, KRAB (Margolin et al., 1994), SNAG, Kid, Ume6, CRP, SID (Ayer et al., 1996). Thus, an engineered zinc-finger protein can be used a transcriptional activator or transcriptional repressor, depending on the requirements of the various embodiments described herein, by fusing an engineered zinc-finger protein with an appropriate transcriptional activator or transcriptional repressor domain. Non-limiting examples of methods of engineering zinc-finger proteins and transcriptional activation domains for fusion are discussed, for example, at Kwang-Hee B. et al, Nature Biotechnology 2003: 21, p. 275-280; R-J Kwon et al., Biotechnology Letters (2006) 28: 9-15; P. Blancafort et al., PNAS, 2005, 102: 33, p. 11716-11721; J. T. Stege et al., The Plant Journal (2002) 32, 1077-1086; J. Y. Lee et al., Nucleic Acids Research, 2008, 36:16; K-S Park et al., Nature Biotechnology, 2003, 21:10, p. 1208-1214; R. R. Beerli et al., PNAS, 2000, 97:4, p. 1495-1500; P. Blancafort et al., Nature Biotechnology 2003: 21, p. 269-274; D-k Lee, et al., Genome Res., 2003, 13: 2708-2716. Interoperability of such fusion engineered zinc-finger proteins can be assessed by combinatorial addition of the different engineered zinc-finger transcription factors to determine how promoter activity is affected.

To enhance cooperativity of engineered zinc-finger-based transcription factors, in some embodiments, engineered zinc-finger-based transcription factors can be further engineered to dimerize, using dimerization domains such as leucine zipper domains. In some embodiments, the affinity of monomeric engineered-zinc finger proteins can be increased or decreased by site-directed mutagenesis of amino acids known to contact the DNA backbone and/or bases. Non-limiting examples of methods to achieve such affinity modification are discussed, for example, at J. L. Pomerantz, et al., Biochemistry, 1998, 37: 4, p. 965-970, and S. A. Wolfe et al., Structure, 2000, 8:7, p. 739-750.

Pairwise combinations of the engineered zinc-finger-based transcriptional repressors can be conducted to identify mutually-repressing transcription factors and test for bistability, for use in the genetic toggle switches and other modules described herein. In some embodiments, the ability to flip genetic toggle switches can be assessed by overexpressing transcriptional repressors one by one. Thresholds for switching between repressors in such genetic toggle switches can be modulated by changing the promoters in the toggle switch to affect, for example, binding efficiency and repression efficiency.

In some embodiments, the rates of protein synthesis of transcriptional repressors for use in the genetic toggle switches described herein can be modified by adding or modifying sequences for a ribosome binding site (RBS). In some embodiments, an RBS is placed downstream of a promoter sequence and upstream of a sequence encoding a transcriptional repressor being transcribed from that promoter.

In some embodiments, a genetic toggle switch can further comprise an output product sequence (OP) that encodes an output product, such as a protein or an RNA molecule, expression of which reflects or is indicative of the state of the genetic toggle switch. In such embodiments, the genetic toggle switch comprises a first repressible promoter sequence ($rP_1$) that drives the transcription of a second repressor sequence ($R_2$) that encodes a repressor specific for the second repressible promoter sequence, and a second repressible promoter sequence ($rP_2$) that drives the transcription of a first repressor sequence ($R_1$), which encodes a repressor specific for the first repressible promoter sequence, as well as the transcription of an output sequence (OP), i.e., the genetic toggle switch comprises $rP_1$-$R_2$ and $rP_2$-$R_1$-OP. In such embodiments, when the second repressible promoter is active and transcribing the first repressor and the output sequence, the toggle switch is considered in the "on" state. In such embodiments, the expression of the output product can be thought of as a digital output 00000001, in the binary system. In some embodiments of various aspects described herein, multiple genetic toggle switches are combined, each having a different output product that represents the state of that particular genetic toggle switch, such that the digital output of that combination of toggle switches is dependent on how many of the genetic toggle switches are in the "ON" state.

As used herein, a "digital output" refers to an output that can be represented in a binary format. The binary numeral system, or base-2 number system represents numeric values using two symbols, 0 and 1. More specifically, the usual base-2 system is a positional notation with a radix of 2. Owing to its implementation in digital electronic circuitry using logic gates, the binary system is used internally by all modern computers. A "bit," as defined herein, is a binary digit. The numeric value represented by a combination of modules of the invention, for example, genetic toggle switches, is dependent upon the value assigned to each module when it is in the "on" state. For example, in those embodiments described herein where a combination of three genetic toggle switches is used, the digital output is represented as 00000000, when no genetic toggle switch is "on". When 1 genetic toggle switch is "on," i.e., transcribing the output product, the state is 00000001. When 2 genetic toggle switches are "ON," the state is 00000010. When all 3 genetic toggle switches are "on," the state is 00000011. A "byte" represents a collection of eight bits. A byte can hence be defined as a collection of 8 bits, such that 256 values or states can be represented, ranging from 0 to 255, i.e., 00000000 to 11111111.

Any such output product as described herein can be utilized. In some embodiments, where the expression of an output product is driven by only one of the two promoters in a toggle switch, the output product can encode a reporter protein or a reporter RNA molecule. In some embodiments, the reporter protein is a fluorescent reporter protein, e.g., green fluorescent protein. In some embodiments, where multiple genetic toggle switches are combined, each output sequence encodes for a different output product. For example, when a combination of three genetic toggle switches are combined, the output product sequences can encode for green fluorescent protein, yellow fluorescent protein, and red fluorescent protein, such that expression of all three fluorescent proteins represents a digital output of 00000011 for that combination of switches. Detection of the output products of the modules described herein can be performed using any method known to one of skill in the art, including, but not limited to, fluorescent detectors, such as microscopes and flow cytometers, luminescent detectors, quantitative PCR, Western blot analysis, etc., based on the nature of the output product being detected.

In other embodiments, each promoter in a genetic toggle switch can drive expression of an output product, such that the expression of one output product represents one digital output and expression of an output product driven by the opposing promoter represents another digital output, i.e., the "on" and "off" states of a single genetic toggle switch are represented by the expression of a different output product, which can be assigned in an arbitrary manner by a skilled artisan or user, or based on the design of the circuit in which the genetic toggle switch is a component. In such embodiments, the designation of which output product expression corresponds to which state, i.e., "on" or "off," can be determined by the skilled artisan.

Single Invertase Memory Modules

Provided herein are biological modules such as single invertase memory modules, comprising different nucleic acid and protein components, such as promoters, transcriptional activators, transcriptional repressors, recombinases, and output products, to be used in the biological circuit chemotactic converters described herein. The ability to manipulate and combine different components and modules provides flexibility in input and output responses of the biological circuit chemotactic converters described herein.

In some aspects, a "single invertase memory module" is provided as a biological module for use in the biological circuit chemotactic converters described herein. A "single invertase memory module (SIMM)," as defined herein, refers to a stable, switchable bit of memory that uses recombinases, such as Cre and $flp_e$, which can invert DNA between two oppositely oriented cognate recombinase recognition sites. A unique feature and advantage of SIMMs, of relevance to their use in the biological circuit chemotactic converters described herein, is the ability to design such SIMMs to lack both "leakiness" and mixtures of inverted and non-inverted states that can be caused by expressing recombinases independently from their cognate recognition sites. Thus, the use of SIMMs in the biological circuit chemotactic converters described herein allows for the maintenance of memory, and provides the ability to control and maintain discrete states by expressing recombinases between their cognate recognition sites.

At a minimum, a SIMM is a nucleic acid-based module comprising a recombinase sequence located between its cognate recombinase recognition sites, i.e., $RRS_{for}$-RC-$RRS_{rev}$, where $RRS_{for}$ is a forward recombinase recognition site; RC is a recombinase sequence encoding a recombinase that recognizes $RRS_{for}$ and $RRS_{rev}$; and $RRS_{rev}$ is a reverse recombinase recognition site. Upon recombinase expression following activation of an upstream promoter, the recombinase causes a single inversion of the nucleic acid between the cognate recognition sites, i.e., the recombinase nucleic acid sequence or $RRS_{for}$-$RC_{inv}$-$RRS_{rev}$. Any further transcription from the upstream promoter yields antisense RNA of the recombinase gene rather then sense RNA, and therefore no further recombinase protein is produced. Thus, the inversion event is discrete and stable, and does not result in a mixture of inverted and non-inverted states. The upstream promoter driving expression of the SIMM can be a promoter sequence within an upstream SIMM, another modular component, a component of the same SIMM, or be an isolated promoter sequence.

In some aspects, the SIMM further comprises an upstream promoter sequence, i.e., P-$RRS_{for}$-RC-$RRS_{rev}$, where P is a promoter sequence. In other aspects, a SIMM comprises the recombinase sequence located between its cognate recombinase recognition sites, and further comprises an inverted inducible promoter sequence upstream of the recombinase sequence, i.e., $RRS_{for}$-$iP_{inv}$ RC-$RRS_{rev}$, where $RRS_{for}$ is a forward recombinase recognition site, $iP_{inv}$ is an inverted promoter sequence, RC is a recombinase sequence, and $RRS_{rev}$ is a reverse recombinase recognition site. Upon recombinase expression following activation of an upstream promoter, the recombinase causes a single inversion of the DNA between the cognate recognition sites, including the nucleic acid sequence encoding itself, i.e., the recombinase nucleic acid sequence. Any further transcription from the upstream promoter yields antisense RNA of the recombinase gene rather then sense RNA, and therefore no further recombinase protein is produced. Further, the inverted promoter is now in the proper orientation to drive transcription of components of any downstream modules, for example, another SIMM. In some embodiments of the aspects described herein, the promoter is a constitutive promoter. In other embodiments of the aspects described herein, the promoter is a inducible promoter. In some embodiments, the inducible promoter is a repressible promoter. In some embodiments, the inducible promoter is activated by an activating agent.

In some embodiments of the aspects described herein, a SIMM can use any recombinase for encoding memory, rather than only unidirectional recombinases. In some embodiments, the recombinase is encoded between its cognate recombinase recognition sequences. In other embodiments, the recombinase is encoded outside of its cognate recombinase recognition sequences. In those embodiments where the recombinase is encoded outside of its cognate recombinase recognition sequences, the SIMM can be used as, for example, a waveform generator, such that the input or inputs that lead to recombinase expression results in constant inversion between the recombinase recognition sequences and is used to generate pulses of outputs. Such outputs can be any of the output products described herein. In some embodiments, the output is a fluorescent protein.

The recombinases and recombination recognition sequences for use in the SIMMs described herein can be selected from any known or variant, i.e., engineered, recombinase or recombinase recognition sequences, as determined by a skilled artisan. In some embodiments of the various aspects described herein, the recombinase is a Cre recombinase and the recombinase recognition sites are LoxP sites or variants thereof. Alternative site-specific recombinases include, but are not limited to, 1) the Flp recombinase of the 2pi plasmid of *Saccharomyces cerevisiae* (Cox (1983) Proc. Natl. Acad. Sci. USA 80:4223) which recognize FRT sites and variants thereof; 2) the integrase of *Streptomyces* phage .PHI.C31 that carries out efficient recombination between the attP site of the phage genome and the attB site of the host chromosome (Groth et al., 2000 Proc. Natl. Acad. Sci. USA, 97: 5995); 3) the Int recombinase of bacteriophage lambda (lambda-int/attP) (with or without Xis) which recognizes att sites (Weisberg et al. In: Lambda II, supra, pp. 211-250); 4) the xerC and xerD recombinases of *E. coli* which together form a recombinase that recognizes the 28 bp dif site (Leslie and Sherratt (1995) EMBO J. 14:1561); 5) the Int protein from the conjugative transposon Tn916 (Lu and Churchward (1994) EMBO J. 13:1541); 6) TpnI and the β-lactamase transposons (Levesque (1990) J. Bacteriol. 172:3745); 7) the Tn3 resolvase (Flanagan et al. (1989) J. Mol. Biol. 206:295 and Stark et al. (1989) Cell 58:779); 8) the SpoIVC recombinase of *Bacillus subtilis* (Sato et al. J. Bacteriol. 172:1092); 9) the Hin recombinase (Galsgow et al. (1989) J. Biol. Chem. 264: 10072); 10) the Cin recombinase (Hafter et al. (1988) EMBO J. 7:3991); 11) the immunoglobulin recombinases (Malynn et al. Cell (1988) 54:453); and 12) the FIMB and FIME recombinases (Blomfield et al., 1997 Mol. Microbiol. 23:705). Additional non-limiting examples of recombinases and their cognate recombinase recognition sequences that are useful for the SIMMs and biological circuit chemotactic converters described herein are provided in SEQ ID NOs: 8-25, SEQ ID NOs: 844-857, and SEQ ID NOs: 1002-1004.

The inverted promoter sequence in a SIMM can be used to drive transcription of downstream components of that SIMM or other biological modules upon recombinase activation and inversion of the promoter to the forward direction. Accordingly, an inverted promoter sequence for use in the SIMMs described herein can be a constitutive or inducible promoter, depending upon the requirements of the biological circuit chemotactic converters. Non-limiting examples of such promoter sequences for use in the SIMMs described herein are provided in SEQ ID NOs: 1-7, SEQ ID NOs: 41-843, and SEQ ID NOs: 1005-1010.

A SIMM can further comprise one or more components, including, but not limited to, ribosome binding sequences, degradation tag sequences, translational terminator sequences, and anti-sense sequences, that are added to, for example, enhance translation of mRNA sequences for protein synthesis, prevent further transcription downstream of the recombinase, or enhance degradation of the recombinase mRNA sequence or protein sequence once the recombinase sequence has been expressed. Such additional 'parts' or components, by enhancing the fidelity and accuracy of the biological modules, such as SIMMs, permit, for example, increased numbers and combinations of biological modules and improve the capabilities of the biological circuit chemotactic converters described herein.

In other embodiments of the aspects described herein, a SIMM can further comprise one or more ribosome binding site sequences (RBSs) to promote efficient and accurate translation of the mRNA sequences for protein synthesis. RBSs are useful components for modulating the efficiency and rates of synthesis of the proteins or other outputs encoded by the biological converter switches described herein. Non-limiting examples of such RBS sequences for use in the SIMMs described herein are provided in SEQ ID NOs: 26-33 and SEQ ID NOs: 858-1001. Accordingly, in some embodiments of these aspects, a SIMM further comprises a ribosome binding site upstream of the recombinase sequence, i.e., the SIMM comprises $RRS_{for}$-RBS-RC-$RRS_{rev}$, where RBS is a ribosome binding site. In other aspects, a SIMM further comprises both an inverted promoter sequence and a ribosome binding site upstream of the recombinase sequence, i.e., the SIMM comprises $RRS_{for}$-$iP_{inv}$-RBS-RC-$RRS_{rev}$, where $iP_{inv}$ is an inverted promoter sequence and RBS is a ribosome binding site sequence.

In other embodiments of the aspects described herein, one or more terminator sequences can be added to a SIMM to prevent activation of downstream genes or modules by an upstream promote sequence. Terminator sequences can be added to the end of, for example, the sequence encoding a recombinase in a SIMM, to prevent further transcription downstream of the recombinase. Thus, terminator sequences are useful in the biological converter switches described herein to prevent unwanted transcription driven by activation of the various modules. Non-limiting examples of such terminators for use in the SIMMs described herein are provided in Tables 1-5. Accordingly, in some embodiments of these aspects, a SIMM further comprises a transcriptional terminator sequence downstream of the recombinase sequence, i.e., $RRS_{for}$-RC-T-$RRS_{rev}$, where T is a terminator sequence. In other embodiments, a SIMM further comprises both an inverted promoter sequence and a terminator sequence upstream and downstream respectively of the recombinase sequence, i.e., the SIMM comprises $RRS_{for}$-$iP_{inv}$-RC-T-$RRS_{rev}$, where $iP_{inv}$ is an inverted promoter sequence and T is a terminator sequence.

Degradation tag sequences are also provided for use in the SIMMs and biological converter switches described herein to enhance degradation of a protein expressing the tag. The ability to add degradation tags to the proteins encoded by the SIMMs and biological converter switches described herein provides an additional layer of regulation and control of the modules. Non-limiting examples of such degradation tag sequences for use in the SIMMs described herein are provided in SEQ ID NOs: 34-40. Accordingly, in some embodiments of the aspects described herein, a SIMM further comprises a protein degradation tag sequence downstream of the recombinase sequence, i.e., the SIMM comprises i.e., the SIMM comprises $RRS_{for}$-RC-D-$RRS_{rev}$, where D is a degradation tag sequence. In other embodiments, a SIMM further comprises both an inverted promoter sequence and a degradation tag sequence upstream and downstream respectively of the recombinase sequence, i.e., the SIMM comprises $RRS_{for}$-$iP_{inv}$-RC-D-$RRS_{rev}$, where $iP_{inv}$ is an inverted promoter sequence and D is a degradation tag sequence.

In further embodiments of these aspects, a SIMM comprises both a ribosome binding site upstream of the recombinase sequence and a protein degradation tag sequence downstream of the recombinase sequence, i.e., the SIMM comprises $RRS_{for}$-RBS-RC-D-$RRS_{rev}$. In some embodiments, a SIMM further comprises an inverted promoter sequence and ribosome binding site upstream of the recombinase sequence, and a protein degradation tag sequence downstream of the recombinase sequence, i.e., the SIMM comprises $RRS_{for}$-$iP_{inv}$-RBS-RC-D-$RRS_{rev}$. In some embodiments of these aspects, a SIMM comprises both a protein degradation tag sequence and a transcriptional terminator sequence downstream of the recombinase sequence, i.e., the SIMM comprises $RRS_{for}$-$iP_{inv}$-RC-D-T-$RRS_{rev}$. In some embodiments, a SIMM further comprises an inverted promoter sequence upstream of the recombinase sequence, and a protein degradation tag sequence and a terminator sequence downstream of the recombinase sequence, i.e., the SIMM comprises $RRS_{for}$-$iP_{inv}$-RC-D-T-$RRS_{rev}$. In some embodiments of these aspects, a SIMM further comprises a ribosome binding site upstream of the recombinase sequence and a terminator sequence downstream of the recombinase sequence, i.e., the SIMM comprises $RRS_{for}$-$iP_{inv}$ RBS-RC-T-$RRS_{rev}$. In some embodiments, a SIMM further comprises an inverted promoter sequence and ribosome binding site upstream of the recombinase sequence, and a terminator sequence downstream of the recombinase sequence, i.e., the SIMM comprises $RRS_{for}$-$iP_{inv}$-RBS-RC-T-$RRS_{rev}$.

In some particular embodiments of these aspects, a SIMM can further comprise a ribosome binding site upstream of the recombinase sequence, and protein degradation tag and transcriptional terminator sequences downstream of the recombinase sequence, i.e., $RRS_{for}$-$iP_{inv}$-RBS-RC-D-T-$RRS_{rev}$. In other such embodiments, a SIMM further comprises an inverted promoter sequence and ribosome binding site upstream of the recombinase sequence, and protein degradation tag and transcriptional terminator sequences downstream of the recombinase sequence, i.e., the SIMM comprises $RRS_{for}$-$iP_{inv}$-RBS-RC-D-T-$RRS_{rev}$. In such embodiments, the combined addition of an RBS, a transcriptional terminator sequence, and a degradation tag to the SIMM provides an enhanced ability to regulate and control expression of the recombinase encoded by the SIMM.

In some embodiments of the aspects described herein, a SIMM can further comprise or be designed to include an antisense RNA sequence downstream of and in an inverted orientation in respect to the sequence encoding the recombinase, which is specific for the recombinase mRNA, i.e., $RRS_{for}$-RC-asRNA$_{inv}$-RRS$_{rev}$, where asRNA$_{inv}$ is an inverted antisense RNA sequence. In such embodiments, upon expression of the recombinase protein, in response, for example, to activation of an upstream promoter, the recombinase flips the sequences in the SIMM flanked by the recombinase recognition sites, such that the recombinase sequence is in the inverted orientation and the sequence encoding the antisense RNA is in the forward direction, i.e., $RRS_{for}$-asRNA-RC$_{inv}$-RRS$_{rev}$. The inversion event prevents further transcription and translation of the recombinase sequence, while transcription of the sequence encoding the antisense RNA specific for the recombinase enhances degradation of any transcribed recombinase mRNA sequence remaining. In further embodiments, the SIMM can further comprise a ribosome binding site upstream of the recombinase sequence, protein degradation tag or transcriptional terminator sequences downstream of the recombinase sequence, or any combination thereof, i.e., $RRS_{for}$-RBS-RC-asRNA$_{inv}$-D-T-RRS$_{rev}$, such that expression of the recombinase is regulated by a combination of elements to ensure accuracy and fidelity of the SIMM.

In some embodiments of these aspects and all such aspects described herein, a SIMM can be designed so that it can be reset by placing an additional promoter sequence in an inverted orientation downstream of the reverse recombinase recognition site, i.e., $RRS_{for}$-RBS-RC-RRS$_{rev}$-iP$_{inv}$; where iP$_{inv}$ is an inverted inducible promoter sequence. Upon activation of the promoter, the state of such a SIMM is flipped from its inverted state back to its original state, when the recombinase sequence is in the inverted orientation. In some embodiments, the same reverse inducible promoter can be used throughout an entire set of SIMMs within an a biological converter switch, such that a single inducer can be used to perform a global reset of all the SIMMs in the biological converter switch.

In some embodiments of these aspects and all such aspects described herein, a SIMM comprises a forward recombinase recognition site sequence, an inverted promoter sequence, a ribosome binding site sequence, a recombinase gene sequence, and a reverse recombinase recognition site sequence, and a sequence encoding an output product, i.e., $RRS_{for}$-P$_{inv}$-RC-RRS$_{rev}$-OP; where $RRS_{for}$ is a forward recombinase recognition sequence; P$_{inv}$ is an inverted promoter sequence; RC is a recombinase gene sequence encoding a recombinase that is specific for $RRS_{for}$ and RRS$_{rev}$; RRS$_{rev}$ is a reverse recombinase recognition sequence, and OP is an output product sequence. In such embodiments, upon expression of the recombinase, the sequence between the two recombinase recognition sites is inverted, resulting in termination of recombinase expression and allowing for the inverted promoter sequence to be in the appropriate direction to drive expression of the output gene sequence and any downstream modules. In some embodiments, the promoter is a inducible promoter. In some embodiments, the inducible promoter is a repressible promoter, or a promoter that can be activated by an activating agent. In such embodiments, the SIMM can further comprise degradation tags, ribosome binding sites, transcriptional terminator sequences, and antisense RNA sequences, as described herein, to add further regulatory capacities to the SIMM.

In other embodiments of these aspects and all such aspects described herein, a SIMM can comprise an inducible promoter sequence (iP), a forward recombinase recognition site sequence ($RRS_{for}$), an inverted sequence of a constitutive promoter (P$_{inv}$), a recombinase gene sequence (RC), a reverse recombinase recognition site sequence (RRS$_{rev}$), and an output product sequence (OP), i.e., iP-$RRS_{for}$-iP$_{inv}$-RC-RRS$_{rev}$-OP. In such embodiments, activation of the inducible promoter drives expression of the recombinase, which inverts the sequence between the two recombinase recognition sites, resulting in termination of recombinase expression, and allowing for the inverted, constitutive promoter sequence to be in the appropriate direction to drive expression of the output product sequence and any downstream modules, for example, one or more additional SIMMs. In some such embodiments, the SIMM can further comprise an additional inducible promoter in inverted orientation between the reverse recombinase recognition site sequence and the output product sequence, i.e., (iP-$RRS_{for}$-iP$_{inv}$-RC-RRS$_{rev}$-iP$_{2, inv}$-OP), such that the upon activation of the reverse promoter, the state of the system is flipped from its inverted state back to its original state. In some such embodiments, the first and second inducible promoters are induced by different agents. In all such embodiments, the SIMM can further comprise one or more components such as degradation tags, ribosome binding sites, transcriptional terminator sequences, and antisense RNA sequences to further regulate the activated and steady-states of the SIMM.

In some embodiments of these aspects and all such aspects described herein, one or more additional components can be added to the SIMMs to increase the utility or functionality of the SIMM for use in the biological circuit chemotactic converters provided herein. In some embodiments, a SIMM comprises a forward promoter sequence, a forward recombinase recognition sequence, a ribosome-binding site sequence, a recombinase gene sequence, a transcriptional terminator sequence, an inverted output product sequence, an inverted ribosome-binding site sequence, and a reverse recombinase recognition site sequence, i.e., P$_{for}$-$RRS_{for}$-RBS-RC-T-OP$_{inv}$-RBS$_{inv}$-RRS$_{rev}$; where P$_{for}$ is a forward promoter sequence; $RRS_{for}$ is a forward recombinase recognition sequence; RBS is a ribosome-binding site sequence; RC is a recombinase gene sequence encoding a recombinase that recognizes $RRS_{for}$ and RRS$_{rev}$; T is a transcriptional terminator sequence; OP$_{inv}$ is the inverted sequence of any gene that can be used as an output; RBS$_{inv}$ is an inverted ribosome-binding site sequence; and RRS$_{rev}$ is a reverse recombinase recognition sequence. In such embodiments, upon activation of the forward promoter (P$_{for}$), the recombinase gene (RC) is expressed, causing inversion of the sequence between the two recombinase recognition sequences ($RRS_{for}$ and RRS$_{rev}$), thus allowing for expression of the output product sequence that is no longer in the inverted direction. In some embodiments, the output product sequence encodes a transcriptional repressor or activator. In some embodiments, the output product sequence encodes a reporter gene.

In other embodiments of these aspects and all such aspects described herein, a SIMM is provided that comprises a forward promoter sequence, a forward recombinase recognition sequence, a ribosome-binding site sequence, a recombinase gene sequence, a ribosome-binding site sequence, an output product sequence, an inverted ribosome-binding site sequence, and a reverse recombinase recognition site sequence, i.e., P$_{for}$-$RRS_{for}$-RBS-RC-RBS-OP-RBS$_{inv}$-RRS$_{rev}$, where P$_{for}$ is a forward promoter; $RRS_{for}$ is a forward recombinase recognition sequence; RBS are ribosome-binding site sequences; RC is a recombinase gene sequence encoding a recombinase that recognizes $RRS_{for}$ and RRS$_{rev}$; OP is the sequence of any output product, such as a protein or RNA molecule; RBS$_{inv}$ is an inverted ribosome-binding site sequence; and RRS$_{rev}$ is a reverse recombinase recognition sequence. In such embodiments, activation of the forward promoter sequence results in expression of both the recombinase and the output product, and then upon inversion of the sequence due to the activity of the recombinase, the expression of the output product is shut off. Thus, in such embodiments, the SIMM creates a single pulse of expression of an output gene product. In some embodiments, the output product sequence encodes a transcriptional repressor or transcriptional activator. In other embodiments, the output product sequence encodes an RNA molecule, such as an iRNA molecule, an antisense RNA molecule, or a microRNA molecule. Other non-limiting examples of output products for use in the SIMMs described herein are reporter proteins (e.g., green fluorescent protein), transcription factors, transcriptional repressors, or RNA molecules, such as riboswitches in prokaryotic and mammalian cells, as well as short-hairpin RNAs, antisense RNA molecules, and microRNA molecules in mammalian cells (F. J. Isaacs, Nat Biotechnol 22, 841 (2004)). Further non-limiting examples of output products for use in the SIMMs described herein, are provided in the sections entitled "Output Products" and "RNA Molecule Components and Output Products."

Biological Circuit Chemotactic Converters

Described herein are novel biological circuit chemotactic converters that provide the ability to convert input signals received into expression of specific "sensory receptors" or "sensors." Expression of such sensors enable a biological system, such as a natural or synthetic (e.g., artificial) cell, to activate the necessary molecular components to move, or chemotaxis, in response to a chemotactic signal. The modular nature of the biological circuit chemotactic converters described herein permits flexibility and expansion of the converters to vary the range and sensitivity of input signals to which the biological circuit chemotactic converters can respond, and increases the numbers and combinations of sensors that are expressed, depending on the specific input signals received. Such signals that can act as input signals to the biological circuit chemotactic converters described herein include, but are not limited to, concentrations of inducing agents, which may include biological agents such as pheromones, hormones, growth factors, metabolites, and the like; concentrations of chemicals, environmental byproducts, metal ions, and other such molecules or agents; light levels; temperature; mechanical stress; or electrical signals, such as currents and voltages.

The biological circuit chemotactic converters provided herein comprise at least five modules—an input module, a genetic toggle switch, a logic module, and at least two sensor modules. The input module comprises an inducible promoter sequence operably linked to a repressor sequence, i.e., $iP_A$-$R_A$. In some embodiments of the aspects described herein, the input module further comprises an enhancer, a ribosome binding site, a degradation tag, an antisense RNA or microRNA sequence, and/or a terminator sequence. In some embodiments of the aspects described herein, the inducible promoter is an engineered promoter. In some embodiments of the aspects described herein, the inducing agent for the inducible promoter is an exogenous chemical, metal ion, toxin, or pollutant.

The genetic toggle switches provided herein are bistable switches that comprise a mutually inhibitory arrangement of repressor sequences, the products of which are specific for the sequence of the promoter sequence the other repressor sequence is operably linked to. In some embodiments of the aspects described herein, the genetic toggle switch comprises a first repressible promoter sequence ($rP_1$) that drives the transcription of a second repressor sequence ($R_2$) that encodes a repressor specific for the second repressible promoter sequence, and a second repressible promoter sequence ($rP_2$) that drives the transcription of a first repressor sequence ($R_1$), that represses transcription from $rP_1$, i.e., the genetic toggle switch (TS) comprises $rP_1$-$R_2$ and $rP_2$-$R_1$. In some embodiments of the aspects described herein, the repressor encoded by the input module $R_A$ acts a repressor for $rP_1$, such that when the input module receives an input and transcribes $R_A$, then transcription driven by $rP_1$ of the genetic toggle switch is repressed, allowing transcription to proceed from $rP_2$, resulting in transcription of $R_1$ of the genetic toggle switch. $R_1$ serves as a further repressor of transcription driven by $rP_1$ of the genetic toggle switch. In some embodiments of the aspects described herein, the repressor of the input module ($R_A$) and the first repressor of the toggle switch ($R_1$) are the same repressor, i.e., $R_A$=$R_1$.

The logic module of the biological circuit chemotactic converters described herein comprises a repressible promoter operably linked to a repressor sequence, i.e., $rP_B$-$R_B$. In some embodiments, the logic module further comprises an enhancer, a ribosome binding site, a degradation tag, an antisense RNA or microRNA sequence, and/or a terminator sequence. In some embodiments of these aspects, the repressible promoter of the logic module ($rP_B$) is repressed by the repressor encoded by the second repressor of the genetic toggle switch, such that $rP_B$ is repressed by $R_2$. In some embodiments of these aspects, the inducing agent for the inducible promoter is a biological agent, such as a pheromone, hormone, growth factor, or metabolite; or an exogenous chemical, metal ion, toxin, or pollutant. In some embodiments of these aspects, $rP_B$=$rP_2$ of the genetic toggle switch. Thus, in such embodiments, in the absence of an inducing agent received by the inducible promoter of the input module ($iP_A$), the genetic toggle switch transcribes the second repressor ($R_2$), which represses both $rP_2$ of the genetic toggle switch and the promoter ($rP_B$) of the logic module.

The sensor modules of the biological circuit chemotactic converter described herein each comprise a repressible promoter operably linked to a sequence encoding a sensor, i.e., $rP_C$-sensor A and $rP_D$-sensor B. In some embodiments, the two sensor sequences encode for a different sensor receptor. In some embodiments, the repressible promoter of one sensor module is repressed by the repressor encoded by the logic module, and the repressible promoter of the other sensor module is repressed by the repressor encoded by the second repressor ($R_2$) of the genetic toggle switch. For example, in such embodiments, $rP_C$ is repressed by $R_B$ of the logic module, which prevents transcription of sensor A, and $rP_C$ is repressed by $R_2$ of the genetic toggle switch, which prevents transcription of sensor B. In some embodiments, $rP_D$=$rP_2$. In some embodiments, $rP_D$=$rP_B$. In some embodiments, $rP_D$=$rP_B$=$rP_2$. Thus, in such biological circuit chemotactic converters, when no input is received by the input module, then the second repressor of the genetic toggle switch ($R_2$) is expressed and inhibits expression of the sensor having a promoter repressible by $R_2$, as well as the first repressor of the genetic toggle switch, and repressor B of the logic module. In the example described herein, in the absence of an input, only sensor A would be expressed.

Accordingly, in such embodiments, upon the input module receiving an appropriate input signal, repressor A of the input module is transcribed, which represses transcription from $rP_1$ of the genetic toggle switch, allowing transcription of the first repressor from $rP_2$ of the genetic toggle switch, and further inhibition of transcription from $rP_1$. In the absence of the second repressor of the genetic toggle switch, repression of the logic module and the $R_2$ repressible sensor module is removed, (i.e., sensor B), thus allowing transcription of repressor B of the logic module, and sensor B. Expression of repressor B of the logic module represses transcription from the sensor module having a promoter that can be repressed by repressor B, i.e., in this example, sensor A.

Figure 1B:
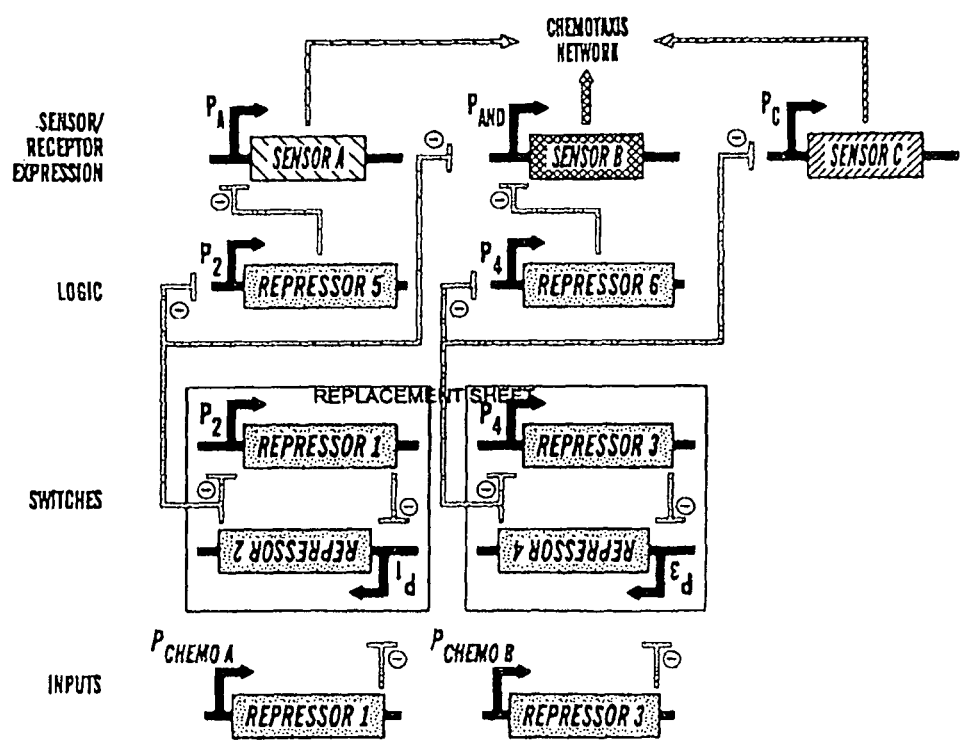
Figure 1C:
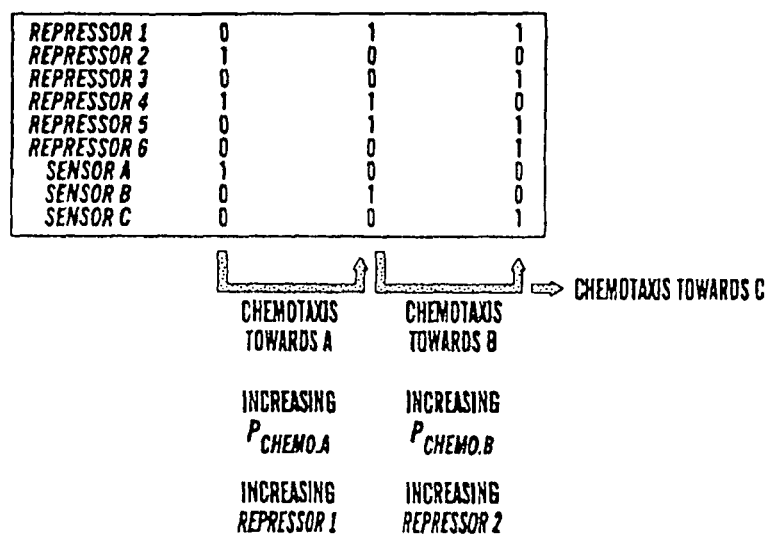
Figure 2A:
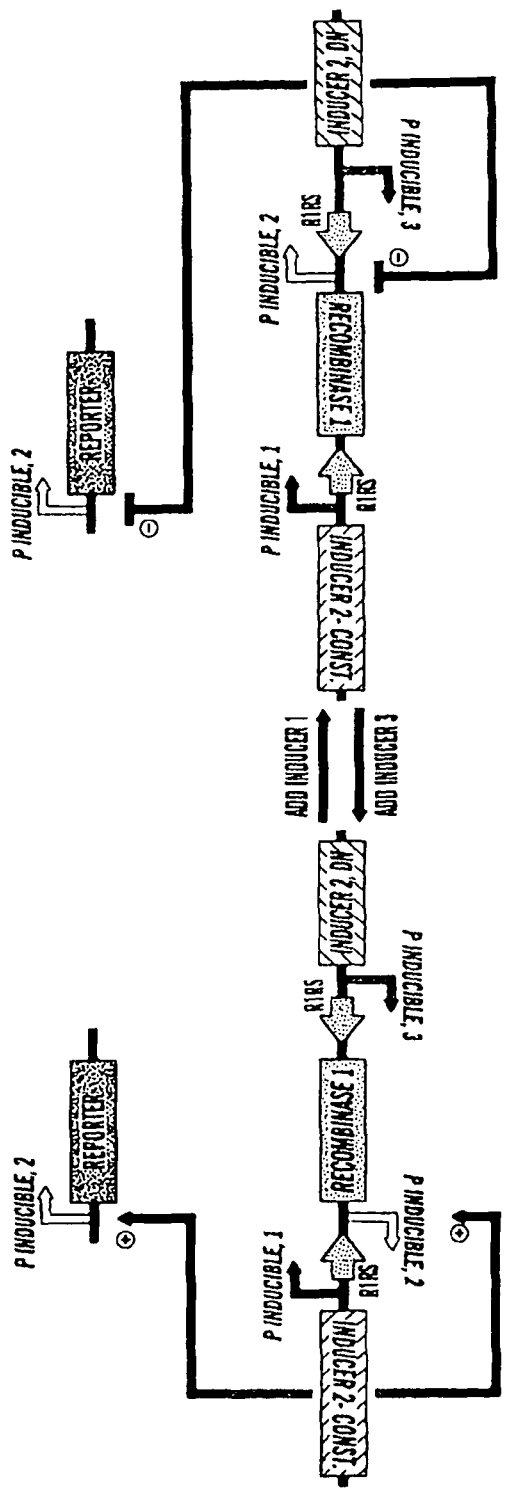
FIGS. 2A-2C depict an exemplary switch-module (SIMM) for use in the converters described herein and data from the exemplary switch module (SIMM).
Figure 2B:
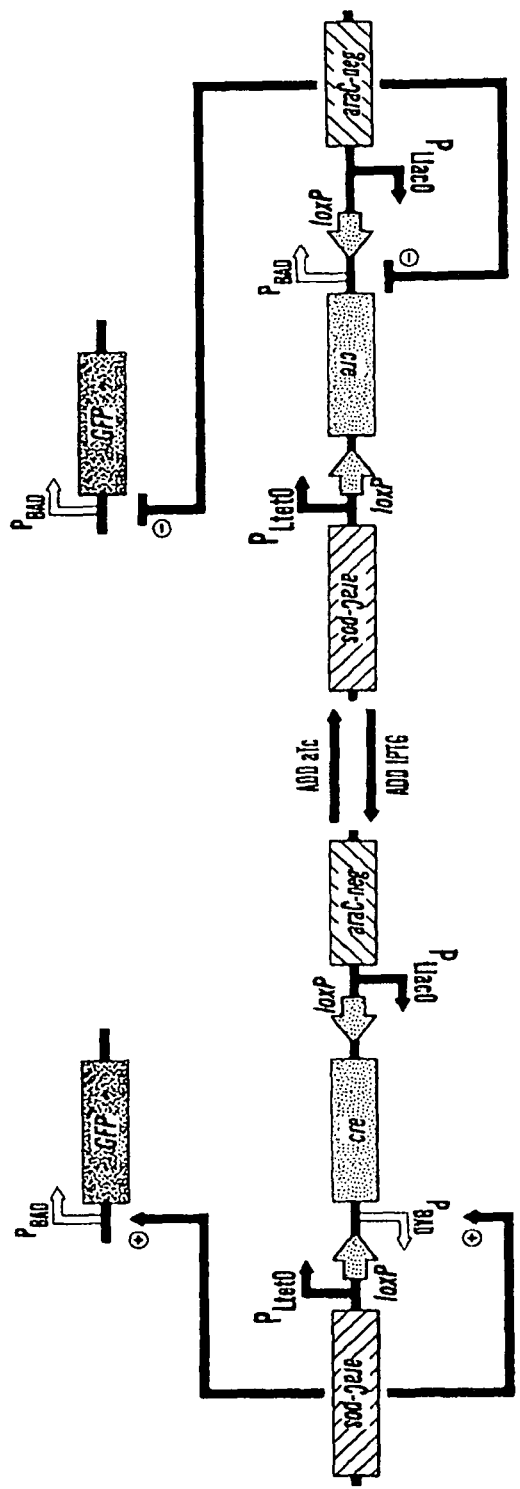
Figure 2C:
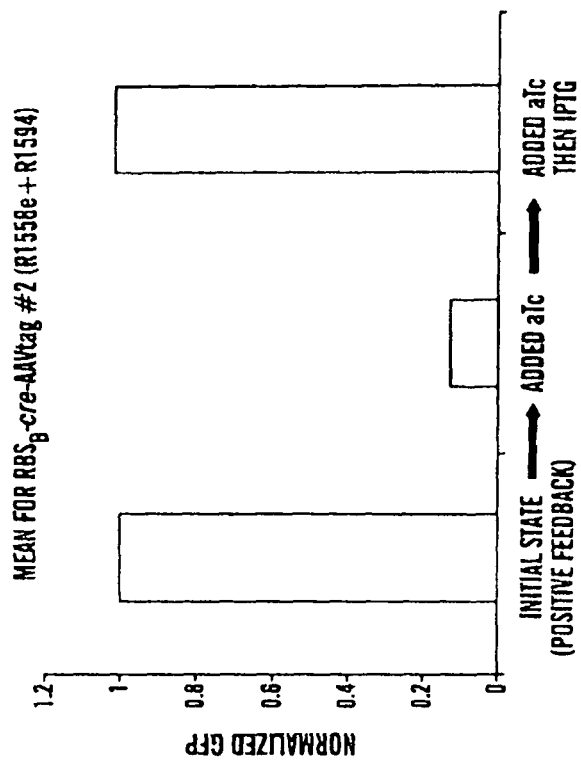

In some embodiments of the aspects described herein, the biological circuit chemotactic converters comprise multiple such modular components to increase the sensitivity and range of chemotactic responses in a biological system, such as a cell or organism. For example, in some embodiments, the biological circuit chemotactic converter comprises at least 2 input modules, at least 2 genetic toggle switches, at least 2 logic modules, and at least 3 sensor modules, as depicted in FIG. 1B. In such an embodiment, upon the input modules receiving appropriate input signals, different sensors are expressed, allowing different chemotactic responses to be achieved. For example, in the embodiment described in FIG. 1B, when neither input module receives an input signal, only sensor A is expressed, and the biological circuit chemotactic converter can be responsive, i.e., undergo chemotaxis, to the chemoattractant recognized by sensor A. Similarly, in the example shown in FIG. 1B, if the first input module, which encodes for repressor 1, receives an appropriate input signal, then the specific combination of repressors expressed results in expression of only sensor B, and the biological circuit chemotactic converter can be responsive to the chemoattractant recognized by sensor B. If the second input module, in the example shown in FIG. 1B, receives an appropriate input signal to begin transcription of repressor 3, than only sensor C is expressed and the biological circuit chemotactic converter can undergo chemotaxis to the chemoattractant recognized by sensor C.

In other embodiments of this aspect and all such aspects described herein, the biological circuit chemotactic converter comprises: at least 3 input modules, at least 3 genetic toggle switches, at least 3 logic modules, and at least 4 sensor modules; at least 4 input modules, at least 4 genetic toggle switches, at least 4 logic modules, and at least 5 sensor modules; at least 5 input modules, at least 5 genetic toggle switches, at least 5 logic modules, and at least 6 sensor modules; at least 6 input modules, at least 6 genetic toggle switches, at least 6 logic modules, and at least 7 sensor modules; at least 7 input modules, at least 7 genetic toggle switches, at least 7 logic modules, and at least 8 sensor modules; at least 8 input modules, at least 8 genetic toggle switches, at least 8 logic modules, and at least 9 sensor modules; at least 9 input modules, at least 9 genetic toggle switches, at least 9 logic modules, and at least 10 sensor modules; at least 10 input modules, at least 10 genetic toggle switches, at least 10 logic modules, and at least 11 sensor modules; at least 10 input modules, at least 10 genetic toggle switches, at least 10 logic modules, and at least 11 sensor modules; at least 11 input modules, at least 11 genetic toggle switches, at least 11 logic modules, and at least 12 sensor modules; at least 12 input modules, at least 12 genetic toggle switches, at least 12 logic modules, and at least 13 sensor modules; at least 13 input modules, at least 13 genetic toggle switches, at least 13 logic modules, and at least 14 sensor modules; at least 14 input modules, at least 14 genetic toggle switches, at least 14 logic modules, and at least 15 sensor modules; at least 15 input modules, at least 15 genetic toggle switches, at least 15 logic modules, and at least 16 sensor modules; at least 16 input modules, at least 16 genetic toggle switches, at least 16 logic modules, and at least 17 sensor modules; at least 17 input modules, at least 17 genetic toggle switches, at least 17 logic modules, and at least 18 sensor modules; at least 18 input modules, at least 18 genetic toggle switches, at least 18 logic modules, and at least 19 sensor modules; at least 19 input modules, at least 19 genetic toggle switches, at least 19 logic modules, and at least 20 sensor modules; at least 20 input modules, at least 20 genetic toggle switches, at least 20 logic modules, and at least 21 sensor modules; at least 50 input modules, at least 50 genetic toggle switches, at least 50 logic modules, and at least 51 sensor modules; at least 100 input modules, at least 100 genetic toggle switches, at least 100 logic modules, and at least 101 sensor modules; or at least n input modules, at least n genetic toggle switches, at least n logic modules, and at least n+1 sensor modules, where n is any integer value greater than or equal to 1.

In all embodiments of the aspects described herein, the modules of the biological circuit chemotactic converters can further comprise additional components such as one or more RBSs, degradation tag sequences, termination sequences, antisense RNA or microRNA sequences, and/or enhancer sequences. In some embodiments, the input module further comprises a ribosome binding sequence, a degradation tag sequence, a termination sequence, an antisense RNA, a microRNA sequence, an enhancer sequence, or any combination thereof. In some embodiments, the genetic toggle switch further comprises a degradation tag sequence, a termination sequence, an antisense RNA, a microRNA sequence, an enhancer sequence, or any combination thereof. In some embodiments, the logic module further comprises a ribosome binding sequence, a degradation tag sequence, a termination sequence, an antisense RNA, a microRNA sequence, an enhancer sequence, or any combination thereof. In some embodiments, the sensor module further comprises a ribosome binding sequence, a degradation tag sequence, a termination sequence, an antisense RNA, a microRNA sequence, an enhancer sequence, or any combination thereof.

Applications of Biological Circuit Chemotactic Converters

Provided herein are biological circuit chemotactic converters for use in engineering complex behavioral phenotypes in cellular systems, such as prokaryotic, eukaryotic, or synthetic cells. The novel biological circuit chemotactic converters described herein combine the power of protein engineering methods with systems biology approaches to elicit targeted responses in cellular systems.

Chemotactic Responses in Cellular Organisms

Chemotaxis in bacteria has been studied as a model system for receptor signaling and intracellular signal transduction. To actively seek energy sources or find optimal physico-chemical environments, bacteria such as *E. coli* employ a system of alternating tumbling and swimming phases. Bacteria such as *E. coli* are unable to choose the direction in which they swim, and are unable to swim in a straight line for more than a few seconds due to rotational diffusion. In the presence of a chemical gradient bacteria will chemotax, or direct their overall motion based on the gradient. If the bacterium senses that it is moving in the correct direction, for example, toward attractant/away from repellent, it keeps swimming in a straight line for a longer time before tumbling. If it is moving in the wrong direction, it tumbles sooner and try a new direction at random. Thus, bacteria like *E. coli* use temporal sensing, to find, for example, the location with the highest concentration of attractant. Even under very high concentrations, it can still distinguish very small differences in concentration. Fleeing from a repellent works with the same efficiency.

The helical nature of the individual flagellar filament is critical for this movement to occur. Some bacteria, such as *E. coli*, have several flagella per cell (4-10 typically), that can rotate in two ways. Counter-clockwise rotation aligns the flagella into a single rotating bundle, causing the bacterium to swim in a straight line. Clockwise rotation breaks the flagella bundle apart such that each flagellum points in a different direction, causing the bacterium to tumble in place. The protein that makes up the flagellar filament, flagellin, is quite similar among all flagellated bacteria.

Some bacteria, such as Vibrio, are monoflagellated and have a single flagellum at one pole of the cell, and used a different method of chemotaxis. Others possess a single flagellum that is kept inside the cell wall. These bacteria move by spinning the whole cell, which is shaped like a corkscrew.

Chemical gradients are sensed through multiple transmembrane receptors, called methyl accepting chemotaxis proteins (MCPs), which vary in the molecules that they detect. In some aspects of the invention, sequences encoding these receptors, or fragments thereof, are used in the sensor modules of the biological circuit chemotactic converters. These receptors can bind attractants or repellents directly or indirectly through interaction with proteins of periplasmatic space. The signals from these receptors are transmitted across the plasma membrane into the cytosol, where Che proteins are activated. The Che proteins alter the tumbling frequency, and alter the receptors.

The proteins CheW and CheA bind to the receptor. The activation of the multiple transmembrane receptor by an external stimulus causes autophosphorylation in the histidine kinase, CheA, at a single highly conserved histidine residue. CheA in turn transfers phosphoryl groups to conserved aspartate residues in the response regulators CheB and CheY. This mechanism of signal transduction is called a "two-component system" and is a common form of signal transduction in bacteria. CheY induces tumbling by interacting with the flagellar switch protein FliM, inducing a change from counter-clockwise to clockwise rotation of the flagellum. Change in the rotation state of a single flagellum can disrupt the entire flagella bundle and cause a tumble.

CheB, when activated by CheA, acts as a methylesterase, removing methyl groups from glutamate residues on the cytosolic side of the receptor. It works antagonistically with CheR, a methyltransferase, which adds methyl residues to the same glutamate residues. The more methyl residues are attached to the receptor, the less sensitive the receptor. As the signal from the receptor induces demethylation of the receptor in a feedback loop, the system is continuously adjusted to environmental chemical levels, remaining sensitive for small changes even under extreme chemical concentrations. This regulation allows the bacterium to 'remember' chemical concentrations from the recent past, a few seconds, and compare them to those it is currently experiencing, thus 'know' whether it is traveling up or down a gradient. Additional regulatory mechanisms such as receptor clustering and receptor-receptor interactions also modulate the signalling pathway.

The mechanism by which eukaryotic cells undergo chemotaxis differs from that in bacteria, however, sensing of chemical gradients is still a crucial step in the process. In contrast to prokaryotes, such as E. coli, the size of eukaryotic cells allows for the possibility of detecting gradients via dynamic and polarized distribution of receptors. Induction of these receptors by chemoattractants or chemorepellents results in migration towards or away from the chemotactic substance.

Levels of receptors, intracellular signalling pathways and the effector mechanisms all represent diverse, eukaryotic type components that are contemplated for use in the modules and biological circuit chemotactic converters described herein. In eukaryotic unicellular cells, ameboid movement and cilium or the eukaryotic flagellum are the main effectors (e.g. Amoeba or Tetrahymena). Some eukaryotic cells of higher vertebrate origin, such as immune cells also move to where they need to be by sensing chemotactic gradients.

Besides immune competent cells (granulocyte, monocyte, lymphocyte) a large group of cells—considered previously to be fixed into tissues—are also motile in special physiological (e.g. mast cell, fibroblast, endothelial cells) or pathological conditions (e.g. metastases). Chemotaxis has high significance in the early phases of embryogenesis as development of germ layers is guided by gradients of biological signal molecules.

In eukaryotic cells, the mechanisms regulating chemotaxis include mechanisms by which an external chemotactic gradient is sensed and turned into an intracellular PIP3 gradient, which results in a gradient and the activation of a signaling pathway, culminating in the polymerisation of actin filaments. The growing distal end of actin filaments develops connections with the internal surface of the plasma membrane via different sets of peptides and results in the formation of pseudopods. Cilia of eukaryotic cells can also produce chemotaxis; in this case it is mainly a Ca2+ dependent induction of the microtubular system of the basal body and the beat of the 9+2 microtubules within cilia. The orchestrated beating of hundreds of cilia is synchronized by a submembranous system built between basal bodies.

For the most part, eukaryotic cells sense the presence of chemotactic stimuli through the use of 7-transmembrane (or serpentine) heterotrimeric G-protein coupled receptors. Accordingly, in some embodiments, heterotrimeric G-protein coupled receptors are contemplated for use in the modules and biological circuit chemotactic converters described herein. Other professional chemotaxis receptors in eukaryotes that can be used in the modules and biological circuit chemotactic converters described herein are those triggered by formyl peptides, i.e., formyl peptide receptors (FPR); chemokines, i.e., chemokine receptors (CCR or CXCR); and leukotriene, i.e., leukotriene receptors (BLT), as described herein. In addition, induction of a wide set of membrane receptors (e.g. amino acids, insulin, vasoactive peptides) can also elicit migration of the cell and be used in the modules and biological circuit chemotactic converters described herein.

While some chemotaxis receptors are expressed in the surface membrane with long-term characteristics as they are determined genetically, others have short-term dynamics as they are assembled ad hoc in the presence of the ligand. The diverse features of the chemotaxis receptors and ligands allows for the possibility of selecting chemotactic responder cells with a simple chemotaxis assay. The main groups of primary ligands in eukaryotic cells include:

Formyl peptides, which are di-, tri-, tetrapeptides of bacterial origin, released from bacteria in vivo or after decomposition of the cell. A typical member of this group is the N-formylmethionyl-leucyl-phenylalanine (fMLF or fMLP). The bacterial origin fMLF as a key component of inflammation has characteristic chemoattractant effects in neutrophil granulocytes and monocytes.

Complement 3a (C3a) and complement 5a (C5a) are intermediate products of the complement cascade. Their synthesis is joined to the three alternative pathways (classical, lectin dependent and alternative) of complement activation by a convertase enzyme. The main target cells of these derivatives are neutrophil granulocytes and monocytes as well.

Chemokines belong to a special class of cytokines. Their groups (C, CC, CXC, CX3C chemokines) represent not only structurally related molecules with a special arrangement of disulfide bridges, but their target cell specificity is also diverse: CC chemokines act on monocytes (e.g. RANTES), CXC chemokines are neutrophil granulocyte specific (e.g. IL-8).

Leukotrienes belong to the group eicosanoids. They are significant lipid mediators of the arachidonic acid cascade converted by 5-lipoxigenase. Their predominant member is leukotriene B4 (LTB4) which elicits adhesion, chemotaxis and aggregation of leukocytes. The characteristic chemoattractant effect of LTB4 is induced via G-protein linked seven-transmembrane spanning leukotriene receptors which are highly expressed in inflammation and allergy.

Engineering Chemotactic Responses in Cellular Organisms

By integrating various modular components to provide specific responses chemotactic pathways, it is possible to engineer a an artificial chemotactic system, as described herein. In some aspects, biological circuit chemotactic converters are provided for use in organisms, such as bacteria, to modulate responses to chemotactic gradients. A variety of processing elements can be integrated at the genetic level to obtain gradient responses in such a converter, such as stable biphasic switches (for example, the genetic toggle switches described herein). Integration with another input can be achieved through biological logic modules, such as AND gates. The usage of such biological circuit chemotactic converters to modulate a system response can be modeled to characterize the dynamics of the genetic circuitry and can also be fine-tuned during empirical testing of the system.

In some aspects, biological circuit chemotactic converters are provided for use in engineering bacteria, such as *E. coli*, to provide directed chemotactic responses. In some embodiments of these aspects, the chemotactic response is further coupled to the production of an output product specific for the chemoattractant response. For example, upon sensing an environmental toxin, an organism engineered with a biological circuit chemotactic converter described herein, can undergo chemotaxis towards the source of the environmental toxin, resulting in an output "elimination response," such as the production of an enzyme that degrades the toxin. In other such embodiments, the biological circuit chemotactic converter can be used to mobilize an engineered organism towards the source of the environmental toxin to allow for visual identification of a region where there is high concentration of a toxin or pollutant, by, for example, coupling the biological circuit chemotactic converter to a reporter gene, such as GFP. In some embodiments, the biological circuit chemotactic converter is used in a response to eliminate a target, such as another bacteria.

In some embodiments of these aspects, fusion or chimeric polypeptides are encoded by the sensor modules of the biological circuit chemotactic converters described herein. Such fusion polypeptides can comprise a sensor domain, a transmembrane domain, and a cytoplasmic domain. In some embodiments, the domains are selected from chemotactic receptors of different organisms, e.g., different bacteria, or e.g., a eukaryotic sensor domain coupled to a prokaryotic cytoplasmic domain.

The methods and uses of the biological circuit chemotactic converters described herein can involve in vivo, ex vivo, or in vitro systems. The term "in vivo" refers to assays or processes that occur in or within an organism, such as a multicellular animal. In some of the aspects described herein, a method or use can be said to occur "in vivo" when a unicellular organism, such as a bacteria, is used. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others. The term "in vitro" refers to assays and methods that do not require the presence of a cell with an intact membrane, such as cellular extracts, and can refer to the introducing of a biological circuit chemotactic converters in a non-cellular system, such as a media not comprising cells or cellular systems, such as cellular extracts.

A cell or cellular system to be engineered for use with the biological circuit chemotactic converters described herein can be any cell. As defined herein, a "cell" is the basic structural and functional unit of all known living organisms. It is the smallest unit of life that is classified as a living thing, and is often called the building block of life. Some organisms, such as most bacteria, are unicellular (consist of a single cell). Other organisms, such as humans, are multicellular.

A "natural cell," as defined herein, refers to any prokaryotic or eukaryotic cell that occurs in nature. A "prokaryotic cell" can comprise a cell envelope and a cytoplasmic region that contains the cell genome (DNA) and ribosomes and various sorts of inclusions. In some embodiments, the cell is a eukaryotic cell. As used herein, a "eukaryotic cell" comprises membrane-bound compartments in which specific metabolic activities take place, such as for example, a nucleus. In some embodiments, the cell is a artificial or synthetic cell. As defined herein, an "artificial cell" or a "synthetic cell" is a minimal cell formed from artificial parts, that can do many things a natural cell can do, such as transcribe and translate proteins and generate ATP.

Host cells of use in the aspects described herein for transformation or transfection with the biological circuit chemotactic converters described herein include any host cell that is capable of supporting the activation and expression of the biological circuit chemotactic converters. In some embodiments of the aspects described herein, the cells are bacterial cells. The term "bacteria" as used herein is intended to encompass all variants of bacteria, for example, prokaryotic organisms and cyanobacteria. Bacteria are small (typical linear dimensions of around 1 m), non-compartmentalized, with circular DNA and ribosomes of 70S. The term bacteria also includes bacteria subdivisions of Eubacteria and Archaebacteria. Eubacteria can be further subdivided on the basis of their staining using Gram stain, and both gram-positive and gram-negative eubacteria, which depends upon a difference in cell wall structure are also included, as well as classified based on gross morphology alone (into cocci, bacilli, etc.).

In some embodiments, the bacterial cells are gram-negative cells and in alternative embodiments, the bacterial cells are gram-positive cells. Non-limiting examples of species of bacterial cells useful for engineering with the biological circuit chemotactic converters of the invention include, without limitation, cell from *Escherichia coli, Bacillus subtilis, Salmonella typhimurium* and various species of *Pseudomonas, Streptomyces*, and *Staphylococcus*. Other examples of bacterial cells that can be genetically engineered for use with the biological circuit chemotactic converters of the invention include, but are not limited to, cells from *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., and *Erysipelothrix* spp. In some embodiments, the bacterial cells are *E. coli* cells. Other examples of organisms from which cells can be transformed or transfected with the biological circuit chemotactic converters described herein include, but are not limited to the following: *Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans,*

*Bacteroides*, cyanobacteria, *Escherichia coli*, *Helobacter pylori*, *Selnomonas ruminatium*, *Shigella sonnei*, *Zymomonas mobilis*, *Mycoplasma mycoides*, or *Treponema denticola*, *Bacillus thuringiensis*, *Staphlococcus lugdunensis*, *Leuconostoc oenos*, *Corynebacterium xerosis*, *Lactobacillus planta* rum, *Streptococcus faecalis*, *Bacillus coagulans*, *Bacillus ceretus*, *Bacillus popillae*, *Synechocystis* strain PCC6803, *Bacillus liquefaciens*, *Pyrococcus abyssi*, *Selenomonas nominantium*, *Lactobacillus hilgardii*, *Streptococcus ferus*, *Lactobacillus pentosus*, *Bacteroides fragilis*, *Staphylococcus epidermidis*, *Staphylococcus epidermidis*, *Zymomonas mobilis*, *Streptomyces phaechromogenes*, *Streptomyces ghanaenis*, *Halobacterium* strain GRB, and *Halobaferax* sp. strain Aa2.2.

Cells of use in the various aspects described herein upon transformation or transfection with the biological circuit chemotactic converters described herein include any cell that is capable of supporting the activation and expression of the biological circuit chemotactic converters. In some embodiments of the aspects described herein, a cell can be from any multicellular or eukaryotic organism. Examples of eukaryotic cells that can be useful in aspects described herein include eukaryotic cells selected from, e.g., mammalian, insect, yeast, or plant cells. The biological circuit chemotactic converters described herein can be introduced into a variety of cells including, e.g., fungal, plant, or animal (nematode, insect, plant, bird, reptile, or mammal (e.g., a mouse, rat, rabbit, hamster, gerbil, dog, cat, goat, pig, cow, horse, whale, monkey, or human)). The cells can be primary cells, immortalized cells, stem cells, or transformed cells. In some embodiments, the cells comprise stem cells. Expression vectors for the components of the biological circuit chemotactic converters generally comprise a promoter and/or an enhancer suitable for expression in a particular host cell of interest. Other cell types also contemplated for use with the biological circuit chemotactic converters described herein, include, but are not limited to, reproductive cells including sperm, ova and embryonic cells, and non-reproductive cells, such as kidney, lung, spleen, lymphoid, cardiac, gastric, intestinal, pancreatic, muscle, bone, neural, brain, and epithelial cells. Also contemplated for use with the biological circuit chemotactic converters described herein are stem cells, including human embryonic stem cells, pluripotent stem cells, multipotent stem cells, and induced pluripotent stem cells (iPSCs), as those terms are understood by one of skill in the art.

As used herein, the term "stem cells" is used in a broad sense and includes traditional stem cells, progenitor cells, preprogenitor cells, reserve cells, and the like. The term "stem cell" or "progenitor cell" are used interchangeably herein, and refer to an undifferentiated cell which is capable of proliferation and giving rise to more progenitor cells having the ability to generate a large number of mother cells that can in turn give rise to differentiated, or differentiable daughter cells. Stem cells for use with the biological circuit chemotactic converters and the methods described herein can be obtained from endogenous sources such as cord blood, or can be generated using in vitro or ex vivo techniques as known to one of skill in the art. For example, a stem cell can be an induced pluripotent stem cell (iPS cell).

Exemplary stem cells include, but are not limited to, embryonic stem cells, adult stem cells, pluripotent stem cells, induced pluripotent stem cells (iPS cells), neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like.

Descriptions of stem cells, including method for isolating and culturing them, can be found in, among other places, Embryonic Stem Cells, Methods and Protocols, Turksen, ed., Humana Press, 2002; Weisman et al., Annu. Rev. Cell. Dev. Biol. 17:387 403; Pittinger et al., Science, 284:143 47, 1999; Animal Cell Culture, Masters, ed., Oxford University Press, 2000; Jackson et al., PNAS 96 (25):14482 86, 1999; Zuk et al., Tissue Engineering, 7:211 228, 2001 ("Zuk et al."); Atala et al., particularly Chapters 33 41; and U.S. Pat. Nos. 5,559, 022, 5,672,346 and 5,827,735. Descriptions of stromal cells, including methods for isolating them, can be found in, among other places, Prockop, Science, 276:71 74, 1997; Theise et al., Hepatology, 31:235 40, 2000; Current Protocols in Cell Biology, Bonifacino et al., eds., John Wiley & Sons, 2000 (including updates through March, 2002); and U.S. Pat. No. 4,963, 489; Phillips B W and Crook J M, Pluripotent human stem cells: A novel tool in drug discovery. BioDrugs. 2010 Apr. 1; 24 (2):99-108; Mari Ohnuki et al., Generation and Characterization of Human Induced Pluripotent Stem Cells, Current Protocols in Stem Cell Biology Unit Number: UNIT 4A., September, 2009.

As indicated above, there are different levels or classes of cells falling under the general definition of a "stem cell." These are "totipotent," "pluripotent" and "multipotent" stem cells. The term "totipotency" or "totipotent" refers to a cell with the degree of differentiation describing a capacity to make all of the cells in the adult body as well as the extra-embryonic tissues including the placenta. The fertilized egg (zygote) is totipotent as are the early cleaved cells (blastomeres)

The term "pluripotent" or a "pluripotent state" as used herein refers to a cell with the capacity, under different conditions, to differentiate to cell types characteristic of all three germ cell layers: endoderm (gut tissue), mesoderm (including blood, muscle, and vessels), and ectoderm (such as skin and nerve). Pluripotent cells are characterized primarily by their ability to differentiate to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. In some embodiments, a pluripotent cell is an undifferentiated cell.

The term "multipotent" when used in reference to a "multipotent cell" refers to a cell that is able to differentiate into some but not all of the cells derived from all three germ layers. Thus, a multipotent cell is a partially differentiated cell. Multipotent cells are well known in the art, and examples of multipotent cells include adult stem cells, such as for example, hematopoietic stem cells and neural stem cells. Multipotent means a stem cell can form many types of cells in a given lineage, but not cells of other lineages. For example, a multipotent blood stem cell such as a "hematopoietic stem cells" refers to all stem cells or progenitor cells found inter alia in bone marrow and peripheral blood that are capable of differentiating into any of the specific types of hematopoietic or blood cells, such as erythrocytes, lymphocytes, macrophages and megakaryocytes. The term "multipotency" refers to a cell with the degree of developmental versatility that is less than totipotent and pluripotent.

In the context of cell ontogeny, the adjectives "differentiated", or "differentiating" are relative terms. The term "differentiation" in the present context means the formation of cells expressing markers known to be associated with cells that are more specialized and closer to becoming terminally differentiated cells incapable of further differentiation. The pathway along which cells progress from a less committed cell, to a cell that is increasingly committed to a particular cell type, and eventually to a terminally differentiated cell is referred to as progressive differentiation or progressive commitment. Cell which are more specialized (e.g., have begun to progress along a path of progressive differentiation) but not yet terminally differentiated are referred to as partially differentiated. Differentiation is a developmental process whereby cells assume a specialized phenotype, e.g., acquire one or more characteristics or functions distinct from other cell types. In some cases, the differentiated phenotype refers to a cell phenotype that is at the mature endpoint in some developmental pathway (a so called terminally differentiated cell). In many, but not all tissues, the process of differentiation is coupled with exit from the cell cycle. In these cases, the terminally differentiated cells lose or greatly restrict their capacity to proliferate. However, we note that in the context of this specification, the terms "differentiation" or "differentiated" refer to cells that are more specialized in their fate or function than at a previous point in their development, and includes both cells that are terminally differentiated and cells that, although not terminally differentiated, are more specialized than at a previous point in their development. The development of a cell from an uncommitted cell (for example, a stem cell), to a cell with an increasing degree of commitment to a particular differentiated cell type, and finally to a terminally differentiated cell is known as progressive differentiation or progressive commitment. A cell that is "differentiated" relative to a progenitor cell has one or more phenotypic differences relative to that progenitor cell. Phenotypic differences include, but are not limited to morphologic differences and differences in gene expression and biological activity, including not only the presence or absence of an expressed marker, but also differences in the amount of a marker and differences in the co-expression patterns of a set of markers.

In other embodiments of the aspects described herein, biological circuit chemotactic converters can be introduced into a non-cellular system such as a virus or phage, by direct integration of the nucleic acid sequences encoding the various components and modules of the biological converter switch, for example, into the viral genome. A virus for use with the biological converter switches described herein can be a dsDNA virus (e.g. Adenoviruses, Herpesviruses, Poxviruses), a ssDNA viruses ((+)sense DNA) (e.g. Parvoviruses); a dsRNA virus (e.g. Reoviruses); a (+)ssRNA viruses ((+) sense RNA) (e.g. Picornaviruses, Togaviruses); (−)ssRNA virus ((−)sense RNA) (e.g. Orthomyxoviruses, Rhabdoviruses); a ssRNA-Reverse Transcriptase viruses ((+)sense RNA with DNA intermediate in life-cycle) (e.g. Retroviruses); or a dsDNA-Reverse Transcriptase virus (e.g. Hepadnaviruses).

Viruses can also include plant viruses and bacteriophages or phages. Examples of phage families that can be used with the biological circuit chemotactic converters described herein include, but are not limited to, Myoviridae (T4-like viruses; P1-like viruses; P2-like viruses; Mu-like viruses; SPO1-like viruses; φH-like viruses); Siphoviridaeλ-like viruses (T1-like viruses; T5-like viruses; c2-like viruses; L5-like viruses; ψM1-like viruses; φC31-like viruses; N15-like viruses); Podoviridae (T7-like viruses; φ29-like viruses; P22-like viruses; N4-like viruses); Tectiviridae (Tectivirus); Corticoviridae (Corticovirus); Lipothrixviridae (Alphalipothrixvirus, Betalipothrixvirus, Gammalipothrixvirus, Deltalipothrixvirus); Plasmaviridae (Plasmavirus); Rudiviridae (Rudivirus); Fuselloviridae (Fusellovirus); Inoviridae (Inovirus, Plectrovirus); Microviridae (Microvirus, Spiromicrovirus, Bdellomicrovirus, Chlamydiamicrovirus); Leviviridae (Levivirus, Allolevivirus) and Cystoviridae (Cystovirus). Such phages can be naturally occurring or engineered phages.

In some embodiments of the aspects described herein, the biological circuit chemotactic converters are introduced into a cellular or non-cellular system using a vector or plasmid. As used herein, the term "vector" is used interchangeably with "plasmid" to refer to a nucleic acid molecule capable of transporting another nucleic acid to which it has been linked Vectors capable of directing the expression of genes and/or nucleic acid sequence to which they are operatively linked are referred to herein as "expression vectors." In general, expression vectors of utility in the methods and biological circuit chemotactic converters described herein are often in the form of "plasmids," which refer to circular double stranded DNA loops which, in their vector form are not bound to the chromosome.

Other expression vectors can be used in different embodiments, for example, but not limited to, plasmids, episomes, bacteriophages or viral vectors, and such vectors can integrate into the host's genome or replicate autonomously in the particular cellular system used. Other forms of expression vectors known by those skilled in the art which serve the equivalent functions can also be used. Expression vectors comprise expression vectors for stable or transient expression encoding the DNA. A vector can be either a self replicating extrachromosomal vector or a vector which integrates into a host genome. One type of vector is a genomic integrated vector, or "integrated vector", which can become integrated into the chromosomal DNA or RNA of a host cell, cellular system, or non-cellular system. In some embodiments, the nucleic acid sequence or sequences encoding the biological circuit chemotactic converters integrates into the chromosomal DNA or RNA of a host cell, cellular system, or non-cellular system along with components of the vector sequence. In other embodiments, the nucleic acid sequence encoding the biological circuit chemotactic converter directly integrates into chromosomal DNA or RNA of a host cell, cellular system, or non-cellular system, in the absence of any components of the vector by which it was introduced. In such embodiments, the nucleic acid sequence encoding the biological circuit chemotactic converter can be integrated using targeted insertions, such as knock-in technologies or homologous recombination techniques, or by non-targeted insertions, such as gene trapping techniques or non-homologous recombination. The number of copies of a biological circuit chemotactic converter that integrate into the chromosomal DNA or RNA of a cellular or non-cellular system can impact the fidelity of the system, and thus it is preferred that only one copy is integrated per cellular system. Accordingly, in some embodiments of the aspects described herein, only one copy of a biological circuit chemotactic converter is integrated in the chromosomal DNA or RNA of a cellular or non-cellular system. In some embodiments, the number of copies is less than 10, less than 9, less than 8, less than 7, less than 6, less than 6, less than 4, less than 3, or less than 2.

Another type of vector is an episomal vector, i.e., a nucleic acid capable of extra-chromosomal replication. Such plasmids or vectors can include plasmid sequences from bacteria, viruses or phages. Such vectors include chromosomal, episomal and virus-derived vectors e.g., vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. A vector can be a plasmid, bacteriophage, bacterial artificial chromosome (BAC) or yeast artificial chromosome (YAC). A vector can be a single or double-stranded DNA, RNA, or phage vector. In some embodiments, the biological circuit chemotactic converters are introduced into a cellular system using a BAC vector.

The vectors comprising the biological circuit chemotactic converters described herein can be "introduced" into cells as polynucleotides, preferably DNA, by techniques well-known in the art for introducing DNA and RNA into cells. The term "transduction" refers to any method whereby a nucleic acid sequence is introduced into a cell, e.g., by transfection, lipofection, electroporation, biolistics, passive uptake, lipid: nucleic acid complexes, viral vector transduction, injection, contacting with naked DNA, gene gun, and the like. The vectors, in the case of phage and viral vectors can also be introduced into cells as packaged or encapsidated virus by well-known techniques for infection and transduction. Viral vectors can be replication competent or replication defective. In the latter case, viral propagation generally occurs only in complementing host cells. In some embodiments, the biological circuit chemotactic converters are introduced into a cell using other mechanisms known to one of skill in the art, such as a liposome, microspheres, gene gun, fusion proteins, such as a fusion of an antibody moiety with a nucleic acid binding moiety, or other such delivery vehicle.

The biological circuit chemotactic converters or the vectors comprising the biological biological circuit chemotactic converters described herein can be introduced into a cell using any method known to one of skill in the art. The term "transformation" as used herein refers to the introduction of genetic material (e.g., a vector comprising a biological circuit chemotactic converters) comprising one or more modules or biological circuit chemotactic converters described herein into a cell, tissue or organism. Transformation of a cell can be stable or transient. The term "transient transformation" or "transiently transformed" refers to the introduction of one or more transgenes into a cell in the absence of integration of the transgene into the host cell's genome. Transient transformation can be detected by, for example, enzyme linked immunosorbent assay (ELISA), which detects the presence of a polypeptide encoded by one or more of the transgenes. Alternatively, transient transformation can be detected by detecting the activity of the protein encoded by the transgene. The term "transient transformant" refers to a cell which has transiently incorporated one or more transgenes.

In contrast, the term "stable transformation" or "stably transformed" refers to the introduction and integration of one or more transgenes into the genome of a cell or cellular system, preferably resulting in chromosomal integration and stable heritability through meiosis. Stable transformation of a cell can be detected by Southern blot hybridization of genomic DNA of the cell with nucleic acid sequences, which are capable of binding to one or more of the transgenes. Alternatively, stable transformation of a cell can also be detected by the polymerase chain reaction of genomic DNA of the cell to amplify transgene sequences. The term "stable transformant" refers to a cell or cellular, which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Transformation also includes introduction of genetic material into plant cells in the form of plant viral vectors involving epichromosomal replication and gene expression, which may exhibit variable properties with respect to meiotic stability. Transformed cells, tissues, or plants are understood to encompass not only the end product of a transformation process, but also transgenic progeny thereof.

Component Parts
Promoters, and Promoter Inducing, Activating and Repressing Agents Provided herein are promoters and promoter sequences are for use in the various modules and components of the biological circuit chemotactic converters described herein.

The term "promoter," as used herein, refers to any nucleic acid sequence that regulates the expression of another nucleic acid sequence by driving transcription of the nucleic acid sequence, which can be a heterologous target gene encoding a protein or an RNA. Promoters can be constitutive, inducible, repressible, tissue-specific, or any combination thereof. A promoter is a control region of a nucleic acid sequence at which initiation and rate of transcription of the remainder of a nucleic acid sequence are controlled. A promoter can also contain genetic elements at which regulatory proteins and molecules can bind, such as RNA polymerase and other transcription factors. In some embodiments of the aspects, a promoter can drive the expression of a transcription factor that regulates the expression of the promoter itself, or that of another promoter used in another modular component of the biological circuit chemotactic converters described herein.

A promoter can be said to drive expression or drive transcription of the nucleic acid sequence that it regulates. The phrases "operably linked," "operatively positioned," "operatively linked," "under control," and "under transcriptional control" indicate that a promoter is in a correct functional location and/or orientation in relation to a nucleic acid sequence it regulates to control transcriptional initiation and/or expression of that sequence. An "inverted promoter," as used herein, refers to a promoter in which the nucleic acid sequence is in the reverse orientation, such that what was the coding strand is now the non-coding strand, and vice versa. Inverted promoter sequences can be used in various embodiments of the invention to regulate the state of a module or a switch. In addition, in various embodiments of the invention, a promoter can be used in conjunction with an "enhancer," which refers to a cis-acting regulatory sequence involved in the transcriptional activation of a nucleic acid sequence downstream of the promoter. The enhancer can be located at any functional location before or after the promoter, and/or the encoded nucleic acid.

A promoter can be one naturally associated with a gene or sequence, as can be obtained by isolating the 5' non-coding sequences located upstream of the coding segment and/or exon of a given gene or sequence. Such a promoter can be referred to as "endogenous." Similarly, in some embodiments, an enhancer can be one naturally associated with a nucleic acid sequence, located either downstream or upstream of that sequence.

Alternatively, certain advantages are gained by positioning a coding nucleic acid segment under the control of a "recombinant promoter" or "heterologous promoter," which refer to a promoter that is not normally associated with the encoded nucleic acid sequence it is operably linked to in its natural environment. A recombinant or heterologous enhancer refers to an enhancer not normally associated with a given nucleic acid sequence in its natural environment. Such promoters or enhancers can include promoters or enhancers of other genes; promoters or enhancers isolated from any other prokaryotic, viral, or eukaryotic cell; and synthetic promoters or enhancers that are not "naturally occurring," i.e., comprise different elements of different transcriptional regulatory regions, and/or mutations that alter expression through methods of genetic engineering that are known in the art. In addition to producing nucleic acid sequences of promoters and enhancers synthetically, promoter sequences can be produced using recombinant cloning and/or nucleic acid amplification technology, including PCR, in connection with the biological converter switches and modules disclosed herein (see, e.g., U.S. Pat. No. 4,683,202, U.S. Pat. No. 5,928,906, each incorporated herein by reference). Furthermore, it is contemplated that control sequences that direct transcription and/or expression of sequences within non-nuclear organelles such as mitochondria, chloroplasts, and the like, can be employed as well.

Inducible Promoters

As described herein, an "inducible promoter" is one that is characterized by initiating or enhancing transcriptional activity when in the presence of, influenced by, or contacted by an inducer or inducing agent. An "inducer" or "inducing agent," as defined herein, can be endogenous, or a normally exogenous compound or protein that is administered in such a way as to be active in inducing transcriptional activity from the inducible promoter. In some embodiments, the inducer or inducing agent, i.e., a chemical, a compound or a protein, can itself be the result of transcription or expression of a nucleic acid sequence (i.e., an inducer can be a transcriptional repressor protein expressed by another component or module), which itself can be under the control or an inducible promoter. In some embodiments, an inducible promoter is induced in the absence of certain agents, such as a repressor. Examples of inducible promoters include but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

Inducible promoters useful in the biological circuit chemotactic converters, systems, and methods described herein are capable of functioning in both prokaryotic and eukaryotic host organisms. In some embodiments of the different aspects described herein, mammalian inducible promoters are included, although inducible promoters from other organisms, as well as synthetic promoters designed to function in a prokaryotic or eukaryotic host can be used. One important functional characteristic of the inducible promoters described herein is their ultimate inducibility by exposure to an externally applied inducer, such as an environmental inducer. Exemplary environmental inducers include exposure to heat (i.e., thermal pulses or constant heat exposure), various steroidal compounds, divalent cations (including $Cu^{2+}$ and $Zn^{2+}$), galactose, tetracycline, IPTG (isopropyl-β-D thiogalactoside), as well as other naturally occurring and synthetic inducing agents and gratuitous inducers.

The promoters for use in the biological circuit chemotactic converters and modules described herein encompass the inducibility of a prokaryotic or eukaryotic promoter by, in part, either of two mechanisms. In some embodiments of these aspects, the biological converter switches and their component modules comprise suitable inducible promoters that can be dependent upon transcriptional activators that, in turn, are reliant upon an environmental inducer. In other embodiments, the inducible promoters can be repressed by a transcriptional repressor, which itself is rendered inactive by an environmental inducer, such as the product of a sequence driven by another promoter. Thus, unless specified otherwise, an inducible promoter can be one that is induced by an inducing agent that positively activates a transcriptional activator, or one which is derepressed by an inducing agent that negatively regulates a transcriptional repressor. In such embodiments of the various aspects described herein where it is required to distinguish between an activating and a repressing inducing agent, explicit distinction will be made.

Inducible promoters that are useful in the biological circuit chemotactic converters and methods of use disclosed herein include those controlled by the action of latent transcriptional activators that are subject to induction by the action of environmental inducing agents. Some non-limiting examples include the copper-inducible promoters of the yeast genes CUP1, CRS5, and SOD1 that are subject to copper-dependent activation by the yeast ACE1 transcriptional activator (see e.g. Strain and Culotta, 1996; Hottiger et al., 1994; Lapinskas et al., 1993; and Gralla et al., 1991). Alternatively, the copper inducible promoter of the yeast gene CTT1 (encoding cytosolic catalase T), which operates independently of the ACE1 transcriptional activator (Lapinskas et al., 1993), can be utilized. The copper concentrations required for effective induction of these genes are suitably low so as to be tolerated by most cell systems, including yeast and *Drosophila* cells. Alternatively, other naturally occurring inducible promoters can be used in the present invention including: steroid inducible gene promoters (see e.g. Oligino et al. (1998) Gene Ther. 5: 491-6); galactose inducible promoters from yeast (see e.g. Johnston (1987) Microbiol Rev 51: 458-76; Ruzzi et al. (1987) Mol Cell Biol 7: 991-7); and various heat shock gene promoters. Many eukaryotic transcriptional activators have been shown to function in a broad range of eukaryotic host cells, and so, for example, many of the inducible promoters identified in yeast can be adapted for use in a mammalian host cell as well. For example, a unique synthetic transcriptional induction system for mammalian cells has been developed based upon a GAL4-estrogen receptor fusion protein that induces mammalian promoters containing GAL4 binding sites (Braselmann et al. (1993) Proc Natl Acad Sci USA 90: 1657-61). These and other inducible promoters responsive to transcriptional activators that are dependent upon specific inducers are suitable for use with the biological circuit chemotactic converters described herein.

Inducible promoters useful in the biological circuit chemotactic converters, methods of use and systems described herein also include those that are repressed by "transcriptional repressors," which are subject to inactivation by the action of environmental, external agents, or the product of another gene. Such inducible promoters can also be termed "repressible promoters" where it is required to distinguish between other types of promoters in a given module or component of the biological switch converters described herein. Examples include prokaryotic repressors molecules that can transcriptionally repress eukaryotic promoters that have been engineered to incorporate appropriate repressor-binding operator sequences. Preferred repressors for use in the modules and methods described herein are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline will cause dissociation of the tet repressor from the engineered promoter and allow transcription of the sequence downstream of the engineered promoter to occur.

An inducible promoter useful in the biological circuit chemotactic converters, methods and systems as described herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent can comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as described herein can be a phage inducible promoter, nutrient inducible promoter, temperature inducible promoter, radiation inducible promoter, metal inducible promoter, hormone inducible promoter, steroid inducible promoter, and/or hybrids and combinations thereof.

Promoters that are inducible by ionizing radiation can be used in certain embodiments, where gene expression is induced locally in a cell by exposure to ionizing radiation, such as UV or x-rays. Radiation inducible promoters include the non-limiting examples of fos promoter, c-jun promoter or at least one CArG domain of an Egr-1 promoter. Further non-limiting examples of inducible promoters include promoters from genes such as cytochrome P450 genes, inducible heat shock protein genes, metallothionein genes, hormone-inducible genes, such as the estrogen gene promoter, and such. In further embodiments, an inducible promoter useful in the methods and systems described herein can be $Zn^{2+}$ metallothionein promoter, metallothionein-1 promoter, human metallothionein IIA promoter, lac promoter, lacO promoter, mouse mammary tumor virus early promoter, mouse mammary tumor virus LTR promoter, triose dehydrogenase promoter, herpes simplex virus thymidine kinase promoter, simian virus 40 early promoter or retroviral myeloproliferative sarcoma virus promoter. Examples of inducible promoters also include mammalian probasin promoter, lactalbumin promoter, GRP78 promoter, or the bacterial tetracycline-inducible promoter. Other examples include phorbol ester, adenovirus E1A element, interferon, and serum inducible promoters.

Inducible promoters useful in the modules and biological circuit chemotactic converters described herein for in vivo uses can include those responsive to biologically compatible agents, such as those that are usually encountered in defined animal tissues. An example is the human PAI-1 promoter, which is inducible by tumor necrosis factor. Further suitable examples include cytochrome P450 gene promoters, inducible by various toxins and other agents; heat shock protein genes, inducible by various stresses; hormone-inducible genes, such as the estrogen gene promoter, and such.

The administration or removal of an inducer or repressor as described herein results in a switch between the "on" or "off" states of the transcription of the operably linked heterologous target gene. Thus, as defined herein, the "on" state of a promoter operably linked to a nucleic acid sequence, refers to the state when the promoter is actively driving transcription of the operably linked nucleic acid sequence, i.e., the linked nucleic acid sequence is expressed. Several small molecule ligands have been shown to mediate regulated gene expressions, either in tissue culture cells and/or in transgenic animal models. These include the FK1012 and rapamycin immunosuppressive drugs (Spencer et al., 1993; Magari et al., 1997), the progesterone antagonist mifepristone (RU486) (Wang, 1994; Wang et al., 1997), the tetracycline antibiotic derivatives (Gossen and Bujard, 1992; Gossen et al., 1995; Kistner et al., 1996), and the insect steroid hormone ecdysone (No et al., 1996). All of these references are herein incorporated by reference. By way of further example, Yao discloses in U.S. Pat. No. 6,444,871, which is incorporated herein by reference, prokaryotic elements associated with the tetracycline resistance (tet) operon, a system in which the tet repressor protein is fused with polypeptides known to modulate transcription in mammalian cells. The fusion protein is then directed to specific sites by the positioning of the tet operator sequence. For example, the tet repressor has been fused to a transactivator (VP16) and targeted to a tet operator sequence positioned upstream from the promoter of a selected gene (Gussen et al., 1992; Kim et al., 1995; Hennighausen et al., 1995). The tet repressor portion of the fusion protein binds to the operator thereby targeting the VP16 activator to the specific site where the induction of transcription is desired. An alternative approach has been to fuse the tet repressor to the KRAB repressor domain and target this protein to an operator placed several hundred base pairs upstream of a gene. Using this system, it has been found that the chimeric protein, but not the tet repressor alone, is capable of producing a 10 to 15-fold suppression of CMV-regulated gene expression (Deuschle et al., 1995).

One example of a repressible promoter useful in the modules and biological circuit chemotactic converters as disclosed herein is the Lac repressor (lacR)/operator/inducer system of E. coli that has been used to regulate gene expression by three different approaches: (1) prevention of transcription initiation by properly placed lac operators at promoter sites (Hu and Davidson, 1987; Brown et al., 1987; Figge et al., 1988; Fuerst et al., 1989; Deuschle et al., 1989; (2) blockage of transcribing RNA polymerase II during elongation by a LacR/operator complex (Deuschle et al. (1990); and (3) activation of a promoter responsive to a fusion between LacR and the activation domain of herpes simples virus (HSV) virion protein 16 (VP16) (Labow et al., 1990; Baim et al., 1991). In one version of the Lac system, expression of lac operator-linked sequences is constitutively activated by a LacR-VP16 fusion protein and is turned off in the presence of isopropyl-β-D-1-thiogalactopyranoside (IPTG) (Labow et al. (1990), cited supra). In another version of the system, a lacR-VP16 variant is used that binds to lac operators in the presence of IPTG, which can be enhanced by increasing the temperature of the cells (Baim et al. (1991), cited supra). Thus, in some embodiments of the aspects described herein, components of the Lac system are utilized. For example, a lac operator (LacO) can be operably linked to tissue specific promoter, and control the transcription and expression of the heterologous target gene and another repressor protein, such as the TetR. Accordingly, the expression of the heterologous target gene is inversely regulated as compared to the expression or presence of Lac repressor in the system.

Components of the tetracycline (Tc) resistance system of E. coli that have also been found to function in eukaryotic cells and been used to regulate gene expression can also be used in the various aspects described herein. For example, the Tet repressor (TetR), which binds to tet operator (tetO) sequences in the absence of tetracycline and represses gene transcription, has been expressed in plant cells at sufficiently high concentrations to repress transcription from a promoter containing tet operator sequences (Gatz, C. et al. (1992) Plant J. 2:397-404). In some embodiments described herein, the Tet repressor system is similarly utilized.

A temperature- or heat-inducible gene regulatory system can also be used the in the biological circuit chemotactic converters and methods described herein, such as the exemplary TIGR system comprising a cold-inducible transactivator in the form of a fusion protein having a heat shock responsive regulator, rheA, fused to the VP16 transactivator (Weber et al., 2003a). The promoter responsive to this fusion thermosensor comprises a rheO element operably linked to a minimal promoter, such as the minimal version of the human cytomegalovirus immediate early promoter. At the permissive temperature of 37° C., the cold-inducible transactivator transactivates the exemplary rheO-CMVmin promoter, permitting expression of the target gene. At 41° C., the cold-inducible transactivator no longer transactivates the rheO promoter. Any such heat-inducible or -regulated promoter can be used in accordance with the modules, biological circuit chemotactic converters, and methods described herein, including but not limited to a heat-responsive element in a heat shock gene (e.g., hsp20-30, hsp27, hsp40, hsp60, hsp70, and hsp90). See Easton et al. (2000) Cell Stress Chaperones 5 (4):276-290; Csermely et al. (1998) Pharmacol Ther 79 (2): 129-1 68; Ohtsuka & Hata (2000) Int J Hyperthermia 16 (3):231-245; and references cited therein. Sequence similarity to heat shock proteins and heat-responsive promoter elements have also been recognized in genes initially characterized with respect to other functions, and the DNA sequences that confer heat inducibility are suitable for use in the disclosed gene therapy vectors. For example, expression of glucose-responsive genes (e.g., grp94, grp78, mortalin/grp75) (Merrick et al. (1997) Cancer Lett 119 (2): 185-1 90; Kiang et al. (1998) FASEB J 12 (14):1571-16-579), calreticulin (Szewczenko-Pawlikowski et al. (1997) Mol Cell Biochem 177 (1-2): 145-152); clusterin (Viard et al. (1999) J Invest Dermatol 112 (3):290-296; Michel et al. (1997) Biochem J 328 (Pt 1):45-50; Clark & Griswold (1997) J Androl 18 (3):257-263), histocompatibility class I gene (HLA-G) (Ibrahim et al. (2000) Cell Stress Chaperones 5 (3):207-218), and the Kunitz protease isoform of amyloid precursor protein (Shepherd et al. (2000) Neuroscience 99 (2):31 7-325) are upregulated in response to heat. In the case of clusterin, a 14 base pair element that is sufficient for heat-inducibility has been delineated (Michel et al. (1997) Biochem J 328 (Pt 1):45-50). Similarly, a two sequence unit comprising a 10- and a 14-base pair element in the calreticulin promoter region has been shown to confer heat-inducibility (Szewczenko-Pawlikowski et al. (1997) Mol Cell Biochem 177 (1-2): 145-1 52).

Other inducible promoters useful in the various embodiments of the aspects described herein include the erythromycin-resistance regulon from *E. coli*, having repressible ($E_{off}$) and inducible ($E_{on}$) systems responsive to macrolide antibiotics, such as erythromycin, clarithromycin, and roxithromycin (Weber et al., 2002). The $E_{off}$ system utilizes an erythromycin-dependent transactivator, wherein providing a macrolide antibiotic represses transgene expression. In the $E_{on}$ system, the binding of the repressor to the operator results in repression of transgene expression. Therein, in the presence of macrolides gene expression is induced.

Fussenegger et al. (2000) describe repressible and inducible systems using a Pip (pristinamycin-induced protein) repressor encoded by the streptogramin resistance operon of *Streptomyces coelicolor*, wherein the systems are responsive to streptogramin-type antibiotics (such as, for example, pristinamycin, virginiamycin, and Synercid). The Pip DNA-binding domain is fused to a VP16 transactivation domain or to the KRAB silencing domain, for example. The presence or absence of, for example, pristinamycin, regulates the $Pip_{ON}$ and $Pip_{OFF}$ systems in their respective manners, as described therein.

Another example of a promoter expression system useful for the modules and biological circuit chemotactic converters described herein utilizes a quorum-sensing (referring to particular prokaryotic molecule communication systems having diffusible signal molecules that prevent binding of a repressor to an operator site, resulting in derepression of a target regulon) system. For example, Weber et al. (2003b) employ a fusion protein comprising the *Streptomyces coelicolor* quorum-sending receptor to a transactivating domain that regulates a chimeric promoter having a respective operator that the fusion protein binds. The expression is fine-tuned with non-toxic butyrolactones, such as SCB1 and MP133.

In some embodiments, multiregulated, multigene gene expression systems that are functionally compatible with one another can be utilized in the aspects described herein (see, for example, Kramer et al. (2003)). For example, in Weber et al. (2002), the macrolide-responsive erythromycin resistance regulon system is used in conjunction with a streptogramin (PIP)-regulated and tetracycline-regulated expression systems.

Other promoters responsive to non-heat stimuli can also be used. For example, the mortalin promoter is induced by low doses of ionizing radiation (Sadekova (1997) Int J Radiat Biol 72 (6):653-660), the hsp27 promoter is activated by 17-β-estradiol and estrogen receptor agonists (Porter et al. (2001) J Mol Endocrinol 26 (1):31-42), the HLA-G promoter is induced by arsenite, hsp promoters can be activated by photodynamic therapy (Luna et al. (2000) Cancer Res 60 (6): 1637-1 644). A suitable promoter can incorporate factors such as tissue-specific activation. For example, hsp70 is transcriptionally impaired in stressed neuroblastoma cells (Drujan & De Maio (1999) 12 (6):443-448) and the mortalin promoter is up-regulated in human brain tumors (Takano et al. (1997) Exp Cell Res 237 (1):38-45). A promoter employed in methods of the present invention can show selective up-regulation in tumor cells as described, for example, for mortalin (Takano et al. (1997) Exp Cell Res 237 (1):38-45), hsp27 and calreticulin (Szewczenko-Pawlikowski et al. (1997) Mol Cell Biochem 177 (1-2): 145-1 52; Yu et al. (2000) Electrophoresis 2 1 (14):3058-3068)), grp94 and grp78 (Gazit et al. (1999) Breast Cancer Res Treat 54 (2): 135-146), and hsp27, hsp70, hsp73, and hsp90 (Cardillo et al. (2000) Anticancer Res 20 (6B):4579-4583; Strik et al. (2000) Anticancer Res 20 (6B): 4457-4552).

As described herein, the promoters in the modular components of the biological circuit chemotactic converters describes herein, such as genetic toggle switches, can drive expression of an operably linked recombinase, repressor, or output product, thus regulating expression and consequent activity of said recombinase, repressor, or output product. In some embodiments of the various aspects described herein, promoter sequences are added to the modules and biological circuit chemotactic converters in order to enumerate and input physiological events and stimuli, such as activation of gene networks or exposure to nutrients, toxins, metabolites, or any environmental exposure.

In some embodiments of the various aspects described herein, the promoter sequence that is added to a module or a biological circuit chemotactic converter is an inducible promoter that allows control of the module or biological circuit chemotactic converter using one or more chemical inducers.

In some embodiments, the inducible promoter comprises an Anhydrotetracycline (aTc)-inducible promoter as provided in PLtetO-1 (Pubmed Nucleotide# U66309) with the sequence comprising (SEQ ID NO: 1)
GCATGCTCCCTATCAGTGATAGAGATTGACATCCCTATCAGTGATAGA

GATACTGAGCACATCAGCAGGACGCACTGACCAGGA.

In some embodiments, the inducible promoter is an arabinose-inducible promoter $P_{BAD}$ comprising the sequence

```
                                           (SEQ ID NO: 2)
AAGAAACCAATTGTCCATATTGCATCAGACATTGCCGTCACTGCGTCT

TTTACTGGCTCTTCTCGCTAACCAAACCGGTAACCCCGCTTATTAAAA

GCATTCTGTAACAAAGCGGGACCAAAGCCATGACAAAAACGCGTAACA

AAAGTGTCTATAATCACGGCAGAAAAGTCCACATTGATTATTTGCACG

GCGTCACACTTTGCTATGCCATAGCATTTTTATCCATAAGATTAGCGG

ATCCTACCTGACGCTTTTTATCGCAACTCTCTACTGTTTCTCCATA.
```

In some embodiments, the inducible promoter is an isopropyl β-D-1-thiogalactopyranoside (IPTG) inducible promoter. In one embodiment, the IPTG-inducible promoter comprises the $P_{T4C}$ sequence found in the vector encoded by PubMed Accession ID #EU546824. In one embodiment, the IPTG-inducible promoter sequence comprises the $P_{Trc-2}$ sequence

```
                                           (SEQ ID NO: 3)
CCATCGAATGGCTGAAATGAGCTGTTGACAATTAATCATCCGGCTCGT

ATAATGTGTGGAATTGTGAGCGGATAACAATTTCACACAGGA.
```

In some embodiments, the IPTG-inducible promoter comprises the $P_{Trc-2}$ sequence found in the vector encoded by PubMed Accession ID #EU546816.

In some embodiments, the IPTG-inducible promoter comprises the $P_{LlacO-1}$

```
sequence:
                                           (SEQ ID NO: 4)
ATAAATGTGAGCGGATAACATTGACATTGTGAGCGGATAACAAGATAC

TGAGCACTCAGCAGGACGCACTGACC.
```

In some embodiments, the IPTG-inducible promoter comprises the $P_{A1lacO-1}$ sequence

```
                                           (SEQ ID NO: 5)
AAAATTTATCAAAAAGAGTGTTGACTTGTGAGCGGATAACAATGATAC

TTAGATTCAATTGTGAGCGGATAACAATTTCACACA.
```

In some embodiments, the IPTG-inducible promoter comprises the $P_{lac/ara-1}$ sequence

```
                                           (SEQ ID NO: 6)
CATAGCATTTTTATCCATAAGATTAGCGGATCCTAAGCTTTACAATTG

TGAGCGCTCACAATTATGATAGATTCAATTGTGAGCGGATAACAATTT

CACACA.
```

In some embodiments, the inducible promoter sequence comprises the $P_{Ls1con}$ sequence of

```
    (SEQ ID NO: 7), SEQ ID NO: 1009, or SEQ ID NO:
                                           1010.
GCATGCACAGATAACCATCTGCGGTGATAAATTATCTCTGGCGGTGTT

GACATAAATACCACTGGCGGTtATAaTGAGCACATCAGCAGG//GTAT

GCAAAGGA
```

Other non-limiting examples of constitutive and inducible promoters that are useful for the modules and biological circuit chemotactic converters described herein can be found in SEQ ID NO: 41-SEQ ID NO: 843, and SEQ ID NO: 1005-SEQ ID NO: 1008.

A variety of constitutive promoter sequences are available for those embodiments of the modules and biological circuit chemotactic converters described herein where constitutive expression of an operably linked sequence is required. Exemplary constitutive E. coli $\sigma^{70}$ promoter sequences can be found in SEQ ID NO: 41-SEQ ID NO: 125 and SEQ ID NO: 1005-SEQ ID NO: 1008. Exemplary constitutive E. coli $\sigma^{S}$ promoter sequences can be found in SEQ ID NO: 126-SEQ ID NO: 127. Exemplary constitutive B. subtilis $\sigma^{32}$ promoter sequences can be found in SEQ ID NO: 128. Exemplary constitutive B. subtilis $\sigma^{A}$ promoter sequences can be found in SEQ ID NO: 129-SEQ ID NO: 130. Exemplary constitutive B. subtilis $\sigma^{B}$ promoter sequences can be found in SEQ ID NO: 131-SEQ ID NO: 133. Exemplary constitutive promoter sequences from miscellaneous prokaryotes can be found in SEQ ID NO: 134-SEQ ID NO: 135. Exemplary constitutive promoter sequences from bacteriophage T7 can be found in SEQ ID NO: 136-SEQ ID NO: 150. An exemplary constitutive promoter sequence from bacteriophage SP6 can be found in SEQ ID NO: 151. Exemplary constitutive promoter sequences from yeast can be found in SEQ ID NO: 152-SEQ ID NO: 164. Exemplary constitutive promoter sequences from miscellaneous eukaryotes can be found in SEQ ID NO: 165-SEQ ID NO: 166.

A variety of inducible (positive and negative) and otherwise regulateable promoter sequences are available for those embodiments of the modules and biological circuit chemotactic converters described herein where inducible (repressible or activatable) expression of an operably linked sequence is required. Exemplary cell signaling promoter sequences can be found in SEQ ID NO: 167-SEQ ID NO: 198. Exemplary metal inducible promoter sequences can be found in SEQ ID NO: 199-SEQ ID NO: 204. Exemplary T7 promoter sequences can be found in SEQ ID NO: 205-SEQ ID NO: 224. Exemplary stress kit promoter sequences can be found in SEQ ID NO: 225-SEQ ID NO: 241. Exemplary logic promoter sequences can be found in SEQ ID NO: 242-SEQ ID NO: 319. Exemplary positively regulated E. coli $\sigma^{70}$ promoter sequences can be found in SEQ ID NO: 320-SEQ ID NO: 424. An exemplary positively regulated E. coli $\sigma^{S}$ promoter sequence can be found in SEQ ID NO: 425. An exemplary positively regulated E. coli $\sigma^{32}$ promoter sequence can be found in SEQ ID NO: 426. An exemplary positively regulated E. coli $\sigma^{54}$ promoter sequence can be found in SEQ ID NO: 427. Exemplary positively regulated B. subtilis $\sigma^{A}$ promoter sequences can be found in SEQ ID NO: 428-SEQ ID NO: 437. Exemplary miscellaneous prokaryotic inducible promoter sequences can be found in SEQ ID NO: 438-SEQ ID NO: 443. Exemplary yeast positive (activatible) promoter sequences can be found in SEQ ID NO: 444-SEQ ID NO: 459. Exemplary eukaryotic positive (activatible) promoter sequences can be found in SEQ ID NO: 460-SEQ ID NO: 464. Exemplary negatively regulated (repressible) E. coli $\sigma^{70}$ promoter sequences can be found in SEQ ID NO: 465-SEQ ID NO: 683. Exemplary negatively regulated (repressible) E. coli $\sigma^{S}$ promoter sequences can be found in SEQ ID NO: 684-SEQ ID NO: 688. Exemplary negatively regulated (repressible) E. coli $\sigma^{32}$ promoter sequences can be found in SEQ ID NO: 689-SEQ ID NO: 692. An exemplary negatively regulated (repressible) E. coli $\sigma^{54}$ promoter sequence can be found in SEQ ID NO: 693. Exemplary negatively regulated (repressible) B. subtilis $\sigma^{A}$ promoter sequences can be found in SEQ ID NO: 694-SEQ ID NO: 696. Exemplary T7 negatively regulated (repressible) promoter sequences can be found in SEQ ID NO: 697-SEQ ID NO: 700. Exemplary yeast negatively regulated (repressible) promoter sequences can be found in SEQ ID NO: 701-SEQ ID NO: 703. Exemplary eukaryotic negatively regulated (repressible) promoter sequences can be found in SEQ ID NO: 704-SEQ ID NO: 710.

In addition, a variety of combination (positive and negative) and otherwise regulateable promoter sequences are available for those embodiments of the modules and biological circuit chemotactic converters described herein where both repressible and activateable expression of an operably linked sequence is required. Exemplary combination activateable and repressible *E. coli* promoter sequences can be found in SEQ ID NO: 711-SEQ ID NO: 833. An exemplary combination activateable and repressible miscellaneous prokaryotic promoter sequence can be found in SEQ ID NO: 834. Exemplary combination activateable and repressible miscellaneous yeast promoter sequences can be found in SEQ ID NO: 835-SEQ ID NO: 839. Exemplary combination activateable and repressible miscellaneous eukaryotic promoter sequences can be found in SEQ ID NO: 840-SEQ ID NO: 843.

Recombinases and Recombination Recognition Sequences

In some aspects, sequences encoding recombinases and recombination recognition sequences are used in the various modules and components of the biological circuit chemotactic converters described herein. Sequences encoding recombinases and recombination recognition sequences are used, in part, to provide a genetically inheritable switch in the state of a module, or any of the biological circuit chemotactic converters described herein. The recombinases in the various modules and components of the biological circuit chemotactic converters s described herein, are preferably expressed between their cognate recognition sites, i.e., recombinase recognition site$_{for}$-recombinase-recombinase recognition site$_{rev}$. As a result, upon recombinase expression following activation of an upstream promoter, the recombinase causes a single inversion of the nucleic acid sequence between the cognate recognition sites, including its own sequence (i.e., recombinase recognition site$_{for}$-inverted recombinase-recombinase recognition site$_{rev}$). Any further transcription from the upstream promoter yields a long antisense RNA molecule of the recombinase gene rather then sense RNA, and therefore no further recombinase protein is produced. Thus, the inversion event is discrete and stable and does not result in a mixture of inverted and non-inverted states.

The advantages of the use of recombinases that mediate site-specific inversion for use in the various aspects of the biological circuit chemotactic converters described herein are the binary dynamics, the sensitivity of the output, the efficiency of DNA usage, and the persistence of the DNA modification. A "recombinase," as defined herein, is a site-specific enzyme that recognizes short DNA sequences, which are typically between about 30 bp and 40 bp, and mediates the recombination between these elements that results in the excision, integration, inversion, or exchange of DNA fragments.

Recombinases can be classified into two distinct families, the integrase and invertase/resolvase families, based on distinct biochemical properties. Members of the integrase family cleave one strand of each of the two DNA molecules involved, then exchange this strand, and subsequently cleave the second DNA strand. Integrase family recombinases use a conserved tyrosine residue to establish a transient covalent bond between the recombinase and the target DNA. Members of the invertase/resolvase family of recombinases cleave all 4 DNA strands and then exchange them, and initiate DNA cleavage by utilizing a serine residue as the catalytic residue. Recombinases have been used for numerous standard biological applications, including the creation of gene knockouts and the solving of sorting problems (N. J. Kilby, Trends Genet 9, 413 (December, 1993); K. A. Haynes, J Biol Eng 2, 8 (2008); T. S. Ham, Biotechnol Bioeng 94, 1 (2006); K. A. Datsenko, Proc Natl Acad Sci USA 97, 6640 (2000)).

Inversion recombination happens between two short inverted repeated DNA sequences, typically less than 30 bp long. The recombinases bind to these inverted repeated sequences, which are specific to each recombinase, and are defined herein as "recombinase recognition sequences" or "recombinase recognition sites." A DNA loop formation, assisted by DNA bending proteins, brings the two repeat sequences together, at which point DNA cleavage and ligation occur. This reaction is ATP independent and requires supercoiled DNA. The end result of such an inversion recombination event is that the stretch of DNA between the repeated site inverts, i.e., the stretch of DNA reverses orientation, such that what was the coding strand is now the non-coding strand and vice versa. In such reactions, the DNA is conserved with no net gain or no loss of DNA.

The recombinases provided herein are not meant to be an exclusive listing. Other examples of recombinases that are useful in the modules and any of the biological circuit chemotactic converters described herein are known to those of skill in the art, and furthermore, any new recombinase that is discovered or generated can be used in the embodiments described herein.

In some embodiments of the aspects described herein, the recombinase comprises the sequence of Cre recombinase of Pubmed Gene ID #2777477 (SEQ ID NO: 1002), and the corresponding loxP recombinase recognition sequences comprise the sequences of SEQ ID NO: 8 and SEQ ID NO: 9.

In some embodiments of the aspects described herein, the recombinase is Flp recombinase comprising the sequences of GenBank ID U46493 or NC_001398 (SEQ ID NO: 1003). In other embodiments, the recombinase is an enhanced Flp recombinase that comprises the sequence of SEQ ID NO: 10. The corresponding recombinase recognition sequences for the Flp and enhanced Flp recombinases comprise FRT sites with sequences comprising SEQ ID NO: 11. In some embodiments, minimal FRT recombinase recognition sites are used, comprising the sequence of SEQ ID NO: 12.

In some embodiments, the recombinase is R recombinase comprising the sequence of GenBank ID # X02398 (SEQ ID NO: 1004) and the corresponding recombinase recognition sequence comprises SEQ ID NO: 13.

In some embodiments, the recombinase comprises the bidirectional FimB recombinase of GeneID: 948832 (SEQ ID NO: 16) and the corresponding recombinase recognition sequences comprise SEQ ID NO: 14 and SEQ ID NO: 15.

In some embodiments, the recombinase is the unidirectional FimE recombinase of GeneID: 948836 (SEQ ID NO: 17) and the corresponding recombinase recognition sequences comprise SEQ ID NO: 14 and SEQ ID NO: 15.

In some embodiments, the recombinase is an Int recombinase. In some embodiments, the Int recombinase comprises a sequence that encodes for an Int recombinase selected from the group consisting of intE, HP1 Int, and HK022 Int.

In some embodiments, the recombinase is the XerC/XerD recombinase comprising the sequence of GeneID: 5387246 (SEQ ID NO: 18) and the corresponding recombinase recognition sequences comprise cer and dif.

In some embodiments, the recombinase is *Salmonella* Hin recombinase comprising the sequence of GeneID: 1254295 (SEQ ID NO: 19) and the corresponding recombinase recognition sequences comprise hixL and hixR.

In regard to the use of the 'Cre recombinase' and corresponding 'Lox' recombination recognition sequences, or the "Cre-Lox system," in the modules and biological circuit chemotactic converters described herein, the Cre protein has been purified to homogeneity (Abremski et al. (1984) J. Mol. Biol. 259:1509) and the cre gene has been cloned and expressed in a variety of host cells (Abremski et al. (1983)). Purified Cre protein is available from a number of suppliers (e.g., Stratagene, Novagen and New England Nuclear/Du Pont). Cre catalyzes the cleavage of the lox site within the spacer region and creates a six base-pair staggered cut (Hoess and Abremski (1985) J. Mol. Biol. 181:351). The two 13 bp inverted repeat domains of the lox site represent binding sites for the Cre protein. If two lox sites differ in their spacer regions in such a manner that the overhanging ends of the cleaved DNA cannot reanneal with one another, Cre cannot efficiently catalyze a recombination event using the two different lox sites. For example, it has been reported that Cre cannot recombine (at least not efficiently) a loxP site and a loxP511 site; these two lox sites differ in the spacer region. Two lox sites which differ due to variations in the binding sites (i.e., the 13 bp inverted repeats) may be recombined by Cre provided that Cre can bind to each of the variant binding sites; the efficiency of the reaction between two different lox sites (varying in the binding sites) may be less efficient that between two lox sites having the same sequence (the efficiency will depend on the degree and the location of the variations in the binding sites). For example, the loxC2 site can be efficiently recombined with the loxP site; these two lox sites differ by a single nucleotide in the left binding site.

In addition to the foregoing examples of sequences that the Cre protein recognizes, Cre also recognizes a number of variant or mutant lox sites (variant relative to the loxP sequence), including the loxB, loxL, loxR, loxA86, and lox.DELTA.117 sites which are found in the E. coli chromosome (Hoess et al. (1982)). Other variant lox sites include loxP511 (SEQ ID NO: 20); Hoess et al. (1986), supra), loxC2 (SEQ ID NO: 21); U.S. Pat. No. 4,959,317), lox66 (SEQ ID NO: 22), lox 71 (SEQ ID NO: 23), and lox BBa_J61046 (SEQ ID NO: 24).

Other alternative site-specific recombinases include: 1) the FLP recombinase of the 2pi plasmid of *Saccharomyces cerevisiae* (Cox (1983) Proc. Natl. Acad. Sci. USA 80:4223) which recognize the frt site which, like the loxP site, comprises two 13 bp inverted repeats separated by an 8 bp spacer (SEQ ID NO: 25). The FLP gene has been cloned and expressed in *E. coli* (Cox, supra) and in mammalian cells (PCT International Patent Application PCT/US92/01899, Publication No.: WO 92/15694, the disclosure of which is herein incorporated by reference) and has been purified (Meyer-Lean et al. (1987) Nucleic Acids Res. 15:6469; Babineau et al (1985) J. Biol. Chem. 260:12313; Gronostajski and Sadowski (1985) J. Biol. Chem. 260:12328); 2) the integrase of *Streptomyces* phage .PHI.C31 that carries out efficient recombination between the attP site of the phage genome and the attB site of the host chromosome (Groth et al., 2000 Proc. Natl. Acad. Sci. USA, 97: 5995); 3) the Int recombinase of bacteriophage lambda (lambda-int/attP) (with or without Xis) which recognizes att sites (Weisberg et al. In: Lambda II, supra, pp. 211-250); 4) the xerC and xerD recombinases of *E. coli* which together form a recombinase that recognizes the 28 bp dif site (Leslie and Sherratt (1995) EMBO J. 14:1561); 5) the Int protein from the conjugative transposon Tn916 (Lu and Churchward (1994) EMBO J. 13:1541); 6) TpnI and the β-lactamase transposons (Levesque (1990) J. Bacteriol. 172: 3745); 7) the Tn3 resolvase (Flanagan et al. (1989) J. Mol. Biol. 206:295 and Stark et al. (1989) Cell 58:779); 8) the SpoIVC recombinase of *Bacillus subtilis* (Sato et al. J. Bacteriol. 172:1092); 9) the Hin recombinase (Galsgow et al. (1989) J. Biol. Chem. 264:10072); 10) the Cin recombinase (Hafter et al. (1988) EMBO J. 7:3991); 11) the immunoglobulin recombinases (Malynn et al. Cell (1988) 54:453); and 12) the FIMB and FIME recombinases (Blomfield et al., 1997 Mol. Microbiol. 23:705).

In the natural *Salmonella* system, the Hin DNA recombinase (BBa_J31000, BBa_J31001) catalyzes an inversion reaction that regulates the expression of alternative flagellin genes by switching the orientation of a promoter located on a 1 kb invertible DNA segment. The asymmetrical palindromic sequences hixL and hixR flank the invertible DNA segment and serve as the recognition sites for cleavage and strand exchange. A ~70 bp cis-acting recombinational enhancer (RE) increases efficiency of protein-DNA complex formation. In some embodiments, rather than hixL and hixR, hixC (BBa_J44000), a composite 26 bp symmetrical hix site that shows higher binding affinity for Hin and a 16-fold slower inversion rate than wild type sites hixL and hixR can be used. In addition, a modified Hin/hix DNA recombination system can be used in vivo to manipulate at least two adjacent hixC-flanked DNA segments. Hin recombinase fused to a C-terminus LVA degradation tag (BBa_J31001) and hixC (BBa_J44000) are sufficient for DNA inversion activity. Exemplary sequences for the recombinational enhancer and modified Hin recombinase recognition sequences include Recombinational Enhancer (RE) for Hin/Hix inverting (SEQ ID NO: 844) and hixC binding site for *Salmonella typhimurium* Hin recombinase (SEQ ID NO: 845).

Bacteriophage λ has long served as a model system for studies of regulated site-specific recombination. In conditions favorable for bacterial growth, the phage genome is inserted into the *Escherichia coli* genome by an 'integrative' recombination reaction, which takes place between DNA attachment sites called attP and attB in the phage and bacterial genomes, respectively. As a result, the integrated λ DNA is bounded by hybrid attachment sites, termed attL and attR. In response to the physiological state of the bacterial host or to DNA damage, λ phage DNA excises itself from the host chromosome. This excision reaction recombines attL with attR to precisely restore the attP and attB sites on the circular λ and *E. coli* DNAs. The phage-encoded λ integrase protein (Int), a tyrosine recombinase, splices together bacterial and phage attachment sites. Int is required for both integration and excision of the λ prophage.

λ recombination has a strong directional bias in response to environmental conditions. Accessory factors, whose expression levels change in response to host physiology, control the action of Int and determine whether the phage genome will remain integrated or be excised. Int has two DNA-binding domains: a C-terminal domain, consisting of a catalytic domain and a core-binding (CB) domain, that interacts with the core recombining sites and an N-terminal domain (N-domain) that recognizes the regulatory arm DNA sites. The heterobivalent Int molecules bridge distant core and arm sites with the help of accessory proteins, such as integration host factor (IHF), which bend the DNA at intervening sites, and appose arm and core sequences for interaction with the Int recombinase. Five arm DNA sites in the regions flanking the core of attP are differentially occupied during integration and excision reactions. The integration products attL and attR cannot revert back to attP and attB without assistance from the phage-encoded factor Xis, which bends DNA on its own or in combination with the host-encoded factor Fis. Xis also inhibits integration, and prevents the attP and attB products of excision from reverting the attP and attB products of excision from reverting to attL and attR. Because the cellular levels of IHF and F is proteins respond to growth conditions, these host-encoded factors have been proposed as the master signals for integration and excision.

Additional exemplary λ recombination recognition sequences and recombinases for the biological converter switches described herein include, but are not limited to, Lambda attB (SEQ ID NO: 846), Lambda attP (SEQ ID NO: 847), attR2 recombination site (SEQ ID NO: 848), and attR2 recombination site-reverse orientation (SEQ ID NO: 849) as λ recombination recognition sequences, and Xis lambda (excisionase from *E. coli* phage lambda (removes prophage from host genome)); Int lambda (integrase from *E. coli* phage lambda); Xis (Xis from bacteriophage lambda, assembly standard 21); a~xis (the bacteriophage lambda xis gene ready to have rbs attached and stop codon; and xis, from bacteriophage lambda; assembly standard 21.

Bacteriophage P22 is a lambdoid phage which infects *Salmonella typhimurium*. P22 can integrate into and excise out of its host chromosome via site-specific recombination. Both integration and excision reactions require the phage-encoded int gene, and excision is dependent on the xis gene as well.

P22 Int is a member of the λ integrase family. The Int proteins of λ and P22 are composed of two domains. The catalytic domain binds to the core region of the phage recombination site, attP, where the actual recombination reactions occur. The smaller amino-terminal domain binds to arm-type sequences which are located on either site of the core within the attP. The active components of λ integrative and excisive recombination are nucleosome-like structures, called intasomes, in which DNA is folded around several molecules of Int and integration host factor (IHF). It has been demonstrated that one monomer of λ integrase can simultaneously occupy both a core-type binding site and an arm-type binding site. Formation of these bridges is facilitated by IHF, which binds to specific sequences and imparts a substantial bend to the DNA.

The attP regions of P22 and λ are also similar in that both contain arm regions, known as the P and P' arms, which contain Int arm-type binding sites and IHF binding sites. However, the arrangement, spacing, and orientation of the Int and IHF binding sites are distinct. The attP region of λ contains two Int arm-type binding sites on the P arm and three on the P' arm. The P arm contains two IHF binding sites, and the P' arm contains a single site. The attP region of P22 contains three Int arm-type binding sites on the P arm and two sites on the P' arm. In addition, IHF binding sites, called H and H', are located on each arm of the P22 attP. Leong et al. showed that the *Escherichia coli* IHF can recognize and bind to these P22 IHF binding sites in vitro. It was also shown that the maximum amount of P22 integrative recombination occurred in the presence of *E. coli* IHF in vitro, whereas in its absence, recombination was detectable but depressed. However, the requirement for IHF or other possible accessory proteins during P22 site-specific recombination in vivo has not been tested. In this study, we assessed the role of IHF in P22 integration and excision in vivo.

Although the attP region of P22 contains strong IHF binding sites, in vivo measurements of integration and excision frequencies showed that infecting P22 phages can perform site-specific recombination to its maximum efficiency in the absence of IHF. In addition, a plasmid integration assay showed that integrative recombination occurs equally well in wild-type and ihfA mutant cells. P22 integrative recombination is also efficient in *Escherichia coli* in the absence of functional IHF. Additional exemplary recombination recognition sequences and recombinases for the biological converter switches described herein include, but are not limited to, recombination recognition sequences P22 "attB", reverse complement (SEQ ID NO: 850) and P22 "attP" (SEQ ID NO: 851), and recombinases Xis P22 (excisionase from *E. coli* phage P22 (removes prophage from host genome)), and Int P22 (integrase from *E. coli* phage P22).

The FLP system of the yeast 2 mm plasmid is one of the most attractive for genomic manipulation because of its efficiency, simplicity, and demonstrated in vivo activity in a wide range of organisms. The Flp system has been used to construct specific genomic deletions and gene duplications, study gene function, promote chromosomal translocations, promote site-specific chromosome cleavage, and facilitate the construction of genomic libraries in organisms including bacteria, yeast, insects, plants, mice, and humans. Site-specific recombination catalyzed by the FLP recombinase occurs readily in bacterial cells.

The yeast FLP system has been studied intensively. The only requirements for FLP recombination are the FLP protein and the FLP recombination target (FRT) sites on the DNA substrates. The minimal functional FRT site contains only 34 bp. The FLP protein can promote both inter- and intramolecular recombination. Exemplary recombination recognition sequences for use with the yeast FLP system include, but are not limited to, FRT (SEQ ID NO: 852) and [FRT] recombination site for flp recombinase in BBb (SEQ ID NO: 853).

The separation and segregation of newly replicated *E. coli* circular chromosomes can also be prevented by the formation of circular chromosome dimers, which can arise during crossing over by homologous recombination. In *E. coli*, these dimers, which arise about once every six generations, are resolved to monomers by the action of the FtsK-XerCD-dif chromosome dimer resolution machinery. Two site-specific recombinases of the tyrosine recombinase family, XerCD, act at a 28 bp recombination site, dif, located in the replication terminus region of the *E. coli* chromosome to remove the crossover introduced by dimer formation, thereby converting dimers to monomers. A complete dimer resolution reaction during recombination at dif requires the action of the C-terminal domain of FtsK (FtsK$_C$). FtsK is a multifunctional protein whose N-terminal domain acts in cell division, while the C-terminal domain functions in chromosome segregation. Therefore, FtsK is well suited to coordinate chromosome segregation and cell division. A purified protein, FtsK$_{50C}$, containing a functional C-terminal domain, can translocate DNA in an ATP-dependent manner and activate Xer recombination at the recombination site dif, thereby reconstituting in vitro the expected in vivo activities of the C-terminal domain of the complete FtsK protein. Additional exemplary recombination recognition sequences for use with the XerCD system are include, but are not limited to dif site with forward orientation (SEQ ID NO: 854) and dif site with reverse orientation (SEQ ID NO: 855).

The fim switch (fimS) comprises a 314 hp DNA element that can be inverted by site-specific recombinases FimB and FimE. In the natural system, fimSc contains a promoter, that when switched to the on orientation, drives transcription of the fim operon. The fim operon is needed for export and structural assembly of type 1 fimbriae. FimB and FimE, required to invert fimS, are members of the λ integrase family of site-specific recombinases. Recombination of fimS is distinct from the related Xer-mediated recombination in that the recombinases act independently to invert fimS. Each inverted repeat (IR) is flanked by overlapping FimB and FimE binding sites, and following occupancy of these sites they recombine the switch within the IR sequence. As for λ phage chromosomal integration and excision, fim recombination also requires accessory proteins, specifically integration host factor (IHF) and the leucine-responsive regulatory protein (Lrp).

These proteins are believed to contribute to the overall architecture of the fim switch that facilitates synapse of the 9 bp IRs.

FimB catalyses inversion in both directions, although with a slight bias for the off-to-on orientation, while FimE predominantly catalyses on-to-off inversion. Control of FimE expression is important in bringing about its orientation bias; as the fim switch is located at the end of fimE, the orientation of fimS determines the length and 3' sequence of the fimE transcript. As a consequence, fimE mRNA is likely to be subject to more rapid 3' to 5' degradation when the switch is in the off orientation than when it is in the on orientation. In addition, FimE preferentially binds to fimS in the on orientation, as has been demonstrated in vitro and in vivo, which adds to the directional bias. A further difference between FimB and FimE is that FimB inversion frequencies are markedly lower than those exhibited by FimE, both in vitro and in vivo. Additional exemplary recombination recognition sequences and recombinases for use with the FimB and FimE system include, but are not limited to, fimE IRR (SEQ ID NO: 856) and fimE IRL (SEQ ID NO: 857).

Ribosome Binding Sites

Ribosome binding sites (RBS) are sequences that promote efficient and accurate translation of mRNAs for protein synthesis, and are also provided for use in the modules and biological circuit chemotactic converters described herein to enable modulation of the efficiency and rates of synthesis of the proteins encoded by the converters, such as recombinases and repressors. An RBS affects the translation rate of an open reading frame in two main ways—i) the rate at which ribosomes are recruited to the mRNA and initiate translation is dependent on the sequence of the RBS, and ii) the RBS can also affect the stability of the mRNA, thereby affecting the number of proteins made over the lifetime of the mRNA. Accordingly, one or more ribosome binding site sequences (RBS) can be added to the modules and biological circuit chemotactic converters described herein to control expression of proteins, such as recombinases or protein output products.

Translation initiation in prokaryotes is a complex process involving the ribosome, the mRNA, and several other proteins, such as initiation factors, as described in Laursen B S, et al., Microbiol Mol Biol Rev 2005 March; 69 (1) 101-23. Translation initiation can be broken down into two major steps—i) binding of the ribosome and associated factors to the mRNA, and ii) conversion of the bound ribosome into a translating ribosome lengthening processing along the mRNA. The rate of the first step can be increased by making the RBS highly complementary to the free end of the 16s rRNA and by ensuring that the start codon is AUG. The rate of ribosome binding can also be increased by ensuring that there is minimal secondary structure in the neighborhood of the RBS. Since binding between the RBS and the ribosome is mediated by base-pairing interactions, competition for the RBS from other sequences on the mRNA, can reduce the rate of ribosome binding. The rate of the second step in translation initiation, conversion of the bound ribosome into an initiation complex is dependent on the spacing between the RBS and the start codon being optimal (5-6 bp).

Thus, a "ribosome binding site" ("RBS"), as defined herein, is a segment of the 5' (upstream) part of an mRNA molecule that binds to the ribosome to position the message correctly for the initiation of translation. The RBS controls the accuracy and efficiency with which the translation of mRNA begins. In prokaryotes (such as *E. coli*) the RBS typically lies about 7 nucleotides upstream from the start codon (i.e., the first AUG). The sequence itself in general is called the "Shine-Dalgarno" sequence after its discoverers, regardless of the exact identity of the bases. Strong Shine-Dalgarno sequences are rich in purines (A's,G's), and the "Shine-Dalgarno consensus" sequence—derived statistically from lining up many well-characterized strong ribosome binding sites—has the sequence AGGAGG. The complementary sequence (CCUCCU) occurs at the 3'-end of the structural RNA ("16S") of the small ribosomal subunit and it base-pairs with the Shine-Dalgarno sequence in the mRNA to facilitate proper initiation of protein synthesis. In some embodiments of the aspects described herein, a ribosome binding site (RBS) is added to a biological circuit chemotactic converter to regulate expression of a recombinase or other protein encoded by the converter, For protein synthesis in eukaryotes and eukaryotic cells, the 5' end of the mRNA has a modified chemical structure ("cap") recognized by the ribosome, which then binds the mRNA and moves along it ("scans") until it finds the first AUG codon. A characteristic pattern of bases (called a "Kozak sequence") is sometimes found around that codon and assists in positioning the mRNA correctly in a manner reminiscent of the Shine-Dalgarno sequence, but does not involve base pairing with the ribosomal RNA.

RBSs can include only a portion of the Shine-Dalgarno sequence. When looking at the spacing between the RBS and the start codon, the aligned spacing rather than just the absolute spacing is important. In essence, if only a portion of the Shine-Dalgarno sequence is included in the RBS, the spacing that matters is between wherever the center of the full Shine-Dalgarno sequence would be and the start codon rather than between the included portion of the Shine-Dalgarno sequence and the start codon.

While the Shine-Dalgarno portion of the RBS is critical to the strength of the RBS, the sequence upstream of the Shine-Dalgarno sequence is also important. One of the ribosomal proteins, S1, is known to bind to adenine bases upstream from the Shine-Dalgarno sequence. As a result, in some embodiments of the modules and biological circuit chemotactic converters described herein, an RBS can be made stronger by adding more adenines to the sequence upstream of the RBS. A promoter may add some bases onto the start of the mRNA that may affect the strength of the RBS by affecting S1 binding.

In addition, the degree of secondary structure can affect the translation initiation rate. This fact can be used to produce regulated translation initiation rates, as described in Isaacs F J et al., Nat Biotechnol 2004 July; 22 (7) 841-7.

In addition to affecting the translation rate per unit time, an RBS can affect the level of protein synthesis in a second way. That is because the stability of the mRNA affects the steady state level of mRNA, i.e., a stable mRNA will have a higher steady state level than an unstable mRNA that is being produced as an identical rate. Since the primary sequence and the secondary structure of an RBS (for example, the RBS could introduce an RNase site) can affect the stability of the mRNA, the RBS can affect the amount of mRNA and hence the amount of protein that is synthesized.

A "regulated RBS" is an RBS for which the binding affinity of the RBS and the ribosome can be controlled, thereby changing the RBS strength. One strategy for regulating the strength of prokaryotic RBSs is to control the accessibility of the RBS to the ribosome. By occluding the RBS in RNA secondary structure, translation initiation can be significantly reduced. By contrast, by reducing secondary structure and revealing the RBS, translation initiation rate can be increased. Isaacs and coworkers engineered mRNA sequences with an upstream sequence partially complementary to the RBS.

Base-pairing between the upstream sequence and the RBS 'locks' the RBS off. A 'key' RNA molecule that disrupts the mRNA secondary structure by preferentially base-pairing with the upstream sequence can be used to expose the RBS and increase translation initiation rate.

Accordingly, in some embodiments of the aspects described herein, a ribosome binding site (RBS) for use in the biological circuit chemotactic converters described herein comprises a sequence that is selected from the group consisting of SEQ ID NO: 26-SEQ ID NO: 33. In some embodiments of the aspects described herein, a ribosome binding site (RBS) comprises a sequence selected from the ribosome binding site sequences provided in SEQ ID NO: 858-SEQ ID NO: 898. In some embodiments of the aspects described herein, a ribosome binding site (RBS) comprises a sequence selected from the community ribosome binding site sequences provided in SEQ ID NO: 899-SEQ ID NO: 906. In some embodiments of the aspects described herein, a ribosome binding site (RBS) comprises a sequence selected from the miscellaneous prokaryotic ribosome binding site sequences provided in SEQ ID NO: 907-SEQ ID NO: 994. In some embodiments of the aspects described herein, a ribosome binding site (RBS) comprises a sequence selected from the regulated prokaryotic ribosome binding site sequences provided in SEQ ID NO: 995-SEQ ID NO: 996. In some embodiments of the aspects described herein, a ribosome binding site (RBS) comprises a sequence selected from the regulated yeast ribosome binding site sequences provided in SEQ ID NO: 997-SEQ ID NO: 998. In some embodiments of the aspects described herein, a ribosome binding site (RBS) comprises a sequence selected from the eukaryotic ribosome binding site sequences provided in SEQ ID NO: 999-SEQ ID NO: 1001. In some embodiments of the aspects described herein, novel ribosome binding sites can be generated using automated design of synthetic ribosome sites, as described in Salis H M et al., Nature Biotechnology 27, 946-950 (2009).

Terminators

Terminators are sequences that usually occur at the end of a gene or operon and cause transcription to stop, and are also provided for use in the modules and biological circuit chemotactic converters described herein to regulate transcription and prevent transcription from occurring in an unregulated fashion, i.e., a terminator sequence prevents activation of downstream modules by upstream promoters. A "terminator" or "termination signal", as described herein, is comprised of the DNA sequences involved in specific termination of an RNA transcript by an RNA polymerase. Thus, in certain embodiments a terminator that ends the production of an RNA transcript is contemplated. A terminator can be necessary in vivo to achieve desirable message levels.

In prokaryotes, terminators usually fall into two categories (1) rho-independent terminators and (2) rho-dependent terminators. Rho-independent terminators are generally composed of palindromic sequence that forms a stem loop rich in G-C base pairs followed by several T bases. Without wishing to be bound by a theory, the conventional model of transcriptional termination is that the stem loop causes RNA polymerase to pause, and transcription of the poly-A tail causes the RNA:DNA duplex to unwind and dissociate from RNA polymerase.

The most commonly used type of terminator is a forward terminator. When placed downstream of a nucleic acid sequence that is usually transcribed, a forward transcriptional terminator will cause transcription to abort. In some embodiments, bidirectional transcriptional terminators are provided. Such terminators will usually cause transcription to terminate on both the forward and reverse strand. Finally, in some embodiments, reverse transcriptional terminators are provided that terminate transcription on the reverse strand only.

In eukaryotic systems, the terminator region can also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in those embodiments involving eukaryotes, it is preferred that a terminator comprises a signal for the cleavage of the RNA, and it is more preferred that the terminator signal promotes polyadenylation of the message. The terminator and/or polyadenylation site elements can serve to enhance message levels and/or to minimize read through between modules of the biological converter switches. As disclosed herein, terminators contemplated for use in the modules, biological circuit chemotactic converters, and methods of use thereof can include any known terminator of transcription described herein or known to one of ordinary skill in the art. Such terminators include, but are not limited to, the termination sequences of genes, such as for example, the bovine growth hormone terminator, or viral termination sequences, such as for example, the SV40 terminator. In certain embodiments, the termination signal encompasses a lack of transcribable or translatable sequence, such as due to a sequence truncation. The terminator used can be unidirectional or bidirectional.

Terminators for use in the modules and biological circuit chemotactic converters described herein can be selected from the non-limiting examples of Tables 1-5.

TABLE 1

Examples of Forward Terminators

| Name | Description | Direction | Efficiency Fwd. | Efficiency Rev. | Length |
|---|---|---|---|---|---|
| BBa_B0010 | T1 from *E. coli* rrnB | Forward | | | 80 |
| BBa_B0012 | TE from coliphage T7 | Forward | 0.309[CC] | −0.368[CC] | 41 |
| BBa_B0013 | TE from coliphage T7 (+/−) | Forward | 0.6[CC] | −1.06[CC] | 47 |
| BBa_B0015 | double terminator (B0010-B0012) | Forward | 0.984[CC] 0.97[JK] | 0.295[CC] 0.62[JK] | 129 |
| BBa_B0017 | double terminator (B0010-B0010) | Forward | | | 168 |
| BBa_B0053 | Terminator (His) | Forward | | | 72 |
| BBa_B0055 | --No description-- | | | | 78 |
| BBa_B1002 | Terminator (artificial, small, % T~ = 85%) | Forward | 0.98[CH] | | 34 |
| BBa_B1003 | Terminator (artificial, small, % T~ = 80) | Forward | 0.83[CH] | | 34 |
| BBa_B1004 | Terminator (artificial, small, % T~ = 55) | Forward | 0.93[CH] | | 34 |
| BBa_B1005 | Terminator (artificial, small, % T~ = 25% | Forward | 0.86[CH] | | 34 |

TABLE 1-continued

Examples of Forward Terminators

| Name | Description | Direction | Efficiency Fwd. | Efficiency Rev. | Length |
|---|---|---|---|---|---|
| BBa_B1006 | Terminator (artificial, large, % T~ > 90) | Forward | 0.99[CH] | | 39 |
| BBa_B1010 | Terminator (artificial, large, % T~ < 10) | Forward | 0.95[CH] | | 40 |
| BBa_I11013 | Modification of biobricks part BBa_B0015 | | | | 129 |
| BBa_I51003 | --No description-- | | | | 110 |
| BBa_J61048 | [rnpB-T1] Terminator | Forward | 0.98[JCA] | | 113 |

TABLE 2

Examples of Bidirectional Terminators

| Name | Description | Direction | Efficiency Fwd. | Efficiency Rev. | Length |
|---|---|---|---|---|---|
| BBa_B0011 | LuxICDABEG (+/−) | Bidirectional | 0.419[CC]/0.95[JK] | 0.636[CC]/0.86[JK] | 46 |
| BBa_B0014 | double terminator (B0012-B0011) | Bidirectional | 0.604[CC]/0.96[JK] | 0.86[JK] | 95 |
| BBa_B0021 | LuxICDABEG (+/−), reversed | Bidirectional | 0.636[CC]/0.86[JK] | 0.419[CC]/0.95[JK] | 46 |
| BBa_B0024 | double terminator (B0012-B0011), reversed | Bidirectional | 0.86[JK] | 0.604[CC]/0.96[JK] | 95 |
| BBa_B0050 | Terminator (pBR322, +/−) | Bidirectional | | | 33 |
| BBa_B0051 | Terminator (yciA/tonA, +/−) | Bidirectional | | | 35 |
| BBa_B1001 | Terminator (artificial, small, % T~ = 90) | Bidirectional | 0.81[CH] | | 34 |
| BBa_B1007 | Terminator (artificial, large, % T~ = 80) | Bidirectional | 0.83[CH] | | 40 |
| BBa_B1008 | Terminator (artificial, large, % T~ = 70) | Bidirectional | | | 40 |
| BBa_B1009 | Terminator (artificial, large, % T~ = 40%) | Bidirectional | | | 40 |
| BBa_K259006 | GFP-Terminator | Bidirectional | 0.604[CC]/0.96[JK] | 0.86[JK] | 823 |

TABLE 3

Examples of Reverse Terminators

| Name | Description | Direction | Efficiency Fwd. | Efficiency Rev. | Length |
|---|---|---|---|---|---|
| BBa_B0020 | Terminator (Reverse B0010) | Reverse | | | 82 |
| BBa_B0022 | TE from coliphage T7, reversed | Reverse | −0.368[CC] | 0.309[CC] | 41 |
| BBa_B0023 | TE from coliphage T7, reversed | Reverse | −1.06[CC] | 0.6[CC] | 47 |
| BBa_B0025 | double terminator (B0015), reversed | Reverse | 0.295[CC]/0.62[JK] | 0.984[CC]/0.97[JK] | 129 |
| BBa_B0052 | Terminator (rrnC) | Forward | | | 41 |
| BBa_B0060 | Terminator (Reverse B0050) | Bidirectional | | | 33 |
| BBa_B0061 | Terminator (Reverse B0051) | Bidirectional | | | 35 |
| BBa_B0063 | Terminator (Reverse B0053) | Reverse | | | 72 |

TABLE 4

Examples of Yeast Terminators

| Name | Description | Direction | Efficiency Fwd. | Efficiency Rev. | Length |
|---|---|---|---|---|---|
| BBa_J63002 | ADH1 terminator from S. cerevisiae | Forward | | | 225 |
| BBa_K110012 | STE2 terminator | Forward | | | 123 |
| BBa_Y1015 | CycE1 | | | | 252 |

TABLE 5

Examples of Eukaryotic Terminators

| Name | Description | Direction | Efficiency Fwd. | Efficiency Rev. | Chassis | Length |
|---|---|---|---|---|---|---|
| BBa_J52016 | eukaryotic -- derived from SV40 early poly A signal sequence | Forward | | | | 238 |
| BBa_J63002 | ADH1 terminator from S. cerevisiae | Forward | | | | 225 |

TABLE 5-continued

Examples of Eukaryotic Terminators

| Name | Description | Direction | Efficiency Fwd. | Rev. | Chassis | Length |
|---|---|---|---|---|---|---|
| BBa_K110012 | STE2 terminator | Forward | | | | 123 |
| BBa_Y1015 | CycE1 | | | | | 252 |

Degradation Tags

In some embodiments of the aspects described herein, a nucleic sequence encoding a protein degradation tag can be added to the modules and biological circuit chemotactic converters described herein to enhance protein degradation of a protein, such as a recombinase or protein output product. As defined herein, a "degradation tag" is a genetic addition to the end of a nucleic acid sequence that modifies the protein that is expressed from that sequence, such that the protein undergoes faster degradation by cellular degradation mechanisms. Thus, such protein degradation tags 'mark' a protein for degradation, thus decreasing a protein's half-life.

One of the useful aspects of degradation tags is the ability to detect and regulate gene activity in a time-sensitive manner. Such protein degradation tags can operate through the use of protein-degrading enzymes, such as proteases, within the cell. In some embodiments, the tags encode for a sequence of about eleven amino acids at the C-terminus of a protein, wherein said sequence is normally generated in *E. coli* when a ribosome gets stuck on a broken ("truncated") mRNA. Without a normal termination codon, the ribosome can't detach from the defective mRNA. A special type of RNA known as ssrA ("small stable RNA A") or tmRNA ("transfer-messenger RNA") rescues the ribosome by adding the degradation tag followed by a stop codon. This allows the ribosome to break free and continue functioning. The tagged, incomplete protein can get degraded by the proteases ClpXP or ClpAP. Although the initial discovery of the number of amino acids encoding for an ssRA/tmRNA tag was eleven, the efficacy of mutating the last three amino acids of that system has been tested. Thus, the tags AAV, ASV, LVA, and LAA are classified by only three amino acids.

In some embodiments of the aspects described herein, the protein degradation tag is an ssrA tag. In some embodiments of the aspects described herein, the ssrA tag comprises a sequence that is selected from the group consisting of sequences that encode for the peptides

```
                                       (SEQ ID NO: 34)
RPAANDENYALAA, (SEQ ID NO: 35)
RPAANDENYALVA, (SEQ ID NO: 36)
RPAANDENYAAAV,
and (SEQ ID NO: 37)
RPAANDENYAASV.
```

In some embodiments of the aspects described herein, the protein degradation tag is an LAA variant comprising the sequence

```
                                       (SEQ ID NO: 38)
GCAGCAAACGACGAAAACTACGCTTTAGCAGCTTAA.
```

In one embodiment, the protein degradation tag is an AAV variant comprising the sequence

```
                                       (SEQ ID NO: 39)
GCAGCAAACGACGAAAACTACGCTGCAGCAGTTTAA.
```

In some embodiments, the protein degradation tag is an ASV variant comprising the sequence

```
                                       (SEQ ID NO: 40)
GCAGCAAACGACGAAAACTACGCTGCATCAGTTTAA.
```

Output Product Sequences and Output Products

Also provided herein are a variety of biological outputs for use in the various modules and biological circuit chemotactic converters described herein. These biological outputs, or "output products," as defined herein, refer to products that can are used as markers of specific states of the modules and biological circuit chemotactic converters described herein. An output sequence can encode for a protein or an RNA molecule that is used to track or mark the state of the cell upon receiving a particular input for a biological circuit chemotactic converters. Such output products can be used to distinguish between various states of a cell. For example, upon an biological circuit chemotactic converter in a cell or cellular system receiving a specific input signal, the output gene product of the biological circuit chemotactic converter can be a sensor receptor. In some embodiments, the input signal causes the biological circuit chemotactic converter to switch from expression of one sensor to another sensor, in response to changes in chemicals in the external environment.

Reporter Outputs

In some embodiments of the aspects described herein, the output products are "reporters.". As defined herein, "reporters" refer to proteins that can be used to measure gene expression. Reporters generally produce a measurable signal such as fluorescence, color, or luminescence. Reporter protein coding sequences encode proteins whose presence in the cell or organism is readily observed. For example, fluorescent proteins cause a cell to fluoresce when excited with light of a particular wavelength, luciferases cause a cell to catalyze a reaction that produces light, and enzymes such as β-galactosidase convert a substrate to a colored product. In some embodiments, reporters are used to quantify the strength or activity of the signal received by the modules or biological converter switches of the invention. In some embodiments, reporters can be fused in-frame to other protein coding sequences to identify where a protein is located in a cell or organism.

There are several different ways to measure or quantify a reporter depending on the particular reporter and what kind of characterization data is desired. In some embodiments, microscopy can be a useful technique for obtaining both spatial and temporal information on reporter activity, particularly at the single cell level. In other embodiments, flow cytometers can be used for measuring the distribution in reporter activity across a large population of cells. In some embodiments, plate readers may be used for taking population average measurements of many different samples over time. In other embodiments, instruments that combine such various functions, can be used, such as multiplex plate readers designed for flow cytometers, and combination microscopy and flow cytometric instruments.

Fluorescent proteins are convenient ways to visualize or quantify the output of a module or a biological circuit chemotactic converter described herein. Fluorescence can be readily quantified using a microscope, plate reader or flow cytometer equipped to excite the fluorescent protein with the appropriate wavelength of light. Since several different fluorescent proteins are available, multiple gene expression measurements can be made in parallel. Non-limiting examples of fluorescent proteins are provided in Table 6.

Luminescence can be readily quantified using a plate reader or luminescence counter. Luciferases can be used as output products for various embodiments described herein, for example, measuring low levels of gene expression, because cells tend to have little to no background luminescence in the absence of a luciferase. Non-limiting examples of luciferases are provided in Table 7.

TABLE 7

Examples of Luciferases

| Name | Description | Length |
|---|---|---|
| BBa_J52011 | dnMyD88-linker-Rluc | 1371 |
| BBa_J52013 | dnMyD88-linker-Rluc-linker-PEST191 | 1872 |
| BBa_I712019 | Firefly luciferase—luciferase from *Photinus pyralis* | 1653 |

In other embodiments, enzymes that produce colored substrates can be quantified using spectrophotometers or other instruments that can take absorbance measurements including plate readers. Like luciferases, enzymes like β-galactosidase can be used for measuring low levels of gene expression because they tend to amplify low signals. Non-limiting examples of such enzymes are provided in Table 8.

TABLE 6

Examples of Fluorescent Protein Reporters

| Name | Protein | Description | Tag | Emission | Excitation | Length |
|---|---|---|---|---|---|---|
| BBa_E0030 | EYFP | enhanced yellow fluorescent protein derived from *A. victoria* GFP | None | 527 | 514 | 723 |
| BBa_E0020 | ECFP | engineered cyan fluorescent protein derived from *A. victoria* GFP | None | 476 | 439 | 723 |
| BBa_E1010 | mRFP1 | highly engineered mutant of red fluorescent protein from Discosoma striata (coral) | None | 607 | 584 | 681 |
| BBa_E2050 | mOrange | derivative of mRFP1, yeast-optimized | None | 562 | 548 | 744 |
| BBa_E0040 | GFPmut3b | green fluorescent protein derived from jellyfish Aequeora victoria wild-type GFP (SwissProt: P42212) | None | 511 | 501 | 720 |
| BBa_J52021 | | dnTraf6-linker-GFP | | | | 1446 |
| BBa_J52026 | | dnMyD88-linker-GFP | | | | 1155 |
| BBa_I715022 | | Amino Portion of RFP | | | | 462 |
| BBa_I715023 | | Carboxyl portion of RFP | | | | 220 |
| BBa_I712028 | | CherryNLS - synthetic construct monomeric red fluorescent protein with nuclear localization sequence | | | | 733 |
| BBa_K125500 | | GFP fusion brick | | | | 718 |
| BBa_K106000 | | GFP, AarI BD part | | | | 714 |
| BBa_K106004 | | mCherry, AarI AB part | | | | 708 |
| BBa_K106005 | | mCherry, AarI BD part | | | | 708 |
| BBa_K106028 | | GFP, AarI AB part | | | | 714 |
| BBa_K165005 | | Venus YFP, yeast optimized for fusion | | | | 744 |
| BBa_K157005 | | Split-Cerulean-cCFP | | | | 261 |
| BBa_K157006 | | Split-Cerulean-nCFP | | | | 483 |
| BBa_K157007 | | Split-Venus-cYFP | | | | 261 |
| BBa_K157008 | | Split-Venus-nYFP | | | | 486 |
| BBa_K125810 | | slr2016 signal sequence + GFP fusion for secretion of GFP | | | | 779 |
| BBa_K082003 | GFP | GFP(+LVA) | | | | 756 |
| BBa_K156009 | | OFP (orange fluorescent protein) | | | | 864 |
| BBa_K156010 | | SBFP2 (strongly enhanced blue fluorescent protein) | | | | 720 |
| BBa_K106671 | | GFP, AarI AD part | | | | 714 |
| BBa_K294055 | GFPmut3b | GFP RFP Hybrid | None | 511 | 501 | 720 |
| BBa_K192001 | | CFP + tgt + lva | | | | 858 |
| BBa_K180001 | GFPmut3b | Green fluorescent protein (+LVA) | LVA | | | 754 |
| BBa_K283005 | | lpp_ompA_eGFP_streptavidin | | | | 1533 |
| BBa_K180008 | mCherry | mCherry (rights owned by Clontech) | | | | 708 |
| BBa_K180009 | mBanana | mBanana (rights owned by Clontech) | | | | 708 |

TABLE 8

Examples of Enzymes that Produce Colored Substrates

| Name | Description | Length |
| --- | --- | --- |
| BBa_I732006 | lacZ alpha fragment | 234 |
| BBa_I732005 | lacZ (encoding beta-galactosidase, full-length) | 3075 |
| BBa_K147002 | xylE | 924 |

Another reporter output product for use in the different aspects described herein includes fluoresceine-A-binding (BBa_K157004).

Transcriptional Outputs:

In some embodiments of the aspects described herein, the output product of a given module or biological circuit chemotactic converter is itself a transcriptional activator or repressor, the production of which by an output product sequence can result in a further change in state of the cell, and provide additional input signals to subsequent or additional modules or biological circuit chemotactic converters. Transcriptional regulators either activate or repress transcription from cognate promoters. Transcriptional activators typically bind nearby to transcriptional promoters and recruit RNA polymerase to directly initiate transcription. Repressors bind to transcriptional promoters and sterically hinder transcriptional initiation by RNA polymerase. Other transcriptional regulators serve as either an activator or a repressor depending on where it binds and cellular conditions. Non-limiting examples of transcriptional regulators as output products are provided in Table 9.

TABLE 9

Examples of Transcriptional Regulators

| Name | Protein | Description | Tag | Direction | Uniprot | Length |
| --- | --- | --- | --- | --- | --- | --- |
| BBa_C0079 | lasR-LVA | lasR activator from *P. aeruginosa* PAO1 (+LVA) | LVA | Forward | P25084 | 756 |
| BBa_C0077 | cinR | cinR activator from *Rhizobium leguminosarum* (+LVA) | LVA | Forward | ~Q84HT2 | 762 |
| BBa_C0179 | lasR | lasR activator from *P. aeruginosa* PAO1 (no LVA) | None | Forward | P25084 | 723 |
| BBa_J07009 | ToxR | toxicity-gene activator from *Vibrio cholerae* | None | Forward | P15795 | 630 |
| BBa_K118001 | | appY coding sequence encoding a DNA-binding transcriptional activator | | | | 753 |
| BBa_K137113 | | rcsA | | | | 624 |
| BBa_K131022 | | LuxO D47E, *Vibrio harveyi* | | | | 1362 |
| BBa_K131023 | | LuxO D47A, *Vibrio harveyi* | | | | 1362 |
| BBa_K082006 | | LuxR-G2F | | | | 753 |
| BBa_K294205 | | This is a coding sequence of heat shock protein from *E. coli* | | | | 402 |
| BBa_S04301 | lasR-LVA | C0079:B0015 | LVA | Forward | P25084 | 918 |
| BBa_K266002 | lasR-LVA | LasR + Term | LVA | Forward | P25084 | 918 |
| BBa_C0012 | LacI | lacI repressor from *E. coli* (+LVA) | LVA | Forward | P03023 | 1128 |
| BBa_C0040 | TetR | tetracycline repressor from transposon Tn10 (+LVA) | LVA | Forward | P04483 | 660 |
| BBa_C0050 | CI HK022 | cI repressor from phage HK022 (+LVA?) | LVA | Forward | P18680 | 744 |
| BBa_C0051 | CI lambda | cI repressor from *E. coli* phage lambda (+LVA) | LVA | Forward | P03034 | 750 |
| BBa_C0052 | CI 434-LVA | cI repressor from phage 434 (+LVA) | LVA | Forward | P16117 | 669 |
| BBa_C0053 | C2 P22 | c2 repressor from *Salmonella* phage P22 (+LVA) | LVA | Forward | P69202 | 687 |
| BBa_C0073 | mnt-weak | mnt repressor (weak) from *Salmonella* phage P22 (+LVA) | LVA | Forward | P03049 | 288 |
| BBa_C0075 | cI TP901 | TP901 cI repressor from phage TP901-1 (+LVA) | LVA | Forward | none | 579 |
| BBa_C0074 | penI | penI repressor from *Bacillus licheniformis* (+LVA) | LVA | Forward | P06555 | 423 |
| BBa_C0072 | mnt | mnt repressor (strong) from *Salmonella* phage P22 (+LVA) | LVA | Forward | P03049 | 288 |
| BBa_C2001 | Zif23-GCN4 | Zif23-GCN4 engineered repressor (+LVA, C2000 codon-optimized for *E. coli*) | LVA | Forward | P03069 | 300 |
| BBa_C0056 | CI 434 | cI repressor from phage 434 (no LVA) | None | Forward | P16117 | 636 |
| BBa_J06501 | LacI-mut2 | LacI repressor (temperature-sensitive mut 265) (+LVA) | LVA | Forward | ~P03023 | 1153 |
| BBa_J06500 | LacI-mut1 | LacI repressor (temperature-sensitive mut 241) (+LVA) | LVA | Forward | ~P03023 | 1153 |
| BBa_C2006 | | MalE.FactorXa.Zif268-GCN4 | | | | 1428 |
| BBa_I715032 | | lacIq reverse | | | | 1128 |
| BBa_I732100 | | LacI | | | | 1086 |
| BBa_I732101 | | LRLa | | | | 1086 |
| BBa_I732105 | | ARL2A0101 | | | | 1086 |
| BBa_I732106 | | ARL2A0102 | | | | 1086 |
| BBa_I732107 | | ARL2A0103 | | | | 1086 |
| BBa_I732110 | | ARL2A0203 | | | | 1086 |
| BBa_I732112 | | ARL2A0301 | | | | 1086 |

TABLE 9-continued

Examples of Transcriptional Regulators

| Name | Protein | Description | Tag | Direction | Uniprot | Length |
|---|---|---|---|---|---|---|
| BBa_I732115 | | ARL4A0604 | | | | 1086 |
| BBa_K091001 | | LsrR gene | | Forward | | 954 |
| BBa_K091121 | | LacI wild-type gene | | | | 1083 |
| BBa_K091122 | | LacI_I12 protein | | | | 1083 |
| BBa_K143033 | | LacI (Lva−, N-terminal deletion) regulatory protein | | | | 1086 |
| BBa_K142000 | | lacI IS mutant (IPTG unresponsive) R197A | | | | 1128 |
| BBa_K142001 | | lacI IS mutant (IPTG unresponsive) R197F | | | | 1128 |
| BBa_K142002 | | lacI IS mutant (IPTG unresponsive) T276A | | | | 1128 |
| BBa_K142003 | | lacI IS mutant (IPTG unresponsive) T276F | | | | 1128 |
| BBa_K106666 | | Lac Repressor, AarI AB part | | | | 1104 |
| BBa_K106667 | | Lac Repressor, AarI BD part | | | | 1107 |
| BBa_K142004 | | lacI IS mutant (IPTG unresponsive) R197A T276A | | | | 1128 |
| BBa_K106668 | | Tet Repressor, AarI AB part | | | | 618 |
| BBa_K106669 | | Tet Repressor, AarI BD part | | | | 621 |
| BBa_K142005 | | lacI IS mutant (IPTG unresponsive) R197A T276F | | | | 1128 |
| BBa_K142006 | | lacI IS mutant (IPTG unresponsive) R197F T276A | | | | 1128 |
| BBa_K142007 | | lacI IS mutant (IPTG unresponsive) R197F T276F | | | | 1128 |
| BBa_K082004 | LacI | LacI-wild type | | | | 1083 |
| BBa_K082005 | LacI | LacI-Mutant | | | | 1083 |
| BBa_C0062 | LuxR | luxR repressor/activator, (no LVA?) | None | Forward | P12746 | 756 |
| BBa_C0071 | rhlR-LVA | rhlR repressor/activator from P. aeruginosa PA3477 (+LVA) | LVA | Forward | P54292 | 762 |
| BBa_C0080 | araC | araC arabinose operon regulatory protein (repressor/activator) from E. coli (+LVA) | LVA | Forward | P0A9E0 | 915 |
| BBa_C0171 | rhIR | rhlR repressor/activator from P. aeruginosa PA3477 (no LVA) | None | Forward | P54292 | 729 |
| BBa_K108021 | | Fis | | | | 297 |

Selection Markers

In other embodiments of the various aspects described herein, genes encoding selection markers are used as output product sequences. "Selection markers," as defined herein, refer to protein coding sequences that confer a selective advantage or disadvantage to a biological unit, such as a cell. For example, a common type of prokaryotic selection marker is one that confers resistance to a particular antibiotic. Thus, cells that carry the selection marker can grow in media despite the presence of antibiotic. For example, most plasmids contain antibiotic selection markers so that it is ensured that the plasmid is maintained during cell replication and division, as cells that lose a copy of the plasmid will soon either die or fail to grow in media supplemented with antibiotic. A second common type of selection marker, often termed a positive selection marker, are those that are toxic to the cell. Positive selection markers are frequently used during cloning to select against cells transformed with the cloning vector and ensure that only cells transformed with a plasmid containing the insert. Non-limiting examples of selection marker output products are provided in Table 10.

| Name | Protein | Description | UniProt | KEGG | Length |
|---|---|---|---|---|---|
| BBa_T9150 | PyrF | orotidine 5 | P08244 | eco:b1281; | 741 |
| BBa_J31002 | AadA-bkw | kanamycin resistance backwards (KanB) [cf. BBa_J23012 & BBa_J31003] | P0AG05 | none | 816 |
| BBa_J31003 | AadA2 | kanamycin resistance forward (KanF) [cf. BBa_J23012 & BBa_J31002] | P0AG05 | none | 816 |
| BBa_J31004 | CAT-bkw | chloramphenicol acetyltransferase (backwards, CmB) [cf. BBa_131005] | P62577 | none | 660 |
| BBa_J31006 | TetA(C)-bkw | tetracycline resistance protein TetA(C) (backwards) [cf. BBa_J31007] | P02981 | | 1191 |
| BBa_J31005 | CAT | chloramphenicol acetyltransferase (forwards, CmF) [cf. BBa_J31004] | P62577 | none | 660 |
| BBa_J31007 | TetA(C) | tetracycline resistance protein TetA(C) (forward), [cf. BBa_J31006] | P02981 | | 1191 |
| BBa_K145151 | | ccdB coding region | | | 306 |
| BBa_K143031 | | Aad9 Spectinomycin Resistance Gene | | | 771 |
| BBa_K156011 | | aadA (streptomycin 3'-adenyltransferase) | | | 789 |

Enzyme Outputs

An output product sequence can encode an enzyme for use in different embodiments the modules and biological circuit chemotactic converters described herein. In some embodiments, an enzyme output can be used as a response to a particular input. For example, in response to a particular input received by a biological circuit chemotactic converter of the invention, such as a certain range of toxin concentration present in the environment, a module of the biological circuit chemotactic converter can "turn on" a modular component that encodes as an output gene product an enzyme that can degrade or otherwise destroy the toxin.

In some embodiments of the aspects described herein, output product sequences encode "biosynthetic enzymes" that catalyze the conversion of substrates to products. For example, such biosynthetic enzymes can be combined together along with or within the modules and biological circuit chemotactic converters described herein to construct pathways that produce or degrade useful chemicals and materials, in response to specific signals. These combinations of enzymes can reconstitute either natural or synthetic biosynthetic pathways. These enzymes have applications in specialty chemicals, biofuels, and bioremediation.

For example, N-Acyl Homoserine lactones (AHLs or N-AHLs) are a class of signaling molecules involved in bacterial quorum sensing. "Quorum sensing" refers to a method of communication between bacteria that enables the coordination of group based behavior based on population density. In synthetic biology, genetic parts derived from quorum sensing systems have been used to create patterns on a lawn of bacteria and to achieve synchronized cell behavior. AHL can diffuse across cell membranes and is stable in growth media over a range of pH values. AHL can bind to transcriptional activators such as LuxR and stimulate transcription from cognate promoters. Several similar quorum sensing systems exists across different bacterial species; thus, there are several known enzymes that synthesize or degrade different AHL molecules that can be used for the modules and biological circuit chemotactic converters described herein.

TABLE 11

Examples of AHLs

| Name | Protein | Description | Direction | Uniprot | KEGG | E.C. | Length |
|---|---|---|---|---|---|---|---|
| BBa_C0061 | luxI-LVA | autoinducer synthetase for AHL | Forward | P12747 | none | none | 618 |
| BBa_C0060 | aiiA-LVA | autoinducer inactivation enzyme from *Bacillus*; hydrolyzes acetyl homoserine lactone | Forward | Q1WNZ5 | none | 3.1.1.— | 789 |
| BBa_C0070 | rhlI-LVA | autoinducer synthetase for N-butyryl-HSL (BHL) and HHL | Forward | Q02QW5 | none | none | 642 |
| BBa_C0076 | cinI | autoinducer synthetase | Forward | Q1MDW1 | none | none | 702 |
| BBa_C0078 | lasI | autoinducer synthetase for PAI from *Pseudomonas aeruginosa* | Forward | P33883 | pae: PA1432 | none | 642 |
| BBa_C0161 | luxI | autoinducer synthetase for AHL (no LVA) | Forward | P12747 | none | none | 585 |
| BBa_C0170 | rhlI | autoinducer synthetase for N-butyryl-HSL (BHL) and HHL (no LVA) | Forward | Q02QW5 | none | none | 609 |
| BBa_C0178 | lasI | autoinducer synthetase for PAI from *Pseudomonas aeruginosa* (no LVA) | Forward | P33883 | pae: PA1432 | none | 609 |
| BBa_K091109 | | LuxS | | | | | 516 |
| BBa_C0060 | aiiA-LVA | autoinducer inactivation enzyme from *Bacillus*; hydrolyzes acetyl homoserine lactone | Forward | Q1WNZ5 | none | 3.1.1.— | 789 |
| BBa_C0160 | aiiA | autoinducer inactivation enzyme aiiA (no LVA) | Forward | Q1WNZ5 | none | 3.1.1.— | 756 |

"Isoprenoids," also known as "terpenoids," refer to a large and highly diverse class of natural organic chemicals with many functions in plant primary and secondary metabolism. Most are multicyclic structures that differ from one another not only in functional groups but also in their basic carbon skeletons. Isoprenoids are synthesized from common prenyl diphosphate precursors through the action of terpene synthases and terpene-modifying enzymes such as cytochrome P450 monooxygenases. Plant terpenoids are used extensively for their aromatic qualities. They play a role in traditional herbal remedies and are under investigation for antibacterial, antineoplastic, and other pharmaceutical functions. Much effort has been directed toward their production in microbial hosts.

There are two primary pathways for making isoprenoids: the mevalonate pathway and the non-mevalonate pathway. Exemplary isoprenoids for use as output products in the modules and biological circuit chemotactic converters described herein are provided in Table 12.

TABLE 12

Examples of Isoprenoids

| Name | Description | Length |
|---|---|---|
| BBa_K118000 | dxs coding sequence encoding 1-deoxyxylulose-5-phosphate synthase | 1866 |
| BBa_K115050 | A-coA -> AA-coA | 1188 |
| BBa_K115056 | IPP -> OPP or DMAPP -> OPP | 552 |
| BBa_K115057 | OPP -> FPP | 903 |

TABLE 12-continued

Examples of Isoprenoids

| Name | Description | Length |
|---|---|---|
| BBa_K118002 | crtB coding sequence encoding phytoene synthase | 933 |
| BBa_K118003 | crtI coding sequence encoding phytoene dehydrogenase | 1482 |
| BBa_K118008 | crtY coding sequence encoding lycopene B-cyclase | 1152 |

Odorants are volatile compounds that have an aroma detectable by the olfactory system. Odorant enzymes convert a substrate to an odorant product. Exemplary odorant enzymes for use as output products in the modules and biological circuit chemotactic converters described herein are provided in Table 13.

TABLE 13

Examples of Odorant Enzymes

| Name | Protein | Description | Uniprot | KEGG | E.C. | Length |
|---|---|---|---|---|---|---|
| BBa_J45001 | SAMT | SAM: salicylic acid carboxyl methyltransferase; converts salicylic acid to methyl salicylate (winter | Q8H6N2 | none | none | 1155 |
| BBa_J45002 | BAMT | SAM: benzoic acid carboxyl methyltransferase; converts benzoic acid to methyl benzoate (floral odor) | Q9FYZ9 | none | 2.1.1.— | 1098 |
| BBa_J45004 | BSMT1 | SAM: benzoic acid/salicylic acid carboxyl methyltransferase I; converts salicylic acid to methyl sali | Q84UB5 | none | none | 1074 |
| BBa_J45008 | BAT2 | branched-chain amino acid transaminase (BAT2); converts leucine to alpha-ketoisocaproate | P47176 | scc: YJR148W | 2.6.1.42 | 1134 |
| BBa_J45014 | ATF1-1148 mutant | alcohol acetyltransferase I; converts isoamyl alcohol to isoamyl acetate (banana odor) | P40353 | scc: YOR377W | 2.3.1.84 | 1581 |
| BBa_J45017 | PchA & PchB | isochorismate pyruvate-lyase and isochorismate synthase (pchBA); converts chorismate to salicylate | | | | 1736 |
| BBa_I742107 | | COMT | | | | 1101 |

The following are exemplary enzymes involved in the biosynthesis of plastic, specifically polyhydroxybutyrate, for use as output products in the modules and biological circuit chemotactic converters described herein.

TABLE 14

Examples of Plastic Biosynthesis Enzymes

| Name | Description | Length |
|---|---|---|
| BBa_K125504 | phaE BioPlastic polyhydroxybutyrate synthesis pathway (origin PCC6803 slr1829) | 996 |
| BBa_K125501 | phaA BioPlastic polyhydroxybutyrate synthesis pathway (origin PCC6803 slr1994) | 1233 |
| BBa_K125502 | phaB BioPlastic polyhydroxybutyrate synthesis pathway (origin PCC6803 slr1993) | 726 |
| BBa_K125503 | phaC BioPlastic polyhydroxybutyrate synthesis pathway (origin PCC6803 slr1830) | 1140 |
| BBa_K156012 | phaA (acetyl-CoA acetyltransferase) | 1182 |

TABLE 14-continued

Examples of Plastic Biosynthesis Enzymes

| Name | Description | Length |
|---|---|---|
| BBa_K156013 | phaB1 (acetyacetyl-CoA reductase) | 741 |
| BBa_K156014 | phaC1 (Poly(3-hydroxybutyrate) polymerase) | |

The following are exemplary enzymes involved in the biosynthesis of butanol and butanol metabolism for use as output products in the modules and biological circuit chemotactic converters described herein.

TABLE 15

Examples of Butanol Biosynthesis Enzymes

| Name | Description | Length |
|---|---|---|
| BBa_I725011 | B-hydroxy butyryl coA dehydrogenase | 870 |
| BBa_I72512 | Enoyl-coa hydratase | 801 |

TABLE 15-continued

Examples of Butanol Biosynthesis Enzymes

| Name | Description | Length |
|---|---|---|
| BBa_I725013 | Butyryl CoA dehyrogenase | 1155 |
| BBa_I725014 | Butyraldehyde dehydrogenase | 2598 |
| BBa_I725015 | Butanol dehydrogenase | 1188 |

Bisphenol A is a toxin that has been shown to leech from certain types of plastic. Recent studies have shown this chemical to have detrimental effects in animal studies and that it can be harmful to humans as well. Exemplary bisphenol A degradation enzymes from *Sphingomonas bisphenolicum* include BisdB and BisdA and can be used, for example, as an output product in the modules and biological circuit chemotactic converters described herein, for the remediation of bisphenol A contamination.

Other exemplary miscellaneous enzymes for use as output products in the modules and biological circuit chemotactic converters described herein are provided in Table 16.

TABLE 16

Examples of Miscellaneous Biosynthetic Enzymes

| Name | Description | Direction | Uniprot | KEGG | E.C. | Length |
|---|---|---|---|---|---|---|
| BBa_K118022 | cex coding sequence encoding Cellulomonas fimi exoglucanase | | | | | 1461 |
| BBa_K118023 | cenA coding sequence encoding Cellulomonas fimi endoglucanase A | | | | | 1353 |
| BBa_K118028 | beta-glucosidase gene bglX (chu_2268) from *Cytophaga hutchinsonii* | | | | | 2280 |
| BBa_C0083 | aspartate ammonia-lyase | Forward | P0AC38 | eco: b4139 | 4.3.1.1 | 1518 |
| BBa_I15008 | heme oxygenase (ho1) from Synechocystis | Forward | P72849 | syn: sll1184 | 1.14.99.3 | 726 |
| BBa_I15009 | phycocyanobilin:ferredoxin oxidoreductase (PcyA) from synechocystis | Forward | Q55891 | syn: slr0116 | 1.3.7.5 | 750 |
| BBa_T9150 | orotidine 5 | Forward | P08244 | eco: b1281; | 4.1.1.23 | 741 |
| BBa_I716153 | hemB | | | | | 975 |
| BBa_I716154 | hemC | | | | | 942 |
| BBa_I716155 | hemD | | | | | 741 |
| BBa_I716152 | hemA (from CFT703) | | | | | 1257 |
| BBa_I742141 | sam5 (coumarate hydroxylase) coding sequence | | | | | 1542 |
| BBa_I742142 | sam8 (tyrosine-ammonia lyase) coding sequence | | | | | 1536 |
| BBa_I723024 | PhzM | | | | | 1019 |
| BBa_I723025 | PhzS | | | | | 1210 |
| BBa_K137005 | pabA (from pABA synthesis) | | | | | 585 |
| BBa_K137006 | pabB (from pABA synthesis) | | | | | 1890 |
| BBa_K137009 | folB (dihydroneopterin aldolase) | | | | | 354 |
| BBa_K137011 | folKE (GTP Cyclohydrolase I + pyrophosphokinase) | | | | | 1053 |
| BBa_K137017 | Galactose Oxidase | | | | | 1926 |
| BBa_K118015 | glgC coding sequence encoding ADP-glucose pyrophosphorylase | | | | | 1299 |
| BBa_K118016 | glgC16 (glgC with G336D substitution) | | | | | 1299 |
| BBa_K123001 | BisdB | | | | | 1284 |
| BBa_K108018 | PhbAB | | | | | 1997 |
| BBa_K108026 | XylA | | | | | 1053 |
| BBa_K108027 | XylM | | | | | 1110 |
| BBa_K108028 | XylB | | | | | 1101 |
| BBa_K108029 | XylS | | | | | 966 |
| BBa_K147003 | ohbA | | | | | 531 |
| BBa_K123000 | BisdA | | | | | 330 |
| BBa_K284999 | Deletar este | | | | | 1431 |
| BBa_I716253 | HPI, katG | | | | | 2181 |
| BBa_K137000 | katE | | | | | 2265 |
| BBa_K137014 | katE + LAA | | | | | 2298 |
| BBa_K137067 | katG | | | | | 2184 |
| BBa_K078102 | dxnB | | | | | 886 |
| BBa_K078003 | one part of the initial dioxygenase of the dioxin degradation pathway | | | | | 1897 |

Other enzymes of use as output products in the modules and biological circuit chemotactic converters described herein include enzymes that phosphorylate or dephosphorylate either small molecules or other proteins, or enzymes that methylate or demethylate other proteins or DNA.

TABLE 17

Examples of Phosphorylation and Methylation-Related Enzymes

| Name | Protein | Description | Direction | Uniprot | KEGG | E.C. | Length |
|---|---|---|---|---|---|---|---|
| BBa_C0082 | tar-envZ | Receptor, tar-envZ | Forward | | | | 1491 |
| BBa_J58104 | | Fusion protein Trg-EnvZ for signal transduction | | | | | 1485 |
| BBa_J58105 | | Synthetic periplasmic binding protein that docks a vanillin molecule | | | | | 891 |
| BBa_I752001 | | CheZ coding sequence (Chemotaxis protein) | | | | | 639 |
| BBa_K091002 | | LsrK gene | Forward | | | | 1593 |

TABLE 17-continued

Examples of Phosphorylation and Methylation-Related Enzymes

| Name | Protein | Description | Direction | Uniprot | KEGG | E.C. | Length |
|---|---|---|---|---|---|---|---|
| BBa_K147000 | | cheZ | | | | | 835 |
| BBa_K118015 | | glgC coding sequence encoding ADP-glucose pyrophosphorylase | | | | | 1299 |
| BBa_K118016 | | glgC16 (glgC with G336D substitution) | | | | | 1299 |
| BBa_K094100 | | cheZ gene | | | | | 695 |
| BBa_K136046 | | envZ* | | | | | 1353 |
| BBa_K283008 | chez | chez_Histag | | | | | 713 |
| BBa_C0024 | CheB | CheB chemotaxis coding sequence (protein glutamate methylesterase) | Forward | P07330 | JW1872 | 3.1.1.61 | 1053 |
| BBa_K108020 | | Dam | | | | | 837 |

Also useful as output products in the modules and biological circuit chemotactic converters described herein are receptors, ligands, and lytic proteins. Receptors tend to have three domains: an extracellular domain for binding ligands such as proteins, peptides or small molecules, a transmembrane domain, and an intracellular or cytoplasmic domain which frequently can participate in some sort of signal transduction event such as phosphorylation. In some embodiments, transporter, channel, or pump gene sequences are used as output products. Transporters are membrane proteins responsible for transport of substances across the cell membrane. Channels are made up of proteins that form transmembrane pores through which selected ions can diffuse. Pumps are membrane proteins that can move substances against their gradients in an energy-dependent process known as active transport. In some embodiments, nucleic acid sequences encoding proteins and protein domains whose primary purpose is to bind other proteins, ions, small molecules, and other ligands are used as output products in the modules and biological circuit chemotactic converters described herein. Exemplary receptors, ligands, and lytic proteins are listed in Table 18.

TABLE 18

Examples of Receptors, Ligands, and Lytic Proteins

| Name | Protein | Description | Tag | Direction | UniProt | Length |
|---|---|---|---|---|---|---|
| BBa_J07009 | ToxR | toxicity-gene activator from Vibrio cholerae | None | Forward | P15795 | 630 |
| BBa_K133063 | | (TIR)TLR3 | | | | 453 |
| BBa_K133064 | | (TIR)TLR9 | | | | 585 |
| BBa_K133065 | | (TMTIR)TLR3 | | | | 600 |
| BBa_K133069 | | (TMTIR)TLR3stop | | | | 603 |
| BBa_K133067 | | (TMTIR)TLR4 | | | | 621 |
| BBa_K133060 | | (TMTIR)TLR9 | | | | 645 |
| BBa_K209400 | | AarI B-C part, hM4D | | | | 1434 |
| BBa_K209401 | | AarI B-C part, Rs1.3 | | | | 1407 |
| BBa_I712002 | | CCR5 | | | | 1059 |
| BBa_I712003 | | CCR5-NUb | | | | 1194 |
| BBa_I712010 | | CD4 sequence without signal peptide | | | | 1299 |
| BBa_I712017 | | Chemokine (CXC motif) receptor 4, fused to N-terminal half of ubiquitin. | | | | 1191 |
| BBa_I15010 | Cph8 | cph8 (Cph1/EnvZ fusion) | None | Forward | | 2238 |
| BBa_I728500 | | CPX Terminal Surface Display Protein with Polystyrene-Binding Peptide | | | | 654 |
| BBa_J52035 | | dnMyD88 | | | | 420 |
| BBa_K259000 | | fhuA - Outer membrane transporter for ferrichrome-iron | | | | 2247 |
| BBa_K259001 | | fiu B Outer Membrane Ferric Iron Transporter | | | | 2247 |
| BBa_J58104 | | Fusion protein Trg-EnvZ for signal transduction | | | | 1485 |
| BBa_K137112 | | lamB | | | | 1339 |
| BBa_C0082 | tar-envZ | Receptor, tar-envZ | LVA | Forward | | 1491 |
| BBa_J58105 | | Synthetic periplasmic binding protein that docks a vanillin molecule | | | | 891 |
| BBa_I712012 | | TIR domain of TLR3 | | | | 456 |
| BBa_K143037 | | YtvA Blue Light Receptor for B. subtilis | | | | 789 |
| BBa_J07006 | | malE | | | | 1191 |
| BBa_J07017 | | FecA protein | | | | 2325 |
| BBa_K141000 | UCP1 | Ucp1 | | | | 924 |
| BBa_K141002 | | Ucp 175 deleted | | | | 921 |
| BBa_K141003 | | Ucp 76 deleted | | | | 921 |
| BBa_K190028 | | GlpF | | | | 846 |

TABLE 18-continued

Examples of Receptors, Ligands, and Lytic Proteins

| Name | Protein | Description | Tag | Direction | UniProt | Length |
|---|---|---|---|---|---|---|
| BBa_I746200 | | FepA L8T Mutant - Large Diffusion pore for E. coli outer membrane. | | | | 2208 |
| BBa_I765002 | | ExbB membrane spanning protein in TonB-ExbB-ExbD complex [Escherichia coli K12] | | | | 735 |
| BBa_I765003 | | TonB ferric siderophore transport system, periplasmic binding protein TonB [Pseudomonas entomophila] | | | | 735 |
| BBa_K090000 | | Glutamate gated K+ channel | | | | 1194 |
| BBa_K284000 | | Lactate Permease from Kluyveromyces lactis | | | | 1873 |
| BBa_K284997 | | Deletar este | | | | 1069 |
| BBa_J22101 | | Lac Y gene | | | | 1288 |
| BBa_K079015 | | LacY transporter protein from E. coli | | | | 1254 |
| BBa_K119003 | | RcnA (YohM) | | | | 833 |
| BBa_K137001 | | LacY | | | | 1254 |
| BBa_I712024 | | CD4 | | | | 1374 |
| BBa_K133061 | | CD4 ecto | | | | 1113 |
| BBa_K136046 | | envZ* | | | | 1353 |
| BBa_K157002 | | Transmembrane region of the EGF-Receptor (ErbB-1) | | | | 87 |
| BBa_K227006 | | puc BA coding region of R. sphaeroides | | forward | | 336 |
| BBa_M12067 | | E1 | | | | 264 |
| BBa_I721002 | | Lead Binding Protein | | | | 399 |
| BBa_K126000 | | TE33 Fab L chain | | | | 648 |
| BBa_K133070 | | gyrEC | | | | 660 |
| BBa_K133062 | | gyrHP | | | | 660 |
| BBa_K157003 | | Anti-NIP singlechain Fv-Fragment | | | | 753 |
| BBa_K211001 | | RI7 | | | | 987 |
| BBa_K211002 | | RI7-odr10 chimeric GPCR | | | | 1062 |
| BBa_K103004 | | protein $Z_{SPA-1}$ | | | | 190 |
| BBa_K128003 | | p1025 | | | | 101 |
| BBa_K133059 | | RGD | | | | 9 |
| BBa_K283010 | | Streptavidin | | | | 387 |
| BBa_K103004 | | protein $Z_{SPA-1}$ | | | | 190 |
| BBa_K128003 | | p1025 | | | | 101 |
| BBa_K133059 | | RGD | | | | 9 |
| BBa_K283010 | | Streptavidin | | | | 387 |
| BBa_K112000 | Holin | T4 holin, complete CDS, berkeley standard | | | | 657 |
| BBa_K112002 | Holin | T4 holin, without stop codon, berkeley standard | | | | 654 |
| BBa_K112004 | | a~T4 holin in BBb | | | | 661 |
| BBa_K112006 | | T4 antiholin in BBb | | | | 294 |
| BBa_K112009 | | in BBb | | | | 288 |
| BBa_K112010 | | a~T4 antiholin in BBb | | | | 298 |
| BBa_K112012 | | T4 lysozyme in BBb | | | | 495 |
| BBa_K112015 | | in BBb | | | | 489 |
| BBa_K112016 | | a~T4 lysozyme in BBb | | | | 499 |
| BBa_K117000 | | Lysis gene (promotes lysis in colicin-producing bacteria strain) | | | | 144 |
| BBa_K124014 | | Bacteriophage Holin Gene pS105 | | | | 317 |
| BBa_K108001 | | SRRz | | | | 1242 |
| BBa_K112300 | | {lambda lysozyme} in BBb format | | | | 477 |
| BBa_K112304 | | {a~lambda lysozyme} in BBb format | | | | 481 |
| BBa_K112306 | | {lambda holin} in BBb format | | | | 318 |
| BBa_K112310 | | {a~lambda holin}; adheres to Berkeley standard | | | | 322 |
| BBa_K112312 | | {lambda antiholin}; adheres to Berkeley standard | | | | 324 |
| BBa_K112316 | | {a~lambda antiholin}; adheres to Berkeley standard | | | | 328 |
| BBa_K124017 | | Bacteriophage Lysis Cassette S105, R, and Rz | | | | 1257 |
| BBa_K112806 | | [T4 endolysin] | | | | 514 |
| BBa_K284001 | | Lysozyme from Gallus gallus | | | | 539 |

Particularly useful for the different embodiments of the various aspects described herein are chemotaxis sensors. Exemplary, non-limiting chemotaxis sensors are provided in Table 19. Such chemotaxis sensors can be further engineered by, in some embodiments, swapping in new sensory domains to allow for chemotaxis towards new chemicals, such as, for example, biological toxins or environmental pollutants. For example, the sensing and transmembrane signaling modules of different chemoreceptors can be swapped to generate functional chimeric receptors with directed changes in ligand specificity. In some embodiments, engineering of chemotactic sensors can be achieved by using other known sensing proteins from two-component pathways from various organisms, including prokaryotes and eukaryotes, and swapping these sensory domains to form novel engineered chemotaxis sensor proteins.

TABLE 19

Examples of Chemotaxis Sensors/Receptors

| Protein | Gene | Location | Monomer Mass (kDa) | Oligomer Number | Monomers/cell | Monomer Concentration (μM) | Affinity ($K_d$) for signaling complex (μM) | References |
|---|---|---|---|---|---|---|---|---|
| Maltose-binding protein | malE | Periplasm | 41 | 1 | 45,000 | 400 | 250 | 1, 2, 11 |
| Galactose/glucose-binding protein | mglB | Periplasm | 33 | 1 | 20,000 | 200 | | 1, 2 |
| Ribose-binding protein | rbsB | Periplasm | 30 | 1 | 40,000 | 400 | | 1, 2 |
| Dipeptide-binding protein | dpp | Periplasm | 57 | 1 | | | | 2 |
| $Ni^{2+}$-binding protein | nikA | Periplasm | 57 | 1 | 20,000 | 200 | | 3 |
| Aspartate receptor | tar | Membrane | 60 | 2 | 1,500 | 2 | | 6, 13, 16, 17 |
| Serine receptor | tsr | Membrane | 59 | (2) | 3,000 | 4 | | 13, 16, 17 |
| Ribose/galactose receptor | trg | Membrane | 59 | 2 | 150 | 0.2 | | 5, 16, 17 |
| Dipeptide receptor | tap | Membrane | 58 | (2) | 150 | 0.2 | | 2, 4, 16, 17 |
| Citrate receptor | tcp | Membrane | 59 | (2) | | | | 7 |

References:
1 Koman et al 1979;
2 Macnab 1987;
3 DePina et al 1995;
4 Stock et al 1991;
5 Hazelbauer & Adler 1971;
6 Milligan & Koshland 1988;
7 Yamamoto & Imae 1993;
(8) Simms and Subbaramaiah 1991;
(9) Kihara et al 1989;
(10) Tang & Blair 1995;
11 Manson et al 1985;
(12) Li et al 1995;
13 Gegner et al 1992;
(14) Sanatinia et al 1995;
(15) Blat & Eisenbach 1996b;
16 Bray et al 1993;
17 Bray & Bourret 1995.

Non-limiting examples of engineered chimeric chemotactic receptors, with swapped domains, for use in the sensor modules and biological circuit chemotactic converters described herein are provided in Table 20.

TABLE 20

Examples of Engineered Chimeric Chemotactic Receptors

| Sensor Domain | Signaling Domain | Source | Details |
|---|---|---|---|
| Tar | Tsr | Krikos et al. (1985) PNAS 82: 1326-1330. | Tar/Tsr chimeras Produced functional chemotactic receptors. |

TABLE 20-continued

Examples of Engineered Chimeric Chemotactic Receptors

| Sensor Domain | Signaling Domain | Source | Details |
| --- | --- | --- | --- |
| NarX | Tar | Ward et al. (2002) Mol. Microbial. 44(3): 709-719. | NarX sensor-Tar signalling domain chimera produced a chemotactic response to nitrate and nitrites. |
| Tar | Human Insulin Receptor | Moe et al. (1989) PNAS 86: 5683-5687. | Tar sensor-Human insulin receptor cytosolic domain produced a tyrosine kinase chimera |
| McpB | McpC | Kristich and Ordal, (2004) J.Bact. 186: 5950-5955. | Domains swapped between B. subtilis chemoreceptors |
| Trg | EnvZ | Baumgartner et al., (1993) J. Bact. 176: 1157-1163. | Recognition of sugar-binding protein ligands by Trg chemoreceptor and ompC promoter activation by EnvZ. |
| Cph1 | EnvZ | Levskaya et al. (2005). Nature 438: 441-442 | Photoreceptor Cph1 from Synechocystis-EnvZ cytoplasmic domain chimera produces light-activated receptor |

RNA Molecule Components and Output Products

Figure 8:
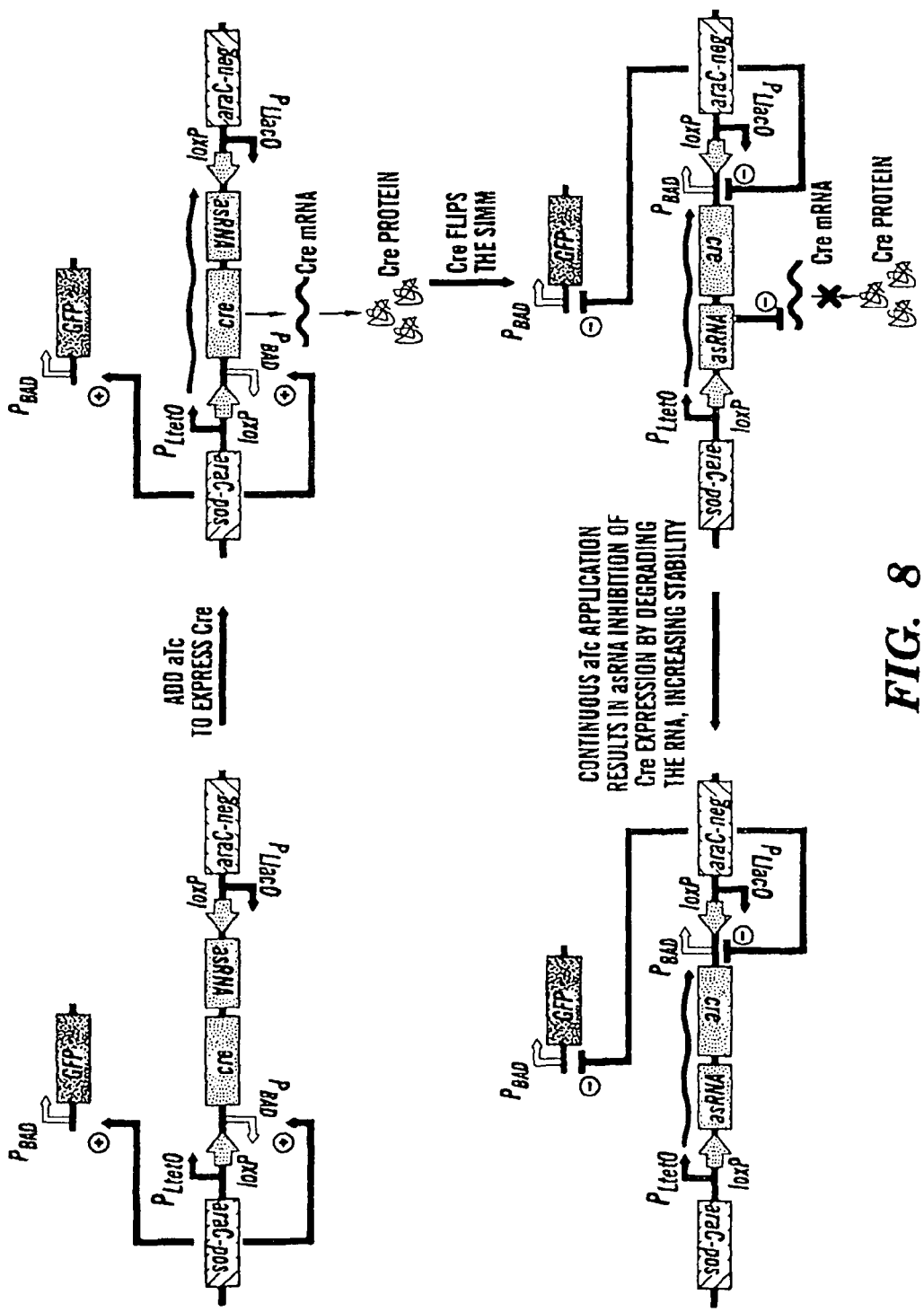
FIG. 8 depicts an exemplary SIMM, as depicted in FIGS. 2A-2C, that further comprises an antisense RNA (asRNA) to enhance the stability of the system. The asRNA is downstream of and in the inverted orientation with respect to the recombinase gene. The asRNA is targeted against the mRNA of the recombinase gene. Thus, when the upstream promoter is expressed, the recombinase is produced and flips the SIMM. Then, further expression from the upstream promoter will produce asRNA targeted against recombinase mRNA and degrade it, thus preventing further recombinase from being produced and preventing the SIMM from being flipped back inadvertently.

Double-stranded (dsRNA) has been shown to direct the sequence-specific silencing of mRNA through a process known as RNA interference (RNAi). The process occurs in a wide variety of organisms, including mammals and other vertebrates. Accordingly, in some embodiments of the aspects described herein, sequences encoding RNA molecules can be used as components or output products in the biological circuit chemotactic converters. Such RNA molecules can be double-stranded or single-stranded and are designed, in some embodiments, to mediate RNAi, e.g., with respect to another output product or, for example, to inhibit a recombinase present in a SIMM (see, for example, FIG. 8). In those embodiments where a sequence encodes an RNA molecule that acts to mediate RNAi, the sequence can be said to encode an "iRNA molecule."

In some embodiments, an iRNA molecule can have any architecture described herein. e.g., it can be incorporate an overhang structure, a hairpin or other single strand structure or a two-strand structure, as described herein. An "iRNA molecule" as used herein, is an RNA molecule which can by itself, or which can be cleaved into an RNA agent that can, downregulate the expression of a target sequence, e.g., a recombinase sequence in a SIMM or an output product encoded by another module or biological circuit chemotactic converter, as described herein. While not wishing to be bound by theory, an iRNA molecule can act by one or more of a number of mechanisms, including post-transcriptional cleavage of a target mRNA sometimes referred to in the art as RNAi, or pre-transcriptional or pre-translational mechanisms. An iRNA molecule can include a single strand or can include more than one strand, e.g., it can be a double stranded iRNA molecule.

The sequence encoding an iRNA molecule should include a region of sufficient homology to a target sequence, and be of sufficient length in terms of nucleotides, such that the iRNA molecule, or a fragment thereof, can mediate down regulation of the target sequence. Thus, the iRNA molecule is or includes a region that is at least partially, and in some embodiments fully, complementary to a target RNA sequence. It is not necessary that there be perfect complementarity between the iRNA molecule and the target sequence, but the correspondence must be sufficient to enable the iRNA molecule t, or a cleavage product thereof, to direct sequence specific silencing, e.g., by RNAi cleavage of the target RNA sequence, e.g., mRNA.

Complementarity, or degree of homology with the target strand, is most critical in the antisense strand. While perfect complementarity, particularly in the antisense strand, is often desired some embodiments can include, particularly in the antisense strand, one or more but preferably 6, 5, 4, 3, 2, or fewer mismatches (with respect to the target RNA). The mismatches, particularly in the antisense strand, are most tolerated in the terminal regions and if present are preferably in a terminal region or regions, e.g., within 6, 5, 4, or 3 nucleotides of the 5' and/or 3' terminus The sense strand need only be sufficiently complementary with the antisense strand to maintain the over all double strand character of the molecule.

iRNA molecules for use in the modules and biological converter switches described herein include: molecules that are long enough to trigger the interferon response (which can be cleaved by Dicer (Bernstein et al. 2001. Nature, 409:363-366) and enter a RISC(RNAi-induced silencing complex); and, molecules that are sufficiently short that they do not trigger the interferon response (which molecules can also be cleaved by Dicer and/or enter a RISC), e.g., molecules that are of a size which allows entry into a RISC, e.g., molecules which resemble Dicer-cleavage products. Molecules that are short enough that they do not trigger an interferon response are termed "sRNA molecules" or "shorter iRNA molecules" herein. Accordingly, a sRNA molecule or shorter iRNA molecule, as used herein, refers to an iRNA molecule, e.g., a double stranded RNA molecule or single strand molecule, that is sufficiently short that it does not induce a deleterious interferon response in a mammalian cell, such as a human cell, e.g., it has a duplexed region of less than 60 but preferably less than 50, 40, or 30 nucleotide pairs. The sRNA molecule, or a cleavage product thereof, can downregulate a target sequence, e.g., by inducing RNAi with respect to a target RNA sequence.

Each strand of an sRNA molecule can be equal to or less than 30, 25, 24, 23, 22, 21, or 20 nucleotides in length. The strand is preferably at least 19 nucleotides in length. For example, each strand can be between 21 and 25 nucleotides in length. Preferred sRNA molecules have a duplex region of 17, 18, 19, 29, 21, 22, 23, 24, or 25 nucleotide pairs, and one or more overhangs, preferably one or two 3' overhangs, of 2-3 nucleotides.

A "single strand iRNA molecule" as used herein, is an iRNA molecule that is made up of a single molecule. It may include a duplexed region, formed by intra-strand pairing, e.g., it may be, or include, a hairpin or pan-handle structure. Single strand iRNA molecules are preferably antisense with regard to the target sequence. A single strand iRNA molecule should be sufficiently long that it can enter the RISC and participate in RISC mediated cleavage of a target mRNA. A single strand iRNA molecule for use in the modules and biological converter switches described herein is at least 14, and more preferably at least 15, 20, 25, 29, 35, 40, or 50 nucleotides in length. It is preferably less than 200, 100, or 60 nucleotides in length.

Hairpin iRNA molecules can have a duplex region equal to or at least 17, 18, 19, 29, 21, 22, 23, 24, or 25 nucleotide pairs. The duplex region is preferably equal to or less than 200, 100, or 50, in length. Preferred ranges for the duplex region are 15-30, 17 to 23, 19 to 23, and 19 to 21 nucleotides pairs in length. The hairpin preferably has a single strand overhang or terminal unpaired region, preferably the 3', and preferably of the antisense side of the hairpin. Preferred overhangs are 2-3 nucleotides in length.

A "double stranded (ds) iRNA molecule" as used herein, refers to an iRNA molecule that includes more than one, and preferably two, strands in which interchain hybridization can form a region of duplex structure. The antisense strand of a double stranded iRNA molecule should be equal to or at least, 14, 15, 16 17, 18, 19, 25, 29, 40, or 60 nucleotides in length. It should be equal to or less than 200, 100, or 50, nucleotides in length. Preferred ranges are 17 to 25, 19 to 23, and 19 to 21 nucleotides in length. The sense strand of a double stranded iRNA molecule should be equal to or at least 14, 15, 16 17, 18, 19, 25, 29, 40, or 60 nucleotides in length. It should be equal to or less than 200, 100, or 50, nucleotides in length. Preferred ranges are 17 to 25, 19 to 23, and 19 to 21 nucleotides in length. The double strand portion of a double stranded iRNA molecule should be equal to or at least, 14, 15, 16 17, 18, 19, 20, 21, 22, 23, 24, 25, 29, 40, or 60 nucleotide pairs in length. It should be equal to or less than 200, 100, or 50, nucleotides pairs in length. Preferred ranges are 15-30, 17 to 23, 19 to 23, and 19 to 21 nucleotides pairs in length.

In some embodiments, the ds iRNA molecule is sufficiently large that it can be cleaved by an endogenous molecule, e.g., by Dicer, to produce smaller ds iRNA agents, e.g., sRNAs agents It is preferred that the sense and antisense strands be chosen such that the ds iRNA molecule includes a single strand or unpaired region at one or both ends of the molecule. Thus, a ds iRNA agent contains sense and antisense strands, preferable paired to contain an overhang, e.g., one or two 5' or 3' overhangs but preferably a 3' overhang of 2-3 nucleotides. Most embodiments have a 3' overhang. Preferred sRNA molecule have single-stranded overhangs, preferably 3' overhangs, of 1 or preferably 2 or 3 nucleotides in length at each end. The overhangs can be the result of one strand being longer than the other, or the result of two strands of the same length being staggered. 5' ends are preferably phosphorylated.

Preferred lengths for the duplexed region is between 15 and 30, most preferably 18, 19, 20, 21, 22, and 23 nucleotides in length, e.g., in the sRNA molecule range discussed above. sRNA molecules can resemble in length and structure the natural Dicer processed products from long dsRNAs. Hairpin, or other single strand structures which provide the required double stranded region, and preferably a 3' overhang are also encompassed within the term sRNA molecule, as used herein.

The iRNA molecules described herein, including ds iRNA molecules and sRNA molecules, can mediate silencing of a target RNA, e.g., mRNA, e.g., a transcript of a sequence that encodes a protein expressed in one or more modules or biological converter switches as described herein. For convenience, such a target mRNA is also referred to herein as an mRNA to be silenced or translationally regulated. Such a sequence is also referred to as a target sequence. As used herein, the phrase "mediates RNAi" refers to the ability to silence, in a sequence specific manner, a target RNA molecule or sequence. While not wishing to be bound by theory, it is believed that silencing uses the RNAi machinery or process and a guide RNA, e.g., an sRNA agent of 21 to 23 nucleotides.

In other embodiments of the aspects described herein, RNA molecules for use in the modules and biological circuit chemotactic converters described herein comprise natural or engineered microRNA sequences. Also provided herein are references and resources, such as programs and databases found on the World Wide Web, that can be used for obtaining information on endogenous microRNAs and their expression patterns, as well as information in regard to cognate microRNA sequences and their properties.

Mature microRNAs (also referred to as miRNAs) are short, highly conserved, endogenous non-coding regulatory RNAs (18 to 24 nucleotides in length), expressed from longer transcripts (termed "pre-microRNAs") encoded in animal, plant and virus genomes, as well as in single-celled eukaryotes. Endogenous miRNAs found in genomes regulate the expression of target genes by binding to complementary sites, termed herein as "microRNA target sequences," in the mRNA transcripts of target genes to cause translational repression and/or transcript degradation. miRNAs have been implicated in processes and pathways such as development, cell proliferation, apoptosis, metabolism and morphogenesis, and in diseases including cancer (S. Griffiths-Jones et al., "miRBase: tools for microRNA genomics." Nuc. Acid. Res., 2007: 36, D154-D158). Expression of a microRNA target sequence refers to transcription of the DNA sequence that encodes the microRNA target sequence to RNA. In some embodiments, a microRNA target sequence is operably linked to or driven by a promoter sequence. In some embodiments, a microRNA target sequence comprises part of another sequence that is operably linked to a promoter sequence, such as a sequence encoding an output product or a recombinase, and is said to be linked to, attached to, or fused to, the sequence encoding the output product or the recombinase.

The way microRNA and their targets interact in animals and plants is different in certain aspects. Translational repression is thought to be the primary mechanism in animals, with transcript degradation the dominant mechanism for plant target transcripts. The difference in mechanisms lies in the fact that plant miRNA exhibits perfect or nearly perfect base pairing with the target but in the case of animals, the pairing is rather imperfect. Also, miRNAs in plants bind to their targets within coding regions cleaving at single sites, whereas most of the miRNA binding sites in animals are in the 3' un-translated regions (UTR). In animals, functional miRNA: miRNA target sequence duplexes are found to be more variable in structure and they contain only short complementary sequence stretches, interrupted by gaps and mismatches. In animal miRNA: miRNA target sequence interactions, multiplicity (one miRNA targeting more than one gene) and cooperation (one gene targeted by several miRNAs) are very common but rare in the case of plants. All these make the approaches in miRNA target prediction in plants and animals different in details (V. Chandra et al., "MTar: a computational microRNA target prediction architecture for human transcriptome." BMC Bioinformatics 2010, 11 (Suppl 1):S2).

Experimental evidence shows that the miRNA target sequence needs enough complementarities in either the 3' end or in the 5' end for its binding to a miRNA. Based on these complementarities of miRNA: miRNA target sequence target duplex, the miRNA target sequence can be divided into three main classes. They are the 5' dominant seed site targets (5' seed-only), the 5' dominant canonical seed site targets (5' dominant) and the 3' complementary seed site targets (3' canonical). The 5' dominant canonical targets possess high complementarities in 5' end and a few complementary pairs in 3' end. The 5' dominant seed-only targets possess high complementarities in 5' end (of the miRNA) and only a very few or no complementary pairs in 3' end. The seed-only sites have a perfect base pairing to the seed portion of 5' end of the miRNA and limited base pairing to 3' end of the miRNA. The 3' complimentary targets have high complementarities in 3' end and insufficient pairings in 5' end. The seed region of the miRNA is a consecutive stretch of seven or eight nucleotides at 5' end. The 3' complementary sites have an extensive base pairing to 3' end of the miRNA that compensate for imperfection or a shorter stretch of base pairing to a seed portion of the miRNA. All of these site types are used to mediate regulation by miRNAs and show that the 3' complimentary class of target site is used to discriminate among individual members of miRNA families in vivo. A genome-wide statistical analysis shows that on an average one miRNA has approximately 100 evolutionarily conserved target sites, indicating that miRNAs regulate a large fraction of protein-coding genes.

At present, miRNA databases include miRNAs for human, *Caenorhabditis elegans, D. melanogaster, Danio rerio* (zebrafish), *Gallus gallus* (chicken), and *Arabidopsis thaliana*. miRNAs are even present in simple multicellular organisms, such as poriferans (sponges) and cnidarians (starlet sea anemone). Many of the bilaterian animal miRNAs are phylogenetically conserved; 55% of *C. elegans* miRNAs have homologues in humans, which indicates that miRNAs have had important roles throughout animal evolution. Animal miRNAs seem to have evolved separately from those in plants because their sequences, precursor structure and biogenesis mechanisms are distinct from those in plants (Kim V N et al., "Biogenesis of small RNAs in animals." Nat Rev Mol Cell Biol. 2009 February; 10 (2):126-39).

miRNAs useful as components and output products for designing the modules and biological circuit chemotactic converters described herein can be found at a variety of databases as known by one of skill in the art, such as those described at "miRBase: tools for microRNA genomics." Nuc. Acid. Res., 2007: 36 (Database Issue), D154-D158; "miRBase: microRNA sequences, targets and gene nomenclature." Nuc. Acid. Res., 2006 34 (Database Issue):D140-D144; and "The microRNA Registry." Nuc. Acid. Res., 2004 32 (Database Issue):D109-D111), which are incorporated herein in their entirety by reference.

Accordingly, in some embodiments of the aspects described herein, a module or biological circuit chemotactic converter can further comprise a sequence encoding an RNA molecule, such as an iRNA molecule or microRNA molecule. In such embodiments, the sequence encoding the RNA molecule can be operably linked to a promoter sequence, or comprise part of another sequence, such as a sequence encoding a protein output. In those embodiments where the RNA molecule comprises part of, is linked to, attached to, or fused to, the sequence encoding, e.g., an output product, transcription of the sequence results in expression of both the mRNA of the output product and expression of the RNA molecule.

DEFINITIONS

The terms "nucleic acids" and "nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or doublestranded, sense or antisense form. As will also be appreciated by those in the art, many variants of a nucleic acid can be used for the same purpose as a given nucleic acid. Thus, a nucleic acid also encompasses substantially identical nucleic acids and complements thereof. Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. shRNAs also can comprise non-natural elements such as non-natural bases, e.g., ionosin and xanthine, nonnatural sugars, e.g., 2'-methoxy ribose, or non-natural phosphodiester linkages, e.g., methylphosphonates, phosphorothioates and peptides.

The term "nucleic acid sequence" or "oligonucleotide" or "polynucleotide" are used interchangeably herein and refers to at least two nucleotides covalently linked together. The term "nucleic acid sequence" is also used inter-changeably herein with "gene," "cDNA,", and "mRNA," unless expressly specified otherwise. As will be appreciated by those in the art, the depiction of a single nucleic acid sequence also defines the sequence of the complementary nucleic acid sequence. Thus, a nucleic acid sequence also encompasses the complementary strand of a depicted single strand. Unless otherwise indicated, a particular nucleic acid sequence also implicitly encompasses conservatively modified variants thereof (e.g., degenerate codon substitutions) and complementary sequences, as well as the sequence explicitly indicated. As will also be appreciated by those in the art, a single nucleic acid sequence provides a probe that can hybridize to the target sequence under stringent hybridization conditions. Thus, a nucleic acid sequence also encompasses a probe that hybridizes under stringent hybridization conditions. The term "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. Nucleic acid sequences can be single stranded or double stranded, or can contain portions of both double stranded and single stranded sequence. The nucleic acid sequence can be DNA, both genomic and cDNA, RNA, or a hybrid, where the nucleic acid sequence can contain combinations of deoxyribo- and ribo-nucleotides, and combinations of bases including uracil, adenine, thymine, cytosine, guanine, inosine, xanthine hypoxanthine, isocytosine and isoguanine. Nucleic acid sequences can be obtained by chemical synthesis methods or by recombinant methods. A nucleic acid sequence will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages in the nucleic acid sequence. Other analog nucleic acids include those with positive backbones; non-ionic backbones, and non-ribose backbones, including those described in U.S. Pat. Nos. 5,235,033 and 5,034,506, which are incorporated by reference. Nucleic acid sequences containing one or more non-naturally occurring or modified nucleotides are also included within one definition of nucleic acid sequences. The modified nucleotide analog can be located for example at the 5'-end and/or the 3'-end of the nucleic acid sequence. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7 deaza-adenosine; O- and N-alkylated nucleotides, e.g. N6-methyl adenosine are suitable. The 2' OH— group can be replaced by a group selected from H, OR, R, halo, SH, SR, NH2, NHR, NR2 or CN, wherein R is C-C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be used; alternatively, mixtures of different nucleic acid analogs, and mixtures of naturally occurring nucleic acids and analogs can be used. Nucleic acid sequences include but are not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc.

The term "oligonucleotide" as used herein refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

In its broadest sense, the term "substantially complementary," when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of at least 10 nucleotides, or at least 11, 12, 13, 14, 15, 16, 17, 18, 19, 20, 21, 22 or up to 50 nucleotides of the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

In its broadest sense, the term "substantially identical," when used herein with respect to a nucleotide sequence, means a nucleotide sequence corresponding to a reference or target nucleotide sequence, wherein the percentage of identity between the substantially identical nucleotide sequence and the reference or target nucleotide sequence is at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of 10-22 nucleotides, such as at least 10, 11, 12, 13, 14, 15, 16, 17, 18, 19, 20, 21, 22 or up to 50 nucleotides of a nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence that is "substantially identical" to a reference nucleotide sequence hybridizes to the exact complementary sequence of the reference nucleotide sequence (i.e. its corresponding strand in a double-stranded molecule) under low stringency conditions, preferably medium stringency conditions, most preferably high stringency conditions (as defined above). Homologues of a specific nucleotide sequence include nucleotide sequences that encode an amino acid sequence that is at least 24% identical, at least 35% identical, at least 50% identical, at least 65% identical to the reference amino acid sequence, as measured using the parameters described above, wherein the amino acid sequence encoded by the homolog has the same biological activity as the protein encoded by the specific nucleotide. The term "substantially non-identical" refers to a nucleotide sequence that does not hybridize to the nucleic acid sequence under stringent conditions.

As used herein, the term "gene" refers to a nucleic acid sequence comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. These definitions generally refer to a single-stranded molecule, but in specific embodiments will also encompass an additional strand that is partially, substantially or fully complementary to the single-stranded molecule. Thus, a nucleic acid sequence can encompass a double-stranded molecule or a double-stranded molecule that comprises one or more complementary strand(s) or "complement(s)" of a particular sequence comprising a molecule. As used herein, a single stranded nucleic acid can be denoted by the prefix "ss", a double stranded nucleic acid by the prefix "ds", and a triple stranded nucleic acid by the prefix "ts."

The term "nucleic acid construct" as used herein refers to a nucleic acid at least partly created by recombinant methods.

The term "DNA construct" refers to a polynucleotide construct consisting of deoxyribonucleotides. The construct can be single or double stranded. The construct can be circular or linear. A person of ordinary skill in the art is familiar with a variety of ways to obtain and generate a DNA construct. Constructs can be prepared by means of customary recombination and cloning techniques as are described, for example, in Maniatis T, Fritsch E F and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands.

The terms "polypeptide", "peptide", "oligopeptide", "polypeptide", "gene product", "expression product" and "protein" are used interchangeably herein to refer to a polymer or oligomer of consecutive amino acid residues.

The term "operable linkage" or "operably linked" are used interchangeably herein, are to be understood as meaning, for example, the sequential arrangement of a regulatory element (e.g. a promoter) with a nucleic acid sequence to be expressed and, if appropriate, further regulatory elements (such as, e.g., a terminator) in such a way that each of the regulatory elements can fulfill its intended function to allow, modify, facilitate or otherwise influence expression of the linked nucleic acid sequence. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. In some embodiments, arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly can be any distance, and in some embodiments is less than 200 base pairs, especially less than 100 base pairs, less than 50 base pairs. In some embodiments, the nucleic acid sequence to be transcribed is located behind the promoter in such a way that the transcription start is identical with the desired beginning of the chimeric RNA of the invention. Operable linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands). However, further sequences may also be positioned between the two sequences. The insertion of sequences may also lead to the expression of fusion proteins, or serves as ribosome binding sites. In some embodiments, the expression construct, consisting of a linkage of promoter and nucleic acid sequence to be expressed, can exist in a vector integrated form and be inserted into a plant genome, for example by transformation.

The terms "promoter," "promoter element," or "promoter sequence" are equivalents and as used herein, refers to a DNA sequence which when operatively linked to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for the host cells (e.g., tissue promoters or pathogens like viruses).

If a promoter is an "inducible promoter", as defined herein, then the rate of transcription is modified in response to an inducing agent or inducer. In contrast, the rate of transcription is not regulated by an inducer if the promoter is a constitutive promoter. The term "constitutive" when made in reference to a promoter means that the promoter is capable of directing transcription of an operably linked nucleic acid sequence in the absence of a stimulus (e.g., heat shock, chemicals, agents, light, etc.). Typically, constitutive promoters are capable of directing expression of a nucleic acid sequence in substantially any cell and any tissue. In contrast, the term "regulateable" or "inducible" promoter referred to herein is one which is capable of directing a level of transcription of an operably linked nucleic acid sequence in the presence of a stimulus (e.g., heat shock, chemicals, light, agent etc.) which is different from the level of transcription of the operably linked nucleic acid sequence in the absence of the stimulus.

A promoter can be regulated in a tissue-specific or tissue preferred manner such that it is only active in transcribing the associated coding region in a specific tissue type(s). The term "tissue specific" as it applies to a promoter refers to a promoter that is capable of directing selective expression of a nucleotide sequence of interest to a specific type of tissue (e.g., liver) in the relative absence of expression of the same nucleotide sequence of interest in a different type of tissue (e.g., kidney). Tissue specificity of a promoter may be evaluated by, for example, operably linking a reporter gene to the promoter sequence to generate a reporter construct, introducing the reporter construct into the genome of an organism, e.g. an animal model such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining or immunohistochemical staining. The term "minimal promoter" as used herein refers to the minimal nucleic acid sequence comprising a promoter element while also maintaining a functional promoter. A minimal promoter may comprise an inducible, constitutive or tissue-specific promoter.

The term "expression" as used herein refers to the biosynthesis of a gene product, preferably to the transcription and/or translation of a nucleotide sequence, for example an endogenous gene or a heterologous gene, in a cell. For example, in the case of a heterologous nucleic acid sequence, expression involves transcription of the heterologous nucleic acid sequence into mRNA and, optionally, the subsequent translation of mRNA into one or more polypeptides. Expression also refers to biosynthesis of an RNA molecule, such as an iRNA molecule, which refers to expression and transcription of an iRNAi molecule such as siRNA, shRNA, microRNA, and antisense DNA but does not require translation to polypeptide sequences. The term "expression construct" and "nucleic acid construct" as used herein are synonyms and refer to a nucleic acid sequence capable of directing the expression of a particular nucleotide sequence, such as the heterologous target gene sequence in an appropriate host cell (e.g., a prokaryotic cell, eukaryotic cell, or mammalian cell). If translation of the desired heterologous target gene is required, it also typically comprises sequences required for proper translation of the nucleotide sequence. The coding region may code for a protein of interest but may also code for a functional RNA of interest, for example antisense RNA, dsRNA, or a nontranslated RNA, in the sense or antisense direction. The nucleic acid construct as disclosed herein can be chimeric, meaning that at least one of its components is heterologous with respect to at least one of its other components.

The term "leakiness" or "leaky" as used in reference to "promoter leakiness" refers to some level of expression of the nucleic acid sequence which is operatively linked to the promoter, even when the promoter is not intended to result in expression of the nucleic acid sequence (i.e. when the promoter is in the "off" state, a background level of expression of the nucleic acid sequence which is operatively linked to such promoter exists). In one illustrative example using inducible promoters, for example a Tet-on promoter, a leaky promoter is where some level of the nucleic acid sequence expression (which is operatively linked to the Tet-on promoter) still occurs in the absence of the inducer agent, tetracycline. Typically, most inducible promoters and tissue-specific promoters have approximately 10%-30% or 10-20% unintended or background nucleic acid sequence expression when the promoter is not active, for example, the background of leakiness of nucleic acid sequence expression is about 10%-20% or about 10-30%. As an illustrative example using a tissue-specific promoter, a "leaky promoter" is one in which expression of the nucleic acid sequence occurs in tissue where a tissue-specific promoter is not active, i.e. expression occurs in a non-specific tissue. Stated in another way using a kidney-specific promoter as an example; if at least some level of the nucleic acid sequence expression occurs in at least one tissue other than the kidney, where the nucleic acid sequence is operably linked to a kidney specific promoter, the kidney specific promoter would be considered a leaky promoter The term "enhancer" refers to a cis-acting regulatory sequence involved in the transcriptional activation of a nucleic acid sequence. An enhancer can function in either orientation and can be upstream or downstream of the promoter. As used herein, the term "gene product(s)" is used to refer to include RNA transcribed from a gene, or a polypeptide encoded by a gene or translated from RNA. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof.

As used herein, the term "comprising" means that other elements can also be present in addition to the defined elements presented. The use of "comprising" indicates inclusion rather than limitation. Accordingly, the terms "comprising" means "including principally, but not necessary solely". Furthermore, variation of the word "comprising", such as "comprise" and "comprises", have correspondingly the same meanings. The term "consisting essentially of" means "including principally, but not necessary solely at least one", and as such, is intended to mean a "selection of one or more, and in any combination". Stated another way, the term "consisting essentially of" means that an element can be added, subtracted or substituted without materially affecting the novel characteristics of the invention. This applies equally to steps within a described method as well as compositions and components therein. In other embodiments, the inventions, compositions, methods, and respective components thereof, described herein are intended to be exclusive of any element not deemed an essential element to the component, composition or method ("consisting of"). For example, a biological converter switch that comprises a sequence encoding a recombinase and a recombinase recognition sequence encompasses both the recombinase and a recombinase recognition sequence of a larger sequence. By way of further example, a composition that comprises elements A and B also encompasses a composition consisting of A, B and C.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, publications, and websites identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The present invention can be defined in any of the following numbered paragraphs:

1. A biological circuit chemotactic converter, the biological circuit chemotactic converter comprising: at least one input module $(IM)_n$, at least one genetic toggle switch $(TS)_n$, at least one logic module $(LM)_n$, and at least two sensor modules $(SM_A$ and $SM_B)_{n+1}$;
   wherein the input module comprises an inducible promoter sequence $(iP_A)$ operably linked to a repressor sequence encoding a repressor protein $(R_A)$;
   wherein the genetic toggle switch comprises a first repressible promoter sequence $(rP_1)$ that drives expression of a second repressor sequence $(R_2)$, and a second repressible promoter sequence $(rP_2)$ that drives expression of a first repressor sequence $(R_1)$, $(rP_1-R_2$ and $rP_2-R_1)$;
   wherein the first and second repressor sequences encode first and second repressors proteins, and wherein the first repressible promoter sequence is inhibited by the first repressor protein and the second repressible promoter sequence is inhibited by the second repressor protein;
   wherein the logic module comprises a repressible promoter sequence $(rP_B)$ operably linked to a repressor sequence $(R_B)$;
   wherein each sensor module comprises a repressible promoter sequence $(rP_C$ and $rP_D)$ operably linked to a nucleic acid sequence encoding a sensor molecule (sensor A and sensor B);
   and wherein $n \geq 1$.
2. The biological circuit chemotactic converter of paragraph 1, wherein the inducible promoter sequence of the input module is induced by a biological agent, a chemical agent, a metal ion, a toxin, or a pollutant.
3. The biological circuit chemotactic converter of any of paragraphs 1-2, wherein the repressor protein encoded by the first repressor sequence of the toggle switch $(R_1)$ and the repressor protein encoded by the input module $(R_A)$ are the same repressor protein.
4. The biological circuit chemotactic converter of any of paragraphs 1-3, wherein the repressor proteins encoded by the logic module and the input module are different repressor proteins.
5. The biological circuit chemotactic converter of any of paragraphs 1-4, wherein the repressor proteins encoded by the logic module and the genetic toggle switch are different repressor proteins.
6. The biological circuit chemotactic converter of any of paragraphs 1-5, wherein the second repressible promoter sequence of the genetic toggle switch $(rP_2)$, the repressible promoter sequence of the logic module $(rP_B)$, and the repressible promoter sequence of one sensor module $(rP_D)$ are repressed by the same repressor protein.
7. The biological circuit chemotactic converter of any of paragraphs 1-6, wherein the second repressible promoter sequence of the genetic toggle switch $(rP_2)$, the repressible promoter sequence of the logic module $(rP_B)$, and the repressible promoter sequence of one sensor module $(rP_D)$ comprise the same repressible promoter sequence.
8. The biological circuit chemotactic converter of any of paragraphs 1-7, wherein the repressible promoter sequence of one sensor module $(rP_C)$ is repressed by the repressor encoded by the logic module $(R_B)$.
9. The biological circuit chemotactic converter of any of paragraphs 1-8, wherein the at least two sensor modules encode for different sensor molecules.
10. The biological circuit chemotactic converter of any of paragraphs 1-9, wherein n is an integer value between and including 1 and 100.
11. The biological circuit chemotactic converter of any of paragraphs 1-10, wherein n is an integer value between and including 1 and 10.
12. The biological circuit chemotactic converter of any of paragraphs 1-11, wherein n is an integer value selected from the group consisting of 1, 2, 3, 4, 5, 6, 7, 8, 9, and 10.
13. The biological circuit chemotactic converter of any of paragraphs 1-12, further comprising at least one ribosome binding sequence.
14. The biological circuit chemotactic converter of any of paragraphs 1-13, further comprising at least one terminator sequence.
15. The biological circuit chemotactic converter of any of paragraphs 1-14, further comprising at least one degradation tag sequence.
16. The biological circuit chemotactic converter of any of paragraphs 1-15, further comprising at least one sequence encoding an iRNA molecule specific for at least one protein encoded by the biological circuit chemotactic converter.
17. The biological circuit chemotactic converter of any of paragraphs 1-16, wherein at least one repressor protein is an engineered zinc-finger protein.
18. The biological circuit chemotactic converter of any of paragraphs 1-17, where the promoter sequence of the inducible and repressible promoters is selected from any of the promoter sequences of SEQ ID NOs: 1-7, SEQ ID NOs: 167-843, and SEQ ID NOs: 1009-1010.
19. The biological circuit chemotactic converter of any of paragraphs 1-18, where the sensor molecule encoded by the nucleic acid sequence of the sensor domain is a chemotaxis receptor or chemotaxis sensor selected from Tables 19 and 20.
20. A system comprising at least one biological circuit chemotactic converter of any of paragraphs 1-19.
21. A method of modulating chemotaxis in a biological system using the biological circuit chemotactic converter or system thereof of any of paragraphs 1-20.
22. The method of paragraph 21, wherein the biological system is a cell.
23. The method of paragraph 22, wherein the biological system is an artificial cell, a prokaryotic cell, or a eukaryotic cell.
24. Any of the above-described paragraphs wherein the biological circuit chemotactic converters, and methods of use thereof consist essentially of the specified components.

EXAMPLES

Synthetic biologists have engineered a wide range of functionality into living systems, including the genetic toggle switch[1] and repressilator[2], genetic switches[1, 3-8], oscillators[2, 9-11], digital logic evaluators[12, 13], counters[14], filters[15-17], sensors[18-20], and cell-cell communicators[16, 18], with varying degrees of success. These functionalities have been demonstrated in proof-of-principle applications, such as in bacteria that invade cancer cells[21], engineered bacteriophages that break up biofilms[22] or enhance antibiotic treatments[23], and synthetic microbial pathways that enable the production of antimalarial drug precursors[24]. However, for all of its successes, many more challenges remain in advancing synthetic biology from low-level gene circuitry to higher-order networks. Herein, we describe the development of novel and useful biological circuit chemotactic converters for use as, and as part of, engineered biological circuits, and the utility of such biological circuit chemotactic converters in various application areas.

Synthetic Gene Networks

The engineering of mechanical, electrical, and chemical systems is enabled by frameworks for handling complexity and reliable means of probing and manipulating system states—tools that are largely lacking in the engineering of biology. Developing properly functioning biological circuits can involve complicated protocols for DNA construction, rudimentary model-guided and rational design, and repeated rounds of trial and error followed by fine-tuning. Limitations in characterizing kinetic processes and interactions between synthetic components and other unknown constituents in vivo make troubleshooting frustrating and prohibitively time-consuming.

Some advances have been made in streamlining the physical construction of artificial biological systems, in the form of resources and methods for building larger engineered DNA systems from smaller defined parts[25-28]. Additionally, large-scale DNA sequencing and synthesis technologies are enabling researchers to directly program whole genes, genetic circuits and eventually genomes, as well as to re-encode DNA sequences with optimal codons and minimal restriction sites.

Despite certain advances in molecular construction, building synthetic gene networks that function as desired remains extremely challenging. Achieving robustness, an important property of engineered systems, requires carefully incorporation of the concepts of feedback, redundancy, and decoupling[29]. For example, robustness in a synthetic gene oscillator composed of linked negative and positive feedback loops was found to be dependent on a time delay in the negative feedback loop[10]. To achieve robustness, synthetic biologists need to adapt designs from natural systems, incorporate feedback and multiple redundant circuits, and seek out evolutionary methods to refine circuit performance. Accelerated, large-scale diversification[30] and the use of characterized component libraries in conjunction with in silico models for a priori design[27] help to fine-tune network performance toward the desired output. However, synthetic biologists are often limited by a dearth of interoperable biological parts and reliable means of characterizing information flow through engineered gene networks.

Thus, as described herein, we have developed next-generation synthetic biology modules and circuits that (1) advance and expand the toolkit of available parts and modules; (2) provide probes for reliably quantifying state values of all the internal nodes of synthetic (and natural) biomolecular systems, and (3) create platforms for characterizing interactions between higher-order networks that have desired functionality for satisfying practical applications. Herein, we describe the development of several next-generation synthetic gene networks and application areas for their use.

Interoperable Parts for Synthetic Gene Networks

While there has been no shortage of novel circuit topologies to construct, limitations in the number of interoperable and well-characterized parts have constrained the development of more complex biological systems[25, 27, 31]. The situation is complicated by the many potential interactions between biological parts, which are derived from a variety of sources within different cellular backgrounds, and which are not well understood or characterized. As a result, the majority of synthetic circuits are still constructed ad hoc from a small number of commonly used components with a significant amount of trial and error.

The biological circuit chemotactic converters we describe herein expand the toolkit of parts for synthetic biological circuits. Promoter libraries with defined transcriptional activities can be created and characterized, plugged into in silico models, and used to develop novel synthetic gene networks that function without significant post-hoc adjustments[27, 32-35]. However, libraries of other biological components, such as transcription factors and recombinases, remain lacking. Automated techniques for assembling and testing multiple potentially interacting parts together within cells, as described herein, can greatly assist in the characterization and development of useful part libraries.

We have discovered and show that nucleic-acid-based parts, such as RNA devices, are essential tools for libraries of interoperable parts and devices, since they can be rationally programmed based on sequence specificity[6, 36, 37]. Novel circuit interconnections can be established using small RNA molecules, such as siRNAs, to control expression of specific components. Further, nucleic-acid-based parts can also be designed to function orthogonally to the wildtype cellular machinery, thus enabling dedication of defined cellular resources to engineered functions[38-40]. Artificial codons and unnatural amino acids, which serve to infuse these biological toolkits with even more orthogonal parts, have enabled new methods for studying existing proteins and the realization of proteins with novel functions[41].

As described herein, we have found that engineered zinc fingers constitute a flexible system for targeting specific DNA sequences, which significantly expands the synthetic biology toolkit for uses in, for example, targeted recombination, control of transcriptional activity, and making circuit interconnections. This technology has seen the greatest use in the creation of zinc-finger nucleases that generate targeted double-strand breaks for genomic modifications[42]. Zinc fingers have also been used to create artificial transcription factors by fusing zinc-finger domains with activation or repression domains[43, 44]. As described herein, libraries of externally controllable transcriptional activators or repressors can be created by engineering protein or RNA ligand-responsive regulators, which control the transcription or translation of zinc-finger-based artificial transcription factors themselves[19]. These libraries enable the construction of basic circuits, such as genetic toggle switches[27, 45], as well as more complex gene networks, such as the biological converter switches, described herein. In fact, several of the higher-order networks we describe herein rely on having multiple reliable and interoperable transcriptional activators and repressors for proper functioning. The greater availability of such transcriptional activators and repressors permits greater flexibility and sensitivity of the biological circuit chemotactic converters described herein.

Probes for Synthetic Gene Networks

Significant advances have been made in the development of new technologies for manipulating biological systems and probing their internal states. At the single-molecule level, for instance, optical tweezers and atomic force microscopes have provided alternative, direct ways to probe the biophysical states of single DNA, RNA, and protein molecules as they undergo conformational changes and other dynamical processes[46-50]. However, we lack similar tools for tracking the in vivo operation of synthetic gene circuits in a high-throughput fashion. Making dynamic measurements of biological networks involves placing sensors at multiple internal nodes, akin to how current and voltage are measured in electrical systems. Furthermore, external manipulation of synthetic biomolecular systems is typically accomplished by the addition of chemical inducers, which can suffer from crosstalk[51], be difficult to remove, and be consumed over time. As a result, inputs are often troublesome to control dynamically. Thus, there is a need in the art to develop and characterize probes for such uses.

Microfluidic devices enable increasingly precise manipulation and measurement of cells, especially since inputs can be modulated over time[52]. These systems allow the rapid addition and removal of chemical inducers, enabling more sophisticated, time-dependent inputs than conventional step functions, while also allowing researchers to track single cells for long periods of time. These developments make possible the wider use in synthetic biology of well-established engineering approaches for analyzing circuits and other systems. For example, frequency-domain analysis, a technique used commonly in electrical engineering, can be utilized with microfluidics to characterize the transfer functions and noise behaviour of synthetic biological circuits[53-55], and small-signal linearization of nonlinear gene circuits can be achieved by applying oscillatory perturbations with microfluidics and measuring responses at the single-cell level[54, 55].

Indeed, microfluidics provides one useful platform for perturbing synthetic gene circuits with well-controlled inputs and observing the outputs in high-resolution fashion. However, without the proper "sensors" (i.e., for quantitatively and simultaneously probing all the internal nodes of a given gene circuit), microfluidic technology alone is not sufficient to bring full, engineering-like characterization to synthetic gene networks.

Thus far, probes enabling quantitative measurements of synthetic gene circuits have primarily focused on the transcriptome, such as the use of fluorescent proteins for in vivo quantitation of promoter activity or protein expression. With the advent of novel mass-spectrometry-based methods that provide global, absolute protein concentrations in cells[56], quantitative transcriptome data can now be merged with proteome data, improving our ability to characterize and model the dynamics of synthetic gene networks. Global proteomic data can also assist synthetic biologists in understanding the metabolic burden that artificial circuits place on the cells they inhabit. Further efforts to devise fluorescent-based and other reporters for the simultaneous monitoring of transcriptome and proteome dynamics in vivo are needed to close the loop on full circuit accounting. Some promising tools under development include tracking protein function by incorporating unnatural amino acids that exhibit fluorescence[57, 58], quantum dots[59], and radiofrequency-controlled nanoparticles[60].

As the field awaits entire-circuit probes, there are, in the meantime, several accessible technologies for increasing the throughput and pace of piece-wise gene-circuit characterization. Recent advances in engineering light-inducible biological parts and systems[61-63] have unlocked the potential for optical-based circuit characterization. For instance, by coupling a synthetic gene network of interest to light-inducible systems as well as fluorescent protein outputs, both control and monitoring could be accomplished via the reliable and high-speed optics that are typically associated with fluorescence microscopy. This prospect, particularly in the context of microfluidic devices, can facilitate the focusing of optical inputs and read-outs to single cells.

Using electrical signals, in lieu of chemical or optical signals, for control and monitoring of biological system also present high-speed advantages. Recently, advances have been made in integrating silicon electronics with lipid bilayers containing transmembrane pores to perform electronic signal conduction[64]. This technology can eventually allow direct communication and control between engineered cells and electronic circuits via ionic flow. The incorporation of these and other technologies to perturb and monitor the in vivo performance of synthetic gene networks can enable us to achieve desired functionality faster and more reliably.

Next-Generation Gene Networks

Advancing synthetic gene circuits into the realm of higher-order networks with programmable functionality is one of the ultimate goals of synthetic biology. Described herein are several next-generation gene circuits and their real-world applications.

Whole-Cell Biosensors and Response Systems

Programmable cells that act as whole-cell biosensors have been created by interfacing engineered gene networks with the cell's natural regulatory circuitry[18] or with other biological components such as light-responsive elements[62, 63]. In some aspects, novel or re-engineered sensory modalities and components, such as those described herein, can be developed to expand the range of applications that programmable cells can address. In some embodiments, proteins or RNAs are engineered to detect a range of small molecules[91, 92]. In other embodiments, protein-based synthetic signaling cascades are designed by rationally rewiring protein-protein interactions and output responses of prokaryotic two-component signal transduction systems[93].

The detection of electrical signals or production of biological energy (e.g., mimicking the operation of electrical electrocytes[94]) can also be enabled, in some aspects, by incorporating natural or synthetic ion channels into engineered cells. Additionally, magneto-responsive bacteria can play useful roles in environmental and medical applications, in some aspects[95]. For example, in some embodiments, synthetic bacteria, designed to form magnetosomes and seek out cancer cells, can be used to enhance imaging, and in other embodiments, magnetic bacteria can be engineered to interact with nanoparticles to enhance the targeting of cancer cells. Moreover, in some embodiments, the introduction of mechanosensitive ion channels (such as MscL from *M. tuberculosis* and MscS from *Escherichia coli*) can be used to endow designer cells with the ability to detect mechanical forces[96]. Such cells can be useful in vivo sensors for studying, in some embodiments, cellular differentiation signals or the effects of external stresses on the body.

In some aspects, programmable cells possessing novel sensory modules described herein can be integrated with mechanical, electrical, and chemical systems to detect, process, and respond to external stimuli, and be utilized for a variety of environmental and medical applications. For example, in some embodiments, bacteria can be engineered to seek out hazardous chemicals in the environment, perform cleanup, and return to their origin to report on the number of hazardous sites encountered via analysis by microfluidic devices. To achieve such complex tasks, in some embodiments, chemotactic bacteria can be programmed to swim from waypoint to waypoint. In such an example, a dish containing gradients of several chemoattractants constitutes the navigational course (FIG. 1A).

At the core of this aspect is a synthetic gene network made up of a series of sequential toggle switches that control the expression of receptors needed for bacterial chemotaxis towards chemoattractants[97] (FIG. 1B). In such aspects, the programmable cells initially express only a single chemoattractant receptor, and therefore migrate up only one of the chemoattractant gradients[97]. To determine that a waypoint has been achieved, in some embodiments, a threshold-based toggle switch is turned ON upon reaching a sufficiently high concentration of the chemoattractant. When the first toggle switch is ON, production of the first chemoattractant receptor is suppressed and production of a second receptor allowed, resulting in cells swimming up the second chemical gradient. In some embodiments, the ON switch additionally primes the next toggle switch in the series to be switched ON when the second waypoint is reached. When that second toggle flips ON, the previous switch is flipped OFF to ensure that only one chemoattractant is being followed at a time. The final chemoattractant leads the bacteria back to its origin so that the engineered cells complete a multi-stop round trip.

Analog-to-Digital and Digital-to-Analog Converters

Electrical engineers have utilized digital processing to achieve reliability and flexibility, even though the world in which digital circuits operate is inherently analog. Although synthetic biological circuits are unlikely to match the computing power of digital electronics, circuits inspired by digital and analog electronics can increase the reliability and programmability of biological behaviours.

Figure 3A:
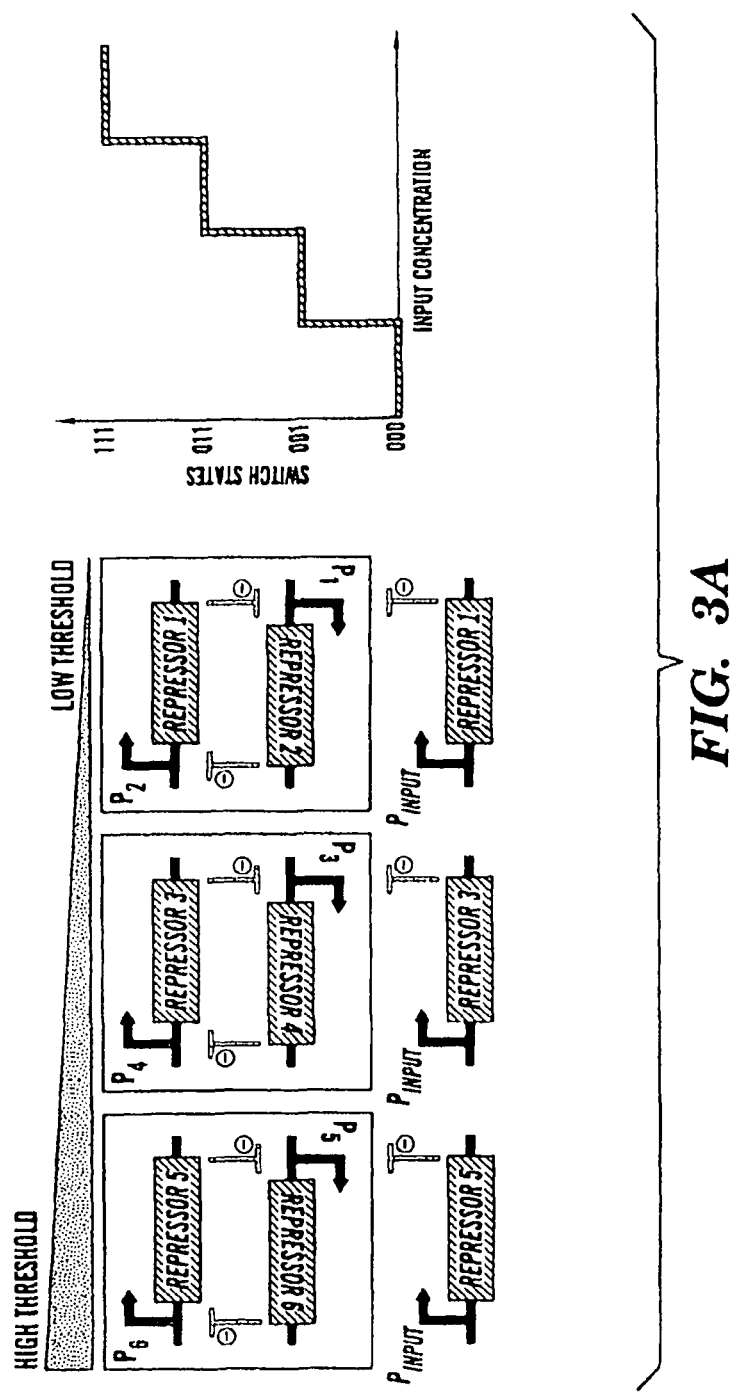
FIGS. 3A-3B depict representative biological converter switches.

In some aspects, biological analog-to-digital converters are provided that translate external analog inputs, such as inducer concentrations or exposure times, into internal digital representations for biological processing. In one embodiment of this aspect, a bank of genetic switches with adjustable thresholds is provided, as depicted in FIG. 3A. In some embodiments, the switches are made out of libraries of artificial transcription factors, as described herein. In such embodiments, discretization of analog inputs into levels of digital output is achieved. In some embodiments, depending on the level of analog inputs received by the biological analog-to-digital converter, different pathways are activated. In some aspects, the biological analog-to-digital converter are used in cells, for use as, for example, biosensors in medical and environmental settings. For example, in one embodiment, whole-cell biosensors[18], resident in the gut, are engineered to generate different reporter molecules depending on the detected level of a physiological input, such as gastrointestinal bleeding, which can be measured in a sample, such as a stool sample. In some embodiments, expressing different reporter molecules rather than a continuous gradient of a single reporter molecule is used to yield more reliable and easily interpretable outputs.

Figure 3B:
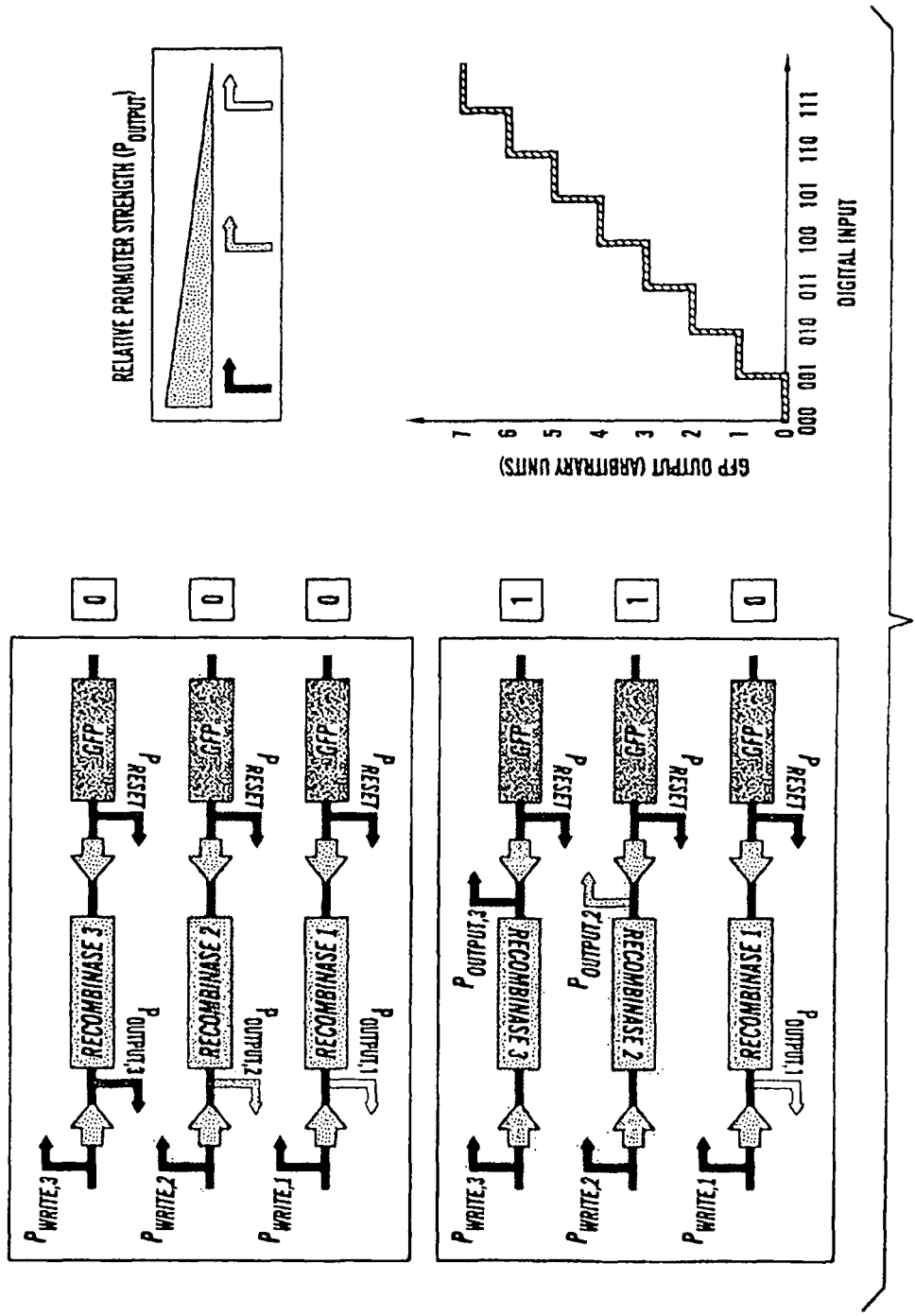

In other aspects, biological digital-to-analog converter switches are provided that translate digital representations back into analog outputs, as represented in FIG. 3B. In some embodiments, such biological digital-to-analog converters are used to reliably set internal system states. For example, in one embodiment, instead of fine-tuning transcriptional activity with varying amounts of chemical inducers, a digital-to-analog converter, composed of a bank of genetic switches, each of which is sensitive to a different inducer, is used to provide better control. If each activated switch enabled transcription from promoters of varying strengths ($P_{output,3} > P_{output,2} > P_{output,1}$), then digital combinations of inducers are used to program defined levels of transcriptional activities, as shown in FIG. 3B. In some aspects, such biological digital-to-analog converter circuits are used in biotechnology applications. For example, in some embodiments, biological digital-to-analog converter circuits are used where reliable expression of different pathways is needed for programming different modes of operation in engineered cells. In other embodiments, digital-to-analog converters can be used for probing synthetic circuits.

Tunable Filters and Noise Generators

Figure 4:
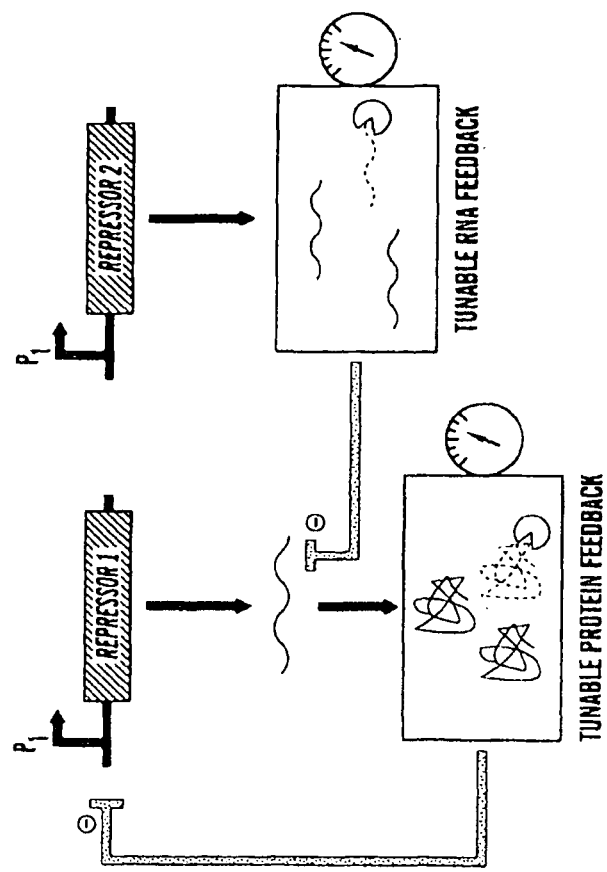
FIG. 4 depicts a tunable genetic filter. Filter characteristics can be adjusted by tuning the degradation of RNA and protein effectors in negative feedback loops. Examples of RNA effectors include small interfering RNAs, riboregulators, and ribozymes. Examples of protein effectors include transcriptional activators and repressors.

Fine-tuning the performance of a synthetic gene network typically means re-engineering its components, be it by replacing or mutating its parts. In some aspects described herein, networks are provided, the responses of which are tuned without re-engineering of their parts, such as, in some embodiments, the biological version of a tunable electronic filter, which enable more sophisticated cellular-based signal processing. Synthetic transcriptional cascades exhibit low-pass filter characteristics[15], and artificial gene circuits with negative autoregulation are capable of pushing the noise spectra of their output to higher frequencies, where it can be filtered by the low-pass characteristics of a downstream gene cascade[65]. In some embodiments, tunable genetic filters with respect to time can be implemented by tuning RNA and/or protein degradation in autoregulated negative feedback circuits, as shown in FIG. 4[53, 66-68]. In certain aspects, these circuits are useful in studying and shaping noise spectra to optimize the performance of artificial gene networks.

Recently, an externally tunable, bacterial bandpass-filter was described[17], which uses low-pass and high-pass filters in series to derive bandpass activity with respect to enzymes and inducer molecules. These types of filters, when coupled, in certain embodiments, to quorum-sensing modules, can be used for spatial patterning applications[16, 17]. In some embodiments, these filters can also be extended to complex multicellular pattern formation, by engineering a suite of different cells, each carrying filters that respond to different inputs. In some embodiments of this aspect, synthetic gene circuits based on tunable filters can be used as platforms for studying cellular differentiation and development, as artificial pattern generation is a model for how natural systems form complex structures[16, 17].

Recent developments in stem cell biology have unlocked important, potential roles for synthetic gene networks[69]. First, it has been shown that stochastic fluctuations in protein expression in embryonic stem cells are important for determining differentiation fates[70]. Stochasticity can be harnessed in differentiation to force population-wide heterogeneity and provide system robustness.

Accordingly, in some embodiments, the effects of stochasticity in stem cell differentiation can be studied with synthetic gene circuits as described herein that act as tunable noise generators. In some embodiments, the mean value and variance of an output can be effectively tuned with two external signals, one for regulating the transcription and the other for regulating the translation of a gene, or in some embodiments, with three external signals, the third for regulating DNA copy number[71]. By varying noise levels while keeping mean expression levels constant, in some embodiments of the aspect, the thresholds at which gene expression noise yields beneficial versus detrimental effects on stem cell differentiation can be elucidated[72].

The discovery of induced pluripotent stem cells (iPSCs), based on the controlled expression of four transcription factors (OCT4, SOX2, KLF2, MYC) in adult fibroblasts, has created a source of patient-specific progenitor cells for engineering[69]. In some aspects, genetic noise generators and basic control circuits are used to dissect the mechanism for inducing pluripotency in differentiated adult cells, by sequentially controlling the mean expression levels of the four iPSC-dependent transcription factors. In some embodiments, timing circuits[27] can be used for higher-efficiency stem cell reprogramming.

Lineage commitment to trophectoderm, ectoderm, mesoderm, and endoderm pathways are controlled by distinct sets of genes[70], and many interacting factors, including growth factors, extracellular matrices and mechanical forces, play important roles in cellular differentiation[73]. Accordingly, in some aspects, synthetic gene cascades can be used to program cellular commitment with increased fidelity, for use in applications in biotechnology and regenerative medicine.

Adaptive Learning Networks

Figure 5A:
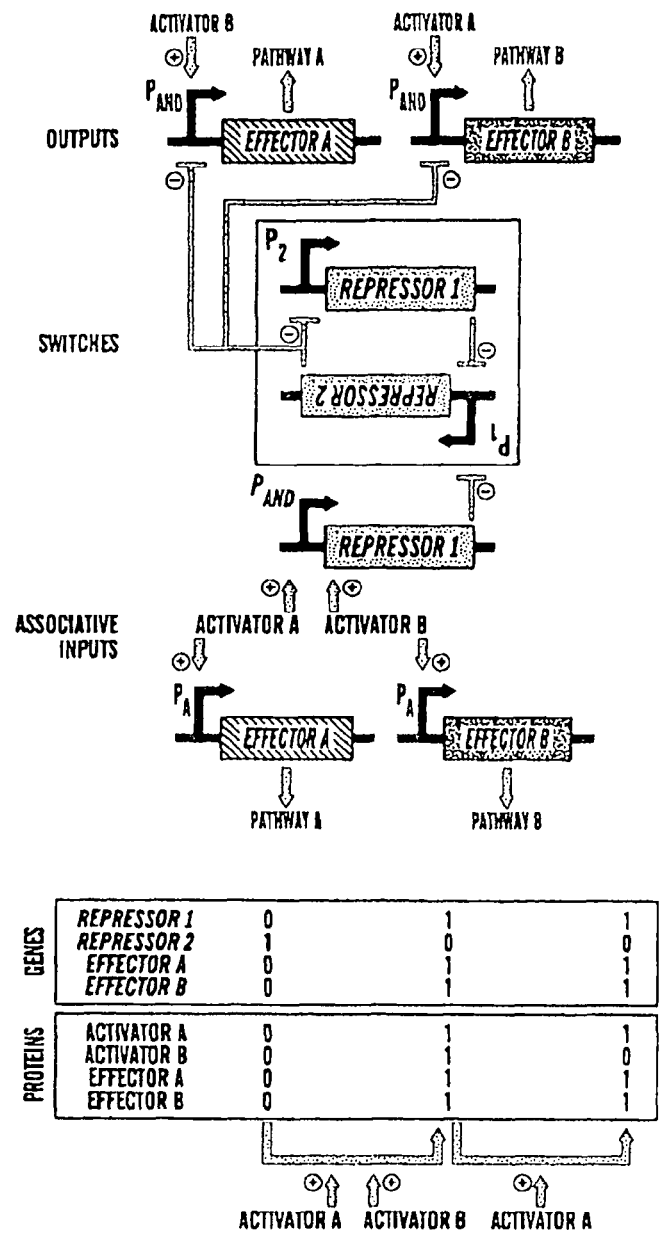
FIG. 5A-5B show exemplary adaptive learning networks.

Endogenous biomolecular networks in bacteria can exhibit anticipatory behaviour for related perturbations in environmental stimuli[74, 75]. This type of behaviour and the associated underlying design principles can, in certain aspects, be harnessed to endow transcriptional networks with the ability to learn[76], much like synaptic interconnections between neurons. In some embodiments, a basic design that enable this functionality involves two transcriptional activators (Activator A and Activator B), each of which is expressed in the presence of a different stimulus (FIG. 5A). In one embodiment, both transcriptional activators drive the expression of effector proteins (Effector A and Effector B), which control distinct genetic pathways. When both transcriptional factors are active, indicating the simultaneous presence of the two stimuli, a toggle switch is flipped ON, creating an associative memory. Subsequently, if either of the transcription factors is activated, AND logic between the ON toggle switch and one transcriptional activator produces the effector protein that controls the pathways of the other activators. Based on such a design, in other aspects and embodiments, cells are programmed to associate simultaneous inputs and exhibit anticipatory behaviour by activating the pathways of associated stimuli, even in, in some embodiments, the presence of only one of the stimuli.

Figure 5B:
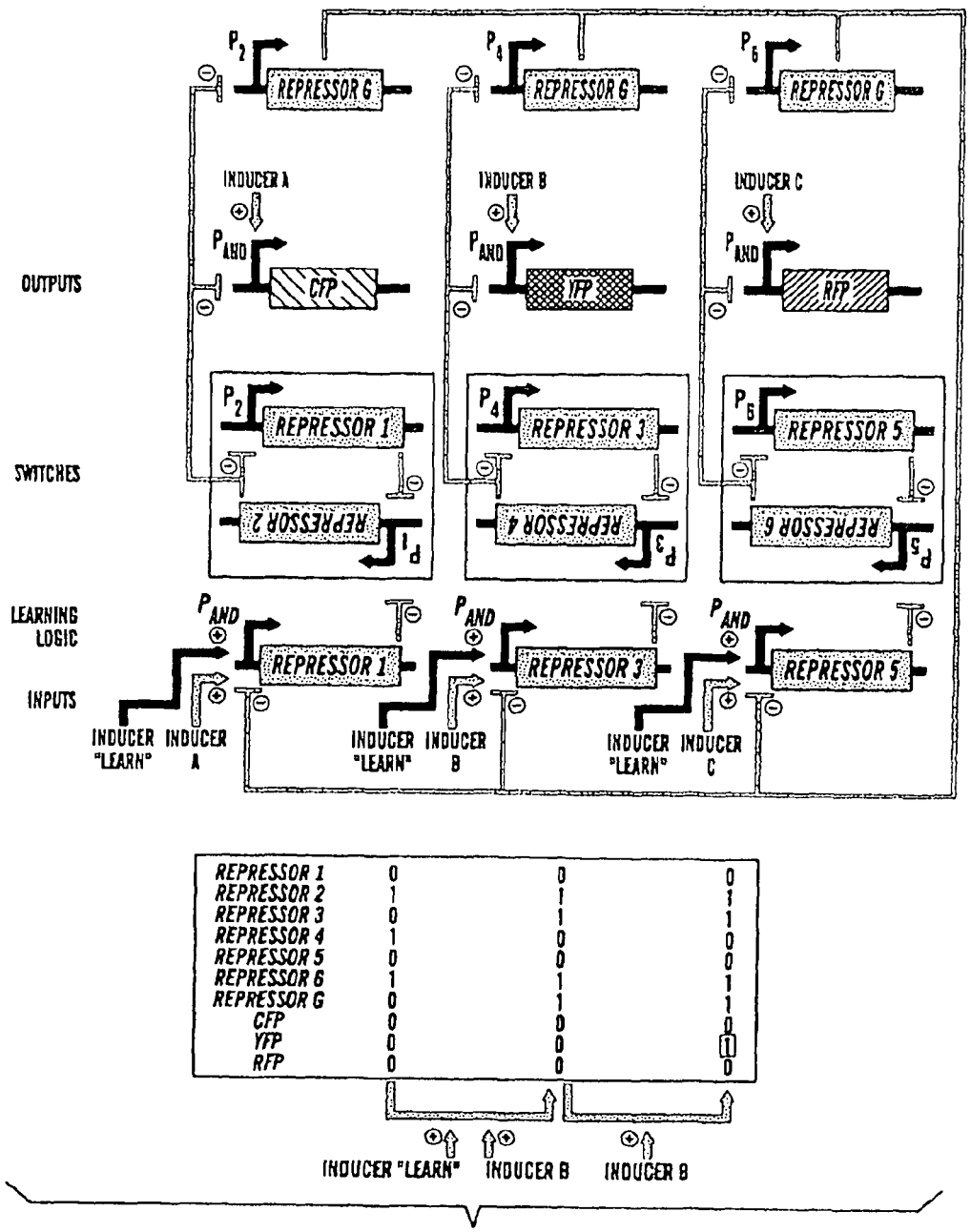

In another aspect of a learning network, bacteria can be engineered that are taught "winner-take-all" behaviour in detecting stimuli, similar to cortical neural processing[77]. In such embodiments, bacteria are exposed to different types of chemical stimuli (Inducers A-C) (FIG. 5B). In some embodiments, an exogenously added inducer (Inducer "Learn") acts as a trigger for learning and serves as one input into multiple, independent transcriptional AND gates, which possess secondary inputs for detecting the presence of each of the different chemical stimuli. Each gate drives an individual toggle switch that, when flipped, suppresses the flipping of the other switches. This creates a winner-take-all system in which the presence of the most abundant chemical stimuli is recorded. Furthermore, in other embodiments, the toggle switch outputs are fed as inputs into transcriptional AND gates, which once again possess secondary inputs for detecting the presence of the different stimuli. If these gates drive different fluorescent reporters when activated, then the overall system associates a single type of stimuli with the learning trigger and responds with an output only in the presence of the single type of stimuli in the future. This system can, in other embodiments, be adapted to make chemotactic bacteria that "remember" a particular location or landmark, and only respond to the gradient of one chemoattractant.

In other aspects of learning networks, synthetic gene circuits are designed to adapt on their own, that is, without external mutagenesis or exogenous nucleic acids. For example, in some embodiments, transcription-based interconnections are dynamically reconfigured based on the expression of DNA recombinases[14]. In another aspect, error-prone RNA polymerases, which create mutant RNAs that can be reverse-transcribed and joined back into the genome, based on double-stranded breaks created by zinc-finger nucleases, are used. Specificity for where the mutations would occur is achieved, in some embodiments, by using promoters that are uniquely read by error-prone RNA polymerases, such as in some embodiments, T7 promoters with a T7 error-prone RNA polymerase, and, in some embodiments, zinc-finger nucleases that define where homologous recombination can occur[78]. In such an aspect, mutagenesis frequency can be targeted to specific regions of the genome.

Protein-Based Computational Circuits

In addition to DNA- and RNA-based circuits, protein-based synthetic systems have the potential to enable flexible and fast computation[79-81]. Protein-based designs can operate on much quicker time scales than genetic circuits because their operation is independent of the transcription and translation machinery. Accordingly, in some aspects described herein, protein-based circuits are described that act as rapidly responding logic gates, smart sensors, or memory elements.

Figure 6A:
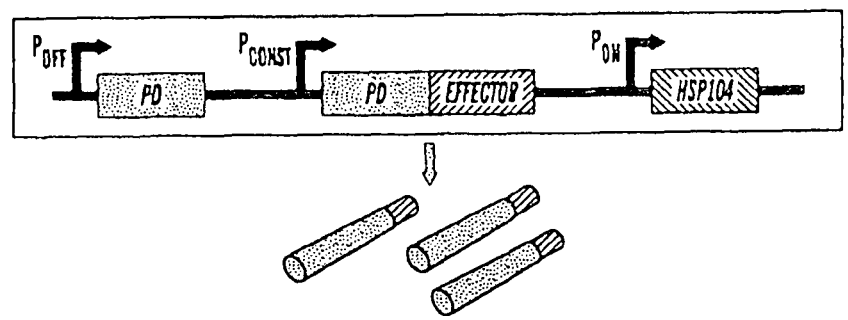
FIGS. 6A-6C shows an amyloid-based memory.
Figure 6B:
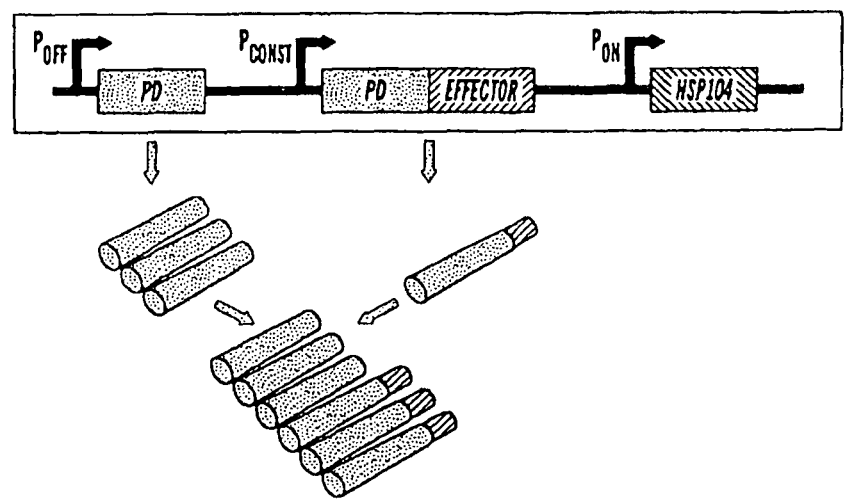
Figure 6C:
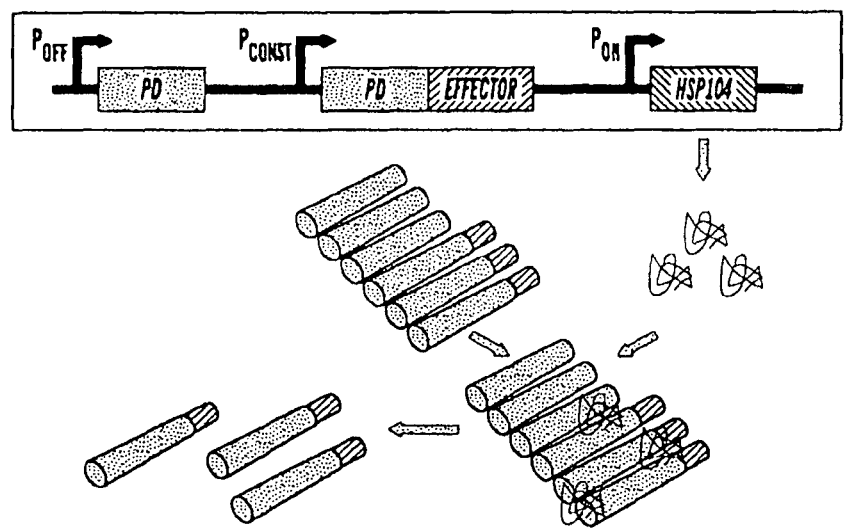

In some embodiments, synthetic amyloids serve as novel components for epigenetic memory circuits. Li and Lindquist demonstrated, by fusing a yeast prion determinant from Sup35 to the rat glucocorticoid receptor, a transcription factor regulated by steroid hormone, that the state of transcriptional activity from the fused protein can be affected and inherited stably in an epigenetic fashion[82]. Given the increasing number of identified prionogenic proteins[83], in some embodiments, amyloid-based memory systems can be created that transmit functionality from one generation to the next (FIG. 6). In some embodiments, aggregation can be induced by the transient overexpression of the prionogenic domain (PD), while, in some embodiments, disaggregation can be achieved by expressing protein remodelling factors such as chaperones (HSP104).

Since genetic (nucleic acid-based) circuits and proteins function on different time scales, in some aspects, synthetic networks that couple both modalities are generated. For example, in some embodiments, the output of protein-based computation can be stored in recombinase-based memory elements[5, 8, 14]. In some embodiments, the two types of networks are coupled to harness their varied filtering capabilities. As a non-limiting example, the mitogen-activated protein kinase cascade contains both positive-feedback and negative-feedback loops that enable rapid activation followed by deactivation[84], thus acting like a high-pass filter. As another non-limiting example, transcription- and translation-based networks operate on slower time scales rendering them effective low-pass filters. Therefore, in some aspects, synthetic kinase/phosphatise circuits that in turn drive gene-based networks are used to design bandpass filters.

Intercell Signaling Circuits and Pulse-Based Processing for Genetic Oscillators

Robust genetic oscillators with tunable periods have been developed via a combination of experimental and computational efforts[10, 11, 86]. In addition to providing design principles guiding the evolution of naturally-occurring biological clocks and circadian rhythms, these synthetic oscillators can have significant utility in biotechnology applications, such as, in some embodiments, optimizing the synthesis and delivery of biologic drugs. As a non-limiting example, glucocorticoid secretion has a circadian and ultradian pattern of release, resulting in transcriptional pulsing in cells that contain glucocorticoid receptors[85]. Therefore, pulsatile administration of synthetic hormones can have therapeutic benefit compared with synthetic hormones applied in a non-ultradian schedule. In some aspects, the biological converter switches described herein can be used as an alternative to electronic-based periodic drug delivery systems. Accordingly, in some embodiments, bacteria that reside in the human gut are engineered to synthesize an active drug at fixed time intervals. In other embodiments, intercell signalling circuits are developed and implemented for synchronizing and entraining synthetic genetic oscillators[87, 88]. Such circuits are based, in some embodiments, on modular components from bacterial quorum sensing systems. In some embodiments, light-sensitive[62, 63] entrainment circuits are engineered for synchronizing mammalian synthetic genetic oscillators. This can aid in the construction of oscillators that can faithfully follow circadian rhythms.

Spike- or pulse-based processing is present in neurons and has been adapted for use in hybrid computation in electrical systems, where interspike times are viewed as analog parameters and spike counts are viewed as digital parameters[89]. In synthetic gene circuits, spike-based processing can be used in novel methods for encoding information in engineered cells. In some embodiments, instead of transmitting information between cells via absolute levels of quorum-sensing molecules, the frequency of a robust genetic oscillator can be modulated. This is useful, for example, in delivering information over longer distances, as frequency information can be less susceptible to decay over distance than absolute molecule levels. Representing signals in this fashion is analogous to frequency modulation encoding in electrical engineering.

Engineered Circuits for Biological Containment

Figure 7:
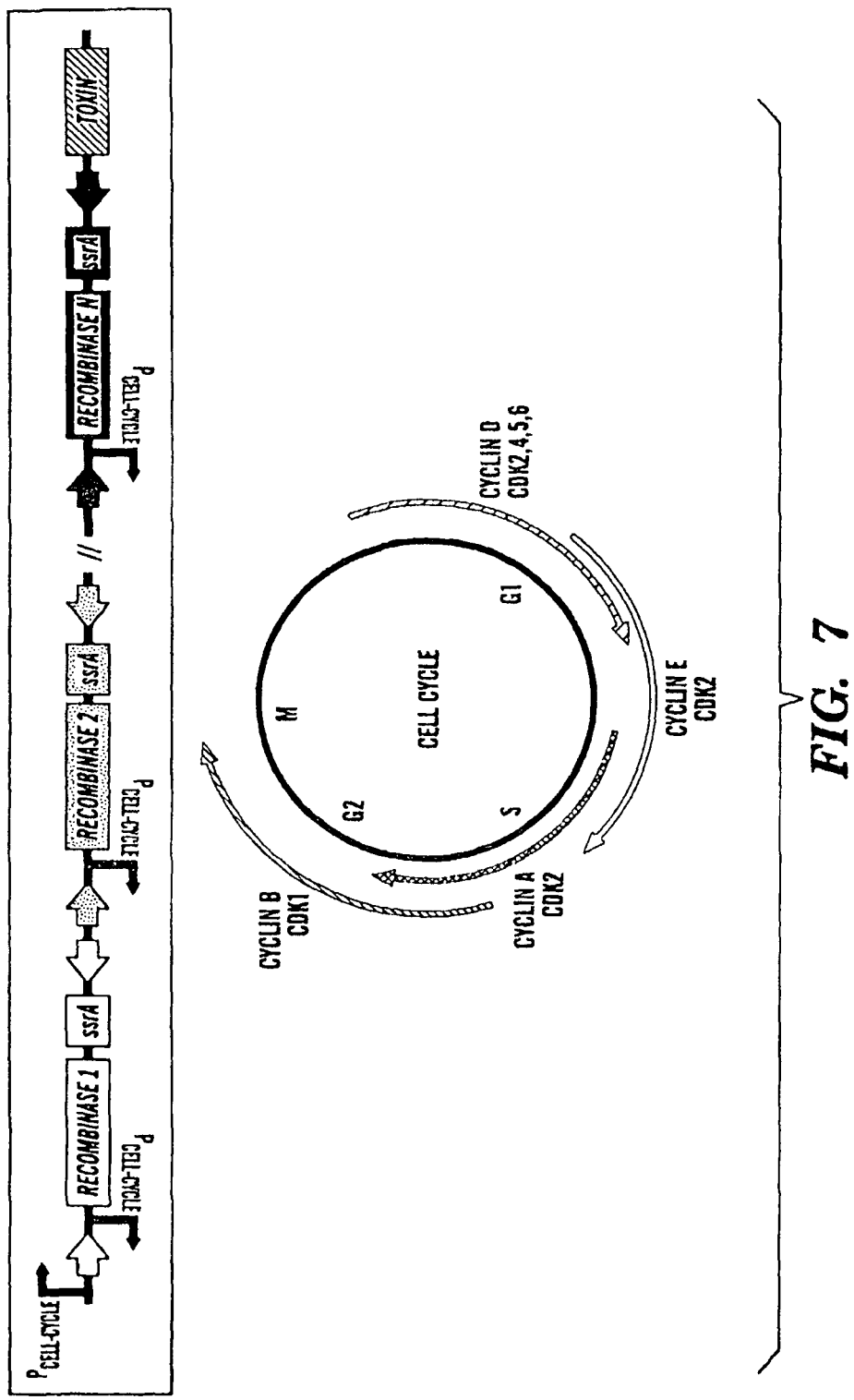
FIG. 7 depicts a cell-cycle counter for biological containment. Cell-cycle counting is accomplished with a cascade of single recombinase-based memory units (e.g., SIMMs), each of which is driven by a cell-cycle-dependent promoter. After N cell-cycle events are counted, the gene circuit unlocks the expression of a toxic protein triggering cell death.

Biological containment can be achieved by passive or active techniques. In aspects related to passive biological containment, cells are engineered to be dependent on exogenous supplementation to compensate for gene defects, while in aspects related to active containment, cells are engineered to directly express toxic compounds when located outside their target environments[90]. Genetic counters or timers for programmed cell death can be used as an active containment tool, in some embodiments. In some embodiments, counting circuits can trigger cell suicide after a defined number of cell cycles or a sequence of events. Recently, we developed two designs for synthetic counters—a recombinase-based cascade of memory units and a riboregulated transcriptional cascade—that can be adapted for this purpose[14]. In some embodiments, promoters that are cell cycle-dependent and replace output reporter proteins with toxic proteins can be incorporated into the counters (FIG. 7). Circuits of this sort enable cells to be programmed to have limited, prescribed lifetimes.

In some aspects, redundant circuits are provided herein that implement digital logic allowing for the conditional survival of engineered cells only within their desired environments, and thus reduce the failure rate of biological containment. By developing a broad set of interoperable parts, in some embodiments, multiple layers of control circuits are built for increased reliability. As in electrical and mechanical engineering, quantitative analysis of failure rates in biological systems enable improved systems-level design and robustness of synthetic gene networks. In some embodiments, synthetic containment circuits can be subjected to stressful conditions that lead to increase mutation rates and improper functioning.

Designer Circuits and Systems for Microbiome Engineering

The human microbiome is fertile ground for the application of engineered organisms as scientific tools and therapeutic agents. There are unique bacterial populations, residing in distinct locations in the human body, that are perturbed in disease states[98, 99]. Each represents an opportunity for re-engineering the human microbiome and designing targeted therapeutics for a range of conditions, including, in some embodiments, dermatologic, genitourinary, gastrointestinal, and immunologic diseases.

Recently, there have been examples in which engineered bacteria were designed to infiltrate cellular communities for the purposes of delivering probes, gene circuits, or chemicals[100, 100]. In a similar fashion, in some aspects, bacteriophages carrying synthetic gene circuits as described herein cab be used to transform existing microbiome bacteria with new functionalities. For example, anaerobic bacteria are known to migrate to hypoxic and necrotic regions of solid tumors[102]. To enhance the specificity of bacterial cancer therapy, in some embodiments, bacteriophages are designed to infect cancer-targeting bacteria. In some embodiments, these bacteriophages encode conditional expression of chemotherapeutic agents using synthetic logic gates or switches, such as ones that are coupled to environmental sensors.

Bhatia and colleagues recently developed nanoparticles that perform Boolean logic based on proteolytic activity[103]. In some aspects, viruses that infect tumor cells or bacteria are used to carry synthetic gene circuits, as described herein, that regulate, in a programmable fashion, the expression of enzymes that trigger nanoparticle activity. In some embodiments, such synthetic gene networks are used in targeted therapies against cancer or infectious diseases that exploit the human microbiome.

Switchboard for Dynamically Controlling the Expression of Multiple Genes

Engineered cells have been used to produce recombinant proteins and chemicals for the biotechnology industry, and one of the major applications of synthetic biology to date has been in enhancing microbial production of biofuels[104] and biomaterials[105-108]. Improving production from cells involves numerous engineering decisions related to the entire organism, including, for example, codon optimization, choosing whether or not to export recombinant proteins[109], rational or evolutionary methods for improving metabolic yields[110], and optimization of growth conditions. Often some or all of the genes required for production are non-optimal for bacterial expression and contain repetitive sequences that are unstable in bacterial hosts. Whole-gene synthesis techniques are increasingly being used to optimize coding sequences for recombinant production[108].

These approaches as well as more traditional knockout techniques, introduce hard-wired changes into the genomes of interest. However, for many industrial and bioprocess applications, for example, there is a need to dynamically modulate and control the expression of multiple genes, depending upon the state of the bioreactor. In some aspects, synthetic switchboards based on the modules, switches and methods described herein can be used. In some embodiments, a synthetic switchboard can tune the expression of many different genes simultaneously and independently. Such a switchboard can comprise, for example, a series of adjustable threshold genetic switches, riboregulators or riboswitches, or a combination thereof, and can be designed to respond, in some embodiments, to different environmental and intracellular variables, such as pH, light intensity, and the metabolic state of the cell. The switchboard design can, in some aspects, integrate novel sensory modalities with tunable, interoperable genetic circuits. Such systems have broad functionality for the biotechnology industry. In some embodiments, a synthetic network is programmed, for example, to shift carbon flux between different pathways depending upon cellular conditions, thereby optimizing the production of biofuels, specialty chemicals, and other materials.

The novel, next-generation synthetic gene networks described herein advance our understanding of natural systems, provide new biological modules and tools allowing for the construction of more complex systems, and satisfy real-world applications in fields such as medicine, biotechnology, bioremediation, and bioenergy.

REFERENCES

1. Gardner, T. S., Cantor, C. R. & Collins, J. J. Construction of a genetic toggle switch in *Escherichia coli*. Nature 403, 339-342 (2000).

2. Elowitz, M. B. & Leibler, S. A synthetic oscillatory network of transcriptional regulators. Nature 403, 335-338 (2000).
3. Isaacs, F. J., Hasty, J., Cantor, C. R. & Collins, J. J. Prediction and measurement of an autoregulatory genetic module. Proc Natl Acad Sci USA 100, 7714-7719 (2003).
4. Kramer, B. P. et al. An engineered epigenetic transgene switch in mammalian cells. Nat Biotechnol 22, 867-870 (2004).
5. Ham, T. S., Lee, S. K., Keasling, J. D. & Arkin, A. P. A tightly regulated inducible expression system utilizing the fim inversion recombination switch. Biotechnol Bioeng 94, 1-4 (2006).
6. Deans, T. L., Cantor, C. R. & Collins, J. J. A tunable genetic switch based on RNAi and repressor proteins for regulating gene expression in mammalian cells. Cell 130, 363-372 (2007).
7. Ajo-Franklin, C. M. et al. Rational design of memory in eukaryotic cells. Genes Dev 21, 2271-2276 (2007).
8. Ham, T. S., Lee, S. K., Keasling, J. D. & Arkin, A. P. Design and construction of a double inversion recombination switch for heritable sequential genetic memory. PLoS ONE 3, e2815 (2008).
9. Fung, E. et al. A synthetic gene-metabolic oscillator. Nature 435, 118-122 (2005).
10. Stricker, J. et al. A fast, robust and tunable synthetic gene oscillator. Nature 456, 516-519 (2008).
11. Tigges, M., Marquez-Lago, T. T., Stelling, J. & Fussenegger, M. A tunable synthetic mammalian oscillator. Nature 457, 309-312 (2009).
12. Rinaudo, K. et al. A universal RNAi-based logic evaluator that operates in mammalian cells. Nat Biotechnol 25, 795-801 (2007).
13. Win, M. N. & Smolke, C. D. Higher-order cellular information processing with synthetic RNA devices. Science 322, 456-460 (2008).
14. Friedland, A. E. et al. Synthetic gene networks that count. Science 324, 1199-1202 (2009).
15. Hooshangi, S., Thiberge, S. & Weiss, R. Ultrasensitivity and noise propagation in a synthetic transcriptional cascade. Proc Natl Acad Sci USA 102, 3581-3586 (2005).
16. Basu, S., Gerchman, Y., Collins, C. H., Arnold, F. H. & Weiss, R. A synthetic multicellular system for programmed pattern formation. Nature 434, 1130-1134 (2005).
17. Sohka, T. et al. An externally tunable bacterial band-pass filter. Proc Natl Acad Sci USA 106, 10135-10140 (2009).
18. Kobayashi, H. et al. Programmable cells: interfacing natural and engineered gene networks. Proc Natl Acad Sci USA 101, 8414-8419 (2004).
19. Bayer, T. S. & Smolke, C. D. Programmable ligand-controlled riboregulators of eukaryotic gene expression. Nat Biotechnol 23, 337-343 (2005).
20. Win, M. N. & Smolke, C. D. A modular and extensible RNA-based gene-regulatory platform for engineering cellular function. Proc Natl Acad Sci USA 104, 14283-14288 (2007).
21. Anderson, J. C., Clarke, E. J., Arkin, A. P. & Voigt, C. A. Environmentally controlled invasion of cancer cells by engineered bacteria. J Mol Biol 355, 619-627 (2006).
22. Lu, T. K. & Collins, J. J. Dispersing biofilms with engineered enzymatic bacteriophage. Proc Natl Acad Sci USA 104, 11197-11202 (2007).
23. Lu, T. K. & Collins, J. J. Engineered bacteriophage targeting gene networks as adjuvants for antibiotic therapy. Proc Natl Acad Sci USA 106, 4629-4634 (2009).
24. Ro, D. K. et al. Production of the antimalarial drug precursor artemisinic acid in engineered yeast. Nature 440, 940-943 (2006).
25. Guido, N. J. et al. A bottom-up approach to gene regulation. Nature 439, 856-860 (2006).
26. Shetty, R. P., Endy, D. & Knight, T. F., Jr. Engineering BioBrick vectors from BioBrick parts. J Biol Eng 2, 5 (2008).
27. Ellis, T., Wang, X. & Collins, J. J. Diversity-based, model-guided construction of synthetic gene networks with predicted functions. Nat Biotechnol 27, 465-471 (2009).
28. Czar, M. J., Cai, Y. & Peccoud, J. Writing DNA with GenoCAD. Nucleic Acids Res 37, W40-47 (2009).
29. Kitano, H. Biological robustness. Nat Rev Genet 5, 826-837 (2004).
30. Wang, H. H. et al. Programming cells by multiplex genome engineering and accelerated evolution. Nature 460, 894-898 (2009).
31. Purnick, P. E. & Weiss, R. The second wave of synthetic biology: from modules to systems. Nat Rev Mol Cell Biol 10, 410-422 (2009).
32. Jensen, P. R. & Hammer, K. Artificial promoters for metabolic optimization. Biotechnol Bioeng 58, 191-195 (1998).
33. Alper, H., Fischer, C., Nevoigt, E. & Stephanopoulos, G Tuning genetic control through promoter engineering. Proc Natl Acad Sci USA 102, 12678-12683 (2005).
34. Hammer, K., Mijakovic, I. & Jensen, P. R. Synthetic promoter libraries—tuning of gene expression. Trends Biotechnol 24, 53-55 (2006).
35. Cox, R. S., 3rd, Surette, M. G. & Elowitz, M. B. Programming gene expression with combinatorial promoters. Mol Syst Biol 3, 145 (2007).
36. Isaacs, F. J. et al. Engineered riboregulators enable post-transcriptional control of gene expression. Nat Biotechnol 22, 841-847 (2004).
37. Win, M. N., Liang, J. C. & Smolke, C. D. Frameworks for programming biological function through RNA parts and devices. Chem Biol 16, 298-310 (2009).
38. Rackham, O. & Chin, J. W. A network of orthogonal ribosome×mRNA pairs. Nat Chem Biol 1, 159-166 (2005).
39. Wang, K., Neumann, H., Peak-Chew, S. Y. & Chin, J. W. Evolved orthogonal ribosomes enhance the efficiency of synthetic genetic code expansion. Nat Biotechnol 25, 770-777 (2007).
40. An, W. & Chin, J. W. Synthesis of orthogonal transcription-translation networks. Proc Natl Acad Sci USA 106, 8477-8482 (2009).
41. Wang, Q., Parrish, A. R. & Wang, L. Expanding the genetic code for biological studies. Chem Biol 16, 323-336 (2009).
42. Maeder, M. L. et al. Rapid "open-source" engineering of customized zinc-finger nucleases for highly efficient gene modification. Mol Cell 31, 294-301 (2008).
43. Beerli, R. R., Dreier, B. & Barbas, C. F., 3rd Positive and negative regulation of endogenous genes by designed transcription factors. Proc Natl Acad Sci USA 97, 1495-1500 (2000).
44. Park, K. S. et al. Phenotypic alteration of eukaryotic cells using randomized libraries of artificial transcription factors. Nat Biotechnol 21, 1208-1214 (2003).
45. Canton, B., Labno, A. & Endy, D. Refinement and standardization of synthetic biological parts and devices. Nat Biotechnol 26, 787-793 (2008).
46. Svoboda, K. & Block, S. M. Biological applications of optical forces. Annu Rev Biophys Biomol Struct 23, 247-285 (1994).

47. Bustamante, C., Bryant, Z. & Smith, S. B. Ten years of tension: single-molecule DNA mechanics. Nature 421, 423-427 (2003).
48. Khalil, A. S. et al. Single M13 bacteriophage tethering and stretching. Proc Natl Acad Sci USA 104, 4892-4897 (2007).
49. Neuman, K. C. & Nagy, A. Single-molecule force spectroscopy: optical tweezers, magnetic tweezers and atomic force microscopy. Nat Methods 5, 491-505 (2008).
50. Khalil, A. S. et al. Kinesin's cover-neck bundle folds forward to generate force. Proc Natl Acad Sci USA 105, 19247-19252 (2008).
51. Lee, S. K. et al. Directed evolution of AraC for improved compatibility of arabinose- and lactose-inducible promoters. Appl Environ Microbiol 73, 5711-5715 (2007).
52. Gulati, S. et al. Opportunities for microfluidic technologies in synthetic biology. J R Soc Interface 6 Suppl 4, S493-506 (2009).
53. Simpson, M. L., Cox, C. D. & Sayler, G. S. Frequency domain analysis of noise in autoregulated gene circuits. Proc Natl Acad Sci USA 100, 4551-4556 (2003).
54. Mettetal, J. T., Muzzey, D., Gomez-Uribe, C. & van Oudenaarden, A. The frequency dependence of osmo-adaptation in *Saccharomyces cerevisiae*. Science 319, 482-484 (2008).
55. Bennett, M. R. et al. Metabolic gene regulation in a dynamically changing environment. Nature 454, 1119-1122 (2008).
56. Malmstrom, J. et al. Proteome-wide cellular protein concentrations of the human pathogen *Leptospira interrogans*. Nature 460, 762-765 (2009).
57. Summerer, D. et al. A genetically encoded fluorescent amino acid. Proc Natl Acad Sci USA 103, 9785-9789 (2006).
58. Wang, J., Xie, J. & Schultz, P. G. A genetically encoded fluorescent amino acid. J Am Chem Soc 128, 8738-8739 (2006).
59. Michalet, X. et al. Quantum dots for live cells, in vivo imaging, and diagnostics. Science 307, 538-544 (2005).
60. Hamad-Schifferli, K., Schwartz, J. J., Santos, A. T., Zhang, S. & Jacobson, J. M. Remote electronic control of DNA hybridization through inductive coupling to an attached metal nanocrystal antenna. Nature 415, 152-155 (2002).
61. Boyden, E. S., Zhang, F., Bamberg, E., Nagel, G. & Deisseroth, K. Millisecond-timescale, genetically targeted optical control of neural activity. Nat Neurosci 8, 1263-1268 (2005).
62. Levskaya, A. et al. Synthetic biology: engineering *Escherichia coli* to see light. Nature 438, 441-442 (2005).
63. Levskaya, A., Weiner, O. D., Lim, W. A. & Voigt, C. A. Spatiotemporal control of cell signalling using a light-switchable protein interaction. Nature (2009).
64. Misra, N. et al. Bioelectronic silicon nanowire devices using functional membrane proteins. Proc Natl Acad Sci USA 106, 13780-13784 (2009).
65. Austin, D. W. et al. Gene network shaping of inherent noise spectra. Nature 439, 608-611 (2006).
66. Mar, D. J., Chow, C. C., Gerstner, W., Adams, R. W. & Collins, J. J. Noise shaping in populations of coupled model neurons. Proc Natl Acad Sci USA 96, 10450-10455 (1999).
67. McGinness, K. E., Baker, T. A. & Sauer, R. T. Engineering controllable protein degradation. Mol Cell 22, 701-707 (2006).
68. Banaszynski, L. A., Chen, L. C., Maynard-Smith, L. A., Ooi, A. G. & Wandless, T. J. A rapid, reversible, and tunable method to regulate protein function in living cells using synthetic small molecules. Cell 126, 995-1004 (2006).
69. Takahashi, K. et al. Induction of pluripotent stem cells from adult human fibroblasts by defined factors. Cell 131, 861-872 (2007).
70. Macarthur, B. D., Ma'ayan, A. & Lemischka, I. R. Systems biology of stem cell fate and cellular reprogramming. Nat Rev Mol Cell Biol (2009).
71. Lu, T., Ferry, M., Weiss, R. & Hasty, J. A molecular noise generator. Phys Biol 5, 36006 (2008).
72. Blake, W. J. et al. Phenotypic consequences of promoter-mediated transcriptional noise. Mol Cell 24, 853-865 (2006).
73. Discher, D. E., Mooney, D. J. & Zandstra, P. W. Growth factors, matrices, and forces combine and control stem cells. Science 324, 1673-1677 (2009).
74. Tagkopoulos, I., Liu, Y. C. & Tavazoie, S. Predictive behavior within microbial genetic networks. Science 320, 1313-1317 (2008).
75. Mitchell, A. et al. Adaptive prediction of environmental changes by microorganisms. Nature 460, 220-224 (2009).
76. Fernando, C. T. et al. Molecular circuits for associative learning in single-celled organisms. J R Soc Interface 6, 463-469 (2009).
77. Lee, D. K., Itti, L., Koch, C. & Braun, J. Attention activates winner-take-all competition among visual filters. Nat Neurosci 2, 375-381 (1999).
78. Brakmann, S. & Grzeszik, S. An error-prone T7 RNA polymerase mutant generated by directed evolution. Chembiochem 2, 212-219 (2001).
79. Yeh, B. J., Rutigliano, R. J., Deb, A., Bar-Sagi, D. & Lim, W. A. Rewiring cellular morphology pathways with synthetic guanine nucleotide exchange factors. Nature 447, 596-600 (2007).
80. Dueber, J. E., Mirsky, E. A. & Lim, W. A. Engineering synthetic signaling proteins with ultrasensitive input/output control. Nat Biotechnol 25, 660-662 (2007).
81. Bashor, C. J., Heiman, N. C., Yan, S. & Lim, W. A. Using engineered scaffold interactions to reshape MAP kinase pathway signaling dynamics. Science 319, 1539-1543 (2008).
82. Li, L. & Lindquist, S. Creating a protein-based element of inheritance. Science 287, 661-664 (2000).
83. Alberti, S., Halfmann, R., King, O., Kapila, A. & Lindquist, S. A systematic survey identifies prions and illuminates sequence features of prionogenic proteins. Cell 137, 146-158 (2009).
84. Bhalla, U. S., Ram, P. T. & Iyengar, R. MAP kinase phosphatase as a locus of flexibility in a mitogen-activated protein kinase signaling network. Science 297, 1018-1023 (2002).
85. Stavreva, D. A. et al. Ultradian hormone stimulation induces glucocorticoid receptor-mediated pulses of gene transcription. Nat Cell Biol 11, 1093-1102 (2009).
86. Tsai, T. Y. et al. Robust, tunable biological oscillations from interlinked positive and negative feedback loops. Science 321, 126-129 (2008).
87. McMillen, D., Kopell, N., Hasty, J. & Collins, J. J. Synchronizing genetic relaxation oscillators by intercell signaling. Proc Natl Acad Sci USA 99, 679-684 (2002).
88. Garcia-Ojalvo, J., Elowitz, M. B. & Strogatz, S. H. Modeling a synthetic multicellular clock: repressilators coupled by quorum sensing. Proc Natl Acad Sci USA 101, 10955-10960 (2004).

89. Sarpeshkar, R. & O'Halloran, M. Scalable hybrid computation with spikes. Neural Comput 14, 2003-2038 (2002).
90. Molin, S. et al. Suicidal genetic elements and their use in biological containment of bacteria. Annu Rev Microbiol 47, 139-166 (1993).
91. Looger, L. L., Dwyer, M. A., Smith, J. J. & Hellinga, H. W. Computational design of receptor and sensor proteins with novel functions. Nature 423, 185-190 (2003).
92. Win, M. N., Klein, J. S. & Smolke, C. D. Codeine-binding RNA aptamers and rapid determination of their binding constants using a direct coupling surface plasmon resonance assay. Nucleic Acids Res 34, 5670-5682 (2006).
93. Skerker, J. M. et al. Rewiring the specificity of two-component signal transduction systems. Cell 133, 1043-1054 (2008).
94. Xu, J. & Lavan, D. A. Designing artificial cells to harness the biological ion concentration gradient. Nat Nanotechnol 3, 666-670 (2008).
95. Jogler, C. & Schuler, D. Genomics, genetics, and cell biology of magnetosome formation. Annu Rev Microbiol 63, 501-521 (2009).
96. Booth, I. R., Edwards, M. D., Black, S., Schumann, U. & Miller, S. Mechanosensitive channels in bacteria: signs of closure? Nat Rev Microbiol 5, 431-440 (2007).
97. Falke, J. J., Bass, R. B., Butler, S. L., Chervitz, S. A. & Danielson, M. A. The two-component signaling pathway of bacterial chemotaxis: a molecular view of signal transduction by receptors, kinases, and adaptation enzymes. Annu Rev Cell Dev Biol 13, 457-512 (1997).
98. Gao, Z., Tseng, C. H., Strober, B. E., Pei, Z. & Blaser, M. J. Substantial alterations of the cutaneous bacterial biota in psoriatic lesions. PLoS One 3, e2719 (2008).
99. Grice, E. A. et al. Topographical and temporal diversity of the human skin microbiome. Science 324, 1190-1192 (2009).
100. Steidler, L. et al. Treatment of murine colitis by *Lactococcus* lactis secreting interleukin-10. Science 289, 1352-1355 (2000).
101. Braat, H. et al. A phase I trial with transgenic bacteria expressing interleukin-10 in Crohn's disease. Clin Gastroenterol Hepatol 4, 754-759 (2006).
102. Wei, M. Q., Mengesha, A., Good, D. & Anne, J. Bacterial targeted tumour therapy-dawn of a new era. Cancer Lett 259, 16-27 (2008).
103. von Maltzahn, G. et al. Nanoparticle self-assembly gated by logical proteolytic triggers. J Am Chem Soc 129, 6064-6065 (2007).
104. Stephanopoulos, G. Challenges in engineering microbes for biofuels production. Science 315, 801-804 (2007).
105. Slotta, U. et al. Spider silk and amyloid fibrils: a structural comparison. Macromol Biosci 7, 183-188 (2007).
106. Rammensee, S., Slotta, U., Scheibel, T. & Bausch, A. R. Assembly mechanism of recombinant spider silk proteins. Proc Natl Acad Sci USA 105, 6590-6595 (2008).
107. Teule, F. et al. A protocol for the production of recombinant spider silk-like proteins for artificial fiber spinning. Nat Protoc 4, 341-355 (2009).
108. Widmaier, D. M. et al. Engineering the *Salmonella* type III secretion system to export spider silk monomers. Mol Syst Biol 5, 309 (2009).
109. Choi, J. H. & Lee, S. Y. Secretory and extracellular production of recombinant proteins using *Escherichia coli*. Appl Microbiol Biotechnol 64, 625-635 (2004).
110. Klein-Marcuschamer, D. & Stephanopoulos, G. Assessing the potential of mutational strategies to elicit new phenotypes in industrial strains. Proc Natl Acad Sci USA 105, 2319-2324 (2008).

We claim:

1. A biological circuit chemotactic converter composition comprising:
   at least one input module $(IM)_n$ nucleic acid comprising an inducible promoter nucleic acid sequence $(iP_A)$ operably linked to a repressor nucleic acid sequence encoding a repressor protein $(R_A)$;
   at least one genetic toggle switch $(T_S)$ n nucleic acid comprising a first repressible promoter nucleic acid sequence $(rP_1)$ that drives expression of a second repressor nucleic acid sequence $(R_2)$ encoding a second repressor protein, and a second repressible promoter nucleic acid sequence $(rP_2)$ that drives expression of a first repressor nucleic acid sequence $(R_1)$ encoding a first repressor protein, $(rP_1-R_2$ and $rP_2-R_1)$, wherein the $rP_1$ is inhibited by the first repressor protein and the $rP_2$ is inhibited by the second repressor protein and wherein $R_A$ of at least one input module acts as a repressor for $rP_1$ of at least one genetic toggle switch;
   at least one logic module $(L_M)_n$ nucleic acid consisting essentially of a repressible promoter nucleic acid sequence $(rP_B)$ operably linked to a repressor nucleic acid sequence $(R_B)$, wherein $rP_B$ is inhibited by the second repressor protein of at least one genetic toggle switch; and
   at least two sensor module $(SM_A$ and $SM_B)_{n+1}$ nucleic acids, wherein each of the two sensor module nucleic acids comprises a repressible promoter nucleic acid sequence $(rP_C$ and $rP_D$, respectively) operably linked to a nucleic acid sequence encoding a sensor molecule (sensor A and sensor B) and wherein n ≥1; wherein the repressible promoter nucleic acid sequence of at least one sensor module is repressed by the repressor protein encoded by at least one logic module, and the repressible promoter nucleic acid sequence of another of the at least two sensor modules is directly repressed by the second repressor protein encoded by at least one genetic toggle switch; and wherein if no input signal is received by the at least one input module nucleic acids, only sensor A is expressed, and wherein if an input signal is received by at least one input module nucleic acid, then sensor A is not expressed; and
   wherein the repressor proteins encoded by any of the logic module nucleic acid sequences are different from the repressor proteins encoded by any of the at least one input module nucleic acid sequences and are different from the repressor proteins encoded by any of the at least one genetic toggle switch nucleic acid sequences.

2. The biological circuit chemotactic converter composition of claim 1, wherein the inducible promoter nucleic acid sequence of the input module is induced by a biological agent, a chemical agent, a metal ion, a toxin, light or a pollutant.

3. The biological circuit chemotactic converter composition of claim 1, wherein the repressor protein encoded by the first repressor nucleic acid sequence of the toggle switch $(R_1)$ and the repressor protein encoded by the input module $(R_A)$ nucleic acid sequence are the same repressor protein.

4. The biological circuit chemotactic converter composition of claim 1, wherein the second repressible promoter nucleic acid sequence of the genetic toggle switch $(rP_2)$, the repressible promoter nucleic acid sequence of the logic module $(rP_B)$, and the repressible promoter nucleic acid sequence of one sensor module $(rP_D)$ are repressed by the same repressor protein.

5. The biological circuit chemotactic converter composition of claim 1, wherein the second repressible promoter nucleic acid sequence of the genetic toggle switch $(rP_2)$, the repressible promoter nucleic acid sequence of the logic module (rP$_B$), and the repressible promoter nucleic acid sequence of one sensor module (rP$_D$) comprise the same repressible promoter nucleic acid sequence.

6. The biological circuit chemotactic converter composition of claim 1, wherein the repressible promoter nucleic acid sequence of one sensor module (rP$_C$) is repressed by the repressor encoded by the logic module (R$_B$) nucleic acid sequence.

7. The biological circuit chemotactic converter composition of claim 1, wherein the at least two sensor module nucleic acids encode for different sensor molecules.

8. The biological circuit chemotactic converter composition of claim 1, wherein n is an integer value between and including 1 and 100.

9. The biological circuit chemotactic converter composition of claim 1, further comprising at least one ribosome binding nucleic acid sequence.

10. The biological circuit chemotactic converter of claim 1, further comprising at least one terminator nucleic acid sequence.

11. The biological circuit chemotactic converter composition of claim 1, further comprising at least one degradation nucleic acid tag sequence.

12. The biological circuit chemotactic converter of composition claim 1, further comprising at least one nucleic acid sequence encoding an iRNA molecule specific for at least one protein encoded by the biological circuit chemotactic converter.

13. The biological circuit chemotactic converter composition of claim 1, wherein at least one repressor protein is an engineered zinc-finger protein.

14. The biological circuit chemotactic converter composition of claim 1, where the promoter nucleic acid sequence of the inducible and repressible promoters is selected from any of the promoter sequences of SEQ ID NOs: 1-7, SEQ ID NOs: 167-843, and SEQ ID NOs: 1009-1010.

15. The biological circuit chemotactic converter composition of claim 1, where the sensor molecule encoded by the nucleic acid sequence of the sensor domain is a chemotaxis receptor or chemotaxis sensor.

16. An isolated cell comprising the biological circuit chemotactic converter nucleic acid composition of claim 1.

17. The cell of claim 16, wherein the cell is an artificial cell, a prokaryotic cell, or a eukaryotic cell.

18. The cell of claim 16 comprising two or more biological circuit chemotactic converter nucleic acid compositions of claim 1 acting together.

19. A vector comprising the biological circuit chemotactic converter nucleic acid composition of claim 1.

20. A biological circuit chemotactic converter composition comprising the circuit depicted in FIG. 1B, the content of which is herein incorporated by reference in its entirety.

* * * * *

SEQUENCE LISTING

```
<160> NUMBER OF SEQ ID NOS: 1010

<210> SEQ ID NO 1
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcatgctccc tatcagtgat agagattgac atccctatca gtgatagaga tactgagcac      60
atcagcagga cgcactgacc agga                                              84

<210> SEQ ID NO 2
<211> LENGTH: 286
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
aagaaaccaa ttgtccatat tgcatcagac attgccgtca ctgcgtcttt tactggctct      60
tctcgctaac caaaccggta accccgctta ttaaaagcat tctgtaacaa agcgggacca     120
aagccatgac aaaaacgcgt aacaaagtg tctataatca cggcagaaaa gtccacattg     180
```

```
attatttgca cggcgtcaca ctttgctatg ccatagcatt tttatccata agattagcgg    240
atcctacctg acgcttttta tcgcaactct ctactgtttc tccata                  286
```

<210> SEQ ID NO 3
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

```
ccatcgaatg gctgaaatga gctgttgaca attaatcatc cggctcgtat aatgtgtgga    60
attgtgagcg gataacaatt tcacacagga                                     90
```

<210> SEQ ID NO 4
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
ataaatgtga gcggataaca ttgacattgt gagcggataa caagatactg agcactcagc    60
aggacgcact gacc                                                      74
```

<210> SEQ ID NO 5
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
aaaatttatc aaaagagtg ttgacttgtg agcggataac aatgatactt agattcaatt     60
gtgagcggat aacaatttca caca                                           84
```

<210> SEQ ID NO 6
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
catagcattt ttatccataa gattagcgga tcctaagctt tacaattgtg agcgctcaca    60
attatgatag attcaattgt gagcggataa caatttcaca ca                       102
```

<210> SEQ ID NO 7
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
gcatgcacag ataaccatct gcggtgataa attatctctg gcggtgttga cataaatacc    60
actggcggtt ataatgagca catcagcagg gtatgcaaag ga                       102
```

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 8
ataacttcgt atagcataca ttatacgaag ttat                              34

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 9
ataacttcgt ataatgtatg ctatacgaag ttat                              34

<210> SEQ ID NO 10
<211> LENGTH: 1272
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 10

| | | |
|---|---|---|
| atgagccaat tgatatatt atgtaaaaca ccacctaagg tcctggttcg tcagtttgtg | 60 |
| gaaaggtttg aaagaccttc aggggaaaaa atagcatcat gtgctgctga actaacctat | 120 |
| ttatgttgga tgattactca taacggaaca gcaatcaaga gagccacatt catgagctat | 180 |
| aatactatca taagcaattc gctgagtttc gatattgtca acaaatcact ccagtttaaa | 240 |
| tacaagacgc aaaaagcaac aattctggaa gcctcattaa agaaattaat tcctgcttgg | 300 |
| gaatttacaa ttattcctta caatggacaa aaacatcaat ctgatatcac tgatattgta | 360 |
| agtagtttgc aattacagtt cgaatcatcg gaagaagcag ataagggaaa tagccacagt | 420 |
| aaaaaaatgc ttaaagcact tctaagtgag ggtgaaagca tctgggagat cactgagaaa | 480 |
| atactaaatt cgtttgagta tacctcgaga tttacaaaaa caaaaacttt ataccaattc | 540 |
| ctcttcctag ctactttcat caattgtgga agattcagcg atattaagaa cgttgatccg | 600 |
| aaaatcattta aattagtcca aaataagtat ctgggagtaa taatccagtg tttagtgaca | 660 |
| gagacaaaga caagcgttag taggcacata tacttcttta gcgcaagggg taggatcgat | 720 |
| ccacttgtat atttggatga attttgagg aactctgaac cagtcctaaa acgagtaaat | 780 |
| aggaccggca attcttcaag caacaaacag gaataccaat tattaaaaga taacttagtc | 840 |
| agatcgtaca caaggctttt gaagaaaaat gcgccttatc caatctttgc tataaagaat | 900 |
| ggcccaaaat ctcacattgg aagacatttg atgacctcat ttctgtcaat gaagggccta | 960 |
| acggagttga ctaatgttgt gggaaattgg agcgataagc gtgcttctgc cgtggccagg | 1020 |
| acaacgtata ctcatcagat aacagcaata cctgatcact acttcgcact agtttctcgg | 1080 |
| tactatgcat atgatccaat atcaaaggaa atgatagcat tgaaggatga gactaatcca | 1140 |
| attgaggagt ggcagcatat agaacagcta aagggtagtg ctgaaggaag catacgatac | 1200 |
| cccgcatgga atgggataat atcacaggag gtactagact acctttcatc ctacataaat | 1260 | agacgcatat aa                                                        1272

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gaagttccta ttccgaagtt cctattctct agaaagtata ggaacttc                   48

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gaagttccta ttctctagaa agtataggaa cttc                                  34

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttgatgaaag aatacgttat tctttcatca a                                     31

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aatacaagac aattggggcc aaactgtcca tatcat                                36

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctctatgagt caaaatggcc ccaaatgttt catcttttg                             39

<210> SEQ ID NO 16
<211> LENGTH: 603
<212> TYPE: DNA
<213> ORGANISM: Escherichia coli

<400> SEQUENCE: 16
atgaagaata aggctgataa caaaaaaagg aacttcctga cccatagtga atcgaatca        60 ctccttaaag cagcaaatac cgggcctcat gcagcacgta attattgtct gactttgctt      120

```
tgttttattc atggtttccg ggcgagtgaa atttgtcgat tgaggatttc ggatattgat    180
cttaaggcaa agtgtatata tatccatcga ttaaaaaaag gcttttcaac aacgcacccg    240
ctattgaata aagaagttca ggctttaaaa aactggttga gtatccgtac ttcgtacccg    300
catgctgaga gcgagtgggt atttttatca cgtaagggga atccgctttc tcggcaacag    360
ttttaccata ttatctcgac ttccggtggt aatgccgggt tgtcactgga gattcatccg    420
cacatgttac gccattcgtg tggttttgct ttggcgaata tgggaataga tacgcgactt    480
atccaggatt atcttgggca tcgcaatatt cgtcatactg tctggtatac cgccagcaat    540
gcagggcgtt tttacggcat ctgggataga gccagaggac gacagcgtca cgctgtttta    600
tag                                                                 603
```

<210> SEQ ID NO 17
<211> LENGTH: 597
<212> TYPE: DNA
<213> ORGANISM: Escherichia coli

<400> SEQUENCE: 17

```
gtgagtaaac gtcgttatct taccggtaaa gaagttcagg ccatgatgca ggcggtttgt     60
tacggggcaa cgggagccag agattattgt cttattctgt tggcatatcg gcatgggatg    120
cgtattagtg aactgcttga tctgcattat caggaccttg accttaatga aggtagaata    180
aatattcgcc gactgaagaa cggattttct accgttcacc cgttacgttt tgatgagcgt    240
gaagccgtgg aacgctggac ccaggaacgt gctaactgga aaggcgctga ccggactgac    300
gctatattta tttctcgccg cgggagtcgg ctttctcgcc agcaggccta tcgcattatt    360
cgcgatgccg gtattgaagc tggaaccgta acgcagactc atcctcatat gttaaggcat    420
gcttgcggtt atgaattggc ggagcgtggt gcagatactc gtttaattca ggattatctc    480
gggcatcgaa atattcgcca tactgtgcgt tataccgcca gtaatgctgc tcgttttgcc    540
ggattatggg aaagaaataa tctcataaac gaaaaattaa aaagagaaga ggtttga       597
```

<210> SEQ ID NO 18
<211> LENGTH: 912
<212> TYPE: DNA
<213> ORGANISM: Yersinia pseudotuberculosis

<400> SEQUENCE: 18

```
atgaccgagt tcagtgcttc actggctcca caggtagagg cttttctccg ttatctcagt     60
attgagcgtc agcttagtcc actgaccgtc accagttatc gccgtcagtt gtctgcgcta    120
atggaaatag gcgaacagat gggcttggct cactggcaga cgctggatgc tgctcaggtc    180
cgttcgttgg tctcccgcag caaacgtgcg ggtttacatg cttcaagcct ggcattacgg    240
ctctccgcat tacgcagttt tctcaactgg ttggtcagcc agggcgtgct gccagccaac    300
cccgctaaag ggggtcagtac gccacgctcg ggccgccacc tgccaaaaaa tattgatgtt    360
gatgaagtca ataaactgct gagtattgat ctgaatgatc cgctggcggt acgtgaccgg    420
gccatgctgg aggtgatgta cggcgcgggg ctgcgtttat ctgaattggt tggcatgaac    480
tgtaaacatg tggatctggc gagcggcgat gtctgggtga tggggaaggg cagtaaagag    540
cgcaaggtgc cgttaggtaa aacggcggtg acctggttac agcattggct ggcgttacgt    600
gagttattcg aaccgcaaga tgacgctatt tttctggcca ataccggcaa gcgtatttca    660
gcccgtaatg tgcagaagcg ctttgccgaa tggggggtga agcagggggt cagtagccac    720
attcacccac ataaattacg tcactctttt gccacgcaca tgctggaatc cagtggtgat    780
```

```
ctacgcgcag tacaagagct actgggccat gccaacctga ccaccacgca aatttataca    840
catctcgact ttcaacatct ggcgacagtg tatgatgctg ctcatccacg ggccaaacga    900
ggcaaatcct ga                                                        912

<210> SEQ ID NO 19
<211> LENGTH: 573
<212> TYPE: DNA
<213> ORGANISM: Salmonella enterica

<400> SEQUENCE: 19
atggctacta ttgggtatat tcgggtgtca acaattgacc aaaatatcga tttacagcgt     60
aatgcgctta ctagtgcaaa ttgtgaccgc atttttgagg accgtatcag tggcaagatt    120
gcaaaccgcc ccggcctgaa acgagcgtta aagtatgtaa ataaaggcga tactcttgtc    180
gtctggaaat tagacagact gggccgcagc gtgaaaaacc tggtggcgtt aatatcagaa    240
ttacatgaac gtggagctca cttccattct ttaaccgata gtattgatac cagtagcgcg    300
atggggcgat tcttttttca tgtaatgtca gcactggccg agatggagcg agaattaatt    360
gtcgagcgaa cccttgccgg actggctgcc gccagagcgc aaggacgact gggagggcgc    420
cctcgggcga tcaacaaaca tgaacaggaa cagattagtc ggctattaga gaaaggccat    480
cctcggcagc aactagctat tattttggt attggcgtat ctaccttata cagatatttt    540
ccggcaagcc gcataaaaaa acgaatgaat taa                                 573

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ataacttcgt atagtataca ttatacgaag ttat                                 34

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
acaacttcgt ataatgtatg ctatacgaag ttat                                 34

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cttggtatag catacattat acgaacggta                                      30

<210> SEQ ID NO 23
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 23
gttcgtatac gatacattat acgaagttat                                              30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cttcgtataa tgtatgctat acgaagttat                                              30

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gaagttccta ttctctagaa agtataggaa cttc                                         34

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aggaggaaaa aaatg                                                              15

<210> SEQ ID NO 27
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aggaatttaa atg                                                                13

<210> SEQ ID NO 28
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aggaaacaga ccatg                                                              15

<210> SEQ ID NO 29
<211> LENGTH: 17
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 29
aggaaaccgg ttcgatg                                                    17

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aggaaaccgg ttatg                                                      15

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aggacggttc gatg                                                       14

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aggaaaggcc tcgatg                                                     16

<210> SEQ ID NO 33
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aggacggccg gatg                                                       14

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Pro Ala Ala Asn Asp Glu Asn Tyr Ala Leu Ala Ala
1               5                   10

<210> SEQ ID NO 35
<211> LENGTH: 13
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 35

Arg Pro Ala Ala Asn Asp Glu Asn Tyr Ala Leu Val Ala
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Pro Ala Ala Asn Asp Glu Asn Tyr Ala Ala Ala Val
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Pro Ala Ala Asn Asp Glu Asn Tyr Ala Ala Ser Val
1               5                   10

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcagcaaacg acgaaaacta cgctttagca gcttaa                                 36

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcagcaaacg acgaaaacta cgctgcagca gtttaa                                 36

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gcagcaaacg acgaaaacta cgctgcatca gtttaa                                 36

<210> SEQ ID NO 41
<211> LENGTH: 30
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 41
gtttatacat aggcgagtac tctgttatgg                                      30

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
agaggttcca actttcacca taatgaaaca                                      30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
taaacaacta acggacaatt ctacctaaca                                      30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
acatcaagcc aaattaaaca ggattaacac                                      30

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gaggtaaaat agtcaacacg cacggtgtta                                      30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
caggccggaa taactcccta taatgcgcca                                      30

<210> SEQ ID NO 47
<211> LENGTH: 30
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 47
ggctagctca gtcctaggta cagtgctagc                                    30

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
agctagctca gtcctaggta ttatgctagc                                    30

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
agctagctca gtcctaggta ctgtgctagc                                    30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
agctagctca gtcctaggga ttatgctagc                                    30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agctagctca gtcctaggta ttgtgctagc                                    30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggctagctca gtcctaggta ctatgctagc                                    30

<210> SEQ ID NO 53
<211> LENGTH: 30
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 53
ggctagctca gtcctaggta tagtgctagc                                           30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ggctagctca gccctaggta ttatgctagc                                           30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
agctagctca gtcctaggta taatgctagc                                           30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
agctagctca gtcctaggga ctgtgctagc                                           30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggctagctca gtcctaggta caatgctagc                                           30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ggctagctca gtcctaggta tagtgctagc                                           30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
agctagctca gtcctaggga ttatgctagc                                              30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ggctagctca gtcctaggga ttatgctagc                                              30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ggctagctca gtcctaggta caatgctagc                                              30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
agctagctca gcccttggta caatgctagc                                              30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
agctagctca gtcctaggga ctatgctagc                                              30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
agctagctca gtcctaggga ttgtgctagc                                              30

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 65
ggctagctca gtcctaggta ttgtgctagc                                    30

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
agctagctca gtcctaggta taatgctagc                                    30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggctagctca gtcctaggta ttatgctagc                                    30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ggctagctca gtcctaggta caatgctagc                                    30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aaagtgtgac gccgtgcaaa taatcaatgt                                    30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gacgaatact taaaatcgtc atacttattt                                    30

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 71
aaacctttcg cggtatggca tgatagcgcc                                      30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tgatagcgcc cggaagagag tcaattcagg                                      30

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ttatttaccg tgacgaacta attgctcgtg                                      30

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
catacgccgt tatacgttgt ttacgctttg                                      30

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ttatgcttcc ggctcgtatg ttgtgtggac                                      30

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ttatgcttcc ggctcgtatg gtgtgtggac                                      30

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77

```
atatatatat atatataatg gaagcgtttt                               30
```

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78

```
atatatatat atatataatg gaagcgtttt                               30
```

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79

```
ccccgaaagc ttaagaatat aattgtaagc                               30
```

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80

```
ccccgaaagc ttaagaatat aattgtaagc                               30
```

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81

```
tgacaatata tatatatata taatgctagc                               30
```

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82

```
acaatatata tatatatata taatgctagc                               30
```

<210> SEQ ID NO 83
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aatatatata tatatatata taatgctagc                                            30

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tatatatata tatatatata taatgctagc                                            30

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tatatatata tatatatata taatgctagc                                            30

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aaaaaaaaaa aaaaaaaata taatgctagc                                            30

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
aaaaaaaaaa aaaaaaaata taatgctagc                                            30

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
caccttcggg tgggcctttc tgcgtttata                                            30

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
caccttcggg tgggcctttc tgcgtttata                                            30

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
caccttcggg tgggcctttc tgcgtttata                                          30

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
caccttcggg tgggcctttc tgcgtttata                                          30

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ggctagctca gtcctaggta cagtgctagc                                          30

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tgctagctac tagagattaa agaggagaaa                                          30

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
cctgttttta tgttattctc tctgtaaagg                                          30

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aaatatttgc ttatacaatc ttcctgtttt                                          30

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gctgataaac cgatacaatt aaaggctcct                                        30

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ctcttctcag cgtcttaatc taagctatcg                                        30

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
atgagccagt tcttaaaatc gcataaggta                                        30

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ctattgattg tgacaaaata aacttattcc                                        30

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gtttcgcgct tggtataatc gctgggggtc                                        30

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ctttgcttct gactataata gtcagggtaa                                        30

```
<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aaaccgatac aattaaaggc tcctgctagc                                          30

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gccggaataa ctccctataa tgcgccacca                                          30

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gccggaataa ctccctataa tgcgccacca                                          30

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ttgacaagct tttcctcagc tccgtaaact                                          30

<210> SEQ ID NO 106
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ttgacagcta gctcagtcct aggtataatg ctagc                                    35

<210> SEQ ID NO 107
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ttgacggcta gctcagtcct aggtacagtg ctagc                                    35

<210> SEQ ID NO 108
```

```
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tttacagcta gctcagtcct aggtattatg ctagc                              35

<210> SEQ ID NO 109
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ttgacagcta gctcagtcct aggtactgtg ctagc                              35

<210> SEQ ID NO 110
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ctgatagcta gctcagtcct agggattatg ctagc                              35

<210> SEQ ID NO 111
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ttgacagcta gctcagtcct aggtattgtg ctagc                              35

<210> SEQ ID NO 112
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tttacggcta gctcagtcct aggtactatg ctagc                              35

<210> SEQ ID NO 113
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tttacggcta gctcagtcct aggtatagtg ctagc                              35

<210> SEQ ID NO 114
<211> LENGTH: 35
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tttacggcta gctcagccct aggtattatg ctagc                               35

<210> SEQ ID NO 115
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ctgacagcta gctcagtcct aggtataatg ctagc                               35

<210> SEQ ID NO 116
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tttacagcta gctcagtcct agggactgtg ctagc                               35

<210> SEQ ID NO 117
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tttacggcta gctcagtcct aggtacaatg ctagc                               35

<210> SEQ ID NO 118
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ttgacggcta gctcagtcct aggtatagtg ctagc                               35

<210> SEQ ID NO 119
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ctgatagcta gctcagtcct agggattatg ctagc                               35

<210> SEQ ID NO 120
<211> LENGTH: 35
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 120
ctgatggcta gctcagtcct agggattatg ctagc                              35

<210> SEQ ID NO 121
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tttatggcta gctcagtcct aggtacaatg ctagc                              35

<210> SEQ ID NO 122
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
tttatagcta gctcagccct tggtacaatg ctagc                              35

<210> SEQ ID NO 123
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ttgacagcta gctcagtcct agggactatg ctagc                              35

<210> SEQ ID NO 124
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ttgacagcta gctcagtcct agggattgtg ctagc                              35

<210> SEQ ID NO 125
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ttgacggcta gctcagtcct aggtattgtg ctagc                              35

<210> SEQ ID NO 126
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 126
ggtttcaaaa ttgtgatcta tatttaacaa                                    30

<210> SEQ ID NO 127
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ggtttcaaaa ttgtgatcta tatttaacaa                                    30

<210> SEQ ID NO 128
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tctattccaa taaagaaatc ttcctgcgtg                                    30

<210> SEQ ID NO 129
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
aaaaatgggc tcgtgttgta caataaatgt                                    30

<210> SEQ ID NO 130
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
aaaaaaagcg cgcgattatg taaaatataa                                    30

<210> SEQ ID NO 131
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
atccttatcg ttatgggtat tgtttgtaat                                    30

<210> SEQ ID NO 132
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 132
taaaagaatt gtgagcggga atacaacaac                                              30

<210> SEQ ID NO 133
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
aaaaaaagcg cgcgattatg taaaatataa                                              30

<210> SEQ ID NO 134
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tacaaaataa ttcccctgca aacattatca                                              30

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tacaaaataa ttcccctgca aacattatcg                                              30

<210> SEQ ID NO 136
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
agggaataca agctacttgt tcttttttgca                                             30

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
taatacgact cactataggg aga                                                     23

<210> SEQ ID NO 138
<211> LENGTH: 28
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 138
gaatttaata cgactcacta tagggaga                                              28

<210> SEQ ID NO 139
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
taatacgact cactatagg                                                        19

<210> SEQ ID NO 140
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gagtcgtatt aatacgactc actatagggg                                            30

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
agtgagtcgt actacgactc actatagggg                                            30

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gagtcgtatt aatacgactc tctatagggg                                            30

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
taatacgact cactataggg aga                                                   23

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ttatacgact cactataggg aga                                              23

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gaatacgact cactataggg aga                                              23

<210> SEQ ID NO 146
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
taatacgtct cactataggg aga                                              23

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
tcatacgact cactataggg aga                                              23

<210> SEQ ID NO 148
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
taatacgact cactataggg agaccacaac                                       30

<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
taattgaact cactaaaggg agaccacagc                                       30

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
cgaagtaata cgactcacta ttagggaaga                              30

<210> SEQ ID NO 151
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
atttaggtga cactataga                                          19

<210> SEQ ID NO 152
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
acaaacacaa atacacacac taaattaata                              30

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ccaagcatac aatcaactat ctcatataca                              30

<210> SEQ ID NO 154
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gatacaggat acagcggaaa caacttttaa                              30

<210> SEQ ID NO 155
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tttcaagcta taccaagcat acaatcaact                              30

<210> SEQ ID NO 156
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
cctttgcagc ataaattact atacttctat					30

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
cctttgcagc ataaattact atacttctat					30

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
cctttgcagc ataaattact atacttctat					30

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cctttgcagc ataaattact atacttctat					30

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cctttgcagc ataaattact atacttctat					30

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ttatctactt tttacaacaa atataaaaca					30

<210> SEQ ID NO 162
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
acaaacacaa atacacacac taaattaata        30

<210> SEQ ID NO 163
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gtttcgaata aacacacata aacaaacaaa        30

<210> SEQ ID NO 164
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
accatcaaag gaagctttaa tcttctcata        30

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
agaacccact gcttactggc ttatcgaaat        30

<210> SEQ ID NO 166
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ggccgttttt ggcttttttg ttagacgaag        30

<210> SEQ ID NO 167
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tgttatagtc gaatacctct ggcggtgata        30

<210> SEQ ID NO 168
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ttttggtaca ctccctatca gtgatagaga        30

-continued

<210> SEQ ID NO 169
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169 cttttttggta cactacctct ggcggtgata                                      30

<210> SEQ ID NO 170
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tacgcaagaa aatggtttgt tatagtcgaa                                       30

<210> SEQ ID NO 171
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
cgtgcgtgtt gataacaccg tgcgtgttga                                       30

<210> SEQ ID NO 172
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
agattgtact aaatcgtata atgacagtga                                       30

<210> SEQ ID NO 173
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gtgttgatgc ttttatcacc gccagtggta                                       30

<210> SEQ ID NO 174
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
agtgtgtgga attgtgagcg gataacaatt                                       30

<210> SEQ ID NO 175
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
acatcttaaa agttttagta tcatattcgt                                      30

<210> SEQ ID NO 176
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tacgcaagaa aatggtttgt tatagtcgaa                                      30

<210> SEQ ID NO 177
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177 atcctcctttt agtcttcccc ctcatgtgtg                                     30

<210> SEQ ID NO 178
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
taaaattatg aaatttgcat aaattcttca                                      30

<210> SEQ ID NO 179
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gtgttgacta ttttacctct ggcggtgata                                      30

<210> SEQ ID NO 180
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
gaaatctggc agtttttggt acacgaaagc                                      30

```
<210> SEQ ID NO 181
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
acaccgtgcg tgttgatata gtcgaataaa                                          30

<210> SEQ ID NO 182
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
aaaattatga aatttgtata aattcttcag                                          30

<210> SEQ ID NO 183
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ggttcttttt ggtacctctg gcggtgataa                                          30

<210> SEQ ID NO 184
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tgtaggatcg tacaggtata aattcttcag                                          30

<210> SEQ ID NO 185
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
caagaaaatg gtttgttata gtcgaataaa                                          30

<210> SEQ ID NO 186
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ctatctcatt tgctagtata gtcgaataaa                                          30

<210> SEQ ID NO 187
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tagtttataa tttaagtgtt ctttaatttc                                        30

<210> SEQ ID NO 188
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
caccttcggg tgggcctttc tgcgtttata                                        30

<210> SEQ ID NO 189
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
aataactctg atagtgctag tgtagatctc                                        30

<210> SEQ ID NO 190
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
caccttcggg tgggcctttc tgcgtttata                                        30

<210> SEQ ID NO 191
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
caccttcggg tgggcctttc tgcgtttata                                        30

<210> SEQ ID NO 192
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ttgacacctg taggatcgta caggtataat                                        30

<210> SEQ ID NO 193
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
caagaaaatg gtttgttata gtcgaataaa                                          30

<210> SEQ ID NO 194
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
cacgcaaaac ttgcgacaaa caataggtaa                                          30

<210> SEQ ID NO 195
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gttagctttc gaattggcta aaaagtgttc                                          30

<210> SEQ ID NO 196
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ccattctgct ttccacgaac ttgaaaacgc                                          30

<210> SEQ ID NO 197
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ggccgcgggt tcttttggt acacgaaagc                                           30

<210> SEQ ID NO 198
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
aagaaaatgg tttgttgata ctcgaataaa                                          30

<210> SEQ ID NO 199
<211> LENGTH: 30
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 199
gaaaaccttg tcaatgaaga gcgatctatg            30

<210> SEQ ID NO 200
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 200
ttctcgttcg actcatagct gaacacaaca            30

<210> SEQ ID NO 201
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 201
atgacaaaat tgtcat            16

<210> SEQ ID NO 202
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 202
accaatgctg ggaacggcca gggcacctaa            30

<210> SEQ ID NO 203
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 203
ctgaaagcgc ataccgctat ggaggggtt            30

<210> SEQ ID NO 204
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 204
tagatatgcc tgaaagcgca taccgctatg            30

<210> SEQ ID NO 205
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 205
agggaataca agctacttgt tcttttttgca                                         30

<210> SEQ ID NO 206
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
taatacgact cactataggg aga                                                 23

<210> SEQ ID NO 207
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
gaatttaata cgactcacta tagggaga                                            28

<210> SEQ ID NO 208
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
taatacgact cactatagg                                                      19

<210> SEQ ID NO 209
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
atttaggtga cactataga                                                      19

<210> SEQ ID NO 210
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
gagtcgtatt aatacgactc actataggggg                                          30

<210> SEQ ID NO 211
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 211
agtgagtcgt actacgactc actatagggg                                        30

<210> SEQ ID NO 212
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gagtcgtatt aatacgactc tctatagggg                                        30

<210> SEQ ID NO 213
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
taatacgact cactataggg aga                                               23

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
ttatacgact cactataggg aga                                               23

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gaatacgact cactataggg aga                                               23

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
taatacgtct cactataggg aga                                               23

<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 217
tcatacgact cactataggg aga                                              23

<210> SEQ ID NO 218
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218 atagggaat tgtgagcgga taacaattcc                                        30

<210> SEQ ID NO 219
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219 atagggaat tgtgagcgga taacaattcc                                        30

<210> SEQ ID NO 220
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220 atagggaat tgtgagcgga taacaattcc                                        30

<210> SEQ ID NO 221
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221 atagggaat tgtgagcgga taacaattcc                                        30

<210> SEQ ID NO 222
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
taatacgact cactataggg agaccacaac                                       30

<210> SEQ ID NO 223
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
taattgaact cactaaaggg agaccacagc                                             30

<210> SEQ ID NO 224
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
cgaagtaata cgactcacta ttagggaaga                                             30

<210> SEQ ID NO 225
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
ttgtgagcgg ataacaagat actgagcaca                                             30

<210> SEQ ID NO 226
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
ttgtgagcgg ataacaattc tgaagaacaa                                             30

<210> SEQ ID NO 227
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ttgtgagcgg ataacaattc tgataaaaca                                             30

<210> SEQ ID NO 228
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
ttgtgagcgg ataacatcta accctttaga                                             30

<210> SEQ ID NO 229
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ttgtgagcgg ataacatagc agataagaaa                                          30

<210> SEQ ID NO 230
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gtttgagcga gtaacgccga aaatcttgca                                          30

<210> SEQ ID NO 231
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gtgtgagcga gtaacgacga aaatcttgca                                          30

<210> SEQ ID NO 232
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
tttgagcgag taacagccga aaatcttgca                                          30

<210> SEQ ID NO 233
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tgtgagcgag taacagccga aaatcttgca                                          30

<210> SEQ ID NO 234
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ttgtgagcga gtggcaccat taagtacgta                                          30

<210> SEQ ID NO 235
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ttgtgagcga gtgacaccat taagtacgta                                              30

<210> SEQ ID NO 236
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
ttgtgagcga gtaacaccat taagtacgta                                              30

<210> SEQ ID NO 237
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
ttgtgagcga gtaacaccat taagtacgta                                              30

<210> SEQ ID NO 238
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
cagtgagcga gtaacaacta cgctgtttta                                              30

<210> SEQ ID NO 239
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
cagtgagcga gtaacaacta cgctgtttta                                              30

<210> SEQ ID NO 240
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
atgtgagcgg ataacactat aattaataga                                              30

<210> SEQ ID NO 241
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
atgtgagcgg ataacactat aattaataga                                      30

<210> SEQ ID NO 242
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
gaattgtgag cggataacaa ttggatccgg                                      30

<210> SEQ ID NO 243
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ggaattgtga gcgctcacaa ttggatccgg                                      30

<210> SEQ ID NO 244
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ggaattgtaa gcgcttacaa ttggatccgg                                      30

<210> SEQ ID NO 245
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ggaattgtaa acgtttacaa ttggatccgg                                      30

<210> SEQ ID NO 246
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ggaattgtga acgttcacaa ttggatccgg                                      30

<210> SEQ ID NO 247
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
ggaattttga gcgctcaaaa ttggatccgg                                      30

<210> SEQ ID NO 248
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
ggaattatga gcgctcataa ttggatccgg                                       30

<210> SEQ ID NO 249
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gggacgactg tatacagtcg tcggatccgg                                       30

<210> SEQ ID NO 250
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ggaattgtga gcgcttacaa ttggatccgg                                       30

<210> SEQ ID NO 251
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
ggaattgtga gcgctcataa ttggatccgg                                       30

<210> SEQ ID NO 252
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
ggaattgtga gctacagtcg tcggatccgg                                       30

<210> SEQ ID NO 253
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
ggaattgtaa gcgctcacaa ttggatccgg                                       30

<210> SEQ ID NO 254
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ggaattgtaa gcgttcacaa ttggatccgg                                            30

<210> SEQ ID NO 255
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
ggaattgtaa gcgctcataa ttggatccgg                                            30

<210> SEQ ID NO 256
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
ggaattgtaa gctacagtcg tcggatccgg                                            30

<210> SEQ ID NO 257
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
ggaattgtga acgctcataa ttggatccgg                                            30

<210> SEQ ID NO 258
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
ggaattgtga actacagtcg tcggatccgg                                            30

<210> SEQ ID NO 259
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
ggaattatga gcgctcacaa ttggatccgg                                            30

```
<210> SEQ ID NO 260
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ggaattgtga gcgctcataa ttggatccgg                                          30

<210> SEQ ID NO 261
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
ggaattgtga gctacagtcg tcggatccgg                                          30

<210> SEQ ID NO 262
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
ggaattgtga acgctcataa ttggatccgg                                          30

<210> SEQ ID NO 263
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ggaattgtga actacagtcg tcggatccgg                                          30

<210> SEQ ID NO 264
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
taaattgtga acgctcataa ttggatccgg                                          30

<210> SEQ ID NO 265
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gaaattgtaa gcgcttacaa ttggatccgg                                          30

<210> SEQ ID NO 266
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
gaaattgtaa gcgcttacaa ttggatccgg                                      30

<210> SEQ ID NO 267
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ggaattgtaa gcgcttacaa ttggatccgg                                      30

<210> SEQ ID NO 268
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
gccaaattaa acaggattaa caggatccgg                                      30

<210> SEQ ID NO 269
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gccaaattaa acaggattaa caggatccgg                                      30

<210> SEQ ID NO 270
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
gccaaattaa acaggattaa caggatccgg                                      30

<210> SEQ ID NO 271
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gccaaattaa acaggattaa caggatccgg                                      30

<210> SEQ ID NO 272
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
gccaaattaa acaggattaa caggatccgg                                     30

<210> SEQ ID NO 273
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
gccaaattaa acaggattaa caggatccgg                                     30

<210> SEQ ID NO 274
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gccaaattaa acaggattaa caggatccgg                                     30

<210> SEQ ID NO 275
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gaaattgtaa gcgcttacaa ttggatccgg                                     30

<210> SEQ ID NO 276
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
taaattgtaa gcgcttacaa ttggatccgg                                     30

<210> SEQ ID NO 277
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
gtaattgtaa gcgcttacaa ttggatccgg                                     30

<210> SEQ ID NO 278
<211> LENGTH: 30
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 278
tcaattgtaa gcgcttacaa ttggatccgg                                30

<210> SEQ ID NO 279
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
aaaattgtaa gcgcttacaa ttggatccgg                                30

<210> SEQ ID NO 280
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
caaattgtaa gcgcttacaa ttggatccgg                                30

<210> SEQ ID NO 281
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
gaaattgtaa gcgcttacaa ttggatccgg                                30

<210> SEQ ID NO 282
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
taaattgtaa gcgcttacaa ttggatccgg                                30

<210> SEQ ID NO 283
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
gtaattgtaa gcgcttacaa ttggatccgg                                30

<210> SEQ ID NO 284
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 284
tcaattgtaa gcgcttacaa ttggatccgg                                        30

<210> SEQ ID NO 285
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
aaaattgtaa gcgcttacaa ttggatccgg                                        30

<210> SEQ ID NO 286
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
caaattgtaa gcgcttacaa ttggatccgg                                        30

<210> SEQ ID NO 287
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
gaaattgtaa gcgcttacaa ttggatccgg                                        30

<210> SEQ ID NO 288
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
taaattgtaa gcgcttacaa ttggatccgg                                        30

<210> SEQ ID NO 289
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
gtaattgtaa gcgcttacaa ttggatccgg                                        30

<210> SEQ ID NO 290
<211> LENGTH: 30
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 290
tcaattgtaa gcgcttacaa ttggatccgg    30

<210> SEQ ID NO 291
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 291
aaaattgtaa gcgcttacaa ttggatccgg    30

<210> SEQ ID NO 292
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 292
caaattgtaa gcgcttacaa ttggatccgg    30

<210> SEQ ID NO 293
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 293
gaaattgtaa gcgcttacaa ttggatccgg    30

<210> SEQ ID NO 294
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 294
taaattgtaa gcgcttacaa ttggatccgg    30

<210> SEQ ID NO 295
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 295
gtaattgtaa gcgcttacaa ttggatccgg    30

<210> SEQ ID NO 296
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 296
tcaattgtaa gcgcttacaa ttggatccgg                                    30

<210> SEQ ID NO 297
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
aaaattgtaa gcgcttacaa ttggatccgg                                    30

<210> SEQ ID NO 298
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
caaattgtaa gcgcttacaa ttggatccgg                                    30

<210> SEQ ID NO 299
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
gaaattgtaa gcgcttacaa ttggatccgg                                    30

<210> SEQ ID NO 300
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
taaattgtaa gcgcttacaa ttggatccgg                                    30

<210> SEQ ID NO 301
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
gtaattgtaa gcgcttacaa ttggatccgg                                    30

<210> SEQ ID NO 302
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 302
tcaattgtaa gcgcttacaa ttggatccgg                                              30

<210> SEQ ID NO 303
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
aaaattgtaa gcgcttacaa ttggatccgg                                              30

<210> SEQ ID NO 304
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
caaattgtaa gcgcttacaa ttggatccgg                                              30

<210> SEQ ID NO 305
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
gaaattgtaa gcgcttacaa ttggatccgg                                              30

<210> SEQ ID NO 306
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
taaattgtaa gcgcttacaa ttggatccgg                                              30

<210> SEQ ID NO 307
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
gtaattgtaa gcgcttacaa ttggatccgg                                              30

<210> SEQ ID NO 308
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 308
tcaattgtaa gcgcttacaa ttggatccgg						30

<210> SEQ ID NO 309
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
aaaattgtaa gcgcttacaa ttggatccgg						30

<210> SEQ ID NO 310
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
caaattgtaa gcgcttacaa ttggatccgg						30

<210> SEQ ID NO 311
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
gaaattgtaa gcgcttacaa ttggatccgg						30

<210> SEQ ID NO 312
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
taaattgtaa gcgcttacaa ttggatccgg						30

<210> SEQ ID NO 313
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
gtaattgtaa gcgcttacaa ttggatccgg						30

<210> SEQ ID NO 314
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
tcaattgtaa gcgcttacaa ttggatccgg                                              30

<210> SEQ ID NO 315
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
aaaattgtaa gcgcttacaa ttggatccgg                                              30

<210> SEQ ID NO 316
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
caaattgtaa gcgcttacaa ttggatccgg                                              30

<210> SEQ ID NO 317
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
gccaaattaa acaggattaa caggatccgg                                              30

<210> SEQ ID NO 318
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
gccaaattaa acaggattaa caggatccgg                                              30

<210> SEQ ID NO 319
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
caaattatga gcgctcacaa ttggatccgg                                              30

<210> SEQ ID NO 320
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
gtttctccat acccgttttt ttgggctagc                                            30

<210> SEQ ID NO 321
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
tgttatagtc gaatacctct ggcggtgata                                            30

<210> SEQ ID NO 322
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
attacaaact ttcttgtata gatttaacgt                                            30

<210> SEQ ID NO 323
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
atttataaat agtggtgata gatttaacgt                                            30

<210> SEQ ID NO 324
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
tttcttgtat agatttacaa tgtatcttgt                                            30

<210> SEQ ID NO 325
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
tttcttgtag atacttacaa tgtatcttgt                                            30

<210> SEQ ID NO 326
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
ctttatgctt ccggctcgta tgttgtgtgg                                            30

<210> SEQ ID NO 327
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327 tttttttgggc tagcaagctt taccatggat                                    30

<210> SEQ ID NO 328
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
tgtttctcca taccgttttt ttgggctagc                                     30

<210> SEQ ID NO 329
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
ttttggtaca ctccctatca gtgatagaga                                     30

<210> SEQ ID NO 330
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330 cttttttggta cactacctct ggcggtgata                                    30

<210> SEQ ID NO 331
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
tacgcaagaa aatggtttgt tatagtcgaa                                     30

<210> SEQ ID NO 332
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
gaaaaccttg tcaatgaaga gcgatctatg                                     30

<210> SEQ ID NO 333
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 333
ctcaaagcgg gccagccgta gccgttacgc                30

<210> SEQ ID NO 334
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 334
ttctcgttcg actcatagct gaacacaaca                30

<210> SEQ ID NO 335
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 335
gttctttaat tatttaagtg ttctttaatt                30

<210> SEQ ID NO 336
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 336
cgtgcgtgtt gataacaccg tgcgtgttga                30

<210> SEQ ID NO 337
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 337
gttacgttta tcgcggtgat tgttacttat                30

<210> SEQ ID NO 338
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 338
gcaaaataaa atggaatgat gaaactgggt                30

```
<210> SEQ ID NO 339
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
gttacgttta tcgcggtgat tgttacttat                                           30

<210> SEQ ID NO 340
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
atttcacact gctattgaga taattcacaa                                           30

<210> SEQ ID NO 341
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
agattgtact aaatcgtata atgacagtga                                           30

<210> SEQ ID NO 342
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gacatctccg gcgcaactga aaataccact                                           30

<210> SEQ ID NO 343
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
gaggatgcgc atcgtcggga aactgatgcc                                           30

<210> SEQ ID NO 344
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
catccgggac tgatggcgga ggatgcgcat                                           30

<210> SEQ ID NO 345
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345 aactttata tattgtgcaa tctcacatgc                                              30

<210> SEQ ID NO 346
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
tgttgtccgg tgtacgtcac aattttctta                                             30

<210> SEQ ID NO 347
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
aatggctgtg tgtttttgt tcatctccac                                              30

<210> SEQ ID NO 348
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
gtgttgatgc ttttatcacc gccagtggta                                             30

<210> SEQ ID NO 349
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
agtgtgtgga attgtgagcg gataacaatt                                             30

<210> SEQ ID NO 350
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
atgacaaaat tgtcat                                                            16

<210> SEQ ID NO 351
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
acatcttaaa agttttagta tcatattcgt                                            30

<210> SEQ ID NO 352
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
ctgaaagcgc ataccgctat ggaggggtt                                             30

<210> SEQ ID NO 353
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
ctgaaagcgc ataccgctat ggaggggtt                                             30

<210> SEQ ID NO 354
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
aacgaatata acaggtggga gatgagagga                                            30

<210> SEQ ID NO 355
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
aatatttcct cattttccac agtgaagtga                                            30

<210> SEQ ID NO 356
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
tacgcaagaa aatggtttgt tatagtcgaa                                            30

<210> SEQ ID NO 357
<211> LENGTH: 30
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 357
atttaattgt tttgatcaat tatttttctg                         30

<210> SEQ ID NO 358
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 358
attattctgc attttgggg agaatggact                         30

<210> SEQ ID NO 359
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 359
ccttgctgga aggtttaacc tttatcacag                         30

<210> SEQ ID NO 360
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 360
atgatgtgtc catggatta                                    19

<210> SEQ ID NO 361
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 361
atgatagacg atgtgcggac aacgtg                            26

<210> SEQ ID NO 362
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 362
cattagccgc caccatgggg ttaagtagca                         30

<210> SEQ ID NO 363
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 363
atttataaat agtggtgata gatttaacgt                                              30

<210> SEQ ID NO 364
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
ataaagccat cacgagtacc atagaggatc                                              30

<210> SEQ ID NO 365
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
tttgtctttt cttgcttaat aatgttgtca                                              30

<210> SEQ ID NO 366
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
tttgtctttt cttgcttaat aatgttgtca                                              30

<210> SEQ ID NO 367
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
atcctccttt agtcttcccc ctcatgtgtg                                              30

<210> SEQ ID NO 368
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
taaaattatg aaatttgcat aaattcttca                                              30

<210> SEQ ID NO 369
<211> LENGTH: 30
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 369
gaaatctggc agttttggt acacgaaagc                                30

<210> SEQ ID NO 370
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
tgccagttct ggcaggtcta aaaagtgttc                                30

<210> SEQ ID NO 371
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
cacagaactt gcatttatat aaagggaaag                                30

<210> SEQ ID NO 372
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
acaccgtgcg tgttgatata gtcgaataaa                                30

<210> SEQ ID NO 373
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
aaaattatga aatttgtata aattcttcag                                30

<210> SEQ ID NO 374
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
ggttcttttt ggtacctctg gcggtgataa                                30

<210> SEQ ID NO 375
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 375
tgtaggatcg tacaggtata aattcttcag                                      30

<210> SEQ ID NO 376
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
caagaaaatg gtttgttata gtcgaataaa                                      30

<210> SEQ ID NO 377
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
ctatctcatt tgctagtata gtcgaataaa                                      30

<210> SEQ ID NO 378
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
gttacgttta tcgcggtgat tgttacttat                                      30

<210> SEQ ID NO 379
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
gttacgttta tcgcggtgat tgttacttat                                      30

<210> SEQ ID NO 380
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
gttacgttta tcgcggtgat tgttacttat                                      30

<210> SEQ ID NO 381
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 381
ataaatgctt gactctgtag cgggaaggcg                                          30

<210> SEQ ID NO 382
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
aaaactggta gtaggactgg agattggtac                                          30

<210> SEQ ID NO 383
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
gggacacaaa catcaagagg atatgagatt                                          30

<210> SEQ ID NO 384
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
gtcaaaatga ccgaaacggg tggtaacttc                                          30

<210> SEQ ID NO 385
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
agtaatctta tcgccagttt ggtctggtca                                          30

<210> SEQ ID NO 386
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
agtaatctta tcgccagttt ggtctggtca                                          30

<210> SEQ ID NO 387
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 387
aattctgaac aacatccgta ctcttcgtgc                                  30

<210> SEQ ID NO 388
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
tcgataagat taccgatctt acctgaagct                                  30

<210> SEQ ID NO 389
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
cgatctattc acctgaaaga gaaataaaaa                                  30

<210> SEQ ID NO 390
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
atcgcaacct atttattaca acactagtgc                                  30

<210> SEQ ID NO 391
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
aaacgttagt ttgaatggaa agatgcctgc                                  30

<210> SEQ ID NO 392
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
tttgcacgaa ccatatgtaa gtatttcctt                                  30

<210> SEQ ID NO 393
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
```
taacacttat ttaattaaaa agaggagaaa                                        30

<210> SEQ ID NO 394
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
tagaaacaaa atgtaacatc tctatggaca                                        30

<210> SEQ ID NO 395
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
acaggaaaca gctatgacca tgattacgcc                                        30

<210> SEQ ID NO 396
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
agcgacgtct gatgacgtaa tttctgcctc                                        30

<210> SEQ ID NO 397
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
gttcactcta taccgctgaa ggtgtaatgg                                        30

<210> SEQ ID NO 398
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
tagtttataa tttaagtgtt ctttaatttc                                        30

<210> SEQ ID NO 399
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
cgagcacttc accaacaagg accatagcat                                    30

<210> SEQ ID NO 400
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
caccttcggg tgggcctttc tgcgtttata                                    30

<210> SEQ ID NO 401
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
catggcatgg atgaactata caaataataa                                    30

<210> SEQ ID NO 402
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
caccttcggg tgggcctttc tgcgtttata                                    30

<210> SEQ ID NO 403
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
caccttcggg tgggcctttc tgcgtttata                                    30

<210> SEQ ID NO 404
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
caccttcggg tgggcctttc tgcgtttata                                    30

<210> SEQ ID NO 405
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
caccttcggg tgggcctttc tgcgtttata                                    30

```
<210> SEQ ID NO 406
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
caccttcggg tgggcctttc tgcgtttata                                        30

<210> SEQ ID NO 407
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
caccttcggg tgggcctttc tgcgtttata                                        30

<210> SEQ ID NO 408
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
caccttcggg tgggcctttc tgcgtttata                                        30

<210> SEQ ID NO 409
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
caccttcggg tgggcctttc tgcgtttata                                        30

<210> SEQ ID NO 410
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
caccttcggg tgggcctttc tgcgtttata                                        30

<210> SEQ ID NO 411
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
caccttcggg tgggcctttc tgcgtttata                                        30
```

```
<210> SEQ ID NO 412
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
caccttcggg tgggcctttc tgcgtttata                                            30

<210> SEQ ID NO 413
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
caccttcggg tgggcctttc tgcgtttata                                            30

<210> SEQ ID NO 414
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
caccttcggg tgggcctttc tgcgtttata                                            30

<210> SEQ ID NO 415
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
caccttcggg tgggcctttc tgcgtttata                                            30

<210> SEQ ID NO 416
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
caccttcggg tgggcctttc tgcgtttata                                            30

<210> SEQ ID NO 417
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
tgtttctcca taccgttttt ttgggctagc                                            30
```

```
<210> SEQ ID NO 418
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
tgtttctcca taccgttttt ttgggctagc                                    30

<210> SEQ ID NO 419
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
ttttatcgca actctctact gtttctccat                                    30

<210> SEQ ID NO 420
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
gtttctccat tactagagaa agagggaca                                     30

<210> SEQ ID NO 421
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
caccttcggg tgggcctttc tgcgtttata                                    30

<210> SEQ ID NO 422
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
aataactctg atagtgctag tgtagatctc                                    30

<210> SEQ ID NO 423
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
caccttcggg tgggcctttc tgcgtttata                                    30

<210> SEQ ID NO 424
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
caccttcggg tgggcctttc tgcgtttata                                    30

<210> SEQ ID NO 425
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
gggacacaaa catcaagagg atatgagatt                                    30

<210> SEQ ID NO 426
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
ataataagcg aagttagcga gatgaatgcg                                    30

<210> SEQ ID NO 427
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
agttggcaca gatttcgctt tatctttttt                                    30

<210> SEQ ID NO 428
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
caagaaaatg gtttgttata gtcgaataaa                                    30

<210> SEQ ID NO 429
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
gtgttgacta ttttacctct ggcggtgata                                    30

<210> SEQ ID NO 430
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
gttagctttc gaattggcta aaaagtgttc                                    30

<210> SEQ ID NO 431
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
ccattctgct ttccacgaac ttgaaaacgc                                    30

<210> SEQ ID NO 432
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
ggccgcgggt tcttttggt acacgaaagc                                     30

<210> SEQ ID NO 433
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
ttttatcgca actctctact gtttctccat                                    30

<210> SEQ ID NO 434
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
attattctgc atttttgggg agaatggact                                    30

<210> SEQ ID NO 435
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
attattctgc atttttgggg agaatggact                                    30

<210> SEQ ID NO 436
<211> LENGTH: 30
<212> TYPE: DNA
```

<213> ORGANISM: Artificial Sequence
<220> FEATURE:
<223> OTHER INFORMATION: Description of Artificial Sequence: Synthetic
    oligonucleotide

<400> SEQUENCE: 436
aacgttagtt tgaatggaaa gatgcctgca                                    30

<210> SEQ ID NO 437
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 437
aagaaaatgg tttgttgata ctcgaataaa                                    30

<210> SEQ ID NO 438
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 438
aacgcagtcg ttaagttcta caaagtcggt                                    30

<210> SEQ ID NO 439
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 439
gtcggtgaca gataacagga gtaagtaatg                                    30

<210> SEQ ID NO 440
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 440
tattggctga ctataataag cgcaaattca                                    30

<210> SEQ ID NO 441

<400> SEQUENCE: 441

000

<210> SEQ ID NO 442
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 442

```
cgaaacggga accctatatt gatctctact                                            30
```

<210> SEQ ID NO 443
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443

```
aagttggcac gcatcgtgct ttatacagat                                            30
```

<210> SEQ ID NO 444
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444

```
gaggaaacta gacccgccgc caccatggag                                            30
```

<210> SEQ ID NO 445
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445

```
gagtaaccaa aaccaaaaca gatttcaacc                                            30
```

<210> SEQ ID NO 446
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446

```
aaagtaagaa tttttgaaaa ttcaatataa                                            30
```

<210> SEQ ID NO 447
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447

```
atacggtcaa cgaactataa ttaactaaac                                            30
```

<210> SEQ ID NO 448
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448

```
cacaaataca cacactaaat taataactag                                            30
```

<210> SEQ ID NO 449
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
cacaaataca cacactaaat taataactag                                      30

<210> SEQ ID NO 450
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
cacaaataca cacactaaat taataactag                                      30

<210> SEQ ID NO 451
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
atactttaac gtcaaggaga aaaaactata                                      30

<210> SEQ ID NO 452
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
accgttaaga accatatcca agaatcaaaa                                      30

<210> SEQ ID NO 453
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
cttcatatat aaaccgccag aaatgaatta                                      30

<210> SEQ ID NO 454
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
atcttcatac aacaataact accaacctta                                      30

<210> SEQ ID NO 455
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
tttcatacac aatataaacg attaaaagaa                                    30

<210> SEQ ID NO 456
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
aaattccagt aaattcacat attggagaaa                                    30

<210> SEQ ID NO 457
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
gggagccaga acgcttctgg tggtgtaaat                                    30

<210> SEQ ID NO 458
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
gcacagactt agattggtat atatacgcat                                    30

<210> SEQ ID NO 459
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
aagtgcaaga aagaccagaa acgcaactca                                    30

<210> SEQ ID NO 460
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
taaaaaaaaa aaaaaaaaaa aaaaaaaaaa                                    30

```
<210> SEQ ID NO 461
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
ggggcgaggg ccccgcctcc ggaggcgggg                                           30

<210> SEQ ID NO 462
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
gaggggacgg ctccggcccc ggggccggag                                           30

<210> SEQ ID NO 463
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
ggggcgaggg ctccggcccc ggggccggag                                           30

<210> SEQ ID NO 464
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
gaggggacgg ccccgcctcc ggaggcgggg                                           30

<210> SEQ ID NO 465
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
tgttatagtc gaatacctct ggcggtgata                                           30

<210> SEQ ID NO 466
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
gatttaacgt atcagcacaa aaaagaaacc                                           30

<210> SEQ ID NO 467
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
attacaaact ttcttgtata gatttaacgt                                              30

<210> SEQ ID NO 468
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
tttcttgtat agatttacaa tgtatcttgt                                              30

<210> SEQ ID NO 469
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
tttcttgtag atacttacaa tgtatcttgt                                              30

<210> SEQ ID NO 470
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
actctgtcaa tgatagagtg gattcaaaaa                                              30

<210> SEQ ID NO 471
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
ttttggtaca ctccctatca gtgatagaga                                              30

<210> SEQ ID NO 472
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472 cttttggta cactacctct ggcggtgata                                               30

<210> SEQ ID NO 473
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
aaacctttcg cggtatggca tgatagcgcc                                      30

<210> SEQ ID NO 474
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
tattttacct ctggcggtga taatggttgc                                      30

<210> SEQ ID NO 475
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
actctcggca tggacgagct gtacaagtaa                                      30

<210> SEQ ID NO 476
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
ttgtgagcgg ataacaatat gttgagcaca                                      30

<210> SEQ ID NO 477
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
cattgagaca cttgtttgca cagaggatgg                                      30

<210> SEQ ID NO 478
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
ttctcgttcg actcatagct gaacacaaca                                      30

<210> SEQ ID NO 479
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 479
gaattgtgag cggataacaa ttggatccgg                                        30

<210> SEQ ID NO 480
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
ggaattgtga gcgctcacaa ttggatccgg                                        30

<210> SEQ ID NO 481
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
ggaattgtaa gcgcttacaa ttggatccgg                                        30

<210> SEQ ID NO 482
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
ggaattgtaa acgtttacaa ttggatccgg                                        30

<210> SEQ ID NO 483
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
ggaattgtga acgttcacaa ttggatccgg                                        30

<210> SEQ ID NO 484
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
ggaattttga gcgctcaaaa ttggatccgg                                        30

<210> SEQ ID NO 485
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 485
ggaattatga gcgctcataa ttggatccgg                                         30

<210> SEQ ID NO 486
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
gggacgactg tatacagtcg tcggatccgg                                         30

<210> SEQ ID NO 487
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
ggaattgtga gcgcttacaa ttggatccgg                                         30

<210> SEQ ID NO 488
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
ggaattgtga gcgctcataa ttggatccgg                                         30

<210> SEQ ID NO 489
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
ggaattgtga gctacagtcg tcggatccgg                                         30

<210> SEQ ID NO 490
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
ggaattgtaa gcgctcacaa ttggatccgg                                         30

<210> SEQ ID NO 491
<211> LENGTH: 30
<212> TYPE: DNA
<213> ORGANISM: Artificial Sequence
<220> FEATURE:
```

<223> OTHER INFORMATION: Description of Artificial Sequence: Synthetic
     oligonucleotide

<400> SEQUENCE: 491
ggaattgtaa gcgttcacaa ttggatccgg                                              30

<210> SEQ ID NO 492
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 492
ggaattgtaa gcgctcataa ttggatccgg                                              30

<210> SEQ ID NO 493
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 493
ggaattgtaa gctacagtcg tcggatccgg                                              30

<210> SEQ ID NO 494
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 494
ggaattgtga acgctcataa ttggatccgg                                              30

<210> SEQ ID NO 495
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 495
ggaattgtga actacagtcg tcggatccgg                                              30

<210> SEQ ID NO 496
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 496
ggaattatga gcgctcacaa ttggatccgg                                              30

<210> SEQ ID NO 497
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 497
ggaattgtga gcgctcataa ttggatccgg                                         30

<210> SEQ ID NO 498
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
ggaattgtga gctacagtcg tcggatccgg                                         30

<210> SEQ ID NO 499
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
ggaattgtga acgctcataa ttggatccgg                                         30

<210> SEQ ID NO 500
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
ggaattgtga actacagtcg tcggatccgg                                         30

<210> SEQ ID NO 501
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
taaattgtga acgctcataa ttggatccgg                                         30

<210> SEQ ID NO 502
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
gaaattgtaa gcgcttacaa ttggatccgg                                         30

<210> SEQ ID NO 503
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 503
gaaattgtaa gcgcttacaa ttggatccgg                                30

<210> SEQ ID NO 504
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
ggaattgtaa gcgcttacaa ttggatccgg                                30

<210> SEQ ID NO 505
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
gccaaattaa acaggattaa caggatccgg                                30

<210> SEQ ID NO 506
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
gccaaattaa acaggattaa caggatccgg                                30

<210> SEQ ID NO 507
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
gccaaattaa acaggattaa caggatccgg                                30

<210> SEQ ID NO 508
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
gccaaattaa acaggattaa caggatccgg                                30

<210> SEQ ID NO 509
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 509
gccaaattaa acaggattaa caggatccgg                                        30

<210> SEQ ID NO 510
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
gccaaattaa acaggattaa caggatccgg                                        30

<210> SEQ ID NO 511
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
gccaaattaa acaggattaa caggatccgg                                        30

<210> SEQ ID NO 512
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
gaaattgtaa gcgcttacaa ttggatccgg                                        30

<210> SEQ ID NO 513
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
taaattgtaa gcgcttacaa ttggatccgg                                        30

<210> SEQ ID NO 514
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
gtaattgtaa gcgcttacaa ttggatccgg                                        30

<210> SEQ ID NO 515
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
```
tcaattgtaa gcgcttacaa ttggatccgg                                              30

<210> SEQ ID NO 516
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
aaaattgtaa gcgcttacaa ttggatccgg                                              30

<210> SEQ ID NO 517
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
caaattgtaa gcgcttacaa ttggatccgg                                              30

<210> SEQ ID NO 518
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
gaaattgtaa gcgcttacaa ttggatccgg                                              30

<210> SEQ ID NO 519
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
taaattgtaa gcgcttacaa ttggatccgg                                              30

<210> SEQ ID NO 520
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
gtaattgtaa gcgcttacaa ttggatccgg                                              30

<210> SEQ ID NO 521
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
tcaattgtaa gcgcttacaa ttggatccgg                                              30

<210> SEQ ID NO 522
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
aaaattgtaa gcgcttacaa ttggatccgg                                              30

<210> SEQ ID NO 523
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
caaattgtaa gcgcttacaa ttggatccgg                                              30

<210> SEQ ID NO 524
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
gaaattgtaa gcgcttacaa ttggatccgg                                              30

<210> SEQ ID NO 525
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
taaattgtaa gcgcttacaa ttggatccgg                                              30

<210> SEQ ID NO 526
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
gtaattgtaa gcgcttacaa ttggatccgg                                              30

<210> SEQ ID NO 527
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
tcaattgtaa gcgcttacaa ttggatccgg                                              30

<210> SEQ ID NO 528
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 528
aaaattgtaa gcgcttacaa ttggatccgg                                    30

<210> SEQ ID NO 529
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 529
caaattgtaa gcgcttacaa ttggatccgg                                    30

<210> SEQ ID NO 530
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 530
gaaattgtaa gcgcttacaa ttggatccgg                                    30

<210> SEQ ID NO 531
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 531
taaattgtaa gcgcttacaa ttggatccgg                                    30

<210> SEQ ID NO 532
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 532
gtaattgtaa gcgcttacaa ttggatccgg                                    30

<210> SEQ ID NO 533
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 533
tcaattgtaa gcgcttacaa ttggatccgg                                    30

<210> SEQ ID NO 534
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
aaaattgtaa gcgcttacaa ttggatccgg                                    30

<210> SEQ ID NO 535
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
caaattgtaa gcgcttacaa ttggatccgg                                    30

<210> SEQ ID NO 536
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
gaaattgtaa gcgcttacaa ttggatccgg                                    30

<210> SEQ ID NO 537
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
taaattgtaa gcgcttacaa ttggatccgg                                    30

<210> SEQ ID NO 538
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
gtaattgtaa gcgcttacaa ttggatccgg                                    30

<210> SEQ ID NO 539
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
tcaattgtaa gcgcttacaa ttggatccgg                                    30

```
<210> SEQ ID NO 540
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
aaaattgtaa gcgcttacaa ttggatccgg                                           30

<210> SEQ ID NO 541
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
caaattgtaa gcgcttacaa ttggatccgg                                           30

<210> SEQ ID NO 542
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
gaaattgtaa gcgcttacaa ttggatccgg                                           30

<210> SEQ ID NO 543
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
taaattgtaa gcgcttacaa ttggatccgg                                           30

<210> SEQ ID NO 544
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
gtaattgtaa gcgcttacaa ttggatccgg                                           30

<210> SEQ ID NO 545
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
tcaattgtaa gcgcttacaa ttggatccgg                                           30

<210> SEQ ID NO 546
```

```
<210> SEQ ID NO 546
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
aaaattgtaa gcgcttacaa ttggatccgg                                           30

<210> SEQ ID NO 547
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
caaattgtaa gcgcttacaa ttggatccgg                                           30

<210> SEQ ID NO 548
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
gaaattgtaa gcgcttacaa ttggatccgg                                           30

<210> SEQ ID NO 549
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
taaattgtaa gcgcttacaa ttggatccgg                                           30

<210> SEQ ID NO 550
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
gtaattgtaa gcgcttacaa ttggatccgg                                           30

<210> SEQ ID NO 551
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
tcaattgtaa gcgcttacaa ttggatccgg                                           30

<210> SEQ ID NO 552
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
aaaattgtaa gcgcttacaa ttggatccgg                                           30

<210> SEQ ID NO 553
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
caaattgtaa gcgcttacaa ttggatccgg                                           30

<210> SEQ ID NO 554
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
gccaaattaa acaggattaa caggatccgg                                           30

<210> SEQ ID NO 555
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
gccaaattaa acaggattaa caggatccgg                                           30

<210> SEQ ID NO 556
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
caaattatga gcgctcacaa ttggatccgg                                           30

<210> SEQ ID NO 557
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
tgatagagat tccctatcag tgatagagat                                           30

<210> SEQ ID NO 558
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 558
tgatagagat tccctatcag tgatagagat                                         30

<210> SEQ ID NO 559
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
gttctttaat tatttaagtg ttctttaatt                                         30

<210> SEQ ID NO 560
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
gttctttaat tatttaagtg ttctttaatt                                         30

<210> SEQ ID NO 561
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
cgtgcgtgtt gataacaccg tgcgtgttga                                         30

<210> SEQ ID NO 562
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
gtgttcttta atatttaagt gttctttaat                                         30

<210> SEQ ID NO 563
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
ggaattgtga gcggataaca atttcacaca                                         30

<210> SEQ ID NO 564
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 564
tgtgtgtaat tgtgagcgga taacaattaa                                    30

<210> SEQ ID NO 565
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
ttttacctct ggcggtgata atggttgcag                                    30

<210> SEQ ID NO 566
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
gtgttgatgc ttttatcacc gccagtggta                                    30

<210> SEQ ID NO 567
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
agtgtgtgga attgtgagcg gataacaatt                                    30

<210> SEQ ID NO 568
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568 aggggggtggg ggcgcgttgg cgcgccacac                                   30

<210> SEQ ID NO 569
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
acatcttaaa agttttagta tcatattcgt                                    30

<210> SEQ ID NO 570
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 570
tattttacct ctggcggtga taatggttgc                                     30

<210> SEQ ID NO 571
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
atttataaat agtggtgata gatttaacgt                                     30

<210> SEQ ID NO 572
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
acccttctcg ttcgactcat agctgaacac                                     30

<210> SEQ ID NO 573
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
tgacttatcc gcttcgaaga gagacactac                                     30

<210> SEQ ID NO 574
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
aggtgttaaa ttgatcacgt tttagaccat                                     30

<210> SEQ ID NO 575
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
caatttggta aaggctccat catgtaataa                                     30

<210> SEQ ID NO 576
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 576
gagaaacaat tggtaaagg ctccatcatg                                     30

<210> SEQ ID NO 577
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
aacgcgcggg gagaggcggt ttgcgtattg                                    30

<210> SEQ ID NO 578
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
cagtgataga gatactgagc acatcagcac                                    30

<210> SEQ ID NO 579
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
ttatgcttcc ggctcgtata atgtttcaaa                                    30

<210> SEQ ID NO 580
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
ggctcgtatg ttgtgtcgac cgagctgcgc                                    30

<210> SEQ ID NO 581
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581
aaacctttcg cggtatggca tgatagcgcc                                    30

<210> SEQ ID NO 582
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
atttgtcact gtcgttacta tatcggctgc                                    30

<210> SEQ ID NO 583
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
gtccaatcaa taaccgcttt aatagataaa                                    30

<210> SEQ ID NO 584
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584
actttattat caataagtta aatcggtacc                                    30

<210> SEQ ID NO 585
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585
gtgttgacta ttttacctct ggcggtgata                                    30

<210> SEQ ID NO 586
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586
gtgttgacta ttttacctct ggcggtgata                                    30

<210> SEQ ID NO 587
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
atacctctgg cggtgatata taatggttgc                                    30

<210> SEQ ID NO 588
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
gtgttgacta ttttacctct ggcggtgata                                    30

<210> SEQ ID NO 589
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
gaaatctggc agtttttggt acacgaaagc                                    30

<210> SEQ ID NO 590
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 590
tgccagttct ggcaggtcta aaaagtgttc                                    30

<210> SEQ ID NO 591
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
agcgctcaca atttaatacg actcactata                                    30

<210> SEQ ID NO 592
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
taataattgt gagcgctcac aattttgaca                                    30

<210> SEQ ID NO 593
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
atccctatca gtgatagaga tactgagcac                                    30

<210> SEQ ID NO 594
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
ttgtgagcgg ataacaagat actgagcaca                                      30

<210> SEQ ID NO 595
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
ggaattgtga gcggataaca atttcacaca                                      30

<210> SEQ ID NO 596
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
ggaattgtga gcggataaca atttcacaca                                      30

<210> SEQ ID NO 597
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
ggaattgtga gcggataaca atttcacaca                                      30

<210> SEQ ID NO 598
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
agaactgtaa tccctatcag tgatagagat                                      30

<210> SEQ ID NO 599
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
tgttgattta tctaacaccg tgcgtgttga                                      30

<210> SEQ ID NO 600
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
acaccgtgcg tgttgatata gtcgaataaa                                           30

<210> SEQ ID NO 601
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
cctttcgcgg tatggcatga tagcgcccgg                                           30

<210> SEQ ID NO 602
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
cctttcgcgg tatggcatga tagcgcccgg                                           30

<210> SEQ ID NO 603
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
cctttcgcgg tatggcatga tagcgcccgg                                           30

<210> SEQ ID NO 604
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
ggttcttttt ggtacctctg gcggtgataa                                           30

<210> SEQ ID NO 605
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
tgtaggatcg tacaggtata aattcttcag                                           30

<210> SEQ ID NO 606
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
ctatctcatt tgctagtata gtcgaataaa                                           30

<210> SEQ ID NO 607
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
gtatatatat acagtataat tgcttcaaca                                      30

<210> SEQ ID NO 608
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
cacaatgtca attgttatcc gctcacaatt                                      30

<210> SEQ ID NO 609
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
aattgtgagc ggataacaat ttcacacaga                                      30

<210> SEQ ID NO 610
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
ccggaagaga gtcaattcag ggtggtgaat                                      30

<210> SEQ ID NO 611
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
acggtgacct agatctccga tactgagcac                                      30

<210> SEQ ID NO 612
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
tggaattgtg agcggataaa atttcacaca                                      30

<210> SEQ ID NO 613
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
tagtagataa tttaagtgtt ctttaatttc                                    30

<210> SEQ ID NO 614
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
ccaacgcgtt cacagcgtac aattactagt                                    30

<210> SEQ ID NO 615
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
aacaaaaaaa cggatcctct agttgcggcc                                    30

<210> SEQ ID NO 616
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
ataaatgctt gactctgtag cgggaaggcg                                    30

<210> SEQ ID NO 617
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
atttcatgat gatacgtgag cggatagaag                                    30

<210> SEQ ID NO 618
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
caaacagaaa gcgttggcgg cagcactggg                                    30

<210> SEQ ID NO 619
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 619
gtcaaaatga ccgaaacggg tggtaacttc                                    30

<210> SEQ ID NO 620
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 620
agtaatctta tcgccagttt ggtctggtca                                    30

<210> SEQ ID NO 621
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 621
agtaatctta tcgccagttt ggtctggtca                                    30

<210> SEQ ID NO 622
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 622
aattctgaac aacatccgta ctcttcgtgc                                    30

<210> SEQ ID NO 623
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 623
tttacgttat cattcacttt acatcagagt                                    30

<210> SEQ ID NO 624
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 624
gtttctccat acccgttttt ttgggctagc                                    30

<210> SEQ ID NO 625

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625
cgatctattc acctgaaaga gaaataaaaa                                           30

<210> SEQ ID NO 626
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
aaacgttagt ttgaatggaa agatgcctgc                                           30

<210> SEQ ID NO 627
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
attgccgaat taatactaag aattattatc                                           30

<210> SEQ ID NO 628
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
acaggaaaca gctatgacca tgattacgcc                                           30

<210> SEQ ID NO 629
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
actggcggtt ataatgagca catcagcagg                                           30

<210> SEQ ID NO 630
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
caccgacaaa caacagataa aacgaaaggc                                           30

<210> SEQ ID NO 631
<211> LENGTH: 30
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
agtgttatta agctactaaa gcgtagtttt                                       30

<210> SEQ ID NO 632
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
gaataagaag gctggctctg caccttggtg                                       30

<210> SEQ ID NO 633
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
ttagcgactt gatgctcttg atcttccaat                                       30

<210> SEQ ID NO 634
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
acatctaaaa cttttagcgt tattacgtaa                                       30

<210> SEQ ID NO 635
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
ttccgacctc attaagcagc tctaatgcgc                                       30

<210> SEQ ID NO 636
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636
caatttttaa acctgtagga tcgtacaggt                                       30

<210> SEQ ID NO 637
<211> LENGTH: 30
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 637
caatttttaa aattaaaggc gttacccaac                                    30

<210> SEQ ID NO 638
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 638
tagtttataa tttaagtgtt ctttaatttc                                    30

<210> SEQ ID NO 639
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 639
gaaaatgtga gcgagtaaca acctcacaca                                    30

<210> SEQ ID NO 640
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 640
caccttcggg tgggcctttc tgcgtttata                                    30

<210> SEQ ID NO 641
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 641
ttttatcgca actctctact gtttctccat                                    30

<210> SEQ ID NO 642
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 642
gtttctccat tactagagaa agagggaca                                     30

<210> SEQ ID NO 643
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
caccttcggg tgggcctttc tgcgtttata                                        30

<210> SEQ ID NO 644
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
caccttcggg tgggcctttc tgcgtttata                                        30

<210> SEQ ID NO 645
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
caccttcggg tgggcctttc tgcgtttata                                        30

<210> SEQ ID NO 646
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
aataactctg atagtgctag tgtagatctc                                        30

<210> SEQ ID NO 647
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
caccttcggg tgggcctttc tgcgtttata                                        30

<210> SEQ ID NO 648
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
caccttcggg tgggcctttc tgcgtttata                                        30

<210> SEQ ID NO 649
<211> LENGTH: 30
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 649
ttgtgagcgg ataacaagat actgagcaca                                    30

<210> SEQ ID NO 650
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
actgagcaca tactagagaa agaggagaaa                                    30

<210> SEQ ID NO 651
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
actgagcaca tactagagaa agaggagaaa                                    30

<210> SEQ ID NO 652
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
tcacacatac tagagattaa agaggagaaa                                    30

<210> SEQ ID NO 653
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 653
ggaattgtga gcggataaca atttcacaca                                    30

<210> SEQ ID NO 654
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 654
ggaattgtga gcggataaca atttcacaca                                    30

<210> SEQ ID NO 655
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 655
ttgtgagcgg ataacaagat actgagcaca                                              30

<210> SEQ ID NO 656
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 656
atccctatca gtgatagaga tactgagcac                                              30

<210> SEQ ID NO 657
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
ccgtcataat atgaaccata agttcaccac                                              30

<210> SEQ ID NO 658
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 658
tattttacct ctggcggtga taatggttgc                                              30

<210> SEQ ID NO 659
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 659
attgtatgaa aatacaagaa agtttgttga                                              30

<210> SEQ ID NO 660
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 660
tagtagataa tttaagtgtt ctttaatttc                                              30

<210> SEQ ID NO 661
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 661
ttgacacctg taggatcgta caggtataat                                30

<210> SEQ ID NO 662
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662
cacgcaaaac ttgcgacaaa caataggtaa                                30

<210> SEQ ID NO 663
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663
gtgttgacta ttttacctct ggcggtgata                                30

<210> SEQ ID NO 664
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 664
tagatctcct atagtgagtc gtattaattt                                30

<210> SEQ ID NO 665
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 665
tactttcaaa gactacattt gtaagatttg                                30

<210> SEQ ID NO 666
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 666
cataaagttc atgaaacgtg aactgaaatt                                30

<210> SEQ ID NO 667
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 667
ccgtgatact atgaaccata agttcaccac                                           30

<210> SEQ ID NO 668
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668
aattttacct ctggcggtga tactggttgc                                           30

<210> SEQ ID NO 669
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 669
attgtatgat actacaagaa agtttgttga                                           30

<210> SEQ ID NO 670
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
tagtagatac tttaagtgtt ctttaatttc                                           30

<210> SEQ ID NO 671
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
tggtcccacg cgcgtgggat actacgtcag                                           30

<210> SEQ ID NO 672
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
attacggtga gatactccca cgcgcgtggg                                           30

<210> SEQ ID NO 673
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 673
```
acgcgcgtgg gatactccca cgcgcgtggg                                               30

<210> SEQ ID NO 674
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 674
gattagattc ataaatttga gagaggagtt                                               30

<210> SEQ ID NO 675
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 675
acttagattc ataaatttga gagaggagtt                                               30

<210> SEQ ID NO 676
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 676
ggttagattc ataaatttga gagaggagtt                                               30

<210> SEQ ID NO 677
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 677
acttagattc ataaatttga gagaggagtt                                               30

<210> SEQ ID NO 678
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 678
aattagattc ataaatttga gagaggagtt                                               30

<210> SEQ ID NO 679
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 679
acttagattc ataaatttga gagaggagtt         30

<210> SEQ ID NO 680
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 680
atttagattc ataaatttga gagaggagtt         30

<210> SEQ ID NO 681
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 681
cacgcgcgtg ggaatgttat aatacgtcag         30

<210> SEQ ID NO 682

<400> SEQUENCE: 682

000

<210> SEQ ID NO 683
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683
actgagcaca tactagagaa agaggagaaa         30

<210> SEQ ID NO 684
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684
cagtgagcga gtaacaacta cgctgtttta         30

<210> SEQ ID NO 685
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685
cagtgagcga gtaacaacta cgctgtttta         30

<210> SEQ ID NO 686
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 686
atgtgagcgg ataacactat aattaataga                                          30

<210> SEQ ID NO 687
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 687
atgtgagcgg ataacactat aattaataga                                          30

<210> SEQ ID NO 688
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688
atttcatgat gatacgtgag cggatagaag                                          30

<210> SEQ ID NO 689
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 689
ttgtgagcga gtggcaccat taagtacgta                                          30

<210> SEQ ID NO 690
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 690
ttgtgagcga gtgacaccat taagtacgta                                          30

<210> SEQ ID NO 691
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 691
ttgtgagcga gtaacaccat taagtacgta                                          30

<210> SEQ ID NO 692
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 692
ttgtgagcga gtaacaccat taagtacgta                                            30

<210> SEQ ID NO 693
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
agttggcaca gatttcgctt tatctttttt                                            30

<210> SEQ ID NO 694
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 694
tggaattgtg agcggataac aattaagctt                                            30

<210> SEQ ID NO 695
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 695
agtttgttta aacaacaaac taataggtga                                            30

<210> SEQ ID NO 696
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
aatgtgtgta attgtgagcg gataacaatt                                            30

<210> SEQ ID NO 697
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 697 atagggaat tgtgagcgga taacaattcc                                             30

<210> SEQ ID NO 698
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 698 atagggaat tgtgagcgga taacaattcc                                30

<210> SEQ ID NO 699
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699 atagggaat tgtgagcgga taacaattcc                                30

<210> SEQ ID NO 700
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700 atagggaat tgtgagcgga taacaattcc                                30

<210> SEQ ID NO 701
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
aaacaaacaa acaaaaaaaa aaaaaaaaaa                                30

<210> SEQ ID NO 702
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
atactttaac gtcaaggaga aaaaactata                                30

<210> SEQ ID NO 703
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 703
tagatacaat tctattaccc ccatccatac                                30

<210> SEQ ID NO 704
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 704
ttagtgaacc gtcagatcac tagtctgcag                                              30

<210> SEQ ID NO 705
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
ttagtgaacc gtcagatcac tagtctgcag                                              30

<210> SEQ ID NO 706
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
ggaaaggacg aaacaccgac tagtctgcag                                              30

<210> SEQ ID NO 707
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
attgtttgtg tattttagac tagtctgcag                                              30

<210> SEQ ID NO 708
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
attgtttgtg tattttagac tagtctgcag                                              30

<210> SEQ ID NO 709
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709
attgtttgtg tattttagac tagtctgcag                                              30

<210> SEQ ID NO 710
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 710
ttagtgaacc gtcagatcac tagtctgcag                                          30

<210> SEQ ID NO 711
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 711
tgttatagtc gaatacctct ggcggtgata                                          30

<210> SEQ ID NO 712
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 712
attacaaact ttcttgtata gatttaacgt                                          30

<210> SEQ ID NO 713
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 713
tttcttgtat agatttacaa tgtatcttgt                                          30

<210> SEQ ID NO 714
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 714
tttcttgtag atacttacaa tgtatcttgt                                          30

<210> SEQ ID NO 715
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 715
ttttggtaca ctccctatca gtgatagaga                                          30

<210> SEQ ID NO 716
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 716
``` cttttttggta cactacctct ggcggtgata                                    30

<210> SEQ ID NO 717
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 717
actctcggca tggacgagct gtacaagtaa                                    30

<210> SEQ ID NO 718
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 718
ttctcgttcg actcatagct gaacacaaca                                    30

<210> SEQ ID NO 719
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 719
ggaattgtga gcgctcataa ttggatccgg                                    30

<210> SEQ ID NO 720
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 720
ggaattgtga gctacagtcg tcggatccgg                                    30

<210> SEQ ID NO 721
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 721
ggaattgtga acgctcataa ttggatccgg                                    30

<210> SEQ ID NO 722
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 722
ggaattgtga actacagtcg tcggatccgg    30

<210> SEQ ID NO 723
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 723
taaattgtga acgctcataa ttggatccgg    30

<210> SEQ ID NO 724
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 724
gaaattgtaa gcgcttacaa ttggatccgg    30

<210> SEQ ID NO 725
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 725
gaaattgtaa gcgcttacaa ttggatccgg    30

<210> SEQ ID NO 726
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 726
ggaattgtaa gcgcttacaa ttggatccgg    30

<210> SEQ ID NO 727
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 727
gccaaattaa acaggattaa caggatccgg    30

<210> SEQ ID NO 728
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 728
gccaaattaa acaggattaa caggatccgg    30

-continued

<210> SEQ ID NO 729
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 729
gccaaattaa acaggattaa caggatccgg                                       30

<210> SEQ ID NO 730
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
gccaaattaa acaggattaa caggatccgg                                       30

<210> SEQ ID NO 731
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
gccaaattaa acaggattaa caggatccgg                                       30

<210> SEQ ID NO 732
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 732
gccaaattaa acaggattaa caggatccgg                                       30

<210> SEQ ID NO 733
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733
gccaaattaa acaggattaa caggatccgg                                       30

<210> SEQ ID NO 734
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 734
gaaattgtaa gcgcttacaa ttggatccgg                                       30

```
<210> SEQ ID NO 735
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735
taaattgtaa gcgcttacaa ttggatccgg                                    30

<210> SEQ ID NO 736
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736
gtaattgtaa gcgcttacaa ttggatccgg                                    30

<210> SEQ ID NO 737
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 737
tcaattgtaa gcgcttacaa ttggatccgg                                    30

<210> SEQ ID NO 738
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 738
aaaattgtaa gcgcttacaa ttggatccgg                                    30

<210> SEQ ID NO 739
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739
caaattgtaa gcgcttacaa ttggatccgg                                    30

<210> SEQ ID NO 740
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 740
gaaattgtaa gcgcttacaa ttggatccgg                                    30
```

-continued

```
<210> SEQ ID NO 741
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741
taaattgtaa gcgcttacaa ttggatccgg                                           30

<210> SEQ ID NO 742
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
gtaattgtaa gcgcttacaa ttggatccgg                                           30

<210> SEQ ID NO 743
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 743
tcaattgtaa gcgcttacaa ttggatccgg                                           30

<210> SEQ ID NO 744
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 744
aaaattgtaa gcgcttacaa ttggatccgg                                           30

<210> SEQ ID NO 745
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 745
caaattgtaa gcgcttacaa ttggatccgg                                           30

<210> SEQ ID NO 746
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 746
gaaattgtaa gcgcttacaa ttggatccgg                                           30

<210> SEQ ID NO 747
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
taaattgtaa gcgcttacaa ttggatccgg                                       30

<210> SEQ ID NO 748
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 748
gtaattgtaa gcgcttacaa ttggatccgg                                       30

<210> SEQ ID NO 749
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 749
tcaattgtaa gcgcttacaa ttggatccgg                                       30

<210> SEQ ID NO 750
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 750
aaaattgtaa gcgcttacaa ttggatccgg                                       30

<210> SEQ ID NO 751
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 751
caaattgtaa gcgcttacaa ttggatccgg                                       30

<210> SEQ ID NO 752
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 752
gaaattgtaa gcgcttacaa ttggatccgg                                       30

<210> SEQ ID NO 753
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 753
taaattgtaa gcgcttacaa ttggatccgg                                         30

<210> SEQ ID NO 754
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 754
gtaattgtaa gcgcttacaa ttggatccgg                                         30

<210> SEQ ID NO 755
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 755
tcaattgtaa gcgcttacaa ttggatccgg                                         30

<210> SEQ ID NO 756
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 756
aaaattgtaa gcgcttacaa ttggatccgg                                         30

<210> SEQ ID NO 757
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 757
caaattgtaa gcgcttacaa ttggatccgg                                         30

<210> SEQ ID NO 758
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 758
gaaattgtaa gcgcttacaa ttggatccgg                                         30

<210> SEQ ID NO 759
<211> LENGTH: 30
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 759
taaattgtaa gcgcttacaa ttggatccgg                                    30

<210> SEQ ID NO 760
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 760
gtaattgtaa gcgcttacaa ttggatccgg                                    30

<210> SEQ ID NO 761
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 761
tcaattgtaa gcgcttacaa ttggatccgg                                    30

<210> SEQ ID NO 762
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 762
aaaattgtaa gcgcttacaa ttggatccgg                                    30

<210> SEQ ID NO 763
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 763
caaattgtaa gcgcttacaa ttggatccgg                                    30

<210> SEQ ID NO 764
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 764
gaaattgtaa gcgcttacaa ttggatccgg                                    30

<210> SEQ ID NO 765
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 765
taaattgtaa gcgcttacaa ttggatccgg                                        30

<210> SEQ ID NO 766
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 766
gtaattgtaa gcgcttacaa ttggatccgg                                        30

<210> SEQ ID NO 767
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 767
tcaattgtaa gcgcttacaa ttggatccgg                                        30

<210> SEQ ID NO 768
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
aaaattgtaa gcgcttacaa ttggatccgg                                        30

<210> SEQ ID NO 769
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 769
caaattgtaa gcgcttacaa ttggatccgg                                        30

<210> SEQ ID NO 770
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 770
gaaattgtaa gcgcttacaa ttggatccgg                                        30

<210> SEQ ID NO 771
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 771
taaattgtaa gcgcttacaa ttggatccgg                                          30

<210> SEQ ID NO 772
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 772
gtaattgtaa gcgcttacaa ttggatccgg                                          30

<210> SEQ ID NO 773
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 773
tcaattgtaa gcgcttacaa ttggatccgg                                          30

<210> SEQ ID NO 774
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 774
aaaattgtaa gcgcttacaa ttggatccgg                                          30

<210> SEQ ID NO 775
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 775
caaattgtaa gcgcttacaa ttggatccgg                                          30

<210> SEQ ID NO 776
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 776
gccaaattaa acaggattaa caggatccgg                                          30

<210> SEQ ID NO 777
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 777
gccaaattaa acaggattaa caggatccgg                    30

<210> SEQ ID NO 778
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 778
caaattatga gcgctcacaa ttggatccgg                    30

<210> SEQ ID NO 779
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 779
tgatagagat tccctatcag tgatagagat                    30

<210> SEQ ID NO 780
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 780
gttctttaat tatttaagtg ttctttaatt                    30

<210> SEQ ID NO 781
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 781
gttctttaat tatttaagtg ttctttaatt                    30

<210> SEQ ID NO 782
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 782
cgtgcgtgtt gataacaccg tgcgtgttga                    30

<210> SEQ ID NO 783
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 783 gtgttctttta atatttaagt gttctttaat                                    30

<210> SEQ ID NO 784
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 784
ggaattgtga gcggataaca atttcacaca                                     30

<210> SEQ ID NO 785
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 785
gttacgttta tcgcggtgat tgttacttat                                     30

<210> SEQ ID NO 786
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 786
gcaaaataaa atggaatgat gaaactgggt                                     30

<210> SEQ ID NO 787
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 787
aacgcgcggg gagaggcggt ttgcgtattg                                     30

<210> SEQ ID NO 788
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 788
gtgttgatgc ttttatcacc gccagtggta                                     30

<210> SEQ ID NO 789
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 789
agtgtgtgga attgtgagcg gataacaatt                                30

<210> SEQ ID NO 790
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 790
acatcttaaa agttttagta tcatattcgt                                30

<210> SEQ ID NO 791
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 791
ctgaaagcgc ataccgctat ggaggggggtt                               30

<210> SEQ ID NO 792
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 792
tattttacct ctggcggtga taatggttgc                                30

<210> SEQ ID NO 793
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 793
atttataaat agtggtgata gatttaacgt                                30

<210> SEQ ID NO 794
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 794
atttataaat agtggtgata gatttaacgt                                30

<210> SEQ ID NO 795
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 795

```
gaaatctggc agttttttggt acacgaaagc                              30
```

<210> SEQ ID NO 796
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 796

```
tgccagttct ggcaggtcta aaaagtgttc                               30
```

<210> SEQ ID NO 797
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 797

```
cacagaactt gcatttatat aaagggaaag                               30
```

<210> SEQ ID NO 798
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 798

```
agttggcaca gatttcgctt tatctttttt                               30
```

<210> SEQ ID NO 799
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 799

```
agcgctcaca atttaatacg actcactata                               30
```

<210> SEQ ID NO 800
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 800

```
ggaattgtga gcggataaca atttcacaca                               30
```

<210> SEQ ID NO 801
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 801
ggaattgtga gcggataaca atttcacaca                                        30

<210> SEQ ID NO 802
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 802
ggaattgtga gcggataaca atttcacaca                                        30

<210> SEQ ID NO 803
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 803
agaactgtaa tccctatcag tgatagagat                                        30

<210> SEQ ID NO 804
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 804
tgttgattta tctaacaccg tgcgtgttga                                        30

<210> SEQ ID NO 805
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 805
acaccgtgcg tgttgatata gtcgaataaa                                        30

<210> SEQ ID NO 806
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 806
ggttcttttt ggtacctctg gcggtgataa                                        30

<210> SEQ ID NO 807
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 807
tgtaggatcg tacaggtata aattcttcag                                        30

<210> SEQ ID NO 808
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 808
ctatctcatt tgctagtata gtcgaataaa                                        30

<210> SEQ ID NO 809
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 809
aattgtgagc ggataacaat ttcacacaga                                        30

<210> SEQ ID NO 810
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 810
gttacgttta tcgcggtgat tgttacttat                                        30

<210> SEQ ID NO 811
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 811
acggtgacct agatctccga tactgagcac                                        30

<210> SEQ ID NO 812
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 812
tggaattgtg agcggataaa atttcacaca                                        30

<210> SEQ ID NO 813
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 813
tagtagataa tttaagtgtt ctttaatttc                                        30

<210> SEQ ID NO 814
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 814
aacaaaaaaa cggatcctct agttgcggcc                                    30

<210> SEQ ID NO 815
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 815
ataaatgctt gactctgtag cgggaaggcg                                    30

<210> SEQ ID NO 816
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 816
atttcatgat gatacgtgag cggatagaag                                    30

<210> SEQ ID NO 817
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 817
gggacacaaa catcaagagg atatgagatt                                    30

<210> SEQ ID NO 818
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 818
gtcaaaatga ccgaaacggg tggtaacttc                                    30

<210> SEQ ID NO 819
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 819
agtaatctta tcgccagttt ggtctggtca                                    30

<210> SEQ ID NO 820
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 820
agtaatctta tcgccagttt ggtctggtca                                         30

<210> SEQ ID NO 821
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 821
aattctgaac aacatccgta ctcttcgtgc                                         30

<210> SEQ ID NO 822
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 822
cgatctattc acctgaaaga gaaataaaaa                                         30

<210> SEQ ID NO 823
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 823
aaacgttagt ttgaatggaa agatgcctgc                                         30

<210> SEQ ID NO 824
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 824
acaggaaaca gctatgacca tgattacgcc                                         30

<210> SEQ ID NO 825
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 825
gttcactcta taccgctgaa ggtgtaatgg                                         30

<210> SEQ ID NO 826

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 826
tagtttataa tttaagtgtt ctttaatttc                                         30

<210> SEQ ID NO 827
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 827
gaaaatgtga gcgagtaaca acctcacaca                                         30

<210> SEQ ID NO 828
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 828
ttttatcgca actctctact gtttctccat                                         30

<210> SEQ ID NO 829
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 829
gtttctccat tactagagaa agaggggaca                                         30

<210> SEQ ID NO 830
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 830
aataactctg atagtgctag tgtagatctc                                         30

<210> SEQ ID NO 831
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 831
caccttcggg tgggcctttc tgcgtttata                                         30

<210> SEQ ID NO 832
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 832
caccttcggg tgggcctttc tgcgtttata                                   30

<210> SEQ ID NO 833
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 833
gtgttgacta ttttacctct ggcggtgata                                   30

<210> SEQ ID NO 834
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 834
cgaaacggga accctatatt gatctctact                                   30

<210> SEQ ID NO 835
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 835
accgttaaga accatatcca agaatcaaaa                                   30

<210> SEQ ID NO 836
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 836
accgttaaga accatatcca agaatcaaaa                                   30

<210> SEQ ID NO 837
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 837
cacaaataca cacactaaat taataactag                                   30

<210> SEQ ID NO 838
<211> LENGTH: 30
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 838
atacggtcaa cgaactataa ttaactaaac                                    30

<210> SEQ ID NO 839
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 839
tagatacaat tctattaccc ccatccatac                                    30

<210> SEQ ID NO 840
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 840
ggggcgaggg ccccgcctcc ggaggcgggg                                    30

<210> SEQ ID NO 841
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 841
gaggggacgg ctccggcccc ggggccggag                                    30

<210> SEQ ID NO 842
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 842
ggggcgaggg ctccggcccc ggggccggag                                    30

<210> SEQ ID NO 843
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 843
gaggggacgg ccccgcctcc ggaggcgggg                                    30

<210> SEQ ID NO 844
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 844
ctttctagtg caaattgtga ccgcattttg                                    30

<210> SEQ ID NO 845
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 845
ttatcaaaaa ccatggtttt tgataa                                        26

<210> SEQ ID NO 846
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 846
accactttgt acaagaaagc tgggt                                         25

<210> SEQ ID NO 847
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 847
tcactatcag tcaaaataaa atcattattt                                    30

<210> SEQ ID NO 848
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 848
gttcagcttt cttgtacaaa gtggttgatc                                    30

<210> SEQ ID NO 849
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 849
aacacaacat atccagtcac tatggtcgac                                    30

<210> SEQ ID NO 850
<211> LENGTH: 27
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 850
acgaccttcg cattacgaat gcgctgc                                              27

<210> SEQ ID NO 851
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 851
gggacatatt tgggacagaa gtaccaaaaa                                           30

<210> SEQ ID NO 852
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 852
ttcctatact ttttagagaa taggaacttc                                           30

<210> SEQ ID NO 853
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 853
ttcctatact ttctagagaa taggaacttc                                           30

<210> SEQ ID NO 854
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 854
tcggtgcgca taatgtatat tatgttaaat                                           30

<210> SEQ ID NO 855
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 855
tcatttaaca taatatacat tatgcgcacc                                           30

<210> SEQ ID NO 856
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 856
gaaacatttg gggccaaact gtccatatta                                    30

<210> SEQ ID NO 857
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 857
gagtcaaaat ggccccaatt gtcttgtatt                                    30

<210> SEQ ID NO 858
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(15)
<223> OTHER INFORMATION: a, c, t, or g
<220> FEATURE:
<221> NAME/KEY: modified_base
<222> LOCATION: (18)..(20)
<223> OTHER INFORMATION: a, c, t, or g

<400> SEQUENCE: 858
tctagagaaa gannngannn actagatg                                      28

<210> SEQ ID NO 859
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 859
tctagagaaa gagggacaa actagatg                                       28

<210> SEQ ID NO 860
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 860
tctagagaaa gacaggaccc actagatg                                      28

<210> SEQ ID NO 861
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 861
tctagagaaa gatccgatgt actagatg                                      28

<210> SEQ ID NO 862
<211> LENGTH: 28
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 862
tctagagaaa gattagacaa actagatg                                          28

<210> SEQ ID NO 863
<211> LENGTH: 28
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 863
tctagagaaa gaagggacag actagatg                                          28

<210> SEQ ID NO 864
<211> LENGTH: 28
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 864
tctagagaaa gacatgacgt actagatg                                          28

<210> SEQ ID NO 865
<211> LENGTH: 28
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 865
tctagagaaa gataggagac actagatg                                          28

<210> SEQ ID NO 866
<211> LENGTH: 28
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 866
tctagagaaa gaagagactc actagatg                                          28

<210> SEQ ID NO 867
<211> LENGTH: 28
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 867
tctagagaaa gacgagatat actagatg                                          28

```
<210> SEQ ID NO 868
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 868
tctagagaaa gactggagac actagatg                                      28

<210> SEQ ID NO 869
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 869
tctagagaaa gaggcgaatt actagatg                                      28

<210> SEQ ID NO 870
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 870
tctagagaaa gaggcgatac actagatg                                      28

<210> SEQ ID NO 871
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 871
tctagagaaa gaggtgacat actagatg                                      28

<210> SEQ ID NO 872
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 872
tctagagaaa gagtggaaaa actagatg                                      28

<210> SEQ ID NO 873
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 873
tctagagaaa gatgagaaga actagatg                                      28

<210> SEQ ID NO 874
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 874
tctagagaaa gaagggatac actagatg                                          28

<210> SEQ ID NO 875
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 875
tctagagaaa gacatgaggc actagatg                                          28

<210> SEQ ID NO 876
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 876
tctagagaaa gacatgagtt actagatg                                          28

<210> SEQ ID NO 877
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 877
tctagagaaa gagacgaatc actagatg                                          28

<210> SEQ ID NO 878
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 878
tctagagaaa gatttgatat actagatg                                          28

<210> SEQ ID NO 879
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 879
tctagagaaa gacgcgagaa actagatg                                          28

<210> SEQ ID NO 880
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 880
tctagagaaa gagacgagtc actagatg                                           28

<210> SEQ ID NO 881
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 881
tctagagaaa gagaggagcc actagatg                                           28

<210> SEQ ID NO 882
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 882
tctagagaaa gagatgacta actagatg                                           28

<210> SEQ ID NO 883
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 883
tctagagaaa gagccgacat actagatg                                           28

<210> SEQ ID NO 884
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 884
tctagagaaa gagccgagtt actagatg                                           28

<210> SEQ ID NO 885
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 885
tctagagaaa gaggtgactc actagatg                                           28

<210> SEQ ID NO 886
<211> LENGTH: 28
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 886
tctagagaaa gagtggaact actagatg                                      28

<210> SEQ ID NO 887
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 887
tctagagaaa gataggactc actagatg                                      28

<210> SEQ ID NO 888
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 888
tctagagaaa gattggacgt actagatg                                      28

<210> SEQ ID NO 889
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 889
tctagagaaa gaaacgacat actagatg                                      28

<210> SEQ ID NO 890
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 890
tctagagaaa gaaccgaatt actagatg                                      28

<210> SEQ ID NO 891
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 891
tctagagaaa gacaggatta actagatg                                      28

<210> SEQ ID NO 892
<211> LENGTH: 28
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 892
tctagagaaa gacccgagac actagatg                                            28

<210> SEQ ID NO 893
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 893
tctagagaaa gaccggaaat actagatg                                            28

<210> SEQ ID NO 894
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 894
tctagagaaa gaccggagac actagatg                                            28

<210> SEQ ID NO 895
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 895
tctagagaaa gagctgagca actagatg                                            28

<210> SEQ ID NO 896
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 896
tctagagaaa gagtagatca actagatg                                            28

<210> SEQ ID NO 897
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 897
tctagagaaa gatatgaata actagatg                                            28

<210> SEQ ID NO 898
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 898
tctagagaaa gattagagtc actagatg                                        28

<210> SEQ ID NO 899
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 899
tctagagttc acacaggaaa cctactagat g                                    31

<210> SEQ ID NO 900
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 900
tctagagatt aaagaggaga aatactagat g                                    31

<210> SEQ ID NO 901
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 901
tctagagtca cacaggaaac ctactagatg                                      30

<210> SEQ ID NO 902
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 902
tctagagtca cacaggaaag tactagatg                                       29

<210> SEQ ID NO 903
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 903
tctagagtca cacaggacta ctagatg                                         27

<210> SEQ ID NO 904
<211> LENGTH: 28
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 904
tctagagaaa gaggagaaat actagatg                28

<210> SEQ ID NO 905
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 905
tctagagatt aaagaggaga atactagatg                30

<210> SEQ ID NO 906
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 906
tctagagaaa gaggggaaat actagatg                28

<210> SEQ ID NO 907
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 907 gtgtg                5

<210> SEQ ID NO 908
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 908
gtgtgtctag                10

<210> SEQ ID NO 909
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 909
tcacacagga aaccggttcg atg                23

<210> SEQ ID NO 910
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 910
tcacacagga aaggcctcga tg                                              22

<210> SEQ ID NO 911
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 911
tcacacagga cggccggatg                                                 20

<210> SEQ ID NO 912
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 912
tctcacgtgt gtcaag                                                     16

<210> SEQ ID NO 913
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 913
tctcacgtgt gt                                                         12

<210> SEQ ID NO 914
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 914 catccct                                                                7

<210> SEQ ID NO 915
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 915
tcacatccct                                                            10

<210> SEQ ID NO 916
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 916
tcacatccct cc                                                         12

<210> SEQ ID NO 917
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 917
actgcacgag gtaacacaag                                                 20

<210> SEQ ID NO 918
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 918
tacgaggagg atgaagagta                                                 20

<210> SEQ ID NO 919
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 919
actttactta tgagggagta                                                 20

<210> SEQ ID NO 920
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 920
acgaagacgg agacttctaa                                                 20

<210> SEQ ID NO 921
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 921
aaccctcagg aggtaaacca                                                 20

<210> SEQ ID NO 922
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 922
```
aagacatgga gacacattta                                                    20

<210> SEQ ID NO 923
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 923
gcacgaggta acacaagatg tgaagagctg                                         30

<210> SEQ ID NO 924
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 924
gaggaggatg aagagtaatg tgaagagctg                                         30

<210> SEQ ID NO 925
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 925
aggaggtcat c                                                             11

<210> SEQ ID NO 926
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 926
gcaagctctt ttttcagttg tctc                                               24

<210> SEQ ID NO 927
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 927
ctgatagtta aaatcaccag catga                                              25

<210> SEQ ID NO 928
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 928
taaaaacaag aggaaaacaa                                              20

<210> SEQ ID NO 929
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 929
tctcctcttt                                                         10

<210> SEQ ID NO 930
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 930
acggagaagc agcgaa                                                  16

<210> SEQ ID NO 931
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 931
gaggttggga caag                                                    14

<210> SEQ ID NO 932
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 932
taaatgtatc cgtttataag gacagcccga                                   30

<210> SEQ ID NO 933
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 933
ctcttaagtg ggagcggct                                               19

<210> SEQ ID NO 934
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 934
ctctaccgga gaaatt                                                  16

<210> SEQ ID NO 935
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 935
ctcatcgtta aagagcgact ac                                              22

<210> SEQ ID NO 936
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 936
ctcagcctgt acctggagag cctttc                                          26

<210> SEQ ID NO 937
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 937
ctcaaggagg                                                            10

<210> SEQ ID NO 938
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 938 gagagg                                                                 6

<210> SEQ ID NO 939
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 939
aggaggatta caa                                                        13

<210> SEQ ID NO 940
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 940
aaagaggaga aa                                                         12

<210> SEQ ID NO 941
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 941
tcacacagga aag                                                          13

<210> SEQ ID NO 942
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 942 ggaagagg                                                                 8

<210> SEQ ID NO 943
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 943
tttctcctct ttaat                                                        15

<210> SEQ ID NO 944
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 944
tcacacagga aaggcctcg                                                    19

<210> SEQ ID NO 945
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 945
attaaagagg agaaattaag c                                                 21

<210> SEQ ID NO 946
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 946
tcgtttctga aaattttcg tttctgaaaa                                         30

```
<210> SEQ ID NO 947
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 947
tggctaacat agggt                                                    15

<210> SEQ ID NO 948
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 948
tggctaactg aggat                                                    15

<210> SEQ ID NO 949
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 949
tggctaaccc agggt                                                    15

<210> SEQ ID NO 950
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 950
tggctaactc aggtg                                                    15

<210> SEQ ID NO 951
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 951
tggctaaccc tggta                                                    15

<210> SEQ ID NO 952
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 952
tggctaactt gggac                                                    15

<210> SEQ ID NO 953
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 953
tggctaacgc aggtc                                                          15

<210> SEQ ID NO 954
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 954
tggctaacat cggtg                                                          15

<210> SEQ ID NO 955
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 955
ttaattaagg aaaagatct                                                      19

<210> SEQ ID NO 956
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 956
cagaagagga tattaata                                                       18

<210> SEQ ID NO 957
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 957
ttgataagga attgta                                                         16

<210> SEQ ID NO 958
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 958
tcagaggaga taattta                                                        17

<210> SEQ ID NO 959
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 959
tgacacgttg agcggtatga                                                   20

<210> SEQ ID NO 960
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 960
acagataaca ggagtaagta                                                   20

<210> SEQ ID NO 961
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 961
taaagggaga aaaat                                                        15

<210> SEQ ID NO 962
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 962
gagtcttgag gtaactat                                                     18

<210> SEQ ID NO 963
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 963
tcaggaatat taaaaacgct                                                   20

<210> SEQ ID NO 964
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 964
atttgaagga aaatatt                                                      17

<210> SEQ ID NO 965
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 965
caaaaacata ctgcaggaat                                                    20

<210> SEQ ID NO 966
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 966
tgccattgca aaggagaaga ct                                                 22

<210> SEQ ID NO 967
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 967 aaggggaat tcaaat                                                         16

<210> SEQ ID NO 968
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 968
aaggggtgca gaat                                                          14

<210> SEQ ID NO 969
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 969
aggtggaatc acag                                                          14

<210> SEQ ID NO 970
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 970
atagataaaa atggtaacaa t                                                  21

<210> SEQ ID NO 971
<211> LENGTH: 24
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 971
gggatatagc ctgaggggcc tgta                                          24

<210> SEQ ID NO 972
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 972
cggcaataac agaggcgatt t                                             21

<210> SEQ ID NO 973
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 973
attaaagagg agaaata                                                  17

<210> SEQ ID NO 974
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 974
tcacacagga aagta                                                    15

<210> SEQ ID NO 975
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 975
aaaggaggtg t                                                        11

<210> SEQ ID NO 976
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 976
agaggtggtg t                                                        11

<210> SEQ ID NO 977
<211> LENGTH: 6
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 977 aggagg                                                                  6

<210> SEQ ID NO 978
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 978 gagg                                                                    4

<210> SEQ ID NO 979
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 979
taaaggagga a                                                           11

<210> SEQ ID NO 980
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 980
aaaggtggtg aa                                                          12

<210> SEQ ID NO 981
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 981
aggaaacaga acc                                                         13

<210> SEQ ID NO 982
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 982
gattgggata aataat                                                      16

<210> SEQ ID NO 983
<211> LENGTH: 16
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 983
atcaaccggg gtacat                                                         16

<210> SEQ ID NO 984
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 984
tttggagatt ttcaac                                                         16

<210> SEQ ID NO 985
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 985
aaaaaaggta attcaa                                                         16

<210> SEQ ID NO 986
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 986
cataaggtaa ttcaca                                                         16

<210> SEQ ID NO 987
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 987
ataaggagtc ttaatc                                                         16

<210> SEQ ID NO 988
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 988
gttccggcta agtaac                                                         16

<210> SEQ ID NO 989
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 989
taatggaaac ttcctc                                                    16

<210> SEQ ID NO 990
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 990
tcgctggggg tcaaag                                                    16

<210> SEQ ID NO 991
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 991
atttgagggg gattca                                                    16

<210> SEQ ID NO 992
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 992
aatttaggtc agaag                                                     15

<210> SEQ ID NO 993
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 993
aatcaatagg agaaatcaat                                                20

<210> SEQ ID NO 994
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 994
ttaaagagga gaaatactag                                                20

<210> SEQ ID NO 995
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 995
tctagagaac tagaatcacc tcttggattt gggtattaaa gaggagatac tagatg      56

<210> SEQ ID NO 996
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 996
tctagagaac tagaatcacc tcttgctttt gggtaagaaa gaggagatac tagatg      56

<210> SEQ ID NO 997
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 997
cccgccgcca ccatggag                                                 18

<210> SEQ ID NO 998
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 998
cccgccgcca ccatggag                                                 18

<210> SEQ ID NO 999
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 999
tctagagcac cactactaga tg                                            22

<210> SEQ ID NO 1000
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1000
tctagagtca caccactact agatg                                         25

<210> SEQ ID NO 1001
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1001
```

```
tctagagtca caccaccccta ctagatg                                          27
```

<210> SEQ ID NO 1002
<211> LENGTH: 1032
<212> TYPE: DNA
<213> ORGANISM: Enterobacteria sp.
<220> FEATURE:
<223> OTHER INFORMATION: Phage P1

<400> SEQUENCE: 1002

```
atgtccaatt tactgaccgt acaccaaaat ttgcctgcat taccggtcga tgcaacgagt        60
gatgaggttc gcaagaacct gatggacatg ttcaggatc gccaggcgtt ttctgagcat        120
acctggaaaa tgcttctgtc cgtttgccgg tcgtgggcgg catggtgcaa gttgaataac       180
cggaaatggt ttcccgcaga acctgaagat gttcgcgatt atcttctata tcttcaggcg       240
cgcggtctgg cagtaaaaac tatccagcaa catttgggcc agctaaacat gcttcatcgt       300
cggtccgggc tgccacgacc aagtgacagc aatgctgttt cactggttat gcggcggatc       360
cgaaaagaaa acgttgatgc cggtgaacgt gcaaacagg ctctagcgtt cgaacgcact        420
gatttcgacc aggttcgttc actcatgaa atagcgatc gctgccagga tatacgtaat         480
ctggcatttc tggggattgc ttataacacc ctgttacgta tagccgaaat tgccaggatc       540
agggttaaag atatctcacg tactgacggt gggagaatgt taatccatat tggcagaacg       600
aaaacgctgg ttagcaccgc aggtgtagag aaggcactta gcctggggt aactaaactg        660
gtcgagcgat ggatttccgt ctctggtgta gctgatgatc cgaataacta cctgttttgc       720
cgggtcagaa aaatggtgt tgccgcgcca tctgccacca gccagctatc aactcgcgcc        780
ctggaaggga tttttgaagc aactcatcga ttgatttacg cgctaaggga tgactctggt       840
cagagatacc tggcctggtc tggacacagt gcccgtgtcg gagccgcgcg agatatggcc       900
cgcgctggag tttcaatacc ggagatcatg caagctggtg gctggaccaa tgtaaatatt       960
gtcatgaact atatccgtaa cctggatagt gaaacagggg caatggtgcg cctgctggaa      1020
gatggcgatt ag                                                         1032
```

<210> SEQ ID NO 1003
<211> LENGTH: 4543
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1003

```
atgaccatga ttacgccaag cttgcatgcc tgcaggtcga ctctagaatt cgctgtctgc        60
gagggccggc tgttggggtg agtactccct ctcaaaagcg ggcatgactt ctgcgctaag       120
attgtcagtt tccaaaaacg aggaggattt gatattcacc tggcccgcgg tgatgccttt       180
gagggtggcc gcgtccatct ggtcagaaaa gacaatcttt tgttgtcaa gcttgaggtg        240
tggcaggctt gagatctggc catacacttg agtgacaatg acatccactt tgcctttctc       300
tccacaggtg tccactccca ggtccaactg cagcccaagc ttccaccatg ccacaatttg       360
atatattatg taaaacacca cctaaggtgc ttgttcgtca gtttgtggaa aggtttgaaa       420
gaccttcagg tgagaaaata gcattatgtg ctgctgaact aacctattta tgttggatga      480
ttacacataa cggaacagca atcaagagag ccacattcat gagctataat actatcaata      540
gcaattcgct gagtttggat attgtcaaca agtcactgca gtttaaatac aagacgcaaa      600
```

```
aagcaacaat tctggaagcc tcattaaaga aattgattcc tgcttgggaa tttacaatta    660
ttccttacta tggacaaaaa catcaatctg atatcactga tattgtaagt agtttgcaat    720
tacagttcga atcatcggaa gaagcagata agggaaatag ccacagtaaa aaaatgctta    780
aagcacttct aagtgagggt gaaagcatct gggagatcac tgagaaaata ctaaattcgt    840
ttgagtatac ttcgagattt acaaaaacaa aaactttata ccaattcctc ttcctagcta    900
ctttcatcaa ttgtggaaga ttcagcgata ttaagaacgt tgatccgaaa tcatttaaat    960
tagtccaaaa taagtatctg ggagtaataa tccagtgttt agtgacagag acaaagacaa   1020
gcgttagtag gcacatatac ttctttagcg caaggggtag gatcgatcca cttgtatatt   1080
tggatgaatt tttgaggaat tctgaaccag tcctaaaacg agtaaatagg accggcaatt   1140
cttcaagcaa caagcaggaa taccaattat taaaagataa cttagtcaga tcgtacaaca   1200
aagctttgaa gaaaaatgcg ccttattcaa tctttgctat aaaaaatggc ccaaaatctc   1260
acattggaag acatttgatg acctcatttc tttcaatgaa gggcctaacg gagttgacta   1320
atgttgtggg aaattggagc gataagcgtg cttctgccgt ggccaggaca acgtatactc   1380
atcagataac agcaatacct gatcactact tcgcactagt ttctcggtac tatgcatatg   1440
atccaatatc aaaggaaatg atagcattga aggatgagac taatccaatt gaggagtggc   1500
agcatataga acagctaaag ggtagtgctg aaggaagcat acgataccc gcatggaatg    1560 ggataatatc acaggaggta ctagactacc tttcatccta cataaataga cgcatataag   1620
tacgcattta agcataaaca cgcactatgc cgttcttctc atgtatatat atatacaggc   1680
aacacgcaga tataggtgcg acgtgaacag tgagctgtat gtgcgggtac cgagctcctc   1740
gaggatcaga catgataaga tacattgatg agtttggaca aaccacaact agaatgcagt   1800
gaaaaaaatg ctttatttgt gaaatttgtg atgctattgc tttatttgta accattataa   1860
agctgcaata aacaagttat cctcgaggag ctcatgagcg cttgtttcgg cgtgggtatg   1920
gtggcaggcc cgtggccggg ggactgttgg gcgccatctc cttgcatgca ccattccttg   1980
cggcggcggt gctcaacggc ctcaacctac tactgggctg cttcctaatg caggagtcgc   2040
ataagggaga gcgtcgacct actagtcggc cgtacgggcc ctttcgtctc gcgcgtttcg   2100
gtgatgacgg tgaaaacctc tgacacatgc agctcccgga cggtcaca gcttgtctgt     2160 aagcggatgc cgggagcaga caagcccgtc agggcgcgtc agcgggtgtt ggcgggtgtc   2220
ggggctggct taactatgcg gcatcagagc agattgtact gagagtgcac catatgcggt   2280
gtgaaatacc gcacagatgc gtaaggagaa ataccgcat caggcggcct taagggcctc    2340
gtgatacgcc tatttttata ggttaatgtc atgataataa tggtttctta gacgtcaggt   2400
ggcacttttc ggggaaatgt gcgcggaacc cctatttgtt tatttttcta aatacattca   2460
aatatgtatc cgctcatgag acaataaccc tgataaatgc ttcaataata ttgaaaaagg   2520
aagagtatga gtattcaaca tttccgtgtc gcccttattc ccttttttgc ggcattttgc   2580
cttcctgttt ttgctcaccc agaaacgctg gtgaaagtaa aagatgctga agatcagttg   2640
ggtgcacgag tgggttacat cgaactggat ctcaacagcg gtaagatcct tgagagtttt   2700
cgccccgaag aacgttttcc aatgatgagc acttttaaag ttctgctatg tggcgcggta   2760
ttatcccgta ttgacgccgg gcaagagcaa ctcggtcgcc gcatacacta ttctcagaat   2820
gacttggttg agtactcacc agtcacagaa aagcatctta cggatggcat gacagtaaga   2880
gaattatgca gtgctgccat aaccatgagt gataacactg cggccaactt acttctgaca   2940
```

| | |
|---|---|
| acgatcggag gaccgaagga gctaaccgct tttttgcaca acatgggggga tcatgtaact | 3000 |
| cgccttgatc gttgggaacc ggagctgaat gaagccatac caaacgacga gcgtgacacc | 3060 |
| acgatgcctg tagcaatggc aacaacgttg cgcaaactat taactggcga actacttact | 3120 |
| ctagcttccc ggcaacaatt aatagactgg atggaggcgg ataaagttgc aggaccactt | 3180 |
| ctgcgctcgg cccttccggc tggctggttt attgctgata aatctggagc cggtgagcgt | 3240 |
| gggtctcgcg gtatcattgc agcactgggg ccagatggta agccctcccg tatcgtagtt | 3300 |
| atctacacga cggggagtca ggcaactatg gatgaacgaa atagacagat cgctgagata | 3360 |
| ggtgcctcac tgattaagca ttggtaactg tcagaccaag tttactcata tactttag | 3420 |
| attgatttaa aacttcattt ttaatttaaa aggatctagg tgaagatcct ttttgataat | 3480 |
| ctcatgacca aaatccctta acgtgagttt tcgttccact gagcgtcaga ccccgtagaa | 3540 |
| aagatcaaag gatcttcttg agatcctttt tttctgcgcg taatctgctg cttgcaaaca | 3600 |
| aaaaaaccac cgctaccagc ggtggtttgt ttgccggatc aagagctacc aactcttttt | 3660 |
| ccgaaggtaa ctggcttcag cagagcgcag ataccaaata ctgtccttct agtgtagccg | 3720 |
| tagttaggcc accacttcaa gaactctgta gcaccgccta catacctcgc tctgctaatc | 3780 |
| ctgttaccag tggctgctgc cagtggcgat aagtcgtgtc ttaccgggtt ggactcaaga | 3840 |
| cgatagttac cggataaggc gcagcggtcg ggctgaacgg ggggttcgtg cacacagccc | 3900 |
| agcttggagc gaacgaccta caccgaactg agatacctac agcgtgagca ttgagaaagc | 3960 |
| gccacgcttc ccgaagggag aaaggcggac aggtatccgg taagcggcag ggtcggaaca | 4020 |
| ggagagcgca cgagggagct tccaggggga aacgcctggt atctttatag tcctgtcggg | 4080 |
| tttcgccacc tctgacttga gcgtcgattt ttgtgatgct cgtcaggggg gcggagccta | 4140 |
| tggaaaaacg ccagcaacgc ggccttttta cggttcctgg ccttttgctg gccttttgct | 4200 |
| cacatgttct ttcctgcgtt atcccctgat tctgtggata accgtattac cgcctttgag | 4260 |
| tgagctgata ccgctcgccg cagccgaacg accgagcgca gcgagtcagt gagcgaggaa | 4320 |
| gcggaagagc gcccaatacg caaaccgcct ctccccgcgc gttggccgat tcattaatgc | 4380 |
| agctggcacg acaggtttcc cgactggaaa gcgggcagtg agcgcaacgc aattaatgtg | 4440 |
| agttagctca ctcattaggc accccaggct ttacacttta tgcttccggc tcgtatgttg | 4500 |
| tgtggaattg tgagcggata caatttcac acaggaaaca gct | 4543 |

<210> SEQ ID NO 1004
<211> LENGTH: 6251
<212> TYPE: DNA
<213> ORGANISM: Zygosaccharomyces rouxii

<400> SEQUENCE: 1004

| | |
|---|---|
| gaattcaaaa cataaagaag agcatgaaaa gactattagt gaacatgtca ccaatcgaag | 60 |
| gactggaaga attgtttttt caggcaagat cgttgggagt accttcccat ttggtagaga | 120 |
| gtgtacgacc acctgtcgat attcatagcg gtaacatgca caggacaggt attagtccga | 180 |
| ggaagcgaac cttacctgaa ccgttcgatg aatcaaacac cataagccac cggagaacta | 240 |
| gaagaaatac caaacaataa cctaaacctg ctatggctaa tagattagga ttgagctact | 300 |
| ggacgggaat tgtggagggg tattgtggaa tggagtgttg tgttgtggaa cggggttaat | 360 |
| tgtaatgata atgataatga taacggtggg ttatagagca ttgcatctgt cgagttacga | 420 |
| tgatagagtt gtaagggcgg cagcgggtat ggcctaaata atttagttta gcttaatata | 480 |
| atttagtttt tctaggcgag atcatatcac tgtggacgtt gatgaaagaa tacgttattc | 540 |

-continued

```
tttcatcaaa tcgttctttc attaattcgt tctttcatca aatcgttctt tcatcaagtc    600
gttctttcat caacccgtac cgcgcagaag ggagcctgcg caggcggttg ctacagaaat    660
taaaccatta ctctatcgaa taaacatttg actacgagaa gcaatgattg gtccagttga    720
tacaccctga cagttactat gctcttgtat ttttattttg ttcctctaaa ctacccgctt    780
gttcctcgta ccttcttgct gaaagtaaag atctacactc aaaatgtaaa ttcttgaaaa    840
taaaataata acccaataaa accctctcta tattgctacc atacaccatc ttgcttcttg    900
gacctcgcct ccgaatttga tttggacatt attgcaatac aaatttatca ttatacccat    960
gatttttata cccttaccta ttacctactg ttacaataag aaaaattaat agtacacggt   1020
ctcaatagtc ttacagaaag gcttaaatta gcaaatgagt ctatccactg gactcagttt   1080
cactttgatc ctcaggatcc ttctcagagc ctcctcttct gttggtgtct ttacctagaa   1140
tgtcacacct gacttgtaac cgaatatcat ccaaagtgtt accttgtgag gtcattttga   1200
tattcaccca aaatccggag aggtgaccag aattgcttgg tttaaggctt acttttaatt   1260
gcccattttg cttgcatctg acacctctat atatgctaaa tttccagctg ctcccaaggc   1320 acccttgag atctagatat agccgagcac gggtatcctt cgtttgcata aaaaaatctt    1380
cttgttcgcg cttatgactc aataaatagc ttgcaagctt cctgcattgt ccgagctgag   1440
ccttagcgga atctgggtca tcctgaagtg cggaaacaat cttatcaaat aactgtgagg   1500
atgtctctgg tgcctctggt gccctttgag cctcttgatc ttgaccagga gatgcagatt   1560
gtgagttctg tacttccaca gaactgccct catcgtcgtc ccctcctccc tcatcaaaac   1620
cataatctgt ttcgttggtg atcatattac acaccatctc tcctacccag agctcccgga   1680
cattggcggc cataaatttga agtttgaagg attgtcctaa cattgctttg gatgatacga   1740
ggatctcaac tttacacaaa ccaacctcga gattttcaac caatgtgcca ttatgaagtt   1800
tttcaaagaa tcgctgcaat cgaggccttg cattcacagg atcaaggaag ttctcattaa   1860
tcgttttggt gacaactcgt tccttcttct gttgacccaa aatttcgtct ttcctcgatt   1920
caggaatgct tacatcagga gcaattaact tatgaagcct ttcagcaaag tcttctttgt   1980
ctttatttgc aaagaactta tgttctttta ggcgcttaag gatagtattt aataccacat   2040
aaggctccgg ccattccaag ttcactggaa ttaccccgta tggtaacttt ttcattaggt   2100
atttcacata gaatattgct aagataggat agtctcggta attctcggct atgttgacca   2160
tacccttagc tgttgaaagc atattctgtg ctggtaggtg tataacagtg taaggatatg   2220
tcataagcac atcgttcatc attctcagct ctctatcggg tctggagtcc ctagcatcct   2280
gactagtaaa catatttaca acatcgccac ttataatcgc cgtttctaaa tgaaatcaga   2340
atccttatgc tttagatttg agaaagtctg agaaaatgat ctgggggatg ttcctttat    2400 atagtcggta cccgtagcat atgacagagt gagaattttg cagagaggat atcccctttt   2460 cgttttaaa cctcagaaaa gttttctttt gtccgcagag cgcacaggga gctcattttc    2520
gtacgtagat atcagaagag gttttcgcgg atagtgcttt ccattttggg atctactaag   2580
gcattgagca agttcattca taaaaccctc agcaaatatt tctgtatttg tgaagcctat   2640
agaagatcta gaactgtctg taaagctcat atggtattta tgtttattaa tagaactcac   2700
agtaaattaa agtgtgttta aagatcctac aaaatatgta atgctattct tagattccca   2760
cgagaggctt gcttttgtac atagacccctc cagaaaacat agtgctgttt atgcagcaca   2820
cagaaggttt ataggtgtga gctacacttt ataggccggg taagtatagt aagatatgtg   2880
```

```
caaattagcc gcggagccat aaacaatcat ctttttaaatt agatgcacag ccttaaaccc      2940
agcaattctg gtcacctctc cggatttttgg gtgaatatca aaatgacctc acaaggtaac      3000
actttggatg atattcggtt acaagtcagg tgtgacattc taggtaaaga caccaacaga      3060
agaggaggct ctgagaagga tcctgaggat caaagtgaaa ctgagtccag tggatagact      3120
catttgctaa tttaagcctt tctgtaagac tattgagacc gtgtactatt aatttttctt      3180
attgtaacag taggtaatag gtaagggtat aaaaatcatg gtataatga taaatttgta      3240 ttgcaataat gtccaaatca aattcggagg cgaggtccaa gaagcaagat ggtgtatggt      3300
agcaatatag agagggtttt attgggttat tattttattt tcaagaattt acattttgag      3360
tgtagatctt tactttcagc aagaaggtac gaggaacaag cgggtagttt agaggaacaa      3420
aataaaaata caagagcata gtaactgtca gggtgtatca actggaccaa tcattgcttc      3480
tcgtagtcaa atgtttattc gatagagtaa tggtttaatt tctgtagcaa ccgcctgcgc      3540 aggctcccctt ctgcgcggta cgggttgatg aaagaacgac ttgatgaaag aacgatttga      3600
tgaaagaacg aattaatgaa agaacgatt tgatgaaaga taacgtattc tttcatcaac      3660
gtccacagtg atatgatctc gcctagaaaa actaaattat attaagctaa actaaattat      3720
ttaggccata cccgctgccg cccttacaac tctatcatcg taactcgaca gatgcaatgc      3780
tctataaccc accgttatca ttatcattat cattacaatt aaccccgttc cacaacacaa      3840
cactccattc cacaataccc ctccacaatt cccgtccagt agctcaaatc tagtgtagaa      3900
tcttaaaaca ttgaatcata aatcgtatat cttacatgac attacattac attacattac      3960
gtgtatatca ttatccagcc tatttaagac gagtctcctg atatatcagg gcatctgttg      4020
aaagataatt cttgagagag caccaacgag cctgtatttg agcaagttac gtcaatgctt      4080
gaaatagagt ccgagtccgg tggtgtgttc ggaggatgtg aaggcttaat cttgtcagga      4140
ggtgtcagga ggtgtcgatg gatcgtccga cgacaatgct aatctttcgg cgcttcacat      4200
gtgccgctgt taacgcgtta taaagtgcag ttctcccatt atccggaaaa tctgggacgc      4260
ctcgggaact tcttgcttgt aacttatact ctttaccttc gttattcttg aacctggcat      4320
agctgctcaa aaaaaccaat acatccattg gtattatttc tgcattcttt ccataccgag      4380
ccatcaatgt ctcgatatct gatatcatag gaatattctt gtcttgttca caagggttgc      4440
tatttggatc aaccaactca cacgcccttt cggctgtgat attataaaac cccgatagaa      4500
acgcaaataa ataagaaggc ggactctttt ctatcgtgtg catgtatcga gccttagcca      4560
cacggctaac accttcttcc cgcgcggcag accaattacc atagagcgtg gcttctttat      4620
ccatctcatt atttgaaaga tatgaagctg tcacatgcct gcctaaatgc gctttcggtc      4680
cattgggtat tttaaagatg ctctcatccg attgtttaga gataaacccg tcatatgagc      4740
ctaacagact gttcctgaga agctggtaat catagcgtgc atcctcatca gtagttcgag      4800
ttttgggaat aggatctgtc cattggaggt atgaatctag tgccaacagc gggtcgcatc      4860
gtcctttaca agggaagaaa tagacaaaac gagtaccagt cttagtctct gggacaaaag      4920
cacgtagcat gcggccaagg tgcttgtctg gaataacttc aaatgtcttg atatcggtat      4980 tcttttaagtc gtctgctcta caacaattca taaaagtcgc ctgaagcaaa agattgtacg      5040
cggcttttgt tgtaggccga gtagttctag cttctattaa gtccatagtc ttcccgacaa      5100 accccccaaat agtttcctgt gtttcagcga ttttagtgat ttcatcatta atcttgttac      5160
ccaaatctct tttccgacct gcttcctttc tcatatgtac agcagataaa tgactcatta      5220
catcatcagg cttttcgtgt accccccacaa caaatctata gggcgataca acatcttcga      5280
```

-continued

```
gtcctttat   tagcttactt   gggtctttca   aatggtattc   aaaggatacc   gtttagtgg    5340 aagaatcgta  ttgcaatgtt  tttgaaatag  acctctggta  tttcaagaaa  gtggagcgct    5400
tgacaggaac  gtcctttctt  ttctgactcg  ccaaattggc  catcaaaatt  atcatcgtca    5460
gatgggaggc  tagttttcc   ttaggtaaag  ggttctcatt  ctccaaaatg  tctttattt     5520 tagagatctg  gtgtaaggga  aggatttgac  taagctcgct  gaagtctgac  atttgtctat    5580
taattgttga  aatttcagta  tccttggtca  attgcattca  aatgcaatta  atcgttgctg    5640
tgagcgctcg  aatttttgc   gtgccatgat  gggccgcctc  tatgaccctg  atttacgaag    5700
aggaggaaat  tcgtccacgg  ccaaaaatga  agctgtgaga  aaaaaaaaaa  catagtactg    5760
tagtatacca  gctgggatta  acaaaactaa  aagggcagac  tattgccaga  tgcaaataca    5820
aaacagtatt  agggcacac   tggaatctaa  tcatggctta  ttagacgttg  actatgtggc    5880
taacctgctc  gaaattat    tgagaacttg  gaaacatggt  aaacccacta  ttaaagtcag    5940
ggaagctatt  cagttagctc  atgcaaaaag  cattaaggta  atttcattat  ggcctcagga    6000
aacctgtagc  ttccgaaatt  ttgatggaaa  tccagaagac  gatccaaatg  tgccctggct    6060
tgtaaggagg  gagaattcgt  cggggccttt  cacacagccg  ggatcagaaa  cgtcttcctt    6120
ggaacagttg  ctaaatggac  tgggatgcat  tgcacgtatt  ctgcgggaga  ataccaacac    6180
agtggaagct  aggagagcga  tagatgacca  cttttgtaag  attaaaaaac  ctgcaaaact    6240
cacaatggtt g                                                              6251
```

<210> SEQ ID NO 1005
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1005
tatatatata tatatata                                                        20

<210> SEQ ID NO 1006
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1006
tatatatata tatata                                                          18

<210> SEQ ID NO 1007
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1007
cccccccccc                                                                 10

<210> SEQ ID NO 1008
<211> LENGTH: 12
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1008
cccccccccc cc                                                              12

<210> SEQ ID NO 1009
<211> LENGTH: 90
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1009
gcatgcacag ataaccatct gcggtgataa attatctctg gcggtgttga cataaatacc          60
actggcggtt ataatgagca catcagcagg                                           90

<210> SEQ ID NO 1010
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1010
gtatgcaaag ga                                                              12
```